US010973486B2

(12) United States Patent
Sjöstrand et al.

(10) Patent No.: US 10,973,486 B2
(45) Date of Patent: Apr. 13, 2021

(54) SYSTEMS AND METHODS FOR RAPID NEURAL NETWORK-BASED IMAGE SEGMENTATION AND RADIOPHARMACEUTICAL UPTAKE DETERMINATION

(71) Applicants: Progenics Pharmaceuticals, Inc., New York, NY (US); EXINI Diagnostics AB, Lund (SE)

(72) Inventors: Karl Vilhelm Sjöstrand, New York, NY (US); Jens Filip Andreas Richter, Lund (SE); Kerstin Elsa Maria Johnsson, Lund (SE); Erik Konrad Gjertsson, Lund (SE)

(73) Assignees: Progenics Pharmaceuticals, Inc., New York, NY (US); EXINI Diagnostics AB, Lund (SE)

(*) Notice: Subject to any disclaimer, the term of this patent is extended or adjusted under 35 U.S.C. 154(b) by 259 days.

(21) Appl. No.: 16/003,006

(22) Filed: Jun. 7, 2018

(65) Prior Publication Data

US 2019/0209116 A1 Jul. 11, 2019

Related U.S. Application Data

(60) Provisional application No. 62/614,935, filed on Jan. 8, 2018.

(51) Int. Cl.
*G06K 9/46* (2006.01)
*A61B 6/00* (2006.01)
(Continued)

(52) U.S. Cl.
CPC ............ *A61B 6/5217* (2013.01); *A61B 6/037* (2013.01); *A61B 6/465* (2013.01); *A61B 6/466* (2013.01);
(Continued)

(58) Field of Classification Search
CPC ......... A61B 6/037; A61B 6/465; A61B 6/466; A61B 6/467; A61B 6/50; A61B 6/5217;
(Continued)

(56) References Cited

U.S. PATENT DOCUMENTS 7,450,747 B2 11/2008 Jabri et al.
7,751,605 B2 7/2010 Gündel et al.
(Continued)

FOREIGN PATENT DOCUMENTS

CN 101528267 A 9/2009
CN 102361594 A 2/2012
(Continued)

OTHER PUBLICATIONS

Cha, Kenny H., et al. "Urinary bladder segmentation in CT urography using deep-learning convolutional neural network and level sets." Medical physics 43.4 (2016): 1882-1896. (Year: 2016).*
(Continued)

*Primary Examiner* — Nirav G Patel
(74) *Attorney, Agent, or Firm* — William R. Haulbrook; Ronen Adato; Choate, Hall & Stewart LLP

(57) ABSTRACT

Presented herein are systems and methods that provide for automated analysis of three-dimensional (3D) medical images of a subject in order to automatically identify specific 3D volumes within the 3D images that correspond to specific organs and/or tissue. In certain embodiments, the accurate identification of one or more such volumes can be used to determine quantitative metrics that measure uptake of radiopharmaceuticals in particular organs and/or tissue regions. These uptake metrics can be used to assess disease state in a subject, determine a prognosis for a subject, and/or determine efficacy of a treatment modality.

55 Claims, 83 Drawing Sheets
(30 of 83 Drawing Sheet(s) Filed in Color)

(51) Int. Cl.
| | |
|---|---|
| *G06T 7/00* | (2017.01) |
| *G06T 5/30* | (2006.01) |
| *A61B 6/03* | (2006.01) |
| *A61K 51/04* | (2006.01) |
| *G06T 15/08* | (2011.01) |
| *G06T 7/143* | (2017.01) |
| *G06T 7/11* | (2017.01) |
| *G06N 3/08* | (2006.01) |
| *G06F 3/0484* | (2013.01) |
| *G06N 3/04* | (2006.01) |

(52) U.S. Cl.
CPC ............... *A61B 6/467* (2013.01); *A61B 6/50* (2013.01); *A61B 6/5223* (2013.01); *A61B 6/5229* (2013.01); *A61B 6/5258* (2013.01); *A61K 51/0478* (2013.01); *G06K 9/4647* (2013.01); *G06T 5/30* (2013.01); *G06T 7/0012* (2013.01); *G06T 7/0014* (2013.01); *G06T 7/11* (2017.01); *G06T 7/143* (2017.01); *G06T 15/08* (2013.01); *G06F 3/04842* (2013.01); *G06K 2209/051* (2013.01); *G06N 3/04* (2013.01); *G06N 3/0454* (2013.01); *G06N 3/08* (2013.01); *G06T 2200/24* (2013.01); *G06T 2207/10081* (2013.01); *G06T 2207/10088* (2013.01); *G06T 2207/10104* (2013.01); *G06T 2207/10108* (2013.01); *G06T 2207/20081* (2013.01); *G06T 2207/30008* (2013.01); *G06T 2207/30081* (2013.01); *G06T 2207/30096* (2013.01)

(58) Field of Classification Search
CPC ... A61B 6/5223; A61B 6/5229; A61B 6/5258; A61K 51/0478; G06F 3/04842; G06K 2209/051; G06K 9/00201; G06K 9/4647; G06K 9/6271; G06N 3/04; G06N 3/0454; G06N 3/08; G06N 3/082; G06T 15/08; G06T 2200/24; G06T 2207/10081; G06T 2207/10088; G06T 2207/10104; G06T 2207/10108; G06T 2207/20081; G06T 2207/30008; G06T 2207/30081; G06T 2207/30096; G06T 5/30; G06T 7/0012; G06T 7/0014; G06T 7/11; G06T 7/143
See application file for complete search history.

(56) References Cited

U.S. PATENT DOCUMENTS

| | | |
|---|---|---|
| 7,935,055 B2 | 5/2011 | Burckhardt |
| 7,970,194 B2 | 6/2011 | Kimura |
| 8,211,401 B2 | 7/2012 | Babich et al. |
| 8,467,856 B2 | 6/2013 | Renisch et al. |
| 8,538,166 B2 | 9/2013 | Gordon et al. |
| 8,705,887 B2 | 4/2014 | Ma et al. |
| 8,778,305 B2 | 7/2014 | Pomper et al. |
| 8,855,387 B2 | 10/2014 | Hamadeh et al. |
| 8,962,799 B2 | 2/2015 | Babich et al. |
| 9,002,081 B2 | 4/2015 | Brown |
| 9,710,915 B2 | 7/2017 | Firouzian et al. |
| 9,721,340 B2 | 8/2017 | Gillies et al. |
| 10,223,610 B1 | 3/2019 | Akselrod-Ballin et al. |
| 10,311,971 B2 | 6/2019 | Opfer et al. |
| 10,339,653 B2 | 7/2019 | Gillies et al. |
| 10,340,044 B2 | 7/2019 | Yao et al. |
| 10,340,046 B2 | 7/2019 | Baker |
| RE47,609 E | 9/2019 | Hamadeh et al. |
| 10,600,184 B2 | 3/2020 | Golden et al. |
| 10,665,346 B2 | 5/2020 | Baker |
| 10,748,652 B2 | 8/2020 | Yao et al. |
| 10,762,993 B2 | 9/2020 | Baker |
| 2003/0215120 A1 | 11/2003 | Uppaluri et al. |
| 2005/0281381 A1 | 12/2005 | Guendel |
| 2006/0062425 A1 | 3/2006 | Shen et al. |
| 2006/0064396 A1 | 3/2006 | Wei et al. |
| 2007/0081712 A1 | 4/2007 | Huang et al. |
| 2007/0081713 A1 | 4/2007 | Jerebko |
| 2007/0100225 A1 | 5/2007 | Maschke |
| 2007/0115204 A1 | 5/2007 | Budz et al. |
| 2008/0027315 A1 | 1/2008 | McGinnis |
| 2009/0309874 A1 | 12/2009 | Salganicoff et al. |
| 2010/0215581 A1 | 8/2010 | Hoffmann |
| 2011/0063288 A1 | 3/2011 | Valadez |
| 2011/0255763 A1 | 10/2011 | Bogoni et al. |
| 2012/0123253 A1 | 5/2012 | Renisch et al. |
| 2013/0038707 A1 | 2/2013 | Cunningham et al. |
| 2013/0211231 A1 | 8/2013 | Sundarapandian et al. |
| 2013/0281841 A1 | 10/2013 | Everett et al. |
| 2015/0110716 A1 | 4/2015 | Armor |
| 2015/0331995 A1 | 11/2015 | Zhao et al. |
| 2016/0203263 A1 | 7/2016 | Maier et al. |
| 2016/0335395 A1 | 11/2016 | Wu et al. |
| 2017/0083682 A1 | 3/2017 | McNutt et al. |
| 2018/0144828 A1 | 5/2018 | Baker |
| 2018/0259608 A1 | 9/2018 | Golden et al. |
| 2018/0360402 A1 | 12/2018 | Carmi |
| 2019/0038239 A1 | 2/2019 | Flohr et al. |
| 2019/0105009 A1 | 4/2019 | Siemionow et al. |
| 2019/0388049 A1 | 12/2019 | Gupta et al. |
| 2020/0027559 A1 | 1/2020 | Baker |
| 2020/0051238 A1 | 2/2020 | El Harouni et al. |
| 2020/0074634 A1 | 3/2020 | Kecskemethy et al. |
| 2020/0085382 A1 | 3/2020 | Taerum et al. |
| 2020/0126666 A1 | 4/2020 | Baker |
| 2020/0193594 A1 | 6/2020 | Georgescu et al. |
| 2020/0193603 A1 | 6/2020 | Golden et al. |
| 2020/0245960 A1 | 8/2020 | Richter et al. |
| 2020/0337658 A1 | 10/2020 | Sjostrand et al. |
| 2020/0342600 A1 | 10/2020 | Sjostrand et al. |
| 2020/0357521 A1 | 11/2020 | Baker |

FOREIGN PATENT DOCUMENTS

| | | |
|---|---|---|
| EP | 1426903 A2 | 6/2004 |
| EP | 1508872 A1 | 2/2005 |
| WO | WO-9905503 A2 | 2/1999 |
| WO | WO-2007/062135 A2 | 5/2007 |
| WO | WO-2009/084995 A1 | 7/2009 |
| WO | WO-2011/077303 A1 | 6/2011 |
| WO | WO-2018/081354 A1 | 5/2018 |
| WO | WO-2019/103912 A2 | 5/2019 |
| WO | WO-2019/136349 A2 | 7/2019 |
| WO | WO-2020/144134 A1 | 7/2020 |
| WO | WO-2020/146032 A1 | 7/2020 |
| WO | WO-2020/190821 A1 | 9/2020 |
| WO | WO-2020/219620 A1 | 10/2020 |

OTHER PUBLICATIONS

Santos-Cuevas, Clara, et al. "99mTc-labeled PSMA inhibitor: Biokinetics and radiation dosimetry in healthy subjects and imaging of prostate cancer tumors in patients." Nuclear Medicine and Biology 52 (2017): 1-6. (Year: 2017).*

Ciernik, I. Frank, et al. "3D-segmentation of the 18F-choline PET signal for target volume definition in radiation therapy of the prostate." Technology in cancer research & treatment 6.1 (2007): 23-30. (Year: 2007).*

Gjertsson, K., Segmentation in Skeletal Scintigraphy Images using Convolutional Neural Networks, Master's Theses in Mathematical Sciences, pp. 39-58, (2017), <https://lup.lub.lu.se/student-papers/search/publication/8916406>. Retrieved on Feb. 24, 2020.

Sjöstrand, K., et al., Automated detection and quantification of Prostatic PSMA uptake in SPECT/CT using a Deep Learning Algorithm for Segmentation of Pelvic Anatomy, The Journal of Nuclear Medicine, 59(1):p. 30, (2018).

Anand, A. et al., Analytic Validation of the Automated Bone Scan Index as an Imaging Biomarker to Standardize Quantitative Changes in Bone Scans of Patients with Metastatic Prostate Cancer, J. Nucl. Med., 57(1):41-45 (2016).

(56) References Cited

OTHER PUBLICATIONS

Anand, A. et al., Automated Bone Scan Index as a quantitative imaging biomarker in metastatic castration-resistant prostate cancer patients being treated with enzalutamide, EJNMMI Research, 6:23, 7 pages (2016).

Anand, A. et al., Translating Prostate Cancer Working Group 2 (PCWG2) Progression Criteria into a Quantitative Response Biomarker in Metastatic Castration Resistant Prostate Cancer (mCRPC), ASCO GU Conference, Poster, presented Feb. 16, 2017.

Anand, A. et al., Translating Prostate Cancer Working Group 2 (PCWG2) progression criteria into a quantitative response biomarker in metastatic castration-resistant prostate cancer (mCRPC), Journal of Clinical Oncology, 35(6):170 (2017).

Armstrong, A. et al., Assessment of the bone scan index in a randomized placebo-controlled trial of tasquinimod in men with metastatic castration-resistant prostate cancer (mCRPC), Urologic Oncology: Seminars and Original Investigations, 32:1308-1316 (2014).

Armstrong, A. et al., Development and validation of a prognostic model for overall survival in chemotherapy-naive men with metastatic castration-resistant prostate cancer (mCRPC) from the phase 3 prevail clinical trial, Journal of Clinical Oncology, 35(Suppl. 6):Abstract 138 (2017).

Armstrong, A. J. et al., Phase 3 prognostic analysis of the automated bone scan index (aBSI) in men with bone-metastatic castration-resistant prostate cancer (CRPC), Meeting Library ASC University. 1 page abstract, (2017).

Belal, S. et al., Association of PET Index quantifying skeletal uptake in NaF PET/CT images with overall survival in prostate cancer patients, ASCO GU 2017, Poster 178, presented Feb. 16, 2017.

Belal, S. et al., PET Index quantifying skeletal uptake in NaF PET/CT images with overall survival in prostate cancer patients, ASCO GU 2017, Abstract (Feb. 13, 2017).

Belal, S. L. et al, 3D skeletal uptake of $^{18}$F sodium fluoride in PET/CT images is associate with overall survival in patients with prostate cancer, EJNMMI Research, 7(15):1-8 (2017).

Belal, S.L. et al., Automated evaluation of normal uptake in different skeletal parts in 18F-sodium fluoride (NaF) PET/CT using a new convolutional neural network method, EJNMMI, EANM '17, 44(Suppl 2):S119-S956, Abstract EP-0116 (2017).

Bushberg, J. T. et al., Essential Physics of Medical Imaging, Essential Physics of Medical Imaging, 19.3: p. 581 (table 15-3), p. 713 paragraph 6, section 19.3 and p. 720, (2011).

Dennis, E. et al., Bone Scan Index: A Quantitative Treatment Response Biomarker for Castration-Resistant Metastatic Prostate Cancer, Journal of Clinical Oncology. 30(5):519-524 (2012).

GE Healthcare, SPECT/CT Cameras, retrieved Oct. 25, 2017: <http://www3.gehealthcare.com.sg/en-gb/products/categories/nuclear_medicine/spect-ct_cameras>.

Giesel, F. L. et al., F-18 labelled PSMA-1007: biodistribution, radiation dosimetry and histopathological validation of tumor lesions in prostate cancer patients, Eur. J. Nucl. Med. Mol. Imaging, 44:678-688 (2017).

Goffin, K. E. et al., Phase 2 study of $^{99m}$Tc-trofolastat SPECT/CT to identify and localize prostate cancer in intermediate- and high-risk patients undergoing radical prostatectomy and extended pelvic lymph node dissection, J. Nucl. Med., 27 pages. (2017).

Goffin, K. E. et al., Phase 2 Study of 99mTc-trofolastat SPECT/CT to identify and localize prostate cancer in intermediate- and high-risk patients undergoing radical prostatectomy and extended pelvic lymph node dissection, Journal of Nuclear Medicine, pp. 1-22 with supplemental data included, (2017).

Guimond, A. et al., Average Brain Models: A Convergence Study, Computer Vision and Image Understanding, 77:192-210 (2000).

Hajnal, J. et al., 4.4 Intensity, Size, and Skew Correction; 7.1 Introduction; 7.2 Methods; 7.3 Image Interpretation—General, In: Medical Image Registration, CRC Press LLC, 80-81:144-148 (2001).

Hiller, S. M. et al., 99mTc-Labeled Small-Molecule Inhibitors of Prostate-Specific Membrane Antigen for Molecular Imaging of Prostate Cancer, Journal of Nuclear Medicine, 54(8):1369-1376 (2013) retrieved Oct. 25, 2017: <http://jnm.snmjournals.org/content/54/8/1369.full>.

Horikoshi, H. et al., Computer-aided diagnosis system for bone scintigrams from Japanese patients: importance of training database, Annals of Nuclear Medicine, 26(8):622-626 (2012).

Huang, J.-H. et al., A Set of Image Processing Algorithms for Computer-Aided Diagnosis in Nuclear Medicine Whole Body Bone Scan Images, IEEE Transactions on Nuclear Science, 54(3):514-522 (2007).

Kaboteh R. et al., Progression of bone metastases in patients with prostate cancer—automated detection of new lesions and calculation of bone scan index, EJNMMI Research, 3:64 (2013).

Kaboteh, R. et al., Convolutional neural network based quantification of choline uptake in PET/CT studies is associated with overall survival in patents with prostate cancer, EJNMMI. EANM '17, 44(Suppl 2):S119-S956, Abstract EP-0642 (2017).

Keiss, et al., Prostate-specific membrane antigen and a target for cancer imaging and therapy, The Quarterly Journal of Nuclear Medicine and Molecular Imaging, 59(3):241-268 (2015).

Kikuchi, A. et al., Automated segmentation of the skeleton in whole-body bone scans: influence of difference in atlas, Nuclear Medicine Communications, 33(9):947-953 (2012).

Kinahan, P.E. et al., PET/CT Standardized Update Values (SUVs) in Clinical Practice and Assessing Response to Therapy, Semin Ultrasound CT MR 31(6):496-505 (2010) retrieved Oct. 25, 2017: <https://www.ncbi.nlm.nih.gov/pmc/articles/PMC3026294/>.

Knutsson, H., and Andersson, M., Morphons: Segmentation using Elastic Canvas and Paint on Priors, IEEE International Conference on Image Processing (ICIP 2005), Genova, Italy, 4 pages (2005).

Kopka, K. et al., Glu-Ureido-Based Inhibitors of Prostate-Specific Membrane Antigen: Lessons Learned During the Development of a Novel Class of Low-Molecular-Weight Theranostic Radiotracers, The Journal of Nuclear Medicine, 58(9)(Suppl. 2):17S-26S, (2017).

Liu, L. et al., Computer-Aided Detection of Prostate Cancer with MRI: Technology and Applications, Acad Radiol. Author manuscript, 50 pages 2016.

Ma, L. et al., Automatic segmentation of the prostate on CT images using deep learning and multi-atlas fusion, Proc. of SPIE vol. 10133:101332O-1-101332O-9 (2017).

Ma, L. et al., Combining Population and Patient-Specific Characteristics for Prostate Segmentation on 3D CT Images, Proc of SPIE 9784:978427-1-8 (2016).

Ma, L. et al., Random Walk Based Segmentation for the Prostate on 3D Transrectal Ultrasound Images, Proc SPIE Int Soc Opt Eng. Author manuscript, 13 pages (2016).

Mayo Clinic Staff, Choline C-11 PET scan, Overview, Mayo Clinic, 4 pages (2017), retrieved Oct. 25, 2017: <https://www.mayoclinic.org/tests-procedures/choline-c-11-pet-scan/home/ovc-20156994>.

Nakajima, K. et al., Enhanced diagnostic accuracy for quantitative bone scan using an artificial neural network system: a Japanese multi-center database project, EJNMMI Research, 3:83 (2013).

National Cancer Institute, NCI Drug Dictionary: gallium Ga 68-labeled PSMA-11, retrieved Oct. 25, 2017: <https://www.cancer.gov/publications/dictionaries/cancer-drug?cdrid=766400>.

National Cancer Institute, NCI Drug Dictionary: technetium Tc 99m methylene diphosphonate, retrieved Oct. 25, 2017: <https://www.cancer.gov/publications/dictionaries/cancer-drug?cdrid=537722>.

Perera, M. et al., Sensitivity, Specificity, and Predictors of Positive 68Ga-Prostate-specific Membrane Antigen Positron Emission Tomography in Advanced Prostate Cancer: A Systematic Review and Meta-analysis, European Urology, 70(6):926-937 (2016).

Polymeri, E. et al., Analytical validation of an automated method for segmentation of the prostate gland in CT images, EJNMMI, EANM '17, 44(Suppl 2):S119-S956, Abstract EP-0641 (2017).

radiologyinfo.org for Patients, Computed Tomography (CT), retrieved Oct. 25, 2017: <https://www.radiologyinfo.org/en/submenu.cfm?pg=ctscan>.

Rowe, S. P. et al., PET Imaging of prostate-specific membrane antigen in prostate cancer: current state of the art and future challenges, Prostate Cancer and Prostatic Diseases, 1-8 (2016).

(56) References Cited

OTHER PUBLICATIONS

Sabbatini, P. et al., Prognostic Significance of Extent of Disease in Bone in Patients With Androgen-Independent Prostate Cancer, Journal of Clinical Oncology, 17(3):948-957 (1999).

Sadik, M. et al., 3D prostate gland uptake of 18F-choline—association with overall survival in patients with hormone-naïve prostate cancer, The Journal of Nuclear Medicine, 58(Suppl. 1):Abstract 544 (2017).

Sadik, M. et al., A new computer-based decision-support system for the interpretation of bone scans, Nuclear Medicine Communications. 27(5):417-423 (2006).

Sadik, M. et al., Automated 3D segmentation of the prostate gland in CT images—a first step towards objective measurements of prostate uptake in PET and SPECT images, Journal of Nuclear Medicine, 58(1) (2017).

Sadik, M. et al., Automated quantification of reference levels in liver and mediastinum (blood pool) for the Deauville therapy response classification using FDG-PET/CT in lymphoma patients, EJNMMI, EANM '17, 44(Suppl 2):S119-S956, Abstract EP-0770 (2017).

Sadik, M. et al., Computer-assisted interpretation of planar whole-body bone scans, Journal Nuclear Medicine, 49(12):1958-65, 2008.

Sadik, M. et al., Convolutional neural networks for segmentation of 49 selected bones in CT images show high reproducibility, EJNMMI, EANM '17, 44(Suppl 2):S119-S956, Abstract OP-657 (2017).

Sadik, M. et al., Improved classifications of planar whole-body bone scans using a computer-assisted diagnosis system: a multicenter, multiple-reader, multiple-case study, Journal of Nuclear Medicine, 50(3): 368-75, 2009.

Sadik, M. et al., Variability in reference levels for Deauville classifications applied to lymphoma patients examined with 18F-FDG-PET/CT, EJNMMI, EANM '17, 44(Suppl 2):S119-S956, Abstract EP-0771 (2017).

Sajn, L. et al., Computerized segmentation of whole-body bone scintigrams and its use in automated diagnostics, Computer Methods and Programs in Biomedicine, 80:47-55 (2005).

Salerno, J. et al., Multiparametric magnetic resonance imaging for pre-treatment local staging of prostate cancer: A Cancer Care Ontario clinical practice guideline, Canadian Urological Association Journal, 10(9-10):332-339 (2016).

Sjöstrand K. et al., Statistical regularization of deformation fields for atlas-based segmentation of bone scintigraphy images, MICCAI 5761:664-671 (2009).

Sluimer, I. et al., Toward Automated Segmentation of the Pathological Lung in CT, IEEE Transactions on Medical Imaging, 24(8):1025-1038 (2005).

Tian, Z. et al., A fully automatic multi-atlas based segmentation method for prostate MR images, Proc SPIE Int Soc Opt Eng. Author manuscript, 12 pages (2015).

Tian, Z. et al., A supervoxel-based segmentation method for prostate MR images, Med. Phys., 44(2):558-569 (2017).

Tian, Z. et al., Deep convolutional neural network for prostate MR segmentation, Proc. of SPIE 10135:101351L-1-101351L-6 (2017).

Tian, Z., et al., Superpixel-based Segmentation for 3D Prostate MR Images, IEEE Trans Med Imaging, Author manuscript, 32 pages, (2016).

Ulmert, D. et al., A Novel Automated Platform for Quantifying the Extent of Skeletal Tumour Involvement in Prostate Cancer Patients Using the Bone Scan Index, European Urology, 62(1):78-84 (2012).

Wrangsjo, A. et al., Non-rigid Registration Using Morphons, Proceedings of the 14th Scandinavian Conference on Image Analysis (SCIA '05), pp. 501-510 (2005).

Yin, T.-K., A Computer-Aided Diagnosis for Locating Abnormalities in Bone Scintigraphy by a Fuzzy System With a Three-Step Minimization Approach, IEEE Transactions on Medical Imaging, 23(5):639-654 (2004).

Litjens, G. et al., A survey on deep learning in medical image analysis, Medical Image Analysis, 42:60-88, (2017).

Partial Search Report and Provisional Opinion, International Application No. PCT/US2019/012486 (Systems and Methods for Rapid Neural Network-Based Image Segmentation and Radiopharmaceutical Uptake Determination, filed Jan. 7, 2019), issued by ISA/European Patent Office, 16 pages, dated May 7, 2019.

Rowe, S. P. et al., PSMA-Based [$^{18}$F]DCFPyL PET/CT is Superior to Conventional Imaging for Lesion Detection in Patients with Metastatic Prostate Cancer, Mol Imaging Biol, 18:411-419, (2016).

Eiber, M. et al., Prostate Cancer Molecular Imaging Standardized Evaluation (PROMISE): Proposed miTNM Classification for the Interpretation of PSMA-Ligand PET/CT, The Journal of Nuclear Medicine, 59(3):469-478, (2018).

International Search Report, International Application No. PCT/US2019/012486 (Systems and Methods for Rapid Neural Network-Based Image Segmentation and Radiopharmaceutical Uptake Determination, filed Jan. 7, 2019), issued by ISA/European Patent Office, 6 pages, dated Jul. 2, 2019.

Written Opinion, International Application No. PCT/US2019/012486 (Systems and Methods for Rapid Neural Network-Based Image Segmentation and Radiopharmaceutical Uptake Determination, filed Jan. 7, 2019), issued by ISA/European Patent Office, 13 pages, dated Jul. 2, 2019.

American College of Radiology (ACR) and the Society for Pediatric Radiology (SPR), ACR-SPR Practice Parameter for the Performance of Skeletal Scintigraphy (Bone Scan), Resolution 28, (2013-Revused2017), available from: http://www.acr.org.

Anand, A. et al., A Pre-Analytical Validation Study of Automated Bone Scan Index: Effect on Accuracy and Reproducibility Due to the Procedural Variabilities in Bone Scan Image Acquisition. J Nucl Med. Jul. 21, 2016. [Epub ahead of print].

Armstrong, A. J. et al., Phase 3 Assessment of the Automated Bone Scan Index as a Prognostic Imaging Biomarker of Overall Survival in Men with Metastatic Castration-Resistant Prostate Cancer: A Secondary Analysis of a Randomized Clinical Trial. JAMA Oncology 4:944-951, (2018).

Bai, P. et. al., Body region localization in whole-body low-dose CT images of PET/CT scans using virtual landmarks, Medical Physics Wiley USA, 46(3): 1286-1299 (2019).

Bombardieri, E. et al., Bone scintigraphy: procedure guidelines for tumour imaging, Eur J. Nucl. Med. Mol. Imaging, 30:BP99-BP106, (2003).

Brynolfsson, J., et. al., Deep Learning based urinary bladder segmentation using 18FDCFPyL (PyL-PSMA) PET/CT images, EPS-145, European Association of Nuclear Medicine, (2020), <http://link.springer.com/article/10.1007/s00259-020-04988-4>. Retrieved Sep. 18, 2020.

Brynolfsson, J., et. al., Deep Learning-Enabled comprehensive detection and quantification of 18FDCFPyL (PyL-PSMA) PET/CT, OP-548, European Association of Nuclear Medicine, (2020), <http://link.springer.com/article/10.1007/s00259-020-04988-4>. Retrieved Sep. 18, 2020.

Dertat, A., Applied Depp Learning—Part 4: Convolutional Neural Networks, Towards Data Science,<http://towardsdatascience.com/applied-deep-learning-part-4-convolutional-neural-networks-584bc134c1e2> (2017).

Gjertsson, K., et. al., A Novel Automated Deep Learning Algorithm for Segmentation of the Skeleton in Low-Dose CT for [(18)F] DCFPyL PET/CT Hybrid Imaging in Patients with Metastatic Prostate Cancer, Annual Congress of the European Association of Nuclear Medicine Oct. 12-16, 2019 Barcelona, Spain. Eur J Nucl Med Mol Imaging 46 (Suppl 1), S1-S952 (2019). Abstract EP-0823, p. S765.

Johnsson, K., et. al., miPSMA Index: Comprehensive and Automated Quantification of 18F-DCFPyL (PyL-PSMA) PET/CT for Prostate Cancer Staging, J Nucl Med., 61: (Supplement 1): 1435, (2020).

Lin, T.Y. et. al., Feature Pyramid Networks for object detection, FAIR, (2016), <https://arxiv.org/abs/1612.03144v1>.

Meyer, A., et. al., Deep learning algorithm improves identification of men with low-risk prostate cancer using PSMA targeted 99mTc-MIP-1404 SPECT/CT, Journal of Clinical Oncology, 37:(15), (2019).

Nickols, N.G., et. al., A deep learning algorithm to predict coexisting metastatic disease using intraprostatic [F18]DCFPYL PSMA image alone in veterans with prostate cancer, Journal of Clinical Oncology 38, (Supplement 6), 2020.

(56) References Cited

OTHER PUBLICATIONS

Ohlsson, M., et. al., Automated decision support for bone scintigraphy, Computer-based medical systems, pp. 1-6, (2009).

Pouliot, F., et. al., Prospective evaluation of a Novel Deep Learning Algorithm (PSMA-AI) in the assessment of 99mTc-MIP-1404 SPECT/CT in patients with low or intermediate risk prostate cancer, Annual Congress of the European Association of Nuclear Medicine Oct. 12-16, 2019 Barcelona, Spain. Eur J Nucl Med Mol Imaging 46 (Suppl 1), S1-S952 (2019). Abstract EP-0804, p. S765.

Ren, S., et. al., Faster R-CNN: Towards Real-Time Object Detection with Region Proposal Networks, (2015), <http://image-net.org/challenges/LSVRC/2015/results>.

Ronneberger, O., et. al., U-Net: Convolutional Networks for Biomedical Image Segmentation, Springer International Publishing, (2015), <http://lmb.informatik.uni-freiburg.de/>. Retrieved on Nov. 18, 2015.

Sjostrand, K., et. al., Automated Assessment of Prostatic PSMA Expression in SPECT/CT using Deep Convolutional Neural Networks—A Prospectively Planned Retrospective Analysis of Phase 3 Study MIP-1404-3301, The Journal of Nuclear Medicine, 60 (Supplement 1): Abstract 401, (2019).

\* cited by examiner

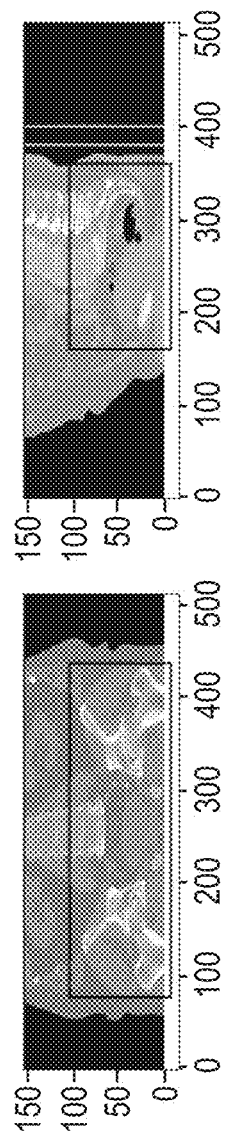
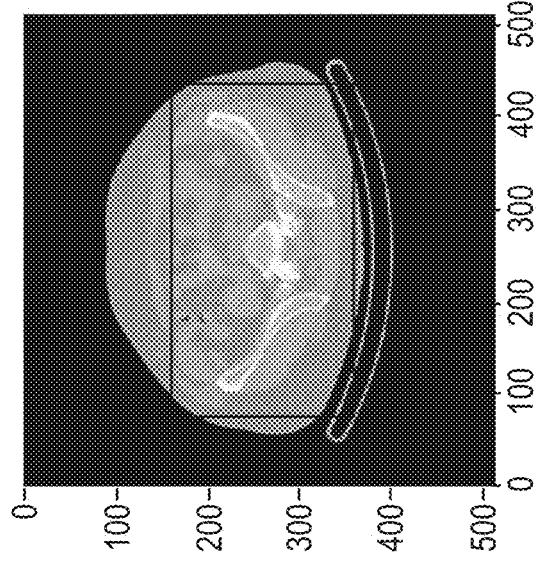
FIG. 5A
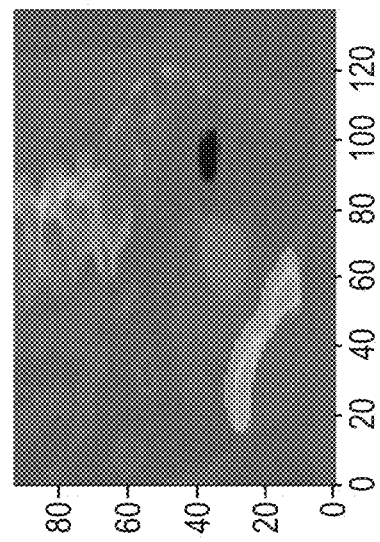
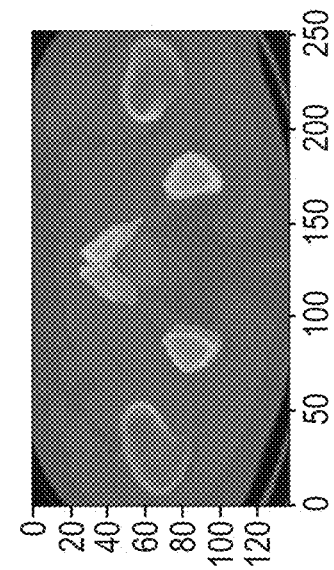
FIG. 5B

TRAD. LOCALIZATION
(MEDIAN CROP SIZE = 94 x 130 x 221)

TRAD. LOCALIZATION
(MEDIAN CROP SIZE = 74 x 116 x 205)

Report

× esc

| | | DIAGNOSTIC DEVICE |
|---|---|---|
| Patient | REPORT DATE | Pioneer Web 1404 CADx |

PATIENT NAME

PATIENT ID

AGE <BIRTH DATE>

Study data

STUDY DATE

INDEX
1.24

PREVIOUS STUDY INDEX
2.62

TECHNICIAN

PHYSICIAN

COMMENT
Lorem ipsum dolor sit amet,
consectetur adipiscing elit. Morbi
cursus nisi enim, ac fringilla sem
accumsan quis. Cras nec arcu sed
nulla elementum tincidunt faucibus a
felis. Aenean a convallis arcu. Cras ac
leo at leo bibendum placerat ac sit STUDY DESCRIPTION
Lorem ipsum dolor sit amet ads Tumor data

| | TUMOR #1 | TUMOR #2 |
|---|---|---|
| Volume (ml) | 7.7 | 7.7 |
| Max (counts/ml) | 29.312 | 29.312 |
| Mean (counts/ml) | 17.336 | 17.336 |
| Median (counts/ml) | 16.402 | 16.402 |
| Max voxel intensity | 3.232 | 3.232 |
| Total (counts) | 133.808 | 133.808 |

Prostate data

NORMAL TISSUE UPTAKE (COUNTS/ML)
731.8

PROSTATE VOLUME (ML)
80.7

TOTAL PROSTATE UPTAKE (COUNTS)
386.933

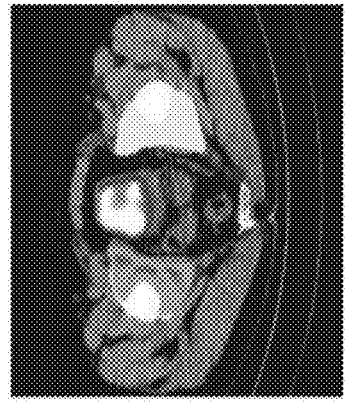

FIG. 24

| Patient name ↓ | Patient id |
|---|---|
| > 28802 | 28802 |
| > 29216 | 29216 |
| > 35660 | 35660 |
| > 41198 | 41198 |
| > 57060 | 57060 |

Items per page: 25 ▾   1 - 5 of 5   < >

FIG. 27A

| > 28802 |
| > 29216 |
| > 35660 |

Report

Export PNG | Export DICOM | X

Report ID

Diagnostic device
Pioneer 1.0.0

CAUTION - Investigation Device. Limited by Federal (or United States) law to investigational use.

Patient

Patient name
29216

Patient ID
29216

Age (Birth date)
-(-)

Study data

Study date
☐

TBR
106.8

Significance
Clinically significant

Quality Control

Quality Control
⊙ Image requirements are met
⊙ Target is correct
⊙ Background is correct
Quality cation
Automatic

} 2918

Pioneer 1.0.0 DOES NOT PROVIDE OR SUBSTITUTE FOR MEDICAL SERVICES OR ADVICE. EXINI PROVIDES Pioneer 1.0.0 FOR INFORMATIONAL PURPOSES ONLY AND Pioneer 1.0.0 DOES NOT CONTAIN OR CONSTITUTE ANY MEDICAL ADVICE OR OPINION. YOU ARE SOLELY RESPONSIBLE FOR ALL DECISIONS OR ACTIONS RESULTING FROM YOUR USE OF Pioneer 1.0.0, INCLUDING, BUT NOT LIMITED TO ANY DECISION TO PROVIDE OR SEEK, OR REFRAIN FROM PROVIDING OR SEEKING, ANY MEDICAL ADVICE OR TREATMENT. Information made available on or through Pioneer 1.0.0 should not be the sole information for making decisions and should be discussed with your healthcare provider prior to making medical decisions or to diagnose or treat a medical or health condition. Your use of Pioneer 1.0.0 does not create a doctor-patient relationship between you and EXINI Report creation
☐

Quality Control approved by
☐

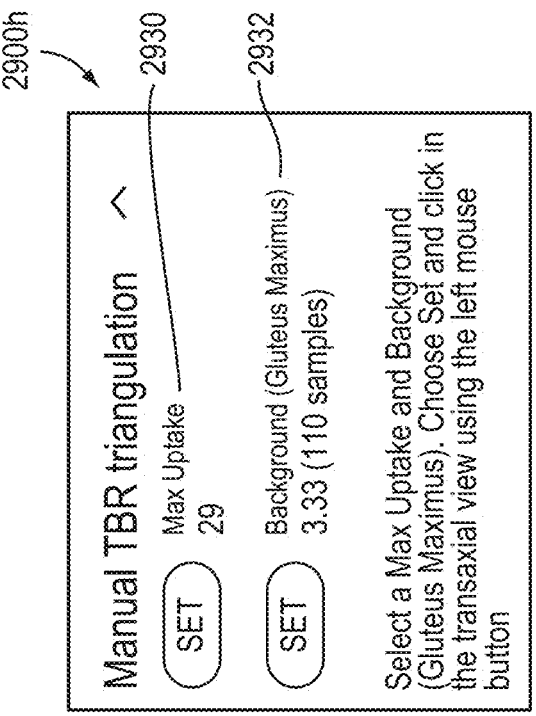
FIG. 29F
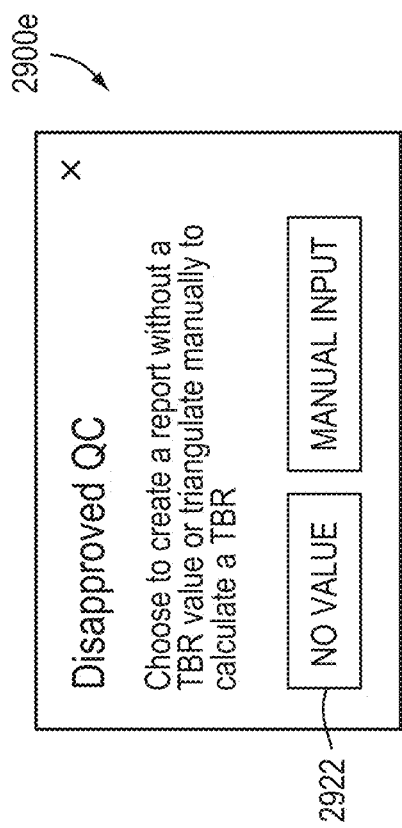
FIG. 29E
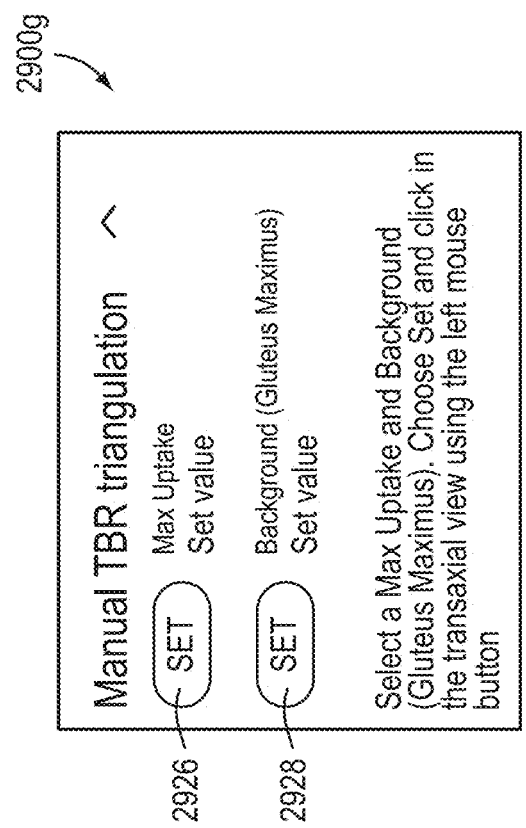
FIG. 29H
FIG. 29G

SYSTEMS AND METHODS FOR RAPID NEURAL NETWORK-BASED IMAGE SEGMENTATION AND RADIOPHARMACEUTICAL UPTAKE DETERMINATION

CROSS REFERENCE TO RELATED APPLICATIONS

This application claims priority to and benefit of U.S. Provisional Application No. 62/614,935, filed Jan. 8, 2018, the content of which is hereby incorporated by reference in its entirety.

FIELD OF THE INVENTION

This invention relates generally to methods, systems, and architectures for automated analysis and/or presentation of medical image data. More particularly, in certain embodiments, the invention relates to automated identification of one or more particular regions of interest (e.g., corresponding to specific organs or tissue) within images of a subject and determination of radiopharmaceutical uptake within such region(s), e.g., for identification and/or staging of disease, e.g., prostate cancer.

BACKGROUND OF THE INVENTION

Targeted image analysis involves the use of radiolabeled small molecules that bind to specific receptors, enzymes and proteins in the body that are altered during the evolution of disease. After administration to a patient, these molecules circulate in the blood until they find their intended target. The bound radiopharmaceutical remains at the site of disease, while the rest of the agent clears from the body. The radioactive portion of the molecule serves as a beacon so that an image may be obtained depicting the disease location and concentration using commonly available nuclear medicine cameras, known as single-photon emission computerized tomography (SPECT) or positron emission tomography (PET) cameras, found in most hospitals throughout the world. Physicians can then use this information to determine the presence and the extent of disease in a patient. The physician can use this information to provide a recommended course of treatment to the patient and to track the progression of disease.

There are a variety of software-based analytical techniques available for analysis and enhancement of PET and SPECT images that can be used by a radiologist or physician. There are also a number of radiopharmaceuticals available for imaging particular kinds of cancer. For example, the small molecule diagnostic 1404 targets the extracellular domain of prostate specific membrane antigen (PSMA), a protein amplified on the surface of >95% of prostate cancer cells and a validated target for the detection of primary and metastatic prostate cancer. 1404 is labeled with technetium-99m, a gamma-emitter isotope that is widely available, relatively inexpensive, facilitates efficient preparation, and has spectrum characteristics attractive for nuclear medicine imaging applications.

Another example radiopharmaceutical is PyL™ (also known as [$^{18}$F]DCFPyL), which is a clinical-stage, fluorinated PSMA-targeted PET imaging agent for prostate cancer. A proof-of-concept study published in the April 2015 issue of the Journal of Molecular Imaging and Biology demonstrated that PET imaging with PyL™ showed high levels of PyL™ uptake in sites of putative metastatic disease and primary tumors, suggesting the potential for high sensitivity and specificity in detecting prostate cancer.

An oncologist may use images from a targeted PET or SPECT study of a patient as input in her assessment of whether the patient has a particular disease, e.g., prostate cancer, what stage of the disease is evident, what the recommended course of treatment (if any) would be, whether surgical intervention is indicated, and likely prognosis. The oncologist may use a radiologist report in this assessment. A radiologist report is a technical evaluation of the PET or SPECT images prepared by a radiologist for a physician who requested the imaging study and includes, for example, the type of study performed, the clinical history, a comparison between images, the technique used to perform the study, the radiologist's observations and findings, as well as overall impressions and recommendations the radiologist may have based on the imaging study results. A signed radiologist report is sent to the physician ordering the study for the physician's review, followed by a discussion between the physician and patient about the results and recommendations for treatment.

Thus, the process involves having a radiologist perform an imaging study on the patient, analyzing the images obtained, creating a radiologist report, forwarding the report to the requesting physician, having the physician formulate an assessment and treatment recommendation, and having the physician communicate the results, recommendations, and risks to the patient. The process may also involve repeating the imaging study due to inconclusive results, or ordering further tests based on initial results.

If an imaging study shows that the patient has a particular disease or condition (e.g., cancer), the physician discusses various treatment options, including surgery, as well as risks of doing nothing or adopting a watchful waiting or active surveillance approach, rather than having surgery.

There are limitations associated with this process, both from the perspective of the physician and from the perspective of the patient. While the radiologist's report is certainly helpful, the physician must ultimately rely on her experience in formulating an assessment and recommendation for her patient. Furthermore, the patient must place a great deal of trust in his physician. The physician may show the patient his PET/SPECT images and may tell the patient a numerical risk associated with various treatment options or likelihood of a particular prognosis, but the patient may very well struggle to make sense of this information. Moreover, the patient's family will likely have questions, particularly if cancer is diagnosed but the patient opts not to have surgery. The patient and/or his family members may search online for supplemental information and may become misinformed about risks of the diagnosed condition. A difficult ordeal may become more traumatic.

Thus, there remains a need for systems and methods for improved analysis of medical imaging studies and communication of those results, diagnoses, prognoses, treatment recommendations, and associated risks to a patient.

SUMMARY OF THE INVENTION

Presented herein are systems and methods that provide for automated analysis of three-dimensional (3D) medical images of a subject in order to automatically identify specific 3D volumes within the 3D images that correspond to specific organs and/or tissue. In certain embodiments, the accurate identification of one or more such volumes are used to automatically determine quantitative metrics that represent uptake of radiopharmaceuticals in particular organs and/or tissue regions. These uptake metrics can be used to assess disease state in a subject, determine a prognosis for a subject, and/or determine efficacy of a treatment modality.

For example, the systems and methods described herein can be used for automated analysis of medical images in order to determine uptake metrics that provide a quantitative measure of uptake of a radiopharmaceutical such as a radionuclide labelled PSMA binding agent (e.g., $^{99m}$Tc-MIP-1404, e.g., [$^{18}$F]DCFPyL) within a prostate of the subject. Such uptake metrics are of relevance for evaluating patient risk for prostate cancer and/or prostate cancer severity/stage within a subject. For example, it has been found that high sensitivities and specificities can be achieved for the automated classification of clinically significant prostate cancer vs. clinically non-significant prostate cancer.

In certain embodiments, the image analysis approaches described herein utilize a combination of 3D anatomical and functional images obtained for the subject. Anatomical images, such as x-ray computed tomography (CT) images, provide detailed anatomical/structural information. Functional images convey information relating to physiological activities within specific organs and/or tissue, such as metabolism, blood flow, regional chemical composition, and/or absorption. Of particular relevance are nuclear medicine images, such as single photon emission computed tomography (SPECT) and/or positron emission tomography (PET) images, which are acquired by detecting emitted radiation from the subject and which can be used to infer spatial distributions of administered radiopharmaceuticals within the subject.

For example, SPECT imaging can be used to evaluate uptake of the radiopharmaceutical $^{99m}$Tc-MIP-1404 (which is 1404 labelled with $^{99m}$Tc). In certain embodiments, in order to evaluate $^{99m}$Tc-MIP-1404 uptake in a prostate of a subject, a CT image and a corresponding SPECT image are obtained for the subject, such that the anatomical/structural information of the CT image can be correlated with the functional information of the corresponding SPECT image. Often the CT and SPECT images are acquired via two separate scans (e.g., a first scan for the CT image and a second scan for the SPECT image) using a single multi-modal imaging system, such that the subject is a substantially fixed position over the duration of the two scans. In this manner, a mapping between voxels of the CT image and those of the SPECT image is established, and volumes identified within the CT image as corresponding to specific organs and/or tissue regions can be used to identify those voxels the SPECT image that correspond to those same specific organs/and or tissue regions.

Accordingly, in certain embodiments, the image analysis approaches described herein utilize convolutional neural networks (CNNs) to accurately identify a prostate volume within the CT image that corresponds to the prostate of the subject. The identified prostate volume can be used to identify those voxels of the SPECT image that also correspond to the subject's prostate. Uptake metrics that provide a measure of uptake of the imaging agent (e.g., a labelled PSMA binding agent, e.g., $^{99m}$Tc-MIP-1404 or [$^{18}$F] DCFPyL) in the prostate can thus be computed using the intensities of SPECT image voxels corresponding to the prostate of the subject. The uptake metrics, then, can be converted to an identification of whether or not the subject has prostate cancer and/or a quantification of risk that the subject has prostate cancer, and/or a staging of the disease (e.g., as part of disease tracking over time), which may be used by the medical practitioner in advising treatment options, and/or monitoring efficacy of administered therapy, for example.

Various advances are described herein that improve the performance of the automated measurement of uptake metrics in the prostate (or, more broadly, a particular organ or tissue region of interest) via this multi-image approach, i.e., analysis of a 3D anatomical image in combination with a 3D functional image. These advances include, for example, the automated identification of a bounding box in the 3D anatomical image (e.g., using a first convolutional neural network, CNN) to identify a pelvic region within which the prostate lies.

For example, a set of 3D anatomical images with identified physiology (e.g., identified pelvic regions) is used to train a first CNN on points representing the boundaries of the pelvic region (e.g., the vertices of a cuboid bounding box) such that the first CNN can be used to automatically identify the pelvic region in a 3D anatomical image of a subject. This provides a more standard-sized initial volumetric region of the 3D anatomical image to be subsequently processed (e.g., via a second CNN) for detailed segmentation of regions of interest within the initial volumetric region—e.g., where the bounding box bounds regions of the image corresponding to the prostate and/or the bladder and/or the rectum, and/or gluteal muscles of the subject. Imaging agent uptake metrics may then be determined from the portions of the 3D functional image that map to one or more of the identified regions of the 3D anatomical image. Note that, as used herein, the 'bounding box' isn't necessarily a cuboid, but may have other shapes. In certain embodiments, the bounding box is a cuboid.

The determination of the bounding box via the first CNN may use, as input, a significantly less dense resolution than is used for segmentation of the prostate and/or other organs within the bounding box by the second CNN. For example, a whole body 3D anatomical image having a first number of voxels (e.g., 81×68×96 voxels) may be processed via the first CNN to find the bounding box, then the second CNN may process an image corresponding to the bounding box region but having a more dense resolution, e.g., many more voxels (e.g., 94×138×253 voxels) than the first number of voxels.

The 'bounding box' approach of identifying one or more portions of a 3D anatomical image that is/are relevant to the analysis at hand, e.g., prior to applying a second CNN (for detailed segmentation), improves computational efficiency by removing a large portion of the initial 3D anatomical image prior to the more computationally intensive subsequent processing. This approach is more computationally efficient than performing the detailed segmentation on the entire initial 3D anatomical image since, for example, identification of the pelvic region (e.g., the vertices of a cuboid bounding box) is simpler than detailed segmentation of a prostate, bladder, and/or other tissues of interest. Not only is this approach more computationally efficient, it also may result in more accurate subsequent processing, e.g., the more detailed segmentation provided by the second CNN. This is because, for example, 3D anatomical images obtained at different medical institutions using different machines vary in size (e.g., where varying size means there are different numbers of voxels of the images, and/or different volumes of the patient tissue represented in the images), and training the second CNN for automated detailed segmentation of the prostate using portions of 3D anatomical training images having a more standardized image volume size, and within which the organs and other tissue regions of interest lie, results in a more robust, accurate segmentation.

Another advance described herein that improves the performance of the automated measurement of uptake metrics in the prostate (or, more broadly, a particular organ or tissue region of interest) via this multi-image approach (i.e., analysis of a 3D anatomical image in combination with a 3D functional image) is the accurate identification of one or more tissue regions in addition to the prostate, and the accounting for imaging agent uptake in those regions in the determination of (i) uptake metrics in the prostate and/or (ii) an identification and/or staging of prostate cancer. Certain imaging agents comprising a PSMA binding agent have high uptake in certain organs, which may affect the identification of diseased tissue (e.g., prostate cancer). For example, uptake of a radionuclide labelled PSMA binding agent by the bladder may result in scattering in the 3D functional image, and may reduce accuracy of the measured imaging agent intensity in the prostate, which is located near the bladder. By training a second CNN for detailed segmentation of both the prostate and the bladder of a subject, it is possible to accurately, automatically account for a 'bleed through' or 'cross-talk' effect and/or other effects caused by uptake of the imaging agent by the bladder. Furthermore, by training the second CNN for identification of a reference region in the 3D anatomical image, e.g., the gluteal muscles, it is possible to more accurately weight/normalize imaging agent intensity measurements and improve the accuracy and diagnostic value of the uptake measurements in the prostate of the subject.

Thus, in certain embodiments, the systems and methods described herein utilize a unique combination of two CNN modules, wherein a first CNN module identifies an initial volume of interest (VOI) within the CT image and a second receives the VOI as input and identifies the prostate volume therein. As described herein, this approach allows the second CNN module to operate on a smaller input size (e.g., the VOI as opposed to the full CT image). The savings in computational resources (e.g., memory; e.g., processing time) by reducing the input size in this manner can be allocated to improving the accuracy of the second CNN module and/or used to improve the speed of the image processing approach.

In certain embodiments, the systems and methods described herein identify, along with the prostate, various additional tissue volumes within the CT image. For example, additional tissue volumes corresponding to pelvic bones, a bladder, a rectum, and gluteal muscles of the subject may be identified in addition to the prostate. As described herein, the identification of such additional tissue volumes can be used for a variety of functions and confers advantages over other approaches, such as a binary classification approach wherein voxels of the CT image are either identified as corresponding to prostate or not. In particular, identification of additional tissue volumes can, for example, (i) improve the accuracy with which the CNN module identifies the prostate volume within the CT image, (ii) provide for identification of reference regions that can be used to compute normalization values for uptake metric calculation, and (iii) allow for intensities of SPECT image voxels corresponding to prostate to be corrected for cross-talk that results, for example, from the accumulation of radiopharmaceutical within the bladder.

In certain embodiments, the image analysis approaches described herein can be used for analysis of a variety of anatomical and functional images and are not limited CT and SPECT images. For example, positron emission tomography (PET) is another functional imaging modality that provides information about the distribution of radiopharmaceutical within a subject. As with SPECT images, PET images can be used in combination with CT images to determine uptake metrics for various organs and tissue regions of interest. The approaches described herein may also be applied to a variety of organs and/or tissue regions of interest, such as bone, lymph nodes, liver, and lungs.

Accordingly, by providing for rapid and accurate identification of specific organs and tissue regions within medical images, the systems and method described herein provide for accurate and automated determination of uptake metrics that provide quantitative measures of radiopharmaceutical uptake within various organs and tissue regions within a subject. Uptake metrics determined in this automated manner provide valuable tools for assessing disease risk, state, and progression within patients, as well as treatment efficacy.

In one aspect, the invention is directed to a method for automatically processing 3D images to identify 3D volumes within the 3D images that correspond to a prostate of a subject and determining one or more uptake metrics indicative of radiopharmaceutical uptake therein (i.e., in the prostate), the method comprising: (a) receiving, by a processor of a computing device, a 3D anatomical image of the subject obtained using an anatomical imaging modality [e.g., x-ray computed tomography (CT) (e.g., a whole-body CT image; e.g., a partial body CT image); e.g., magnetic resonance imaging (MRI); e.g., 3D ultra-sound], wherein the 3D anatomical image comprises a graphical representation of tissue (e.g., soft-tissue and/or bone) within a subject, at least a portion of which corresponds to a pelvic region of the subject; (b) receiving, by the processor, a 3D functional image of the subject obtained using a functional imaging modality [e.g., single-photon emission computed tomography (SPECT); e.g., positron emission tomography (PET)], wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the pelvic region of the subject; (c) determining, by the processor, using a first module (e.g., a first machine learning module), an initial volume of interest (VOI) within the 3D anatomical image (e.g., a parallelepiped, e.g., a cuboid), the initial VOI corresponding to tissue within the pelvic region of the subject and excluding tissue outside the pelvic region of the subject (e.g., wherein the VOI excludes more voxels of the 3D anatomical image than it includes; e.g., wherein the VOI includes less than 25% of the voxels of the 3D anatomical image; e.g., wherein a majority of voxels within the VOI represent physical volumes within the pelvic region of the subject); (d) identifying, by the processor, using a second module (e.g., a second machine learning module), a prostate volume within the initial VOI corresponding to the prostate of the subject; and (e) determining, by the processor, (e.g., and displaying) the one or more uptake metrics using the 3D functional image and the prostate volume identified within the initial VOI of the 3D anatomical image [e.g., computing a quantity of radiopharmaceutical in the prostate of the subject based on intensity values of voxels of the 3D functional image that correspond to the prostate volume identified within the initial VOI of the 3D anatomical image; e.g., computing a sum (e.g., a weighted sum), an average, and/or a maximum of intensities of voxels of the 3D functional image representing a physical volume occupied by the prostate of the subject] [e.g., wherein the one or more uptake metrics comprises a tumor to background ratio (TBR) value and/or wherein the method comprises determining (e.g., and displaying) a prostate cancer classification status of either (i) clinically significant or (ii) clinically non-significant based at least in part on the TBR value].

In certain embodiments, the first module receives the 3D anatomical image as input and outputs a plurality of coordinate values representing opposite corners of a rectangular volume within the 3D anatomical image (e.g., two sets of coordinate values that represent the opposite corners of the rectangular volume).

In certain embodiments, step (c) comprises determining, using the first module, a 3D pelvic bone mask that identifies a volume of the 3D anatomical image corresponding to pelvic bones (e.g., one or more (up to all) of a sacrum, a coccyx, a left hip bone, and a right hip bone) of the subject.

In certain embodiments, the first module is a Convolutional Neural Network (CNN) module (e.g., a Neural Network module that utilizes one or more convolution layers).

In certain embodiments, step (d) comprises using the second module to identify one or more additional tissue volumes within the 3D anatomical image, each volume corresponding to a specific tissue region within the subject, wherein the one or more additional tissue volumes correspond(s) to one or more specific tissue regions selected from the group consisting of: a pelvic bone (e.g., a sacrum; e.g., a coccyx; e.g., a left hip bone; e.g., a right hip bone) of the subject; a bladder of the subject; a rectum of the subject; and a gluteal muscle (e.g., a left gluteal muscle; e.g., a right gluteal muscle) of the subject.

In certain embodiments, step (d) comprises using the second module to classify each voxel within the initial VOI as corresponding a particular tissue region of a set of (predetermined) different tissue regions {e.g., the set comprising the prostate and, optionally, one or more additional tissue regions [e.g., a pelvic bone (e.g., a sacrum; e.g., a coccyx; e.g., a left hip bone; e.g., a right hip bone) of the subject; a bladder of the subject; a rectum of the subject; and a gluteal muscle (e.g., a left gluteal muscle; e.g., a right gluteal muscle]} within the subject. In certain embodiments, classifying each voxel within the initial VOI comprises: determining, via the second module, for each of a plurality of voxels within the initial VOI, a set of likelihood values, wherein the set of likelihood values comprises, for each of one or more tissue regions of the tissue region set, a corresponding likelihood value that represents a likelihood (e.g., as computed by the second module) that the voxel represents a physical volume within the tissue region; and for each of the plurality of voxels within the initial VOI, classifying the voxel as corresponding to the particular tissue region based on the set of likelihood values determined for the voxel. In certain embodiments, the second module receives as input the initial VOI (e.g., the entire initial VOI) and outputs a plurality of values comprising, for each voxel within the initial VOI, at least one of (i), (ii), and (iii) as follows: (i) a value classifying the voxel [e.g., classifying the voxel as corresponding to a specific tissue region, e.g., a region selected from a predetermined set of different tissue regions, e.g., the prostate of the subject; e.g., a pelvic bone (e.g., a sacrum; e.g., a coccyx; e.g., a left hip bone; e.g., a right hip bone) of the subject; a bladder of the subject; a rectum of the subject; and a gluteal muscle (e.g., a left gluteal muscle; e.g., a right gluteal muscle) of the subject]; (ii) a set of likelihood values for the voxel [e.g., a likelihood the voxel corresponds to a specific tissue region, e.g., a region selected from a predetermined set of different tissue regions, e.g., the prostate of the subject; e.g., a pelvic bone (e.g., a sacrum; e.g., a coccyx; e.g., a left hip bone; e.g., a right hip bone) of the subject; a bladder of the subject; a rectum of the subject; and a gluteal muscle (e.g., a left gluteal muscle; e.g., a right gluteal muscle) of the subject]; and (iii) a value identifying the voxel as not corresponding to (e.g., or as likely not corresponding to, or identifying a likelihood the voxel does not correspond to) any of a predetermined set of different tissue regions (e.g., identifying the voxel as corresponding to or as likely corresponding to, or a likelihood the voxel corresponds to, a background area, e.g., that is not of diagnostic interest) (e.g., such that the second module classifies and/or computes likelihood values for the entire VOI in one round, as opposed to operating on each voxel one at a time). In certain embodiments, the (predetermined) set of different tissue regions comprises one or more tissue regions selected from the group consisting of: the prostate of the subject; a pelvic bone (e.g., a sacrum; e.g., a coccyx; e.g., a left hip bone; e.g., a right hip bone) of the subject; a bladder of the subject; a rectum of the subject; and a gluteal muscle (e.g., a left gluteal muscle; e.g., a right gluteal muscle) of the subject.

In certain embodiments, step (d) comprises using the second module to identify a set of one or more base tissue volumes, the one or more base tissue volumes comprising the identified prostate volume and the one or more additional tissue volumes, and wherein the method further comprises: identifying, by the processor, using one or more auxiliary modules (e.g., auxiliary machine learning modules), one or more auxiliary tissue volumes within the 3D anatomical image, each auxiliary tissue volume corresponding [e.g., representing a same specific tissue region [e.g., the prostate of the subject; e.g., a pelvic bone (e.g., a sacrum; e.g., a coccyx; e.g., a left hip bone; e.g., a right hip bone) of the subject; a bladder of the subject; a rectum of the subject; and a gluteal muscle (e.g., a left gluteal muscle; e.g., a right gluteal muscle) of the subject] to a base tissue volume identified by the second module; and merging, by the processor, each auxiliary tissue volume with the corresponding base tissue volume identified by the second module (e.g., adding to the corresponding base tissue volume by incorporating portions of the corresponding auxiliary tissue volume not included in the original base tissue volume).

In certain embodiments, the method comprises: identifying, by the processor, (e.g., using the second module) a reference volume within the 3D anatomical image (e.g., within the initial VOI), the reference volume corresponding to a reference tissue region within the subject (e.g., a gluteal muscle); and at step (e), determining at least one of the one or more uptake metrics using the 3D functional image and the reference volume identified within the 3D anatomical image (e.g., computing a normalization value based on intensity values of voxels of the 3D functional image that correspond to the reference volume identified within the 3D anatomical image). In certain embodiments, the at least one of the one or more uptake metrics determined using the 3D functional image and the reference volume comprises a tumor to background ratio (TBR) value, wherein determining the TBR value comprises: determining a target intensity value using intensity values of one or more voxels of the 3D functional image that correspond to the prostate volume identified within the initial VOI of the 3D anatomical image (e.g., wherein the target intensity value is a maximum of intensities of the voxels of the 3D functional image that correspond to the prostate volume); determining a background intensity value using intensity values of one or more voxels of the 3D functional image that correspond to the reference volume identified within the 3D anatomical image [e.g., wherein the background intensity value is an average intensity of a plurality (e.g., all) of the voxels of the 3D functional image that correspond to the identified reference volume; and determining, as the TBR value, a ratio of the target intensity value to the background intensity value. In certain embodiments, the method comprises determining a prostate cancer status for the subject based on the TBR value in comparison with one or more threshold values (e.g., predetermined threshold values). In certain embodiments, the one or more threshold values are determined using a plurality of reference TBR values [e.g., each reference TBR value having been determined from a corresponding set of reference images (e.g., a reference 3D anatomical image and a reference 3D functional image; e.g., a CT/SPECT image set)], each reference TBR value associated with a particular classification prostate cancer status (e.g., assigned by a medical practitioner)[e.g., a Gleason grade having been determined (e.g., based on histopathology from a radical prostatectomy) for a same subject for which the reference TBR value was determined]. In certain embodiments, the one or more threshold values are determined using a receiver operating characteristic (ROC) curve [e.g., using area under the curve (AUC) analysis; e.g., to provide a specific sensitivity value and/or a specific specificity value]. In certain embodiments, the method comprises determining the prostate cancer status for the subject to be (i) clinically significant if the TBR value is above a cutoff threshold or (ii) clinically non-significant if the TBR value is below the cutoff threshold.

In certain embodiments, the method comprises identifying, by the processor, (e.g., using the second module) a bladder volume within the 3D anatomical image (e.g., within the initial VOI) corresponding to a bladder of the subject; and at step (e), correcting for cross-talk from the bladder (e.g., scattering and/or partial volume effects through which radiopharmaceutical uptake in the bladder influences intensity values of voxels of the 3D functional image that represent physical volumes within the prostate) using intensities of voxels of the 3D functional image corresponding to the identified bladder volume within the 3D anatomical image [e.g., by adjusting intensities of voxels of the 3D functional image that correspond to the prostate volume based on their proximity to the identified bladder volume and/or a bladder uptake (e.g., determined based on intensities of voxels of the 3D functional image that correspond to the bladder volume); e.g., by using intensities of voxels of the 3D functional image to establish a model of radiation scattering from the bladder and adjusting intensities of voxels of the 3D functional image based on the model]. In certain embodiments, correcting for cross-talk from the bladder comprises: determining one or more bladder intensity bleed functions that model a contribution of intensity originating from radiopharmaceutical within the bladder of the subject to intensity of one or more voxels of the 3D functional image corresponding to one or more regions of the 3D anatomical image that are outside of the identified bladder volume, wherein the one or more bladder intensity bleed functions model said contribution as a function of distance from the identified bladder volume [e.g., wherein each of the one or more bladder intensity bleed functions models intensity bleed along a particular direction and is obtained by fitting a template function (e.g., an n-th degree polynomial) to intensities of voxels of the 3D functional image corresponding to the identified bladder volume within the 3D anatomical image and lying along the particular direction]; and for each of one or more voxels of the 3D functional image corresponding to the identified prostate volume within the 3D anatomical image, adjusting an intensity of the voxel for bladder cross-talk using the one or more bladder intensity bleed functions [e.g., by evaluating the one or more bladder intensity bleed functions to determine a bladder intensity bleed value for the voxel and subtracting the bladder intensity bleed value from the intensity of the voxel to obtain a corrected voxel intensity].

In certain embodiments, the method comprises: identifying, by the processor, (e.g., using the second module) a bladder volume within the 3D anatomical image (e.g., within the initial VOI) corresponding to a bladder of the subject; determining, by the processor, a dilated bladder volume by applying a morphological dilation operation to the identified bladder volume; and at step (e), determining the one or more uptake metrics using intensity values of voxels of the 3D functional image that (i) correspond to the prostate volume identified within the VOI of the 3D anatomical image, but (ii) do not correspond to regions of the 3D anatomical image within the dilated bladder volume (e.g., thereby omitting from the computation of the one or more uptake metrics those voxels of the 3D functional image that correspond to locations in the 3D anatomical image within a predefined distance from the identified bladder volume; e.g., and, accordingly, are excessively close to the identified bladder volume).

In certain embodiments, the 3D functional image is a nuclear medicine image (e.g., a single-photon emission computerized tomography (SPECT) scan; e.g., an positron emission tomography (PET) scan) of the subject following administration to the subject of the radiopharmaceutical. In certain embodiments, the radiopharmaceutical comprises a PSMA binding agent (e.g., $^{99m}$Tc-MIP-1404; e.g., [$^{18}$F] DCFPyL). In certain embodiments, the nuclear medicine image is a single-photon emission computerized tomography (SPECT) scan of the subject obtained following administration to the subject of the radiopharmaceutical. In certain embodiments, the radiopharmaceutical comprises $^{99m}$Tc-MP-1404.

In certain embodiments, the method comprises determining, based on at least a portion of the one or more uptake metrics, one or more diagnostic or prognostic values [e.g., a value that provides a measure of disease state, progression, life expectancy (e.g., overall survival), treatment efficacy, and the like for the subject (e.g., Gleason score)] for the subject. In certain embodiments, determining at least one of the one or more diagnostic or prognostic values comprises comparing an uptake metric to one or more threshold value(s). In certain embodiments, at least one of the one or more diagnostic or prognostic values estimates a risk for clinically significant prostate cancer in the subject.

In certain embodiments, the method comprises: (f) causing, by the processor, display of an interactive graphical user interface (GUI) for presentation to the user of a visual representation of the 3D anatomical image and/or the 3D functional image; and (g) causing, by the processor, graphical rendering of, within the GUI, the 3D anatomical image and/or the 3D functional image as selectable and superimposable layers, such that either can be selected for display (e.g., via a corresponding user-selectable graphical control element (e.g., a toggle element)) and rendered separately, or both selected for display and rendered together by overlaying the 3D anatomical image with the 3D functional image. In certain embodiments, step (g) comprises causing graphical rendering of a selectable and superimposable segmentation layer comprising one or more identified specific tissue volumes within the 3D anatomical image, wherein upon selection of the segmentation layer for display, graphics representing the one or more specific tissue volumes are overlaid on the 3D anatomical image and/or the 3D functional image (e.g., as outlines; e.g., as semi-transparent color-coded volumes). In certain embodiments, the one or more specific tissue volumes comprise(s) the identified prostate volume. In certain embodiments, the method comprises, at step (g), causing rendering of a 2D cross sectional view of the 3D anatomical image and/or the 3D functional image within an interactive 2D viewer, such that a position of the 2D cross sectional view is adjustable by the user. In certain embodiments, the method comprises, at step (g), causing rendering of an interactive (e.g., rotatable; e.g., sliceable) 3D view of the 3D anatomical image and/or the 3D functional image. In certain embodiments, the method comprises causing display of, within the GUI, a graphical element (e.g., a cross-hair, a target, a colored marker, etc.) indicating a location corresponding to a voxel of the identified prostate volume (e.g., said location also corresponding to a voxel of the 3D functional image having a maximal intensity, e.g., a maximal corrected intensity, in comparison with other voxels of the 3D functional image corresponding to the identified prostate volume), thereby facilitating user review and/or quality control of the method (e.g., allowing a medical practitioner to verify the identified location corresponds to an expected physical location of the prostate of the subject). In certain embodiments, the method comprises causing display of, within the GUI, text and/or graphics representing the one or more uptake metrics determined in step (e) (e.g., and, optionally, one or more prognostic values determined therefrom) along with a quality control graphical widget for guiding the user through a quality control and reporting workflow for review and/or updating of the one or more uptake metrics (e.g., wherein the quality control graphical widget comprises a selectable graphical control element for receipt of a user input corresponding to (i) approval of the one or more uptake metrics as determined, automatically, by the processor or (ii) disapproval of the automated determination of the one or more uptake metrics). In certain embodiments, the method comprises: receiving, via the quality control graphical widget, a user input corresponding to an approval of automated determination of the one or more uptake metrics (e.g., and any prognostic values determined therefrom); and responsive to the receipt of the user input corresponding to the approval of the automated determination of the one or more uptake metrics, generating, by the processor, a report for the subject comprising a representation of the one or more automatically determined uptake metrics [e.g., the report comprising: an identification of the subject (e.g., an anonymized patient ID number); a representation (e.g., text) of the one or more determined uptake metrics (e.g., and any prognostic values determined therefrom); and a representation (e.g., graphics and/or text) of the user approval the automated determination of the one or more uptake metrics (e.g., and any prognostic values determined therefrom)].

In certain embodiments, the method comprises: receiving, via the quality control graphical widget, a user input corresponding to disapproval of automated determination of the one or more uptake metrics (e.g., and any prognostic values determined therefrom); responsive to receipt of the user input corresponding to the disapproval of the automated determination of the one or more uptake metrics, causing, by the processor, display of a voxel selection graphical element (e.g., a cursor; e.g., an adjustable cross-hair) for user selection of one or more voxels of the 3D functional image (e.g., directly or indirectly, e.g., through selection of voxels of the 3D anatomical image and subsequent determination of corresponding voxels of the 3D functional image) for use in determining updated values of the one or more uptake metrics; receiving, via the voxel selection graphical element, the user selection of one or more voxels of the 3D functional image for use in determining updated values of the one or more uptake metrics [e.g., wherein the user selection is one or more corrected background intensity measurement location(s) and/or one or more corrected prostate intensity location(s), e.g., where a user overrides automated identification of a location of the prostate and/or where the user overrides automated identification of a location of a background area, e.g., gluteal muscle]; updating, by the processor, values of the one or more uptake metrics using the user selected voxels; and generating, by the processor, a report for the subject comprising a representation (e.g., text) of the one or more updated uptake metrics [e.g., the report comprising: an identification of the subject (e.g., an anonymized patient ID number); a representation (e.g., text) of the one or more determined uptake metrics (e.g., and any prognostic values determined therefrom); and a representation (e.g., graphics and/or text) of the user approval of the determination of the one or more uptake metrics (e.g., and any prognostic values determined therefrom) using the user selected voxels (e.g., text indicating that the uptake metrics were determined via semi-automated analysis, with manual selection of voxels from the user)].

In certain embodiments, the method comprises: receiving, via the quality control graphical widget, a user input corresponding to disapproval of automated determination of the one or more uptake metrics (e.g., and any prognostic values determined therefrom); receiving, via the quality control graphical widget, a user input corresponding to a rejection of quality control (e.g., due to low image quality); and generating, by the processor, a report for the subject, wherein the report comprises an identification of the rejection of quality control.

In certain embodiments, voxels of the 3D functional image are related to voxels of the 3D anatomical image via a known relationship [e.g., each voxel of the 3D functional image is associated with one or more voxels of the 3D anatomical image; e.g., each of a plurality of sets of one or more voxels of the 3D functional image is associated with a set of one or more voxels of the 3D anatomical image; e.g., coordinates associated with voxels of the 3D functional image are related to coordinates associated with voxels of the anatomical 3D image via a known functional relationship (e.g., via a known spatial relationship between the first and second imaging modalities)].

In certain embodiments, the first module is a first CNN (convolutional neural network) module and the second module is a second CNN module, wherein the second CNN module comprises a greater number of convolutional filters than the first CNN module (e.g., at least 1.5 times as many, e.g., at least twice as many, e.g., approximately twice as many, e.g., at least three times as many, e.g., approximately three times as many).

In certain embodiments, the method comprises performing steps (a) and (c) for each of a plurality of 3D anatomical images to determine a plurality of initial VOIs, each within one of the plurality of 3D anatomical images, wherein a variability in sizes of the initial VOIs is less than (e.g., substantially less than) a variability in sizes of the 3D anatomical images (e.g., wherein variability in "sizes" means either or both of (i) and (ii) as follows: (i) variability in one or more dimensions of the anatomical volume represented in the image, e.g., as measured in mm, and (ii) variability in the number of voxels in the image along each of one or more dimensions of the image) (e.g., wherein the sizes of the 3D anatomical images (each full image from which each VOI is determined) vary by at least 200 mm, and/or by at least 300 mm, and/or by at least 400 mm, and/or by at least 500 mm, and/or by as much as 400 mm, and/or by as much as 500 mm, and/or by as much as 1000 mm, and/or by as much as 1500 mm) along each of one or more dimensions; e.g., wherein the sizes of the 3D anatomical images (each full image from which each VOI is determined) vary by at least 25 voxels, and/or by at least 50 voxels, and/or by at least 100 voxels, and/or by at least 250 voxels, and/or by at least 300 voxels, and/or by as much as 250 voxels, and/or by as much as 300 voxels, and/or by as much as 500 voxels) along each of one or more dimensions; e.g., wherein the sizes of the VOIs vary by less than or equal to 200 mm (e.g., less than or equal to 100 mm; e.g., less than or equal to 50 mm) along each of one or more dimensions; e.g. wherein the sizes of the VOIs vary by less than or equal to 250 voxels (e.g., less than or equal to 200 voxels; e.g., less than or equal to 150 voxels) along each of one or more dimensions].

In another aspect, the invention is directed to a method for automatically processing 3D images to identify 3D volumes within the 3D images that correspond to a target tissue region within a subject and determining one or more uptake metrics indicative of radiopharmaceutical uptake therein, the method comprising: (a) receiving, by a processor of a computing device, a 3D anatomical image of the subject obtained using an anatomical imaging modality [e.g., x-ray computed tomography (CT); e.g., magnetic resonance imaging (MRI); e.g., ultra-sound], wherein the 3D anatomical image comprises a graphical representation of tissue (e.g., soft-tissue and/or bone) within a pelvic region of the subject; (b) receiving, by the processor, a 3D functional image of the subject obtained using a functional imaging modality [e.g., single-photon emission computed tomography (SPECT); e.g., positron emission tomography (PET)], wherein the 3D functional image comprises a plurality of voxels, each representing a particular physical volume within the subject and having an intensity value that represents detected radiation emitted from a the particular physical volume, wherein at least a portion of the plurality of voxels of the 3D functional image represent physical volumes within the pelvic region of the subject; (c) determining, by the processor, using a first module (e.g., a first machine learning module), an initial volume of interest (VOI) within the 3D anatomical image (e.g., a rectangular prism), the initial VOI corresponding to an anatomical sub-region (e.g., a group of related tissue, such as a pelvic region, a chest region, a head and/or neck region, and the like) comprising the target region (e.g., wherein the VOI excludes more voxels of the 3D anatomical image than it includes; e.g., wherein the VOI includes less than 25% of the voxels of the 3D anatomical image; e.g., wherein a majority of voxels within the VOI represent physical volumes within the anatomical sub-region); (d) identifying, by the processor, using a second module (e.g., a second machine learning module), a target volume within the initial VOI corresponding to the target tissue region of the subject; and (e) determining, by the processor, the one or more uptake metrics using the 3D functional image and the target volume identified within the VOI of the 3D anatomical image [e.g., computing a quantity of radiopharmaceutical in the target tissue region of the subject based on intensity values of voxels of the 3D functional image that correspond to the target volume identified within the VOI of the 3D anatomical image; e.g., computing a sum (e.g., a weighted sum), an average, and/or a maximum of intensities of voxels of the 3D functional image representing a physical volume occupied by the target tissue region of the subject].

In certain embodiments, the method has one or more of the features articulated in paragraphs above.

In another aspect, the invention is directed to a method of automatically analyzing a 3D functional image [e.g., a nuclear medicine image (e.g., a SPECT image; e.g., a PET image)] to correct prostate voxel intensities for cross-talk from radiopharmaceutical uptake into a bladder, the method comprising: (a) receiving, by a processor of a computing device, a 3D anatomical image of the subject obtained using an anatomical imaging modality [e.g., x-ray computed tomography (CT); e.g., magnetic resonance imaging (MRI); e.g., 3D ultra-sound], wherein the 3D anatomical image comprises a graphical representation of tissue (e.g., soft-tissue and/or bone) within a subject, at least a portion of which corresponds to a bladder and a prostate of the subject; (b) receiving, by the processor, the 3D functional image of the subject, wherein the 3D functional image comprises a plurality of voxels, each representing a particular physical volume within the subject and having an intensity value that represents detected radiation emitted from a the particular physical volume, wherein at least a portion of the plurality of voxels of the 3D functional image represent physical volumes within the bladder and/or the prostate of the subject; (c) automatically identifying, by the processor, within the 3D anatomical image: (i) a prostate volume corresponding to a prostate of the subject and (ii) a bladder volume corresponding to a bladder of the subject; (d) automatically identifying, by the processor, within the 3D functional image, (i) a plurality of prostate voxels corresponding to the identified prostate volume and (ii) a plurality of bladder voxels corresponding to the identified bladder volume; (e) adjusting, by the processor, one or more measured intensities of the prostate voxels (e.g., one or more cumulative measurements and/or peak measurements and/or mean measurements and/or median measurements of intensity corresponding to the identified prostate volume and/or corresponding to each of, and/or cumulatively of, a plurality of regions of the identified prostate volume) based on one or more measured intensities of the bladder voxels (e.g., one or more cumulative measurements and/or peak measurements and/or mean measurements and/or median measurements of intensity corresponding to the identified bladder volume and/or corresponding to each of, and/or cumulatively of, a plurality of regions of the identified bladder volume); and (f) determining, by the processor, one or more uptake metrics indicative of radiopharmaceutical uptake within the prostate of the subject using the adjusted intensities of the prostate voxels.

In certain embodiments, the method has one or more of the features articulated in the paragraphs above.

In another aspect, the invention is directed to a method of detecting a prostate cancer status, and/or quantifying a prostate cancer risk, of a subject based on automated analysis of a 3D functional image (e.g., a SPECT image) of a portion of the subject, the method comprising: (a) acquiring, following administration to the subject of a radiopharmaceutical comprising a PSMA binding agent, the 3D functional image (e.g., a SPECT image); (b) identifying, by a processor of a computing device, a 3D target volume within the 3D functional image, the 3D target volume corresponding to a prostate of the subject; (c) determining, by the processor, using intensities of voxels of the 3D target volume, a target to background ratio (TBR) value; and (d)

causing, by the processor, graphical rendering of text and/or graphics representing the determined TBR value for display within an interactive graphical user interface (GUI) [e.g., wherein the method comprises determining (e.g., and displaying) a prostate cancer classification status of either (i) clinically significant or (ii) clinically non-significant based at least in part on the TBR value].

In certain embodiments, the method has one or more of the features articulated in the paragraphs above.

In another aspect, the invention is directed to a system for automatically processing 3D images to identify 3D volumes within the 3D images that correspond to a prostate of a subject and determining one or more uptake metrics indicative of radiopharmaceutical uptake therein (i.e., in the prostate), the system comprising: a processor; and a memory (e.g., external to or embedded in the processor) having instructions stored thereon, wherein the instructions, when executed by the processor, cause the processor to: (a) receive a 3D anatomical image of the subject obtained using an anatomical imaging modality [e.g., x-ray computed tomography (CT) (e.g., a whole-body CT image; e.g., a partial body CT image); e.g., magnetic resonance imaging (MRI); e.g., 3D ultra-sound], wherein the 3D anatomical image comprises a graphical representation of tissue (e.g., soft-tissue and/or bone) within a subject, at least a portion of which corresponds to a pelvic region of the subject; (b) receive a 3D functional image of the subject obtained using a functional imaging modality [e.g., single-photon emission computed tomography (SPECT); e.g., positron emission tomography (PET)], wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the pelvic region of the subject; (c) determine, using a first module (e.g., a first machine learning module), an initial volume of interest (VOI) within the 3D anatomical image (e.g., a parallelepiped, e.g., a cuboid), the initial VOI corresponding to tissue within the pelvic region of the subject and excluding tissue outside the pelvic region of the subject (e.g., wherein the VOI excludes more voxels of the 3D anatomical image than it includes; e.g., wherein the VOI includes less than 25% of the voxels of the 3D anatomical image; e.g., wherein a majority of voxels within the VOI represent physical volumes within the pelvic region of the subject); (d) identify, using a second module (e.g., a second machine learning module), a prostate volume within the initial VOI corresponding to the prostate of the subject; and (e) determine (e.g., and display) the one or more uptake metrics using the 3D functional image and the prostate volume identified within the initial VOI of the 3D anatomical image [e.g., compute a quantity of radiopharmaceutical in the prostate of the subject based on intensity values of voxels of the 3D functional image that correspond to the prostate volume identified within the initial VOI of the 3D anatomical image; e.g., compute a sum (e.g., a weighted sum) and/or an average and/or a maximum of intensities of voxels of the 3D functional image representing a physical volume occupied by the prostate of the subject] [e.g., wherein the one or more uptake metrics comprises a tumor to background ratio (TBR) value, and wherein the instructions, when executed by the processor, cause the processor to determine (e.g., and display) a prostate cancer classification status of either (i) clinically significant or (ii) clinically non-significant based at least in part on the TBR value].

In certain embodiments, the system has one or more of the features articulated in the paragraphs above.

In another aspect, the invention is directed to a system for automatically processing 3D images to identify 3D volumes within the 3D images that correspond to a target tissue region within a subject and determining one or more uptake metrics indicative of radiopharmaceutical uptake therein (i.e., in the target tissue region), the system comprising: a processor; and a memory (e.g., external to or embedded in the processor) having instructions stored thereon, wherein the instructions, when executed by the processor, cause the processor to: (a) receive a 3D anatomical image of the subject obtained using an anatomical imaging modality [e.g., x-ray computed tomography (CT); e.g., magnetic resonance imaging (MRI); e.g., ultra-sound], wherein the 3D anatomical image comprises a graphical representation of tissue (e.g., soft-tissue and/or bone) within a pelvic region of the subject; (b) receive a 3D functional image of the subject obtained using a functional imaging modality [e.g., single-photon emission computed tomography (SPECT); e.g., positron emission tomography (PET)], wherein the 3D functional image comprises a plurality of voxels, each representing a particular physical volume within the subject and having an intensity value that represents detected radiation emitted from a the particular physical volume, wherein at least a portion of the plurality of voxels of the 3D functional image represent physical volumes within the pelvic region of the subject; (c) determine, using a first module (e.g., a first machine learning module), an initial volume of interest (VOI) within the 3D anatomical image (e.g., a rectangular prism), the initial VOI corresponding to an anatomical sub-region (e.g., a group of related tissue, such as a pelvic region, a chest region, a head and/or neck region, and the like) comprising the target region (e.g., wherein the VOI excludes more voxels of the 3D anatomical image than it includes; e.g., wherein the VOI includes less than 25% of the voxels of the 3D anatomical image; e.g., wherein a majority of voxels within the VOI represent physical volumes within the anatomical sub-region); (d) identify, using a second module (e.g., a second machine learning module), a target volume within the initial VOI corresponding to the target tissue region of the subject; and (e) determine the one or more uptake metrics using the 3D functional image and the target volume identified within the VOI of the 3D anatomical image [e.g., compute a quantity of radiopharmaceutical in the target tissue region of the subject based on intensity values of voxels of the 3D functional image that correspond to the target volume identified within the VOI of the 3D anatomical image; e.g., compute a sum (e.g., a weighted sum), and/or an average, and/or a maximum of intensities of voxels of the 3D functional image representing a physical volume occupied by the target tissue region of the subject] [e.g., wherein the one or more uptake metrics comprises a tumor to background ratio (TBR) value, and wherein the instructions, when executed by the processor, cause the processor to determine (e.g., and display) a cancer classification status of either (i) clinically significant or (ii) clinically non-significant based at least in part on the TBR value].

In certain embodiments, the system has one or more of the features articulated in the paragraphs above .

In another aspect, the invention is directed to a system for detecting a prostate cancer status, and/or quantifying a prostate cancer risk, of a subject based on automated analysis of a 3D functional image (e.g., a SPECT image) of a portion of the subject, the system comprising: a processor; and a memory (e.g., external to or embedded in the processor) having instructions stored thereon, wherein the instructions, when executed by the processor, cause the processor to: (a) receive the 3D functional image (e.g., a SPECT image) of the portion (e.g., any or all) of the subject following administration to the subject of a radiopharmaceutical comprising a PSMA binding agent; (b) identify a 3D target volume within the 3D functional image, the 3D target volume corresponding to a prostate of the subject; (c) determine, using intensities of voxels of the 3D target volume, a target to background ratio (TBR) value; and (d) cause graphical rendering of text and/or graphics representing the determined TBR value for display within an interactive graphical user interface (GUI) [e.g., wherein the instructions, when executed by the processor, cause the processor to determine (e.g., and display) a prostate cancer classification status of either (i) clinically significant or (ii) clinically non-significant based at least in part on the TBR value].

In certain embodiments, the system has one or more of the features articulated in the paragraphs above.

In certain embodiments, the invention is directed to a computer-aided detection (CADe) device comprising any of the systems described herein. In certain embodiments, the instructions cause the processor to identify a classification of either clinically significant prostate cancer or clinically non-significant prostate cancer for the subject.

In certain embodiments, the invention is directed to a computer-aided diagnostic (CADx) device comprising any of the systems described herein. In certain embodiments, the instructions cause the processor to identify a classification of either clinically significant prostate cancer or clinically non-significant prostate cancer for the subject.

In certain embodiments, the invention is directed to a combination product comprising: (a) a radiolabeled PSMA binding agent (e.g., $^{99m}$Tc-MIP-1404; e.g., [$^{18}$F]DCFPyL, e.g., other known PSMA binding agent); and (b) a computer-aided detection (CADe) device comprising any of the systems described herein. In certain embodiments, the combination product comprises a label specifying usage of the radiolabeled PSMA binding agent with the computer aided detection device.

Features of embodiments described with respect to one aspect of the invention may be applied with respect to another aspect of the invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

The foregoing and other objects, aspects, features, and advantages of the present disclosure will become more apparent and better understood by referring to the following description taken in conjunction with the accompanying drawings, in which:

FIG. 5A is a set of images showing 2D cross sectional views of a CT image of a subject and a cuboidal region identified as an initial volume of interest within the CT image, according to an illustrative embodiment.

FIG. 5B is a set of images showing 2D cross sectional views of a CT image of a subject along with identified tissue volumes corresponding to pelvic bones and a prostate of the subject.

FIG. 16A is a screenshot of a graphical user interface (GUI) for reviewing patient image data showing a window for selecting subjects for whom to analyze and/or review data, according to an illustrative embodiment.

FIG. 16B is a screenshot of a graphical user interface (GUI) for reviewing patient image data showing a window for selecting subjects for whom to analyze and/or review data, along with a graphical control element for initiating processing of and reviewing patient image data, according to an illustrative embodiment.

FIG. 16C is a screenshot of a graphical user interface (GUI) for reviewing patient image data showing a window for selecting subjects for whom to analyze and/or review data, along with a graphical control element for initiating processing of and reviewing patient image data, according to an illustrative embodiment.

FIG. 24 is a screenshot of a GUI for reviewing patient image data showing a window comprising a generated report for a subject, according to an illustrative embodiment.

FIG. 27A is a screenshot of a view of a GUI window showing a listing of patients, according to an illustrative embodiment.

FIG. 27B is screenshot of a view of a GUI window showing a listing of patients, according to an illustrative embodiment.

FIG. 29B is a screenshot of a GUI for reviewing patient image data showing a quality control graphical widget, according to an illustrative embodiment.

FIG. 29D is a screenshot showing a generated report (e.g., an auto-generated report), according to an illustrative embodiment.

FIG. 29E is a screenshot of a view of a quality control graphical widget displayed in respond to a user input of disapproval of automated determination of an uptake metric, according to an illustrative embodiment.

FIG. 29F is a screenshot of a portion of a generate report showing a graphical indication of rejection of quality control, according to an illustrative embodiment.

FIG. 29G is a screenshot of a quality control graphical widget allowing a user to manually update one or more values used in determination of an uptake metric, according to an illustrative embodiment.

FIG. 29H is a screenshot of a quality control graphical widget allowing a user to manually update one or more values used in determination of an uptake metric, according to an illustrative embodiment.

Figure 1:
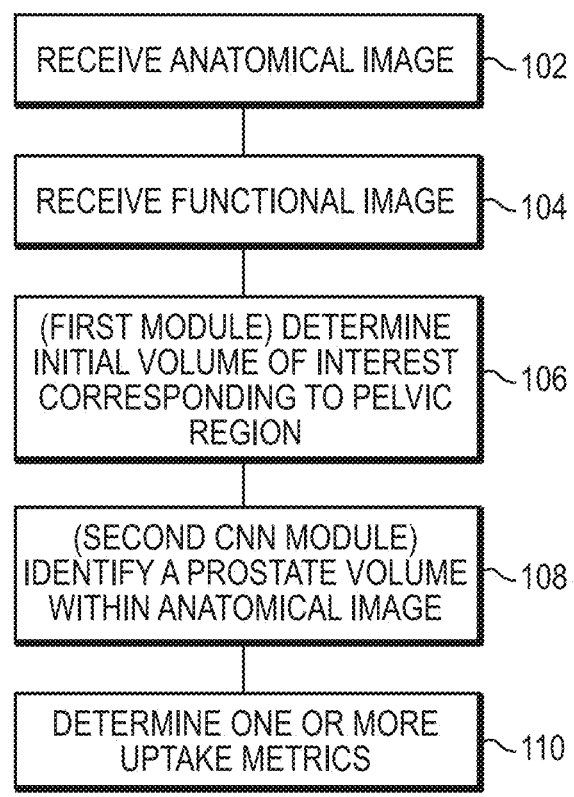
FIG. 1 is a block diagram showing a process for automatically identifying 3D volumes within 3D images that correspond to a prostate of a subject and determining uptake metrics indicative of radiopharmaceutical uptake therein, according to an illustrative embodiment.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Documents are incorporated herein by reference as noted. Where there is any discrepancy in the meaning of a particular term, the meaning provided in the Definition section above is controlling.

Headers are provided for the convenience of the reader—the presence and/or placement of a header is not intended to limit the scope of the subject matter described herein.

As used herein, "radionuclide" refers to a moiety comprising a radioactive isotope of at least one element. Exemplary suitable radionuclides include but are not limited to those described herein. In some embodiments, a radionuclide is one used in positron emission tomography (PET). In some embodiments, a radionuclide is one used in single-photon emission computed tomography (SPECT). In some embodiments, a non-limiting list of radionuclides includes $^{99m}$Tc, $^{111}$In, $^{64}$Cu, $^{67}$Ga, $^{68}$Ga, $^{186}$Re, $^{188}$Re, $^{153}$Sm, $^{177}$Lu, $^{67}$Cu, $^{123}$I, $^{124}$I, $^{125}$I, $^{126}$I, $^{131}$I, $^{11}$C, $^{13}$N, $^{15}$O, $^{18}$F, $^{153}$Sm, $^{166}$Ho, $^{177}$Lu, $^{149}$Pm, $^{90}$Y, $^{213}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{105}$Ru, $^{111}$Ag, $^{89}$Zr, $^{225}$Ac, $^{82}$Rb, $^{75}$Br, $^{76}$Br, $^{77}$Br, $^{80}$Br, $^{80m}$Br, $^{82}$Br, $^{83}$Br, $^{211}$At and $^{192}$Ir.

As used herein, the term "radiopharmaceutical" refers to a compound comprising a radionuclide. In certain embodiments, radiopharmaceuticals are used for diagnostic and/or therapeutic purposes. In certain embodiments, radiopharmaceuticals include small molecules that are labeled with one or more radionuclide(s), antibodies that are labeled with one or more radionuclide(s), and antigen-binding portions of antibodies that are labeled with one or more radionuclide(s).

As used herein, "3D" or "three dimensional" with reference to an "image" means conveying information about three dimensions. A 3D image may be rendered as a dataset in three dimensions and/or may be displayed as a set of two-dimensional representations, or as a three-dimensional representation.

As used herein, an "image"—for example, a 3-D image of a subject—includes any visual representation, such as a photo, a video frame, streaming video, as well as any electronic, digital or mathematical analogue of a photo, video frame, or streaming video. Any apparatus described herein, in certain embodiments, includes a display for displaying an image or any other result produced by the processor. Any method described herein, in certain embodiments, includes a step of displaying an image or any other result produced via the method.

As used herein, a "subject" means a human or other mammal (e.g., rodent (mouse, rat, hamster), pig, cat, dog, horse, primate, rabbit, and the like).

As used herein, "administering" an agent means introducing a substance (e.g., an imaging agent) into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments.

As used herein, the terms "filter", and "filtering", as in a "filtering function" or a "filter", refer to a function that operates on localized portions of an input array (e.g., a multi-dimensional array) of data (e.g., image data, e.g., values computed by a layer of a CNN), referred to herein as "subpatches", computing, for a given subpatch, a response value. In general, a filter is applied in a sliding window fashion across the array to compute a plurality of response values for the array. In particular, for a given multidimensional array, a subpatch of the array can be a rectangular region of the array having a specific size (e.g., having the same number of dimensions as the array). For example, for a 6×3×3 array, a given 3×3×3 subpatch refers to a given 3×3×3 set of adjacent values (e.g., a neighborhood) of the array, such that there are five distinct 3×3×3 subpatches in the 6×3×3 array (each patch shifted one position over along the first dimension).

For example, a filtering function can compute, for a given subpatch of an array, a response value using the values of the subpatch. A filtering function can be applied in a sliding window fashion across an array, computing, for each of a plurality of subpatches of the array, a response value. The computed response values can be stored in an output array such that the positional correspondence between response values and the subpatches of the input array is maintained.

For example, at a first step, beginning with a subpatch in a corner of an input array, a filter can compute a first response value, and store the first response value in a corresponding corner of an output array. In certain embodiments, at a second step, the filter then computes a second response value for a second subpatch, shifted one position over along a specific dimension of the input array. The second response value can be stored in a corresponding position of the output array—that is, shifted one position over along a same dimension of the output array. The step of shifting position of the subpatch, computing a response value, and storing the response value in a corresponding position of the output array can be repeated for the full input array, along each dimension of the input array. In certain embodiments (e.g., a strided filtering approach), the subpatch for which the filter computes a response value is shifted more than one position at a time along a given dimension, such that response values are not computed for every possible subpatch of the input array.

As used herein, the term "convolutional neural network (CNN)" refers to a type of artificial neural network where at least one layer performs one or more filtering functions. As used herein, the term "convolution layer" refers to a layer of a CNN that receives as input an input array and computes an output array, wherein values of the output array are computed by applying one or more filters to the input array. In particular, in certain embodiments, a convolution layer receives as input an input array having n+1 dimensions and produces an output array also having n+1 dimensions. The first n dimensions of input and output arrays operated on by filtering layers of a CNN are referred to herein as "spatial dimensions". The $(n+1)^{th}$ dimension of the input is referred to herein as the "input channel" dimension. The size of the input channel dimension is referred to herein as the "number of input channels". The $(n+1)^{th}$ dimension of the output is referred to herein as the "output channel" dimension. The size of the input channel dimension is referred to herein as the "number of output channels".

In certain embodiments, a convolution layer computes response values by applying a filter that operates on subpatches that are smaller than the input array along the spatial dimensions, but extend across the full output channel dimension. For example, an $N \times M \times L \times K_O$ size input array, has three spatial dimensions and $K_O$ output channels. Filters of a convolution layer may operate on subpatches having sizes of $N_f \times M_f \times L_f \times K_O$, where $N_f \leq N$, $M_f \leq M$ and $L_f \leq L$. Often, a filter of a convolutional layer operates on subpatches having sizes where $N_f < N$, $M_f < M$ and/or $L_f < L$. For example, in certain embodiments, $N_f << N$, $M_f << M$ and/or $L_f << L$.

Accordingly, for each of one or more filters applied by a convolution layer, response values computed by a given filter are stored in a corresponding output channel. Accordingly, a convolution layer that receives an input array having n+1 dimensions computes an output array also having n+1 dimensions, wherein the $(n+1)^{th}$ dimension represents the output channels corresponding to the one or more filters applied by the convolution layer. In this manner, an output array computed by a given convolution layer can be received as input by a subsequent convolution layer.

As used herein, the term "size" in reference to a filter of a convolution layer refers to a size along spatial dimensions of subpatches on which the filter operates (e.g., the subpatch size along the output channel dimension is taken as the full number of output channels). As used herein, the term "size", in reference to a convolution layer, as in "size of a convolution layer" refers to a size of filters of the convolution layer (e.g., each filter of the convolution layer having a same size). In certain embodiments, a filter of a convolution layer has a number of variable parameters that are determined via a machine learning training process. In certain embodiments, the number of parameters of a given filter equals the number of values in a subpatch that the given filter operates on. For example, a size $N_f \times M_f \times L_f$ filter that operates on an input array with $K_O$ output channels has $N_f \times M_f \times L_f \times K_O$ parameters. In certain embodiments, a filter is implemented as an array, and the response value determined by the filter for a given subpatch is computed as a dot product between the filter and the given subpatch.

As used herein, the term "fully convolutional neural network (FCNN)" refers to a CNN wherein each layer of the CNN is a convolution layer.

As used herein, the term "volume", as used in reference to an input or output of a layer of a CNN refers to an input array received or an output array computed by a CNN layer.

As used herein, the term "CNN module" refers to a computer implemented process that implements a specific CNN in order to determine, for a given input, such as an image (e.g., a 2D image; e.g., a 3D image) one or more output values. For example, a CNN module may receive as input a 3D image of a subject (e.g., a CT image; e.g., an MRI), and for each voxel of the image, determine a value that represents a likelihood that the voxel lies within a region of the 3D image that corresponds to a representation of a particular organ or tissue of the subject. A CNN module may be software and/or hardware. For example, a CNN module may be implemented entirely as software, or certain functions of a CNN module may be carried out via specialized hardware (e.g., via an application specific integrated circuit (ASIC)).

As used herein, the term "tissue" refers to bone (osseous tissue) as well as soft-tissue.

The systems and methods described herein provide for automated analysis of medical images of a subject in order to automatically identify regions of interest that correspond to particular organs and/or tissue that are represented in the images. In certain embodiments, convolutional neural network (CNN) modules are employed in order to accurately segment images. In certain embodiments, the accurate automated identification of particular organs and/or tissue in images of a subject allows for quantitative metrics that measure uptake of radiopharmaceuticals (e.g., radiolabeled small molecules; e.g., radiolabeled antibodies; e.g., radiolabeled antigen-binding portions of antibodies) in particular organs to be determined.

In certain embodiments, the systems and methods described herein facilitate automated identification of regions of interest that correspond to particular organs or tissue in which tumors and/or tumor metastases may be present. Radionuclide labelled molecules that selectively bind to specific tumor cell surface proteins may be utilized in combination with the approaches described herein for imaging tumors. For example, the molecule 1404 binds specifically to Prostate Specific Membrane Antigen (PSMA), which is over expressed on many cancer cells. The molecule 1404 may be labelled with a radionuclide, such as $^{99m}$Tc, for use in single-photon emission computed tomography (SPECT) imaging.

In certain embodiments, uptake metrics of radiopharmaceuticals are relevant to assessing disease state and prognosis in a subject.

A. Identifying Prostate Volumes and Determining Uptake Metrics

FIG. 1 shows a process 100 for automatically processing 3D images to identify 3D volumes that correspond to a prostate of a subject and determining one or more uptake metrics indicative of radiopharmaceutical uptake therein.

Figure 2A:
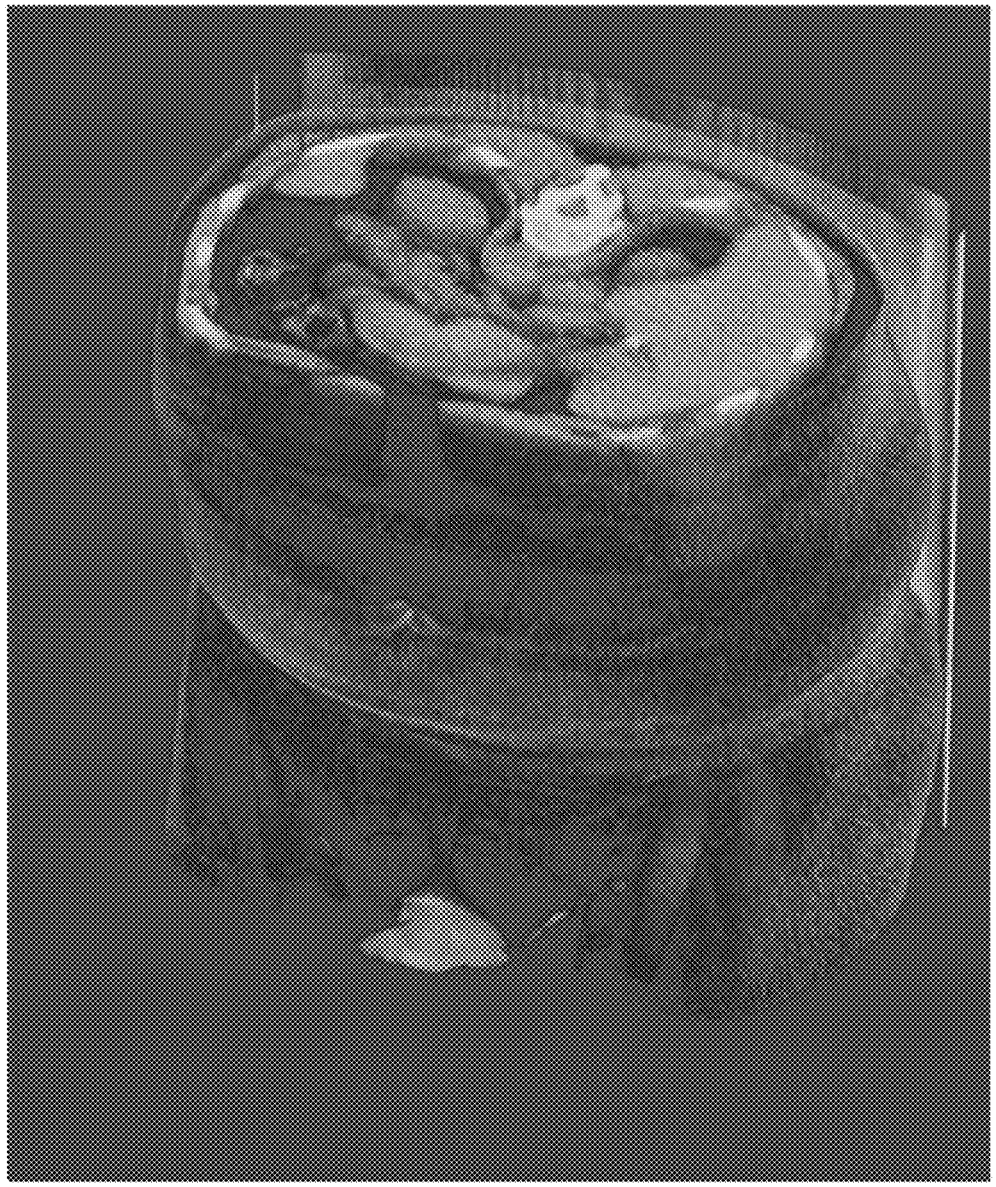
FIG. 2A is an image showing 3D view of a CT image comprising a graphical representation of soft-tissue, according to an illustrative embodiment.
Figure 2B:
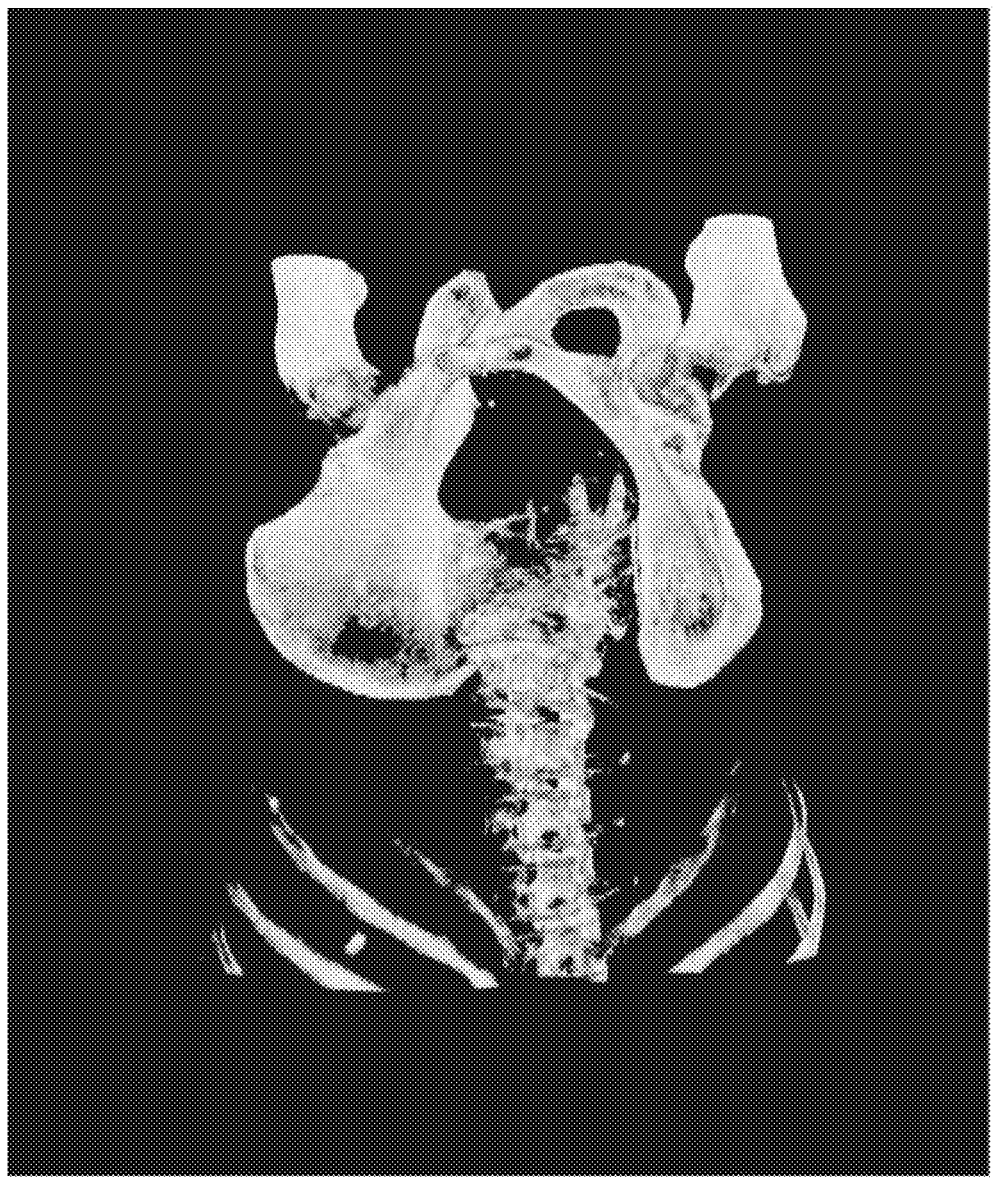
FIG. 2B is an image showing a 3D view of a CT image comprising a graphical representation of bone, according to an illustrative embodiment.
Figure 2C:
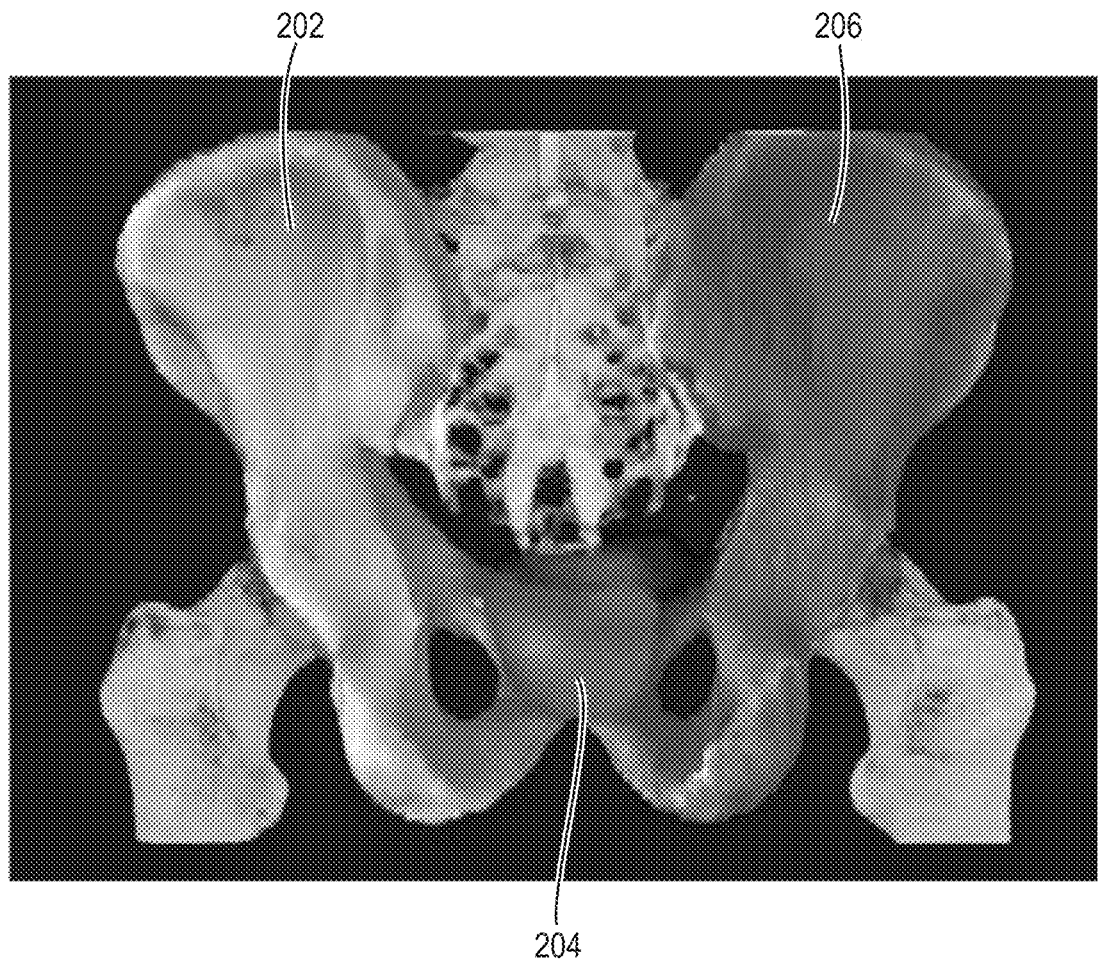
FIG. 2C is an image showing a 3D view of a CT image comprising a graphical representation of bone overlaid with a SPECT image and graphics representing an identified tissue volume corresponding to a prostate organ within pelvic bones of a subject, according to an illustrative embodiment.
Figure 2D:
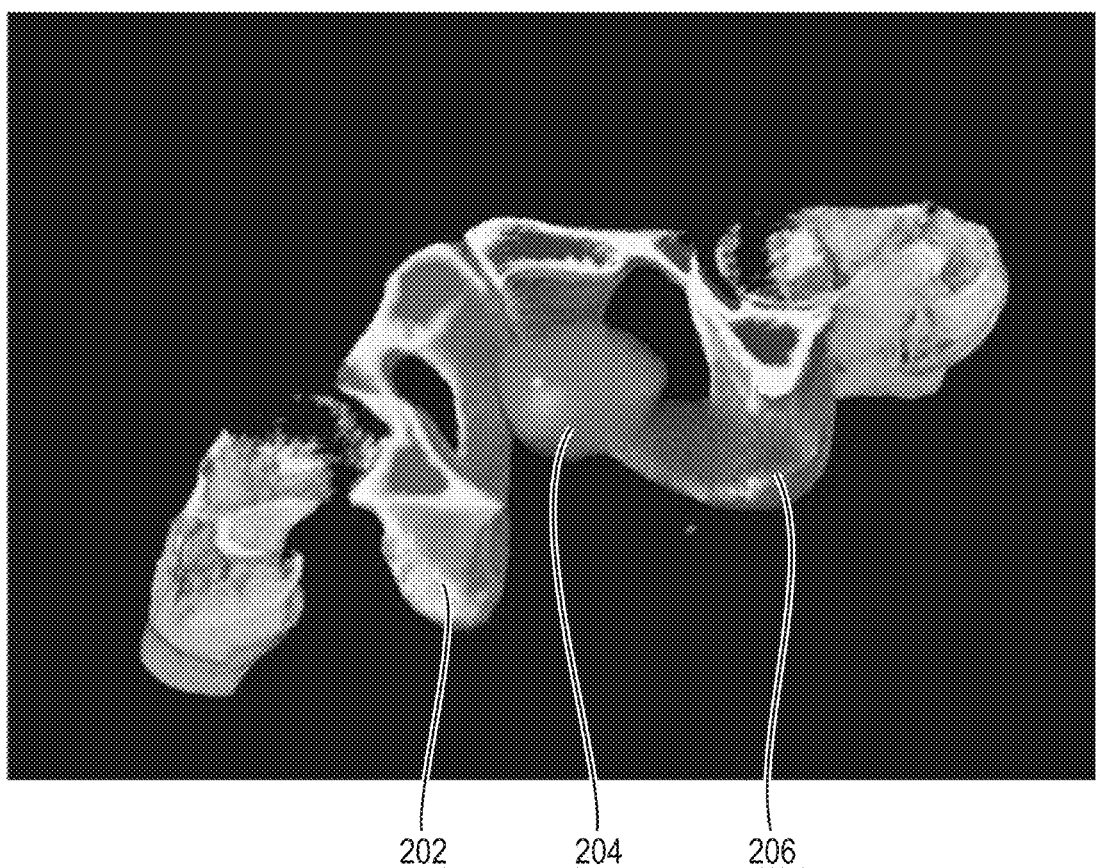
FIG. 2D is an image showing 3D view of a CT image comprising a graphical representation of bone overlaid with a SPECT image and graphics representing an identified tissue volume corresponding to a prostate organ within pelvic bones of a subject, according to an illustrative embodiment.
Figure 2E:
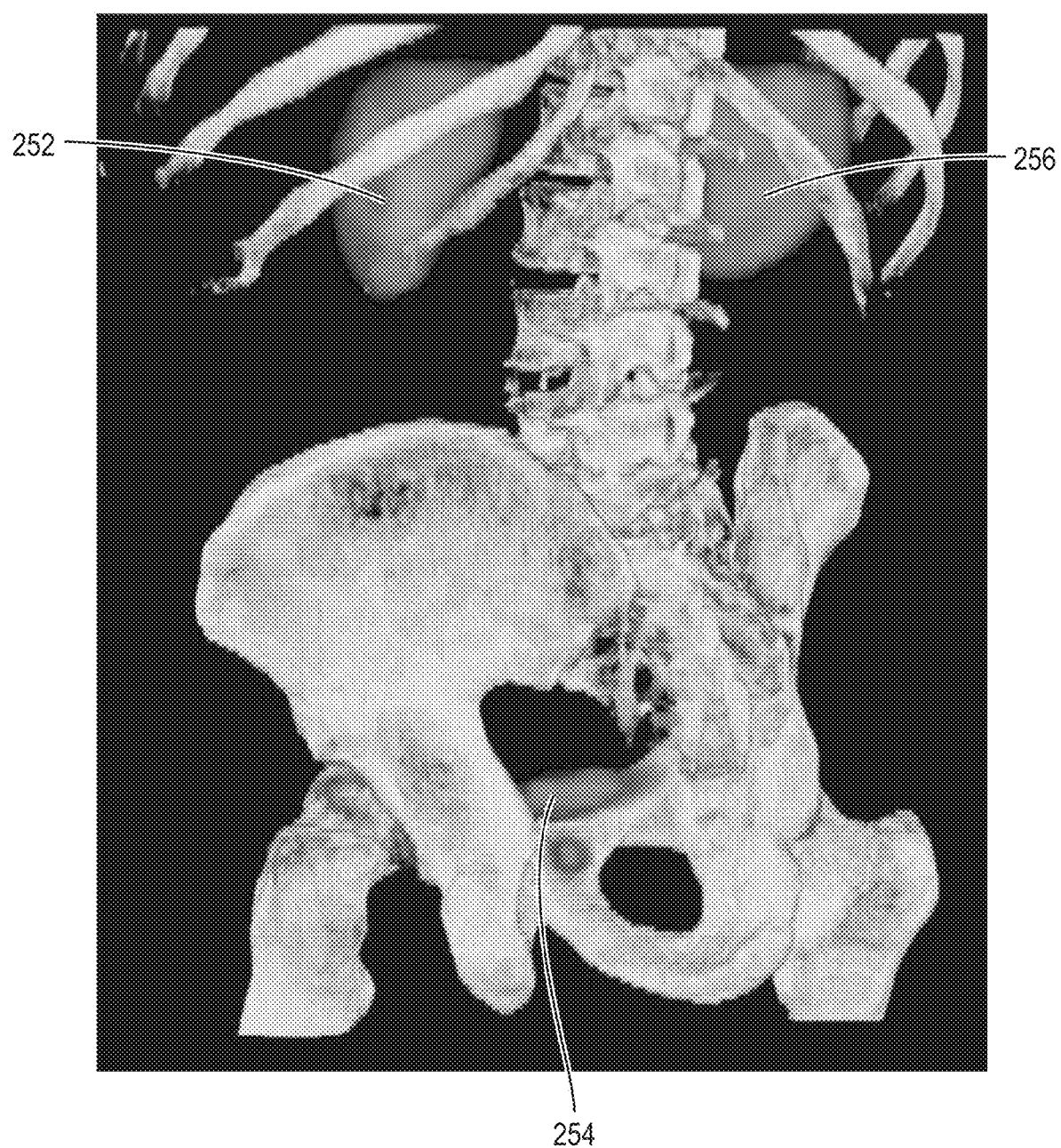
FIG. 2E is an image showing a 3D view of a CT image comprising a graphical representation of bone overlaid with a SPECT image, according to an illustrative embodiment.

Referring to Steps 102 and 104 of Process 100 in FIG. 1:

The various panels of FIG. 2 illustrate CT images (FIG. 2A and FIG. 2B) showing bone and soft-tissue, and highlight the pelvic bones (green 202 and blue 206 in FIGS. 2C and 2D) and prostate (purple 204 in FIGS. 2C and 2D). The highlighted regions are automatically generated by the systems and methods described herein, and identify the pelvic bones and prostate. FIG. 2E shows a SPECT image (the bright pink and purple regions 252, 254, and 256) overlaid on a CT image. As can be seen, the CT image provides detailed anatomical information, while the anatomical/structural information in the SPECT image is more limited. Accordingly, it is possible to segment the CT image, and use a mapping between voxels of the CT image and those of the SPECT image to identify particular voxels of the SPECT image that correspond to tissue volumes of interest, such as the prostate, bladder, rectum, and gluteal muscle, for example.

Referring to Steps 106 and 108 of Process 100 in FIG. 1:

The approach of identifying the prostate volume within the CT image first uses a first machine learning module (e.g., a CNN module) to identify an initial volume of interest within the CT image. This produces a standardized input to a second machine learning module (e.g., a second CNN module) that is responsible for identifying the prostate volume. The second CNN module may also identify other tissue volumes, such as pelvic bones, gluteal muscles, rectum, and bladder. The first and second machine learning modules may be combined and implemented as a single module and/or a single software application. The first and second machine learning modules may also be implemented separately, e.g., as separate software applications.

i. Bounding Box Generation (Localization Machine)

Figure 3A:
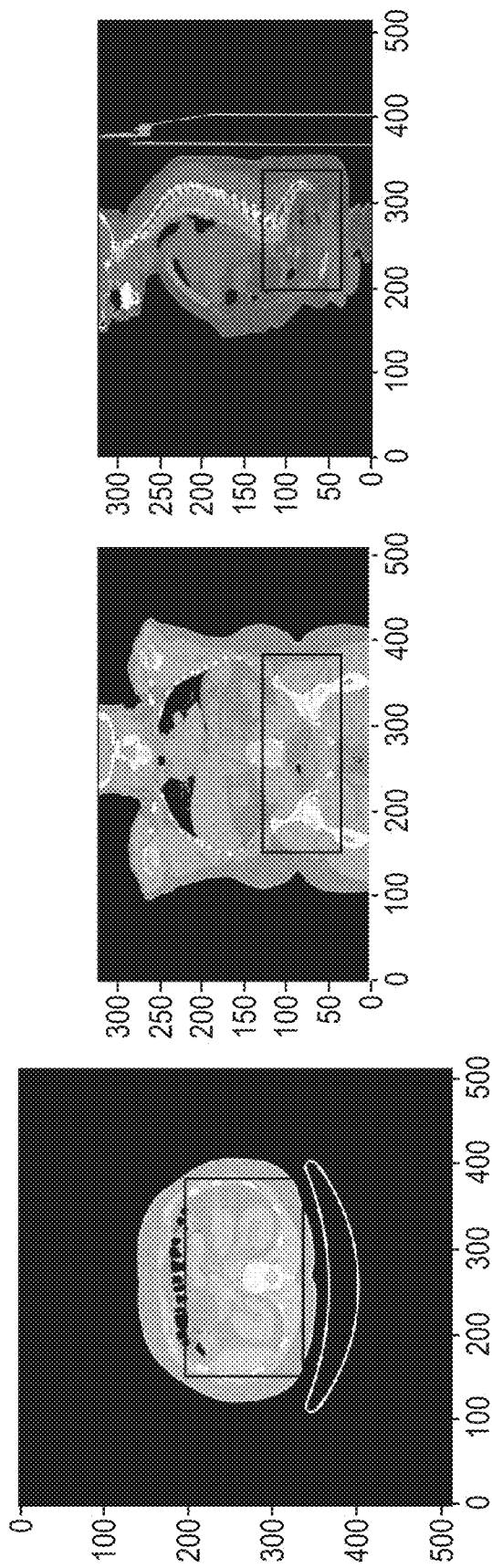
FIG. 3A is a set of images, each image showing a 2D cross-sectional view of a 3D CT image overlaid with graphics representing an identified initial volume of interest (VOI) within the 3D CT image, according to an illustrative embodiment.
Figure 3B:
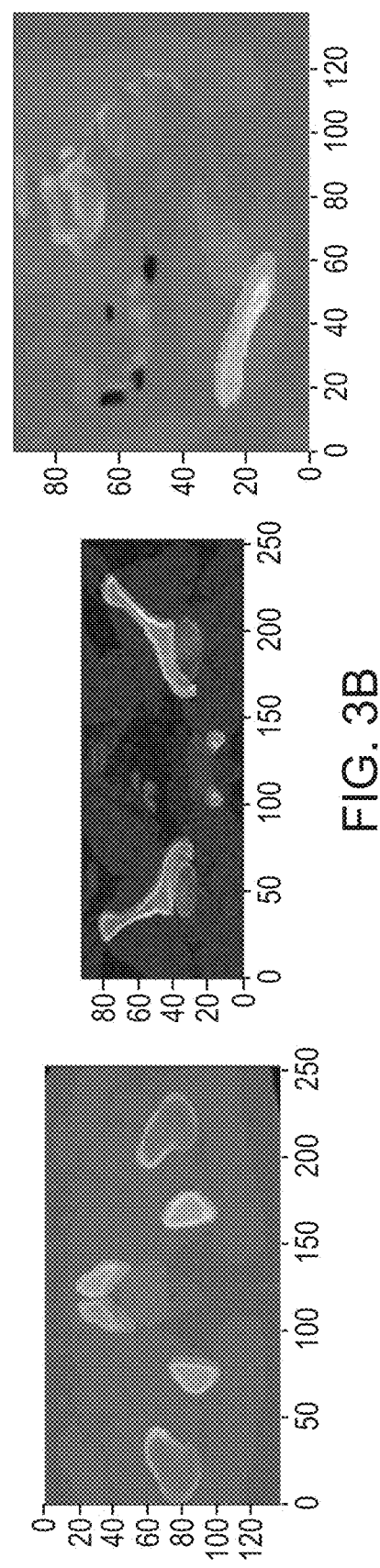
FIG. 3B is a set images, each image showing a 2D cross-sectional view of a 3D CT image overlaid with graphics representing an identified initial volume of interest (VOI) within the 3D CT image, according to an illustrative embodiment.
Figure 4A:
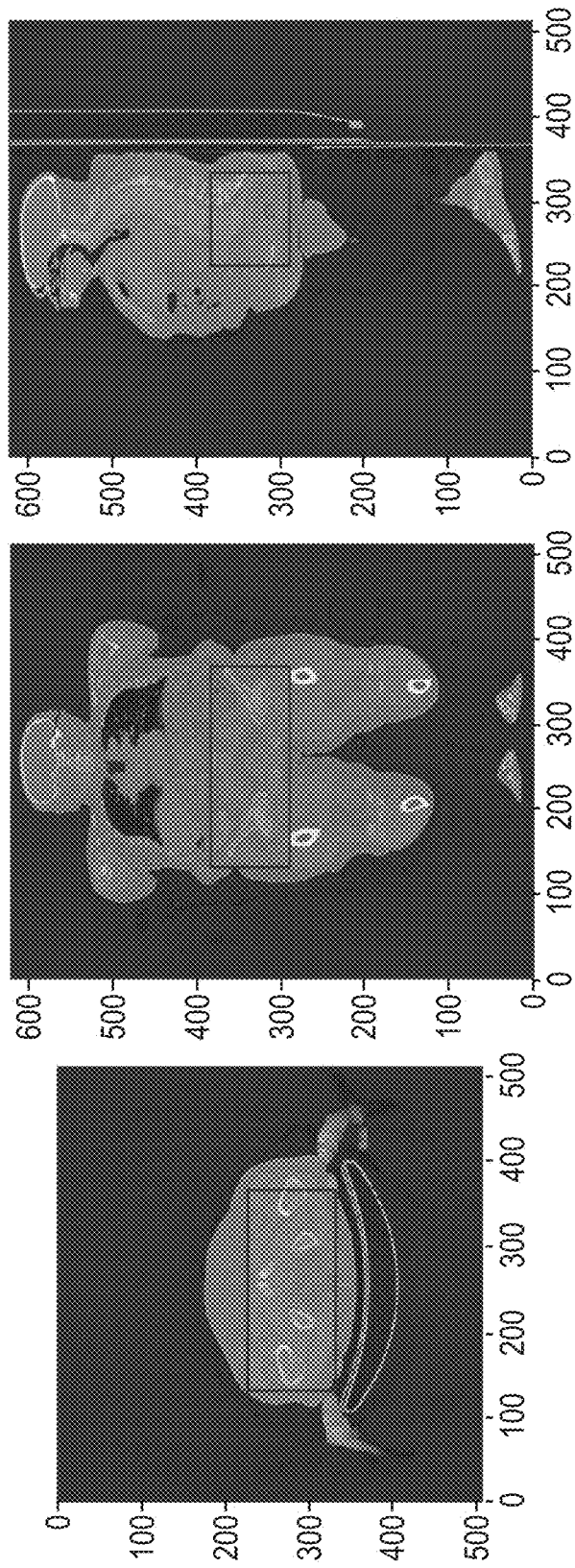
FIG. 4A is a set of images showing 2D cross sectional views of a CT image of a subject and a cuboidal region identified as an initial volume of interest within the CT image, according to an illustrative embodiment.
Figure 4B:
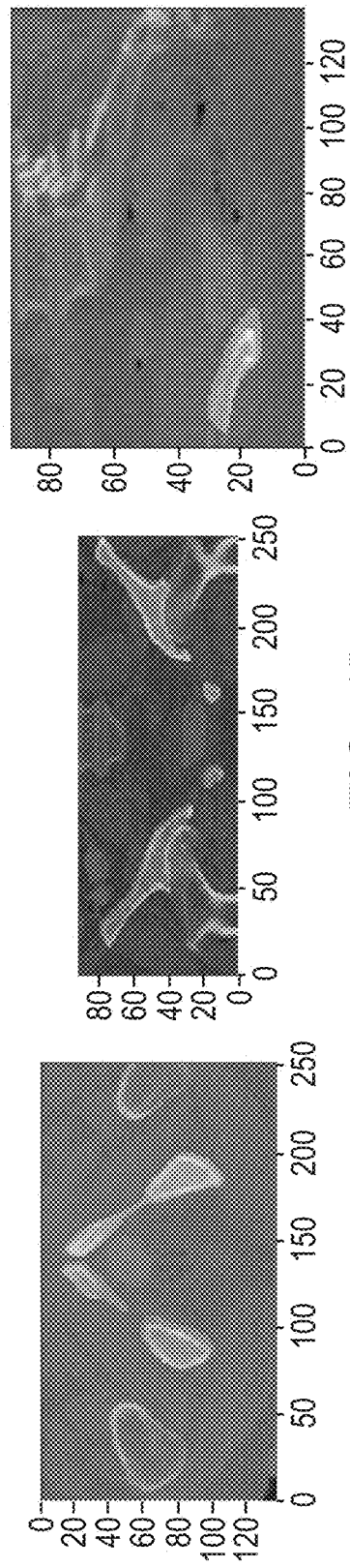
FIG. 4B is a set of images showing 2D cross sectional views of a CT image of a subject along with identified tissue volumes corresponding to pelvic bones and a prostate of the subject.

FIGS. 3-5 present examples of the processing of various CT images showing, first, the identification of the initial volume of interest (VOI) (panels A) and, second, the segmentation of the prostate and pelvic bones (the prostate volume is represented by the blue-green volume in the middle). As shown in these examples, the initial CT image size can substantially depending on the imaging system used, the imaging protocol followed by the radiologist, and other factors, but the initial VOI size is fairly standard.

For example, initial 3D anatomical images may range in size from as large as 700 mm×700 mm×1870 mm (depth× width×height) (i.e. a full body scan), or even larger, to as small as 180 mm×240 mm×290 mm (covering the pelvic bone), or even smaller. In the examples described herein, the smallest tested matrix size of an initial 3D anatomical image is 256×256×76 pixels. The bounding boxes (e.g., identified by the first CNN) for the examples described herein have approximate size ranges of 180-220 mm×240-320 mm×290-380 mm. Matrix sizes of the bounding boxes for the example described herein are in the range of 80-220×150-390×50-300 pixels.

In the example, 3D anatomical images for training the first CNN to detect pelvic region bounding boxes had the following image dimensions:

Training Images (3D Anatomical Images):
rows: 247-512 (sp 1.37), size (mm): 340-700
columns: 319-512 (sp 1.37), size (mm): 430-700
slices: 274-624 (sp 3.0), size (mm): 820-1870

In the example, 3D anatomical images for validating the first CNN for detection of bounding boxes had the following image dimensions, with the resulting range in dimensions of bounding boxes identified by the first CNN:

Validation Images (3D Anatomical Images):
rows: 256-512, size (mm): 500-600
columns: 256-512, size (mm): 500-600
slices: 76-427, size (mm): 380-1070
Bounding Boxes:
rows: 82-222, size (mm): 180-220
columns: 148-386, size (mm): 240-320
slices: 50-295, size (mm): 290-380

The following are three example approaches for automatically generating a bounding box (cuboid) for the pelvic region from an initial 3D anatomical image, for use in subsequent processing for detailed identification of the prostate.

In a first approach, the first CNN receives as input the grayscale CT image (a single input channel) and outputs coordinates of the opposite corners of the bounding box.

In a second approach, the grayscale CT image is processed via thresholding to produce a thresholded image with a rough identification of the pelvic region. In this second approach, the first CNN receives two input channels—one being the grayscale CT image and the other being the thresholded image. The second CNN outputs coordinates of opposite corners of the bounding box.

In a third approach, the first CNN is essentially a rough version of the second CNN—that is, the first CNN identifies a prostate, pelvic bones, and a sacrum (and background). The bounding box is generated using the identified pelvic bones (e.g., by drawing the smallest box that fits the pelvic bones, or maybe adding some buffer distance). A distinction here is that the output of the first CNN is not merely coordinates of cuboid vertices. In this approach, likelihood values are automatically determined for each voxel of the image that give the likelihood as to how the voxel is classified—e.g., whether the voxel is prostate, left/right pelvic bone, sacrum, or background, for example.

In one illustrative embodiment of this third approach, the localization and segmentation networks are very similar. The localization network segments left and right pelvic bones, sacrum and the background (4 classes in all) in very downsampled images. Based on this rough segmentation of the pelvic bones, a bounding box is created. The segmentation network then segments the pelvic bones, the prostate, and the background within this bounding box and at higher resolution. The localization CNN and the segmentation CNN have identical architectures. The differences are in what input shape they require, where the localization network resize images to size (81, 68, 96) and the segmentation CNN resize pelvic images (as output from the localization network) to size (94, 138, 253). Also, the number of convolutional filters differs. The segmentation network has 20 convolutional filters in the first layer whereas the localization network only has 8. The size and number of filters of subsequent layers are scaled, as is shown in the flow charts herein. To create the bounding box after the localization network, the method finds the corners of the first segmentation and draws a square around it with a margin. The input images to the localization network are small because they have been downsampled to a lower resolution, whereas the segmentation process a cropped version of the CT image in the original resolution.

Figure 6A:
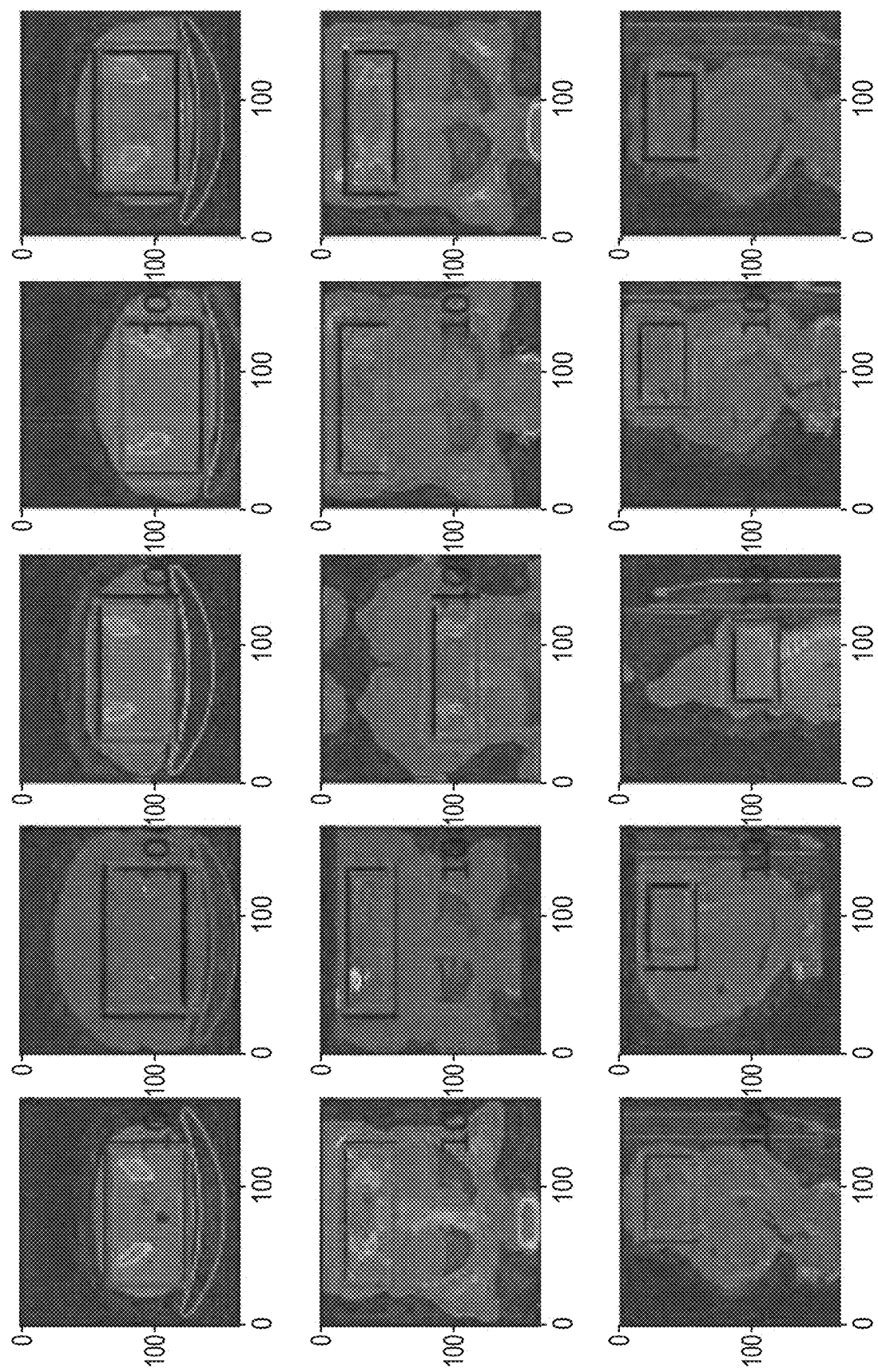
FIG. 6A is a set of images showing 2D cross sectional views of a CT image of a subject and a cuboidal region identified as an initial volume of interest within the CT image, according to an illustrative embodiment.
Figure 6B:
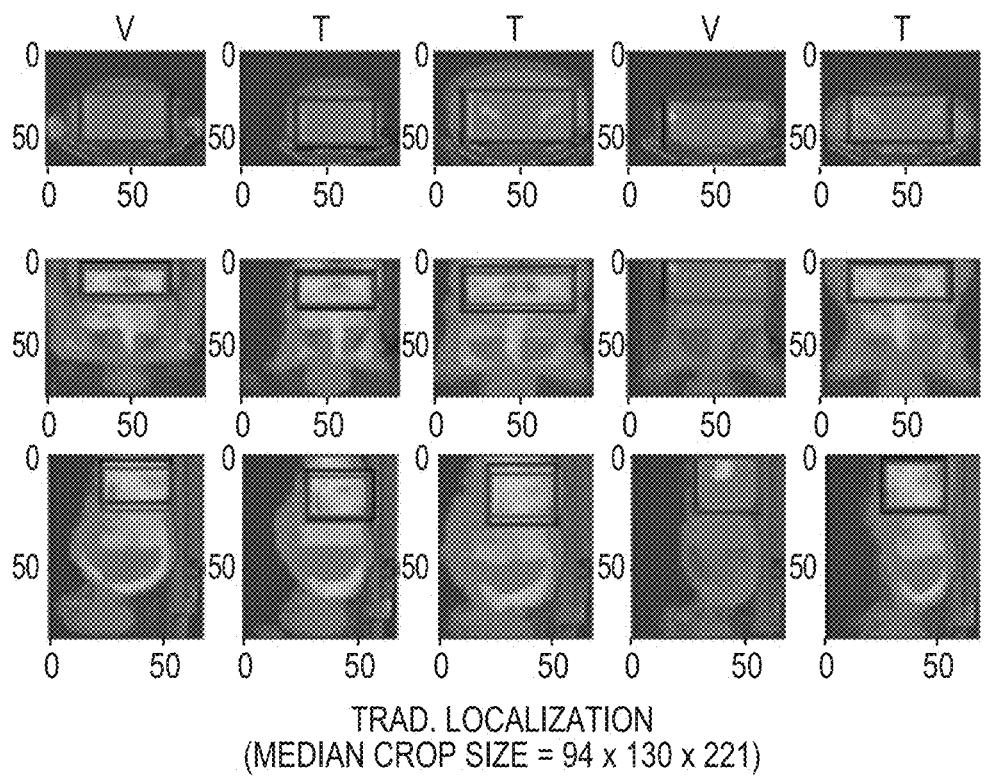
FIG. 6B is a set of images, each image showing a 2D cross-sectional view of a 3D CT image overlaid with graphics representing an identified initial volume of interest (VOI) within the 3D CT image, according to an illustrative embodiment.
Figure 6C:
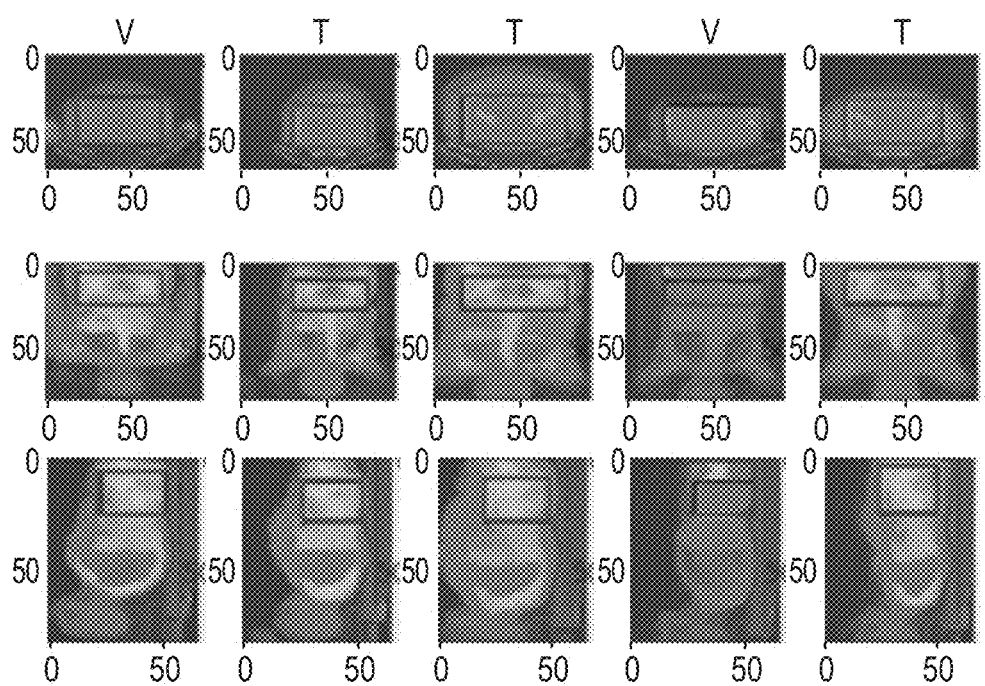
FIG. 6C is a set of images, each image showing a 2D cross-sectional view of a 3D CT image overlaid with graphics representing an identified initial volume of interest (VOI) within the 3D CT image, according to an illustrative embodiment.
Figure 7A:
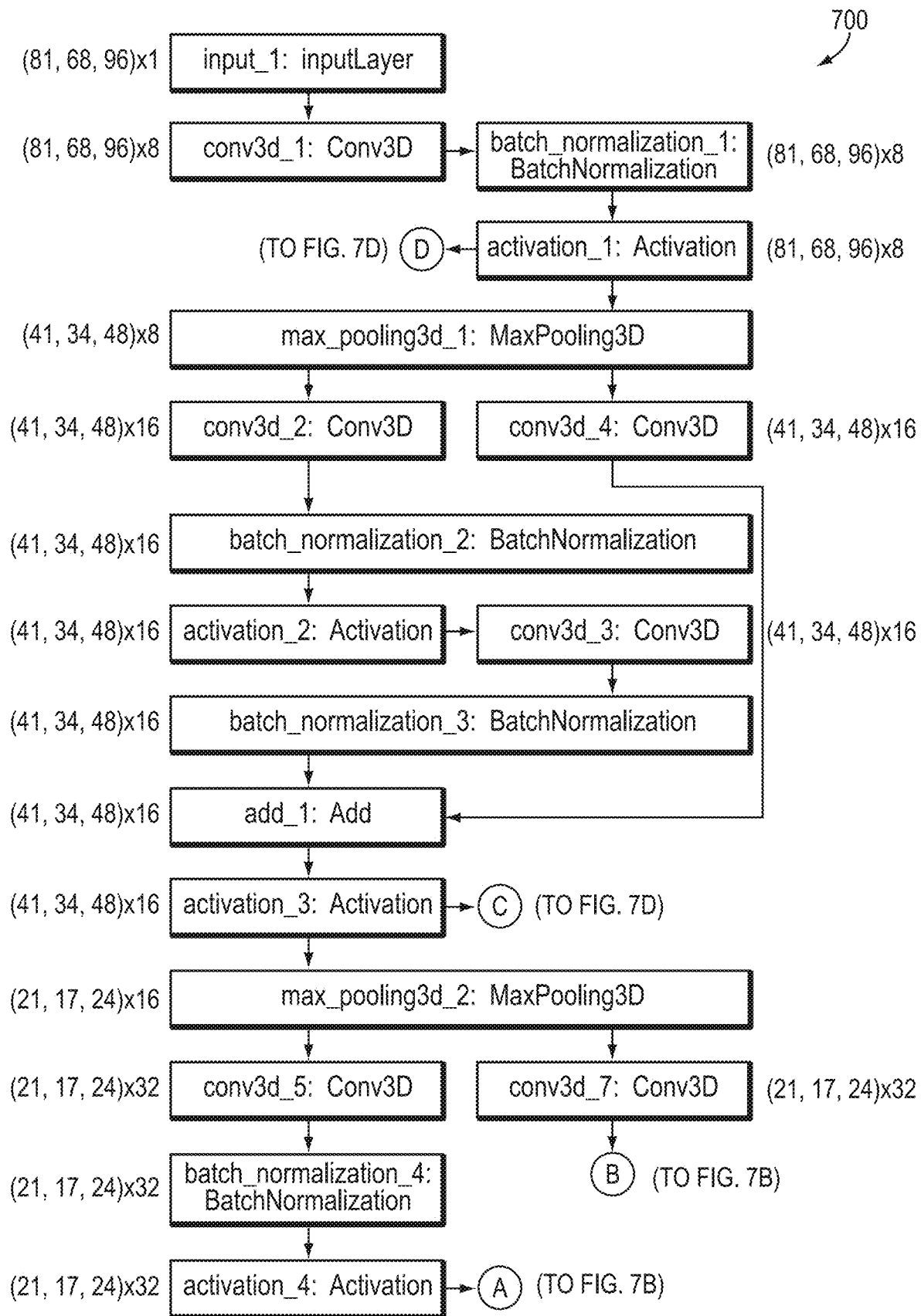
FIGS. 7A-7E present a block diagram of a CNN module architecture (localization network) for identifying a volume of interest (e.g., VOI) corresponding to a pelvic region within a CT image of a subject (wherein the VOI is subsequently processed by a second CNN module for more detailed segmentation/identification of the prostate and/or other tissues within the pelvic region), according to an illustrative embodiment.
Figure 7B:
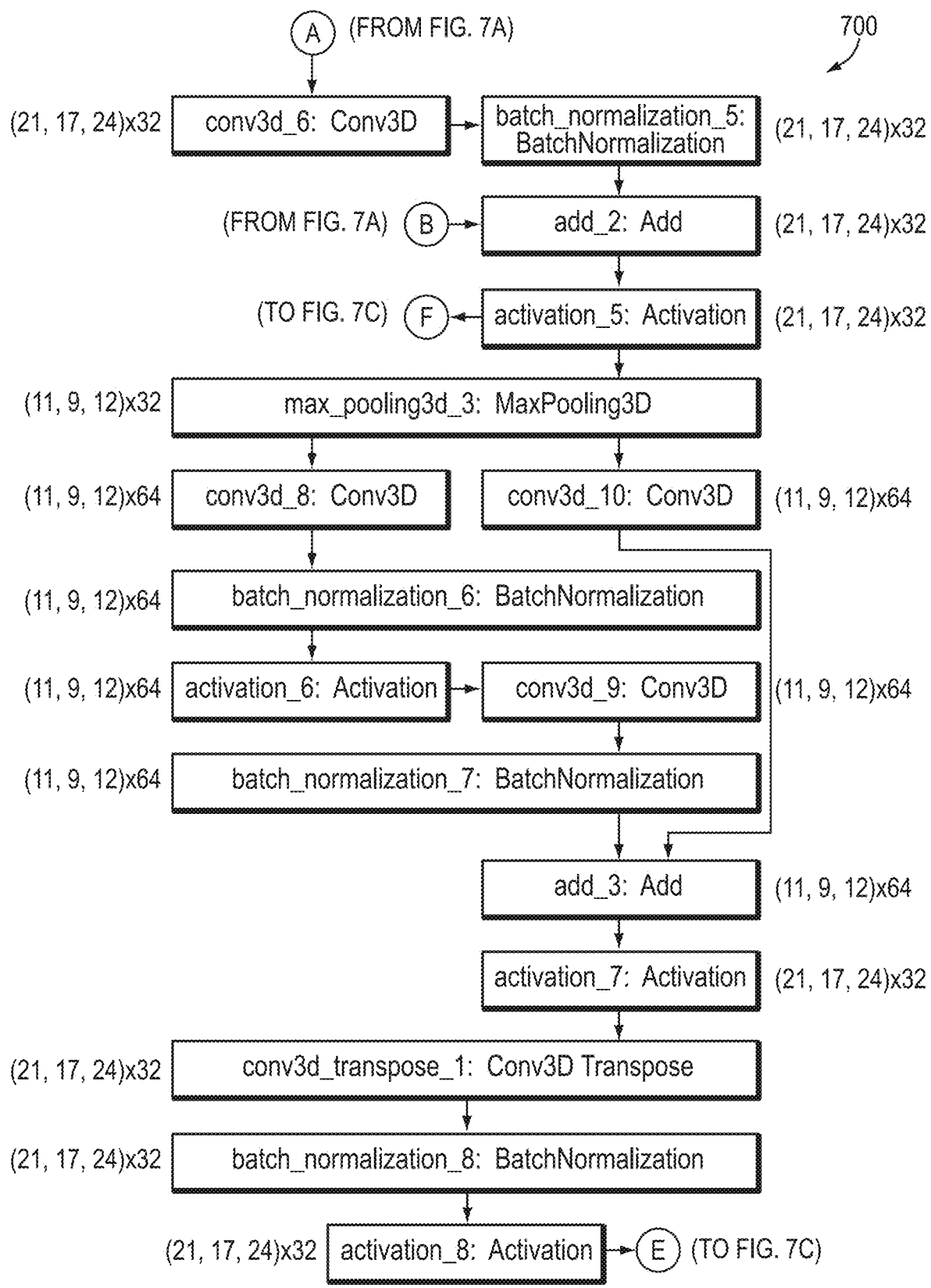
Figure 7C:
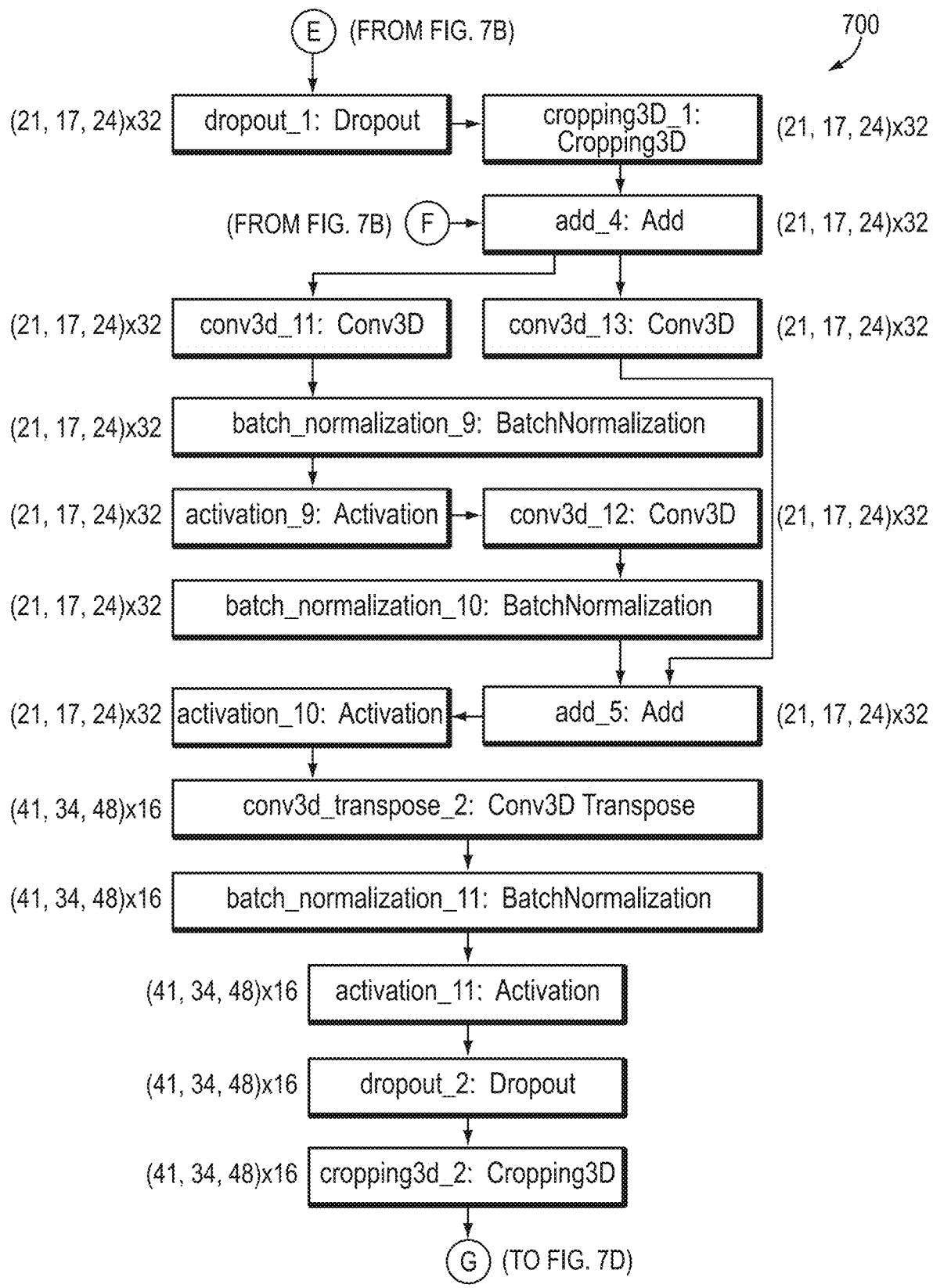
Figure 7D:
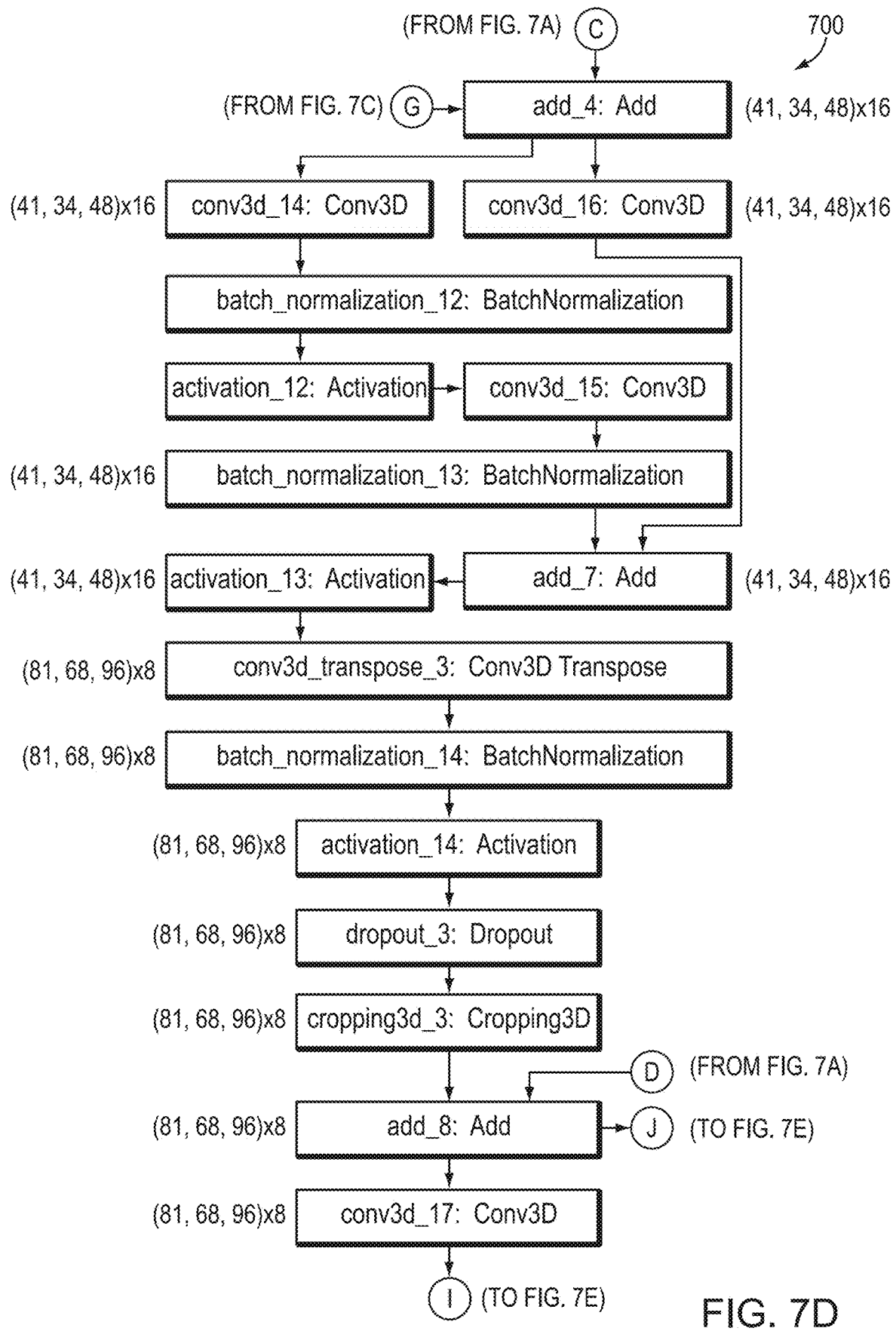
Figure 7E:
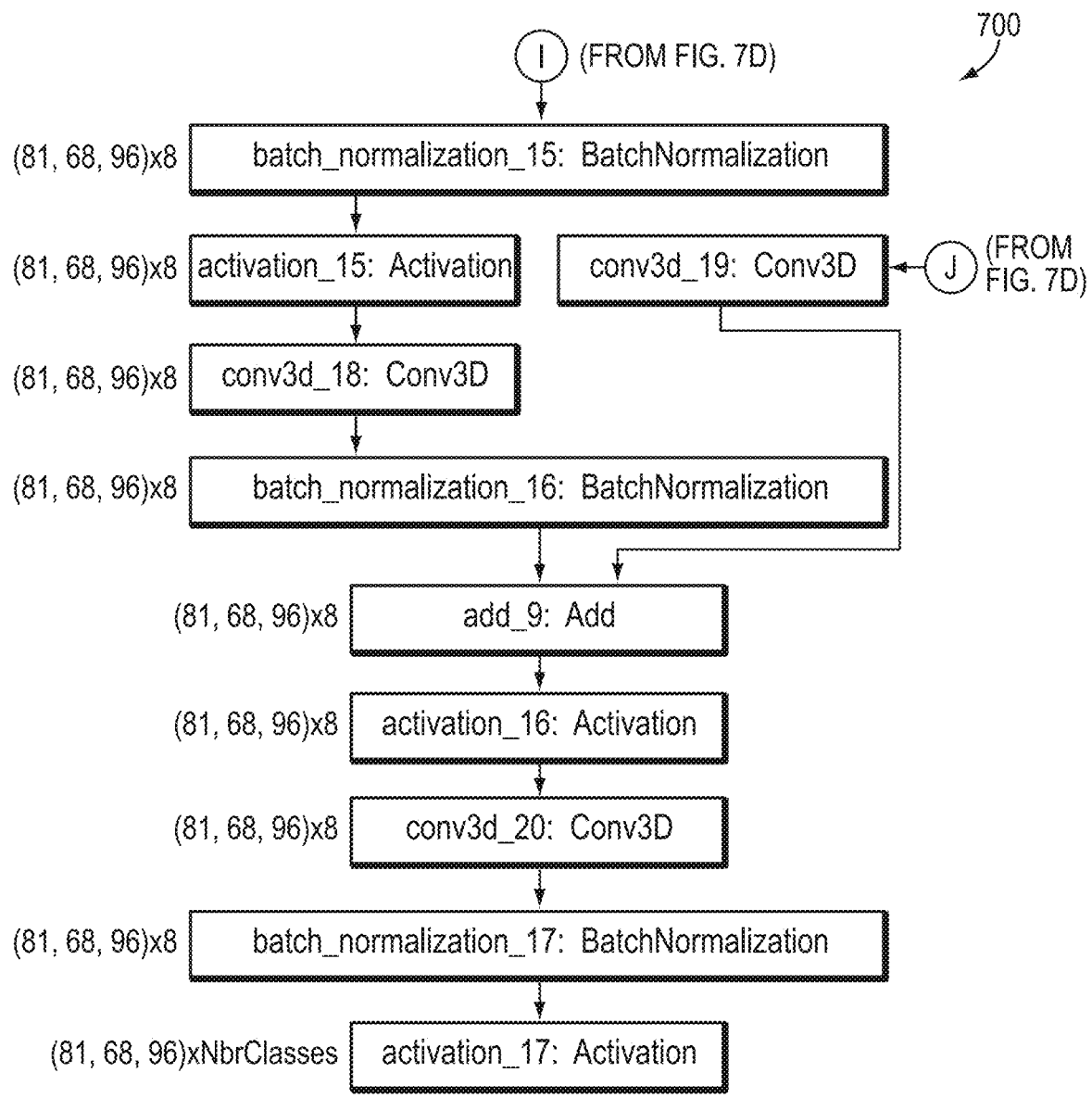
Figure 7F:
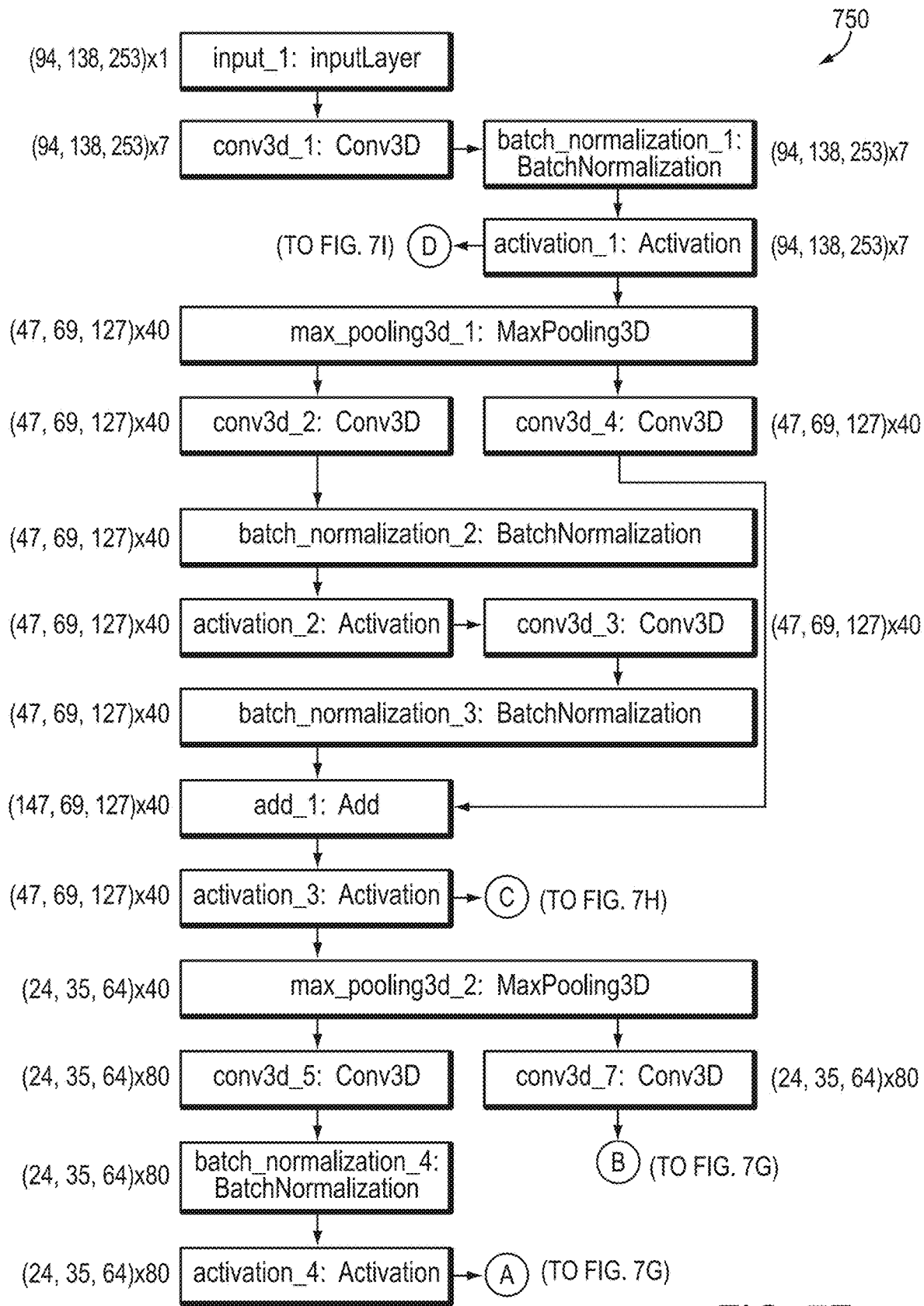
FIGS. 7F-7J present a block diagram of a CNN module architecture (segmentation network) for processing the previously-identified VOI for precise segmentation of the prostate and/or other tissues within the pelvic region, according to an illustrative embodiment.
Figure 7G:
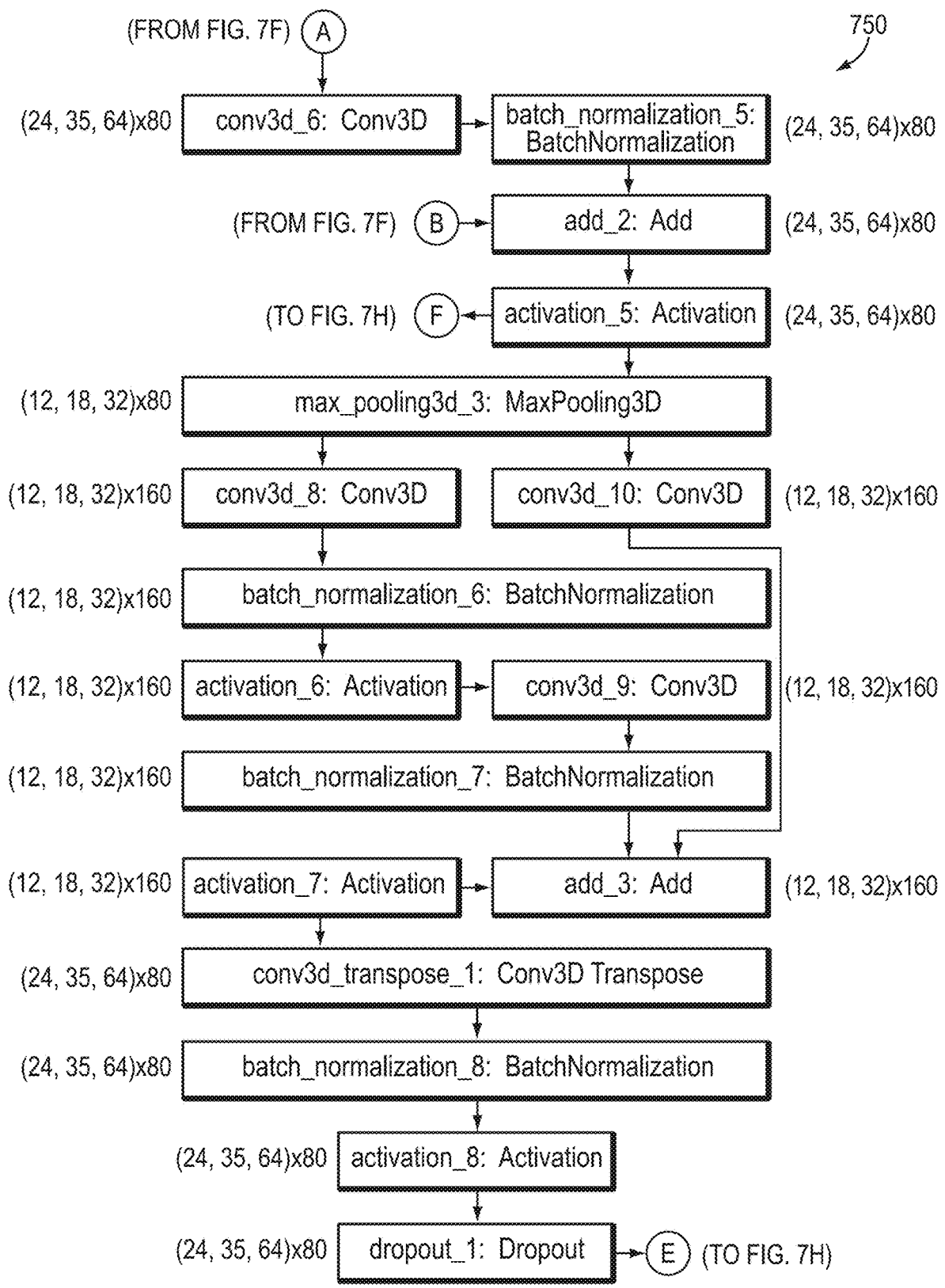
Figure 7H:
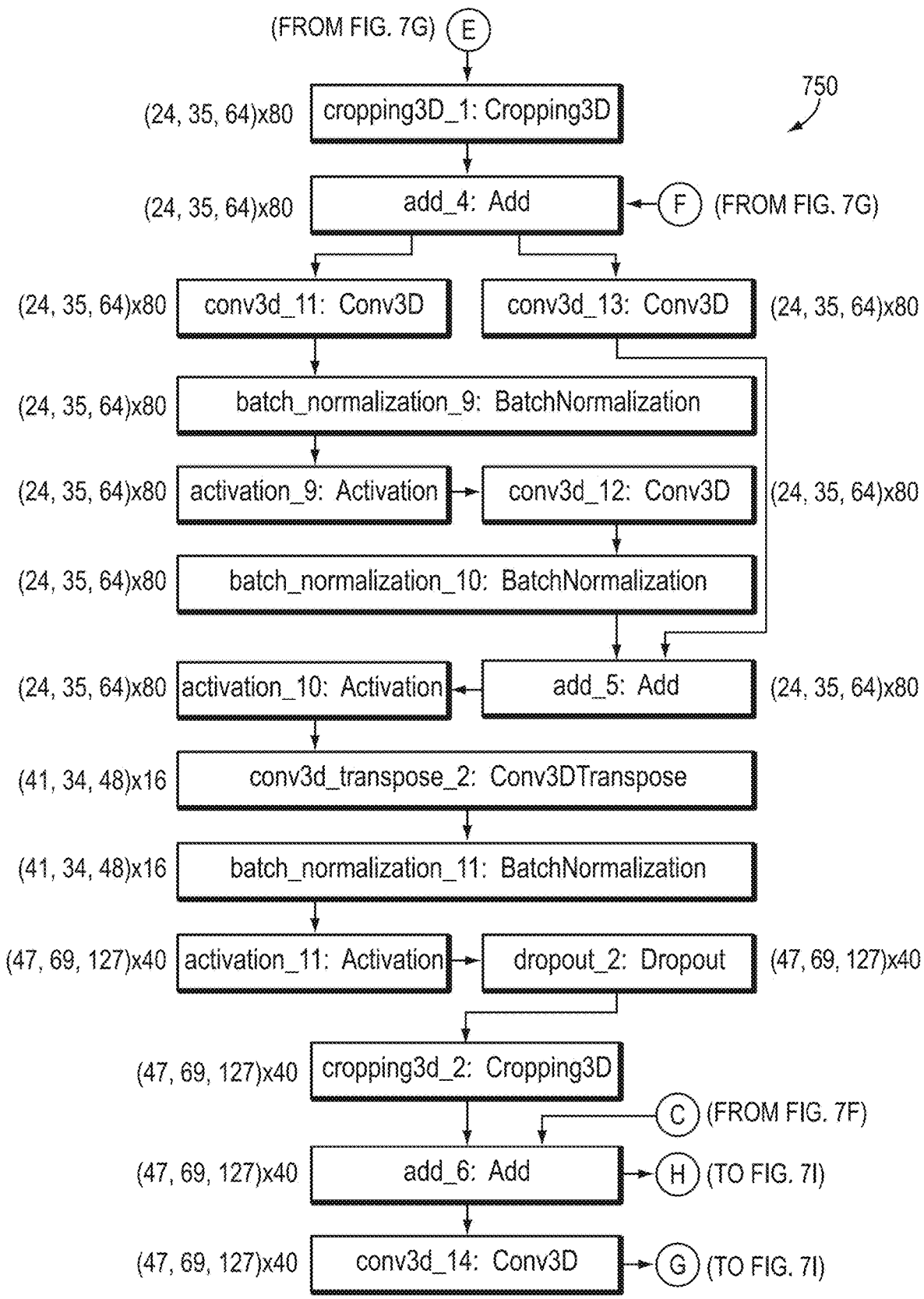
Figure 7I:
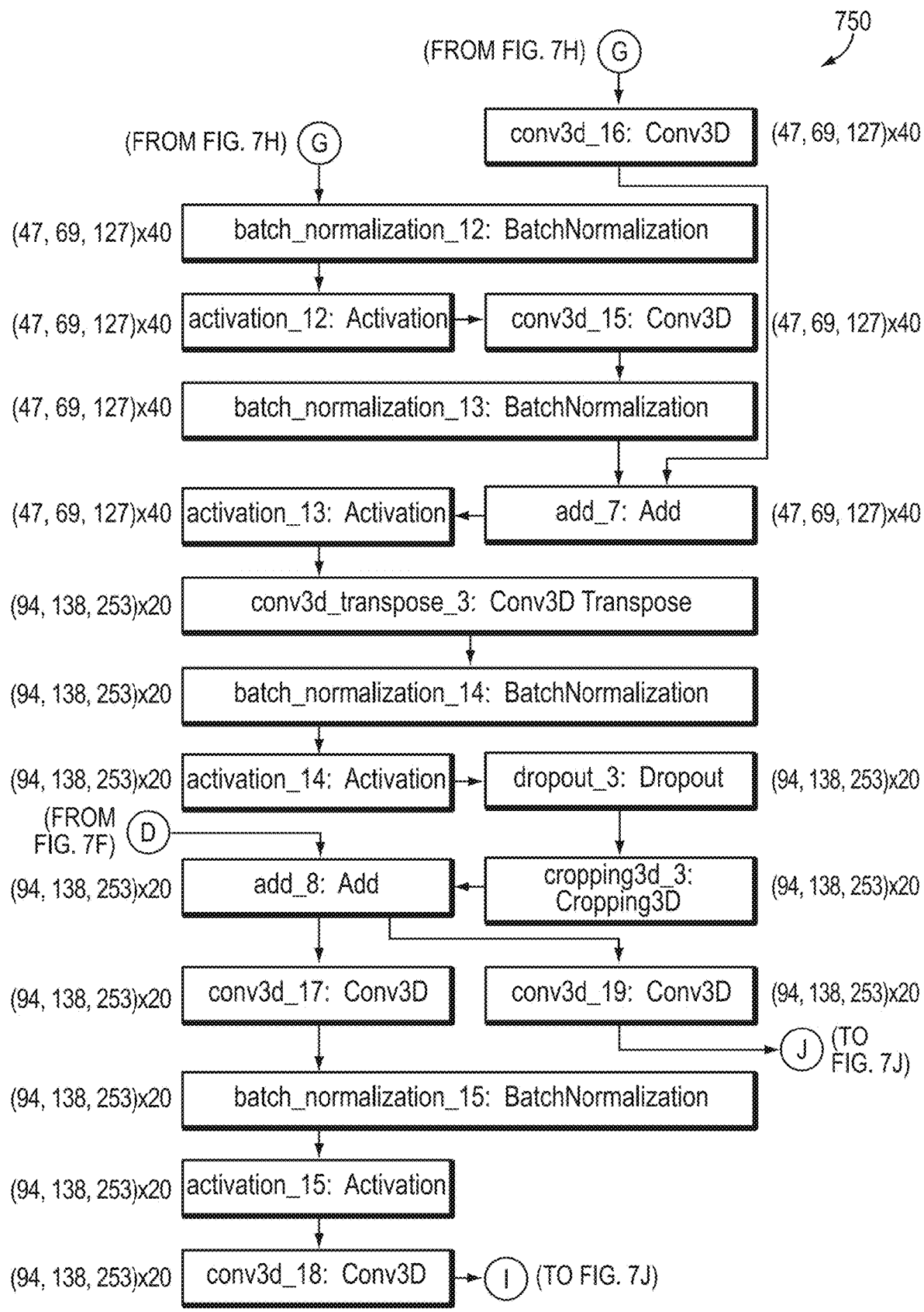
Figure 7J:
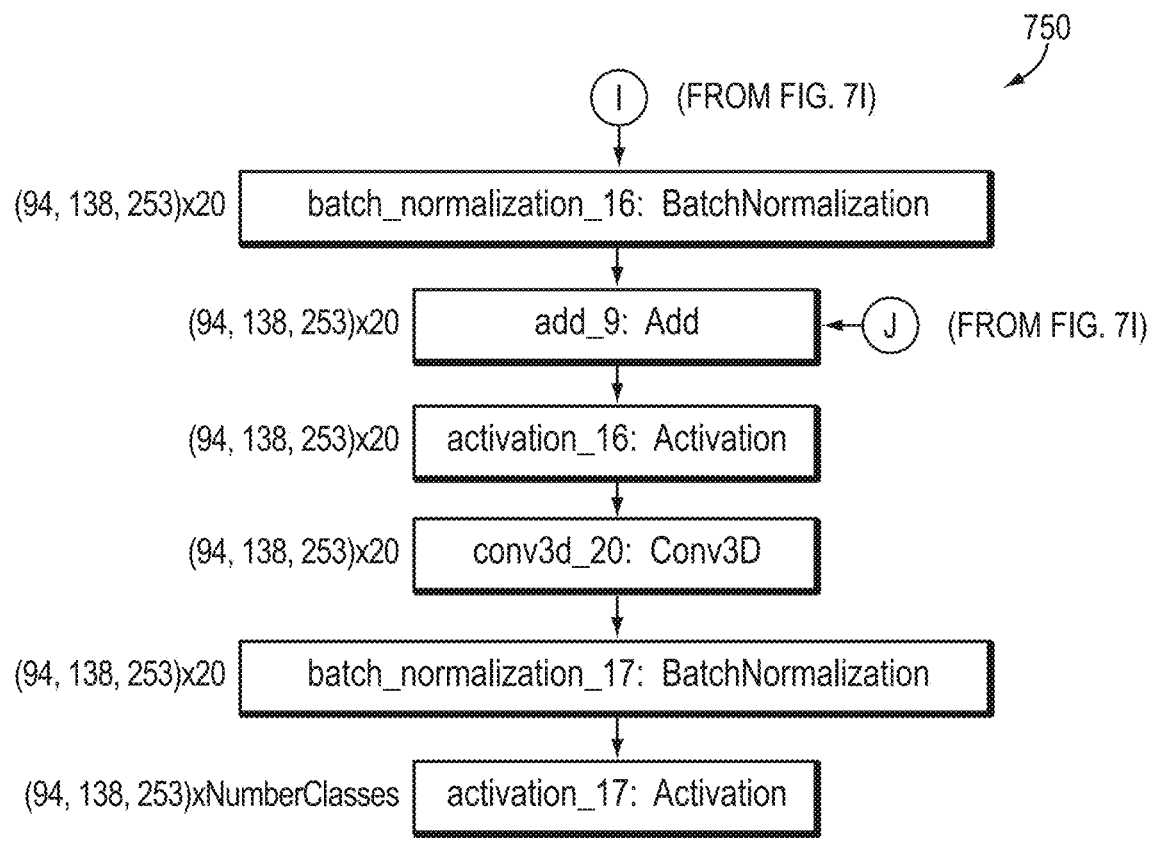

The FIG. 6A shows an example of approach 1. FIG. 6B and FIG. 6C show a comparison between approach 1 and approach 3.

FIGS. 7A-E show an example architecture 700 of the first CNN network described herein. The CNN module architecture (localization network) is used for identifying a volume of interest (e.g., VOI) corresponding to a pelvic region within a CT image of a subject (wherein the VOI is subsequently processed by a second machine learning module (e.g., a second CNN module) for more detailed segmentation/identification of the prostate and/or other tissues within the pelvic region).

ii. Prostate Volume and Additional Tissue Volume Determination (Single Segmentation Machine)

FIGS. 7F-J show an example architecture 750 of the second CNN network described herein. As noted above, the second CNN operates on the VOI to identify a prostate volume, as well as various additional tissue volumes. Additional tissue volumes can include left/right pelvic bones, a sacrum, a bladder, gluteal muscles, and a rectum. Identifying multiple tissue volumes, as opposed to performing a binary classification (e.g., where voxels are simply identified as prostate or background) improves the accuracy of the classification approach.

Figure 8A:
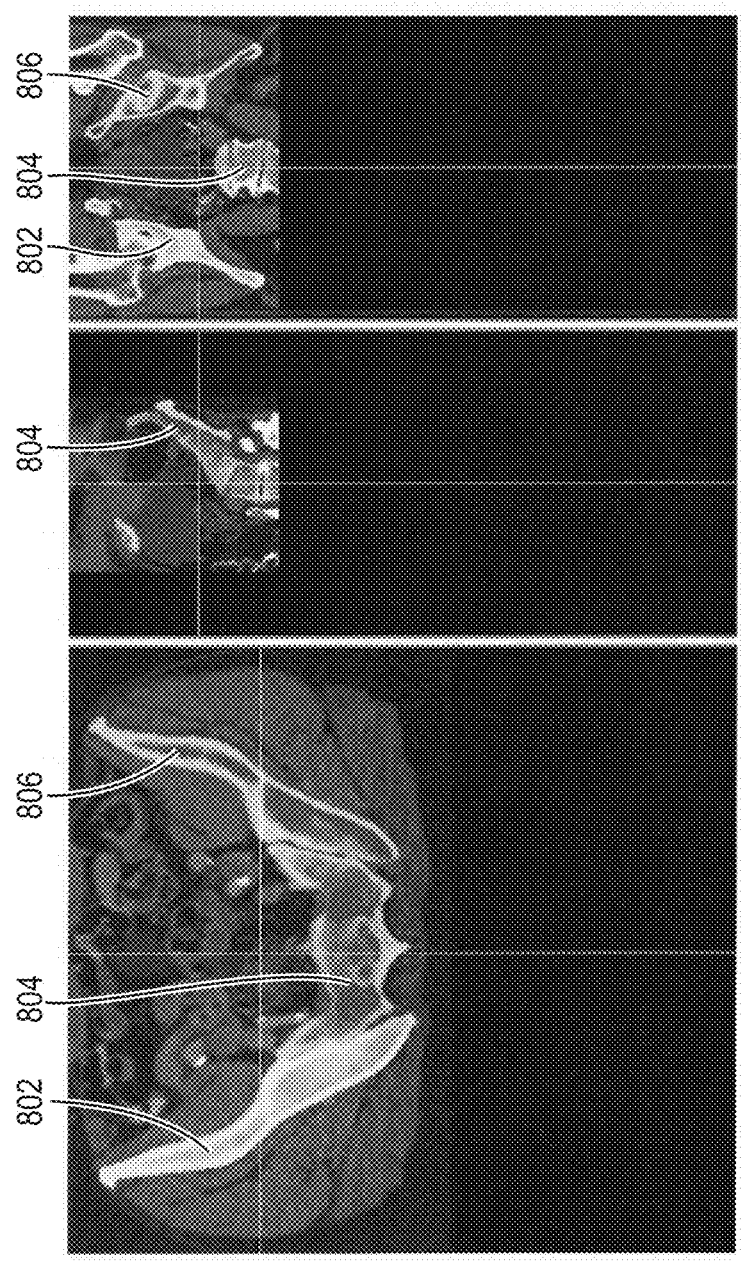
FIG. 8A is a set images, each showing a 2D cross-sectional view of a 3D CT image overlaid with graphics representing identified tissue volumes corresponding to three different pelvic bones (left and right hip bones and the sacrum), according to an illustrative embodiment.
Figure 8B:
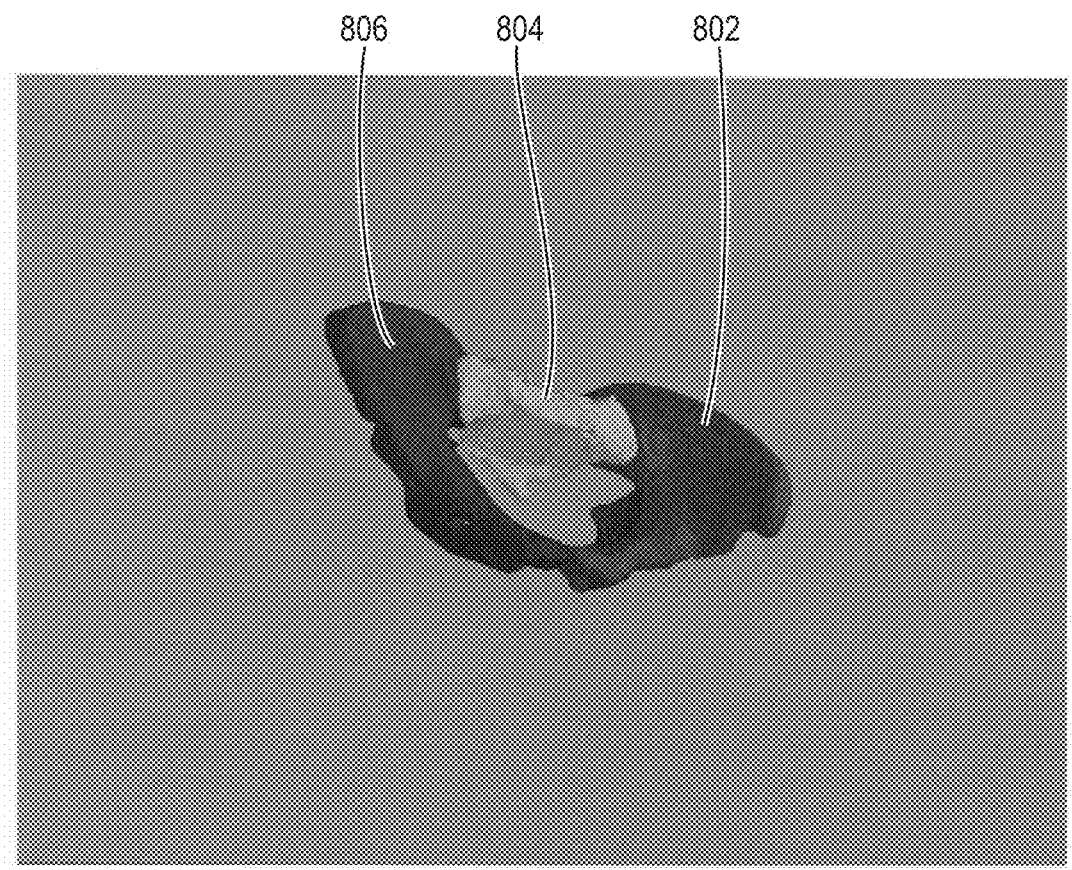
FIG. 8B is an image showing a 3D view of a 3D CT image overlaid with graphics representing identified tissue volumes corresponding to three different pelvic bones (left and right hip bones and the sacrum), according to an illustrative embodiment.

FIG. 8A shows left and right pelvic bones (blue, 806 and yellow, 802) and the sacrum (red, 804) in 2D, and FIG. 8B shows the same in 3D.

Figure 9A:
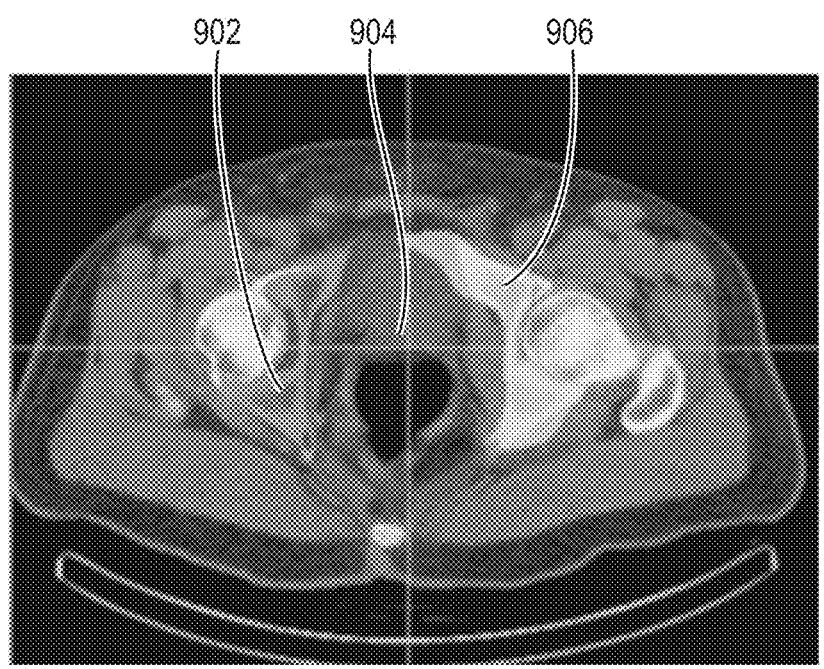
FIG. 9A is an image showing a 2D cross-sectional view of a 3D CT image overlaid with graphics representing identified tissue volumes corresponding to pelvic bones (left and right hip bones) and a prostate of a subject, according to an illustrative embodiment.

FIG. 9A shows left and right pelvic bones (red, 902 and yellow, 906) and a prostate (blue, 904).

Figure 9B:
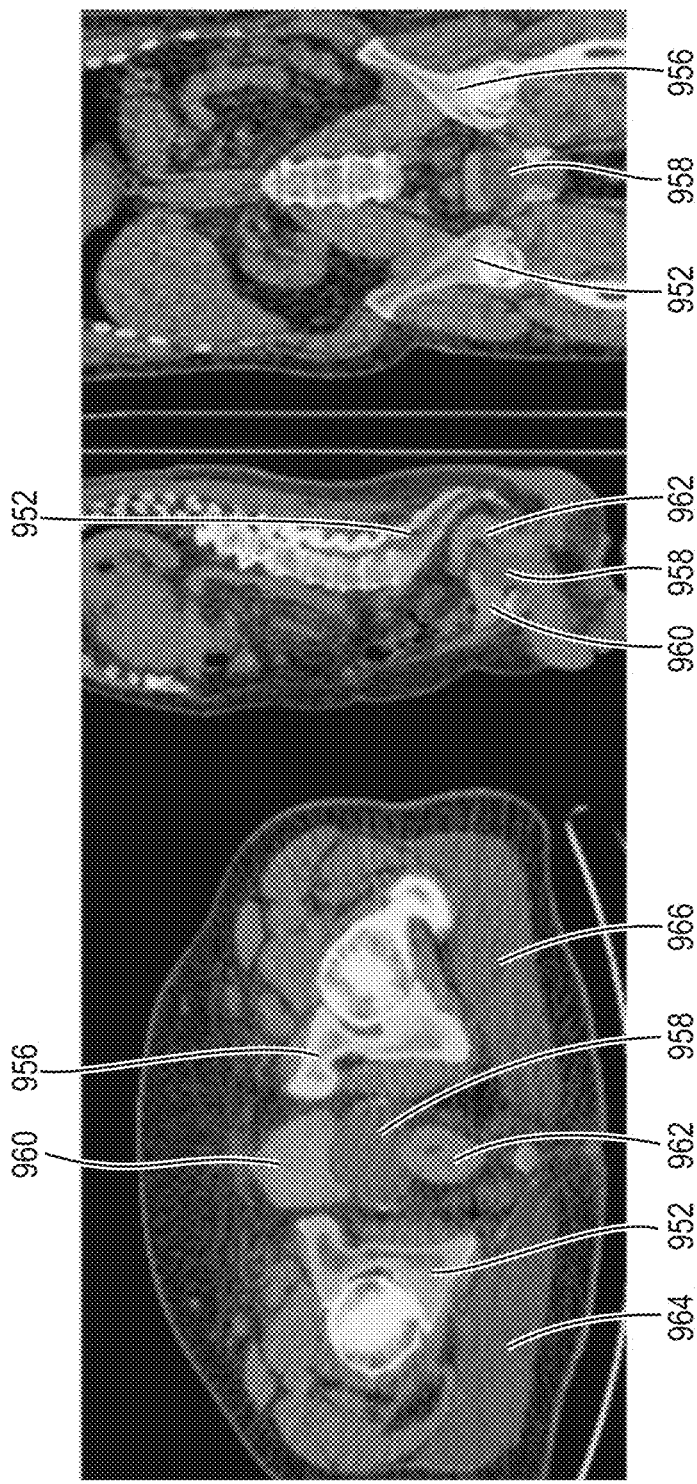
FIG. 9B is a set of images showing different 2D cross sectional views of a 3D CT image overlaid with graphics representing identified tissue volumes corresponding to pelvic bones, gluteal muscles, a rectum, a prostate, and a bladder of a subject, according to an illustrative embodiment.

FIG. 9B shows segmentation of left and right pelvic bones (two lighter green regions, 952 and 956), prostate (dark green, 958), bladder (greenish beige, 960), a rectum (brown, 962), and gluteal muscles (blue, 964 and red, 966).

Figure 10:
FIG. 10 is an image showing a 2D cross sectional view of a low quality 3D CT image overlaid with graphics representing identified tissue volumes corresponding to pelvic bones and a prostate of a subject, according to an illustrative embodiment.

FIG. 10 shows a low quality CT image, where segmentation still worked.

iii. Segmentation Module Architecture

Data Input and Output

Figure 11:
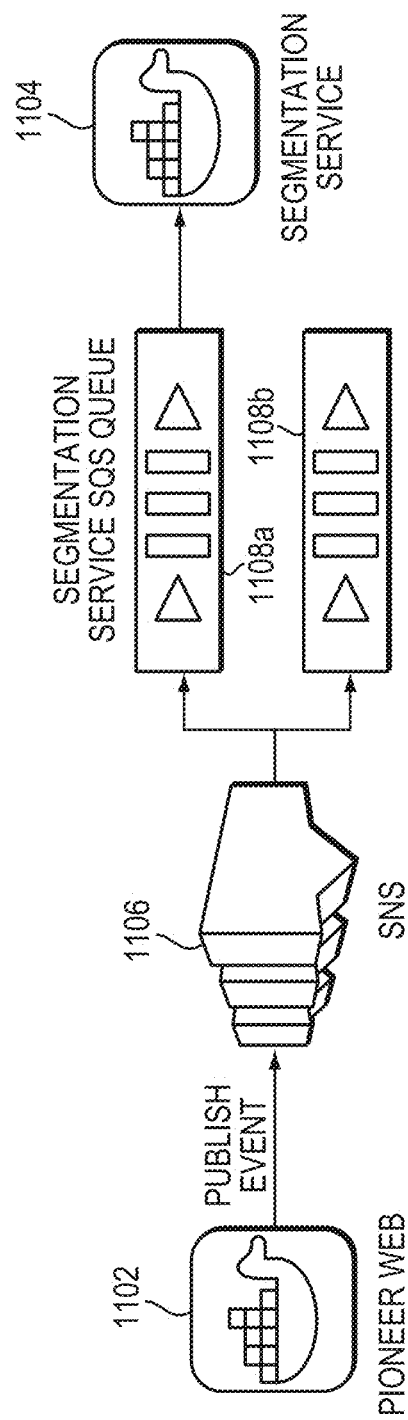
FIG. 11 is a schematic showing an example architecture wherein image segmentation for identification of a prostate volume as described herein is performed by a dedicated module, according to an illustrative embodiment.

FIG. 11 shows an example architecture 1100 in which image segmentation as described herein is performed by a Segmentation Service module 1104 that receives requests to process images (e.g., perform segmentation as described herein) from a client facing module, Pioneer Web 1102.

The particular example architecture 1100 shown in FIG. 11 is used in an embodiment of the image segmentation and analysis systems and methods described herein, in particular a cloud-based software application, referred to as Pioneer. Pioneer is a software device to assist in the assessment and characterization of prostate cancer in the prostate gland using MIP-1404 SPECT/CT image data. The software uses artificial intelligence to automatically segment the image data into distinct anatomical regions and then analyzes the volumetric regions of interest (ROI). Pioneer extracts quantitative data from ROIs to assist in determining the presence or absence of clinically significant prostate cancer.

The architecture and module organization shown in FIG. 11, as well as other architectures and module organizations described herein with respect to Pioneer, may be adapted for use with other imaging modalities and/or other radiopharmaceuticals. For example, a variety of radiopharmaceuticals suitable for use with SPECT imaging are described herein, in section M "Imaging Agents" below. Various 3D functional imaging modalities may also be used for imaging radiopharmaceutical uptake in a subject, and combined with a 3D anatomical imaging modality, such as, but not limited to CT imaging, and analyzed via adapted versions of the approached described herein with respect to Pioneer. For example, various nuclear medicine imaging modalities, such as PET imaging may be used to image radiopharmaceutical uptake. Like SPECT imaging, PET imaging may be performed in combination with CT imaging to obtain an image set comprising a PET image and a CT image—a CT/PET image. Accordingly, the approaches described herein with respect to Pioneer, and CT/SPECT images may also be adapted for use with CT/PET images. Various radiopharmaceuticals suitable for use with PET imaging are also described in section M "Imaging Agents", below.

Turning again to FIG. 11, as shown in FIG. 11, Pioneer is implemented as a cloud based service using Amazon Web Services, in which Simple Notification Service (SNS) and Simple Queue Service (SQS) messaging is used to handle requests. The Segmentation Service 1104 listens for requests on a dedicated SQS queue. Events that occur in Pioneer Web 1102 are published to a dedicated SNS topic "Pioneer Events" 1106. To allow for parallel asynchronous processing, a fanout pattern may be used, such that SNS messages are sent to a topic and then replicated and pushed to multiple Amazon SQS queues 1108a, 1108b, of which the Segmentation Service is a consumer.

The Segmentation Service 1104 may download input data (e.g., image data) from source Uniform Resource Locators (URLs) provided by the requester (e.g., Pioneer Web 1102) and that link to datasets in a local filesystem. In certain embodiments, the input data comprises a pre-processed 3D anatomical image, such as a CT image and a 3D functional image, such as a SPECT scan. Image metadata may also be included, along with the 3D anatomical and functional images.

In certain embodiments, CT and SPECT images have resolutions meeting particular requirements, established for the system. For example, CT images with resolutions ranging from 1.0 to 2.2 mm in x and y directions and between 1.0 and 5.0 mm in a z (slice) direction may be used. In certain embodiments, SPECT images with resolutions ranging from 2.9 to 4.8 mm in all directions are used.

Once Segmentation Service 1104 has performed image segmentation to identify a prostate volume and any additional tissue volumes in a particular CT image, as described herein, Segmentation Service 1104 provides segmentation output data that identifies the prostate volume within the particular CT image for storage and/or further processing (e.g., display in a GUI; e.g., computation of uptake metrics). In certain embodiments, a request issued to the Segmentation Service 1104 includes a target URL that specifies a storage location for the segmentation output data. Accordingly, the Segmentation Service 1104 may upload segmentation output data to the target URL included in the request.

The segmentation output data may include data such as a segmentation mask set, that identifies each voxel of the 3D anatomical image (e.g., CT image) as corresponding to a particular tissue region or as background, as determined by the second machine learning module described herein. The segmentation mask set may include, or be used to determine, for each particular tissue region, a corresponding segmentation mask that identifies voxels of the CT image classified as belonging to that particular tissue region. For example, a segmentation mask set may be stored in a .tiled.png format, with voxels labelled with different numerical labels identifying different particular tissue regions or background. An example set of labels for various tissue regions is shown below, with voxels identified as background labeled with 0:

```
{'prostate': 1,
'gluteus_maximus_left': 2,
'gluteus_maximus_right': 3,
'rectum': 4,
'urinary_bladder': 5,
'sacrum_and_coccyx': 6,
'hip_bone_left': 7,
'hip_bone_right': 8
}
```

In certain embodiments, the segmentation mask set identifies a prostate volume and a reference volume (e.g., a left gluteal muscle) and labels all other voxels as background.

In certain embodiments, segmentation mask metadata is also included in the segmentation output data. Segmentation mask metadata may be used to store information about the particular image(s) processed, such as a number of voxels in each direction (e.g., a number of rows, columns, and slices) and their spacing.

In certain embodiments, the Segmentation Service 1104 also performs quantification using results of the segmentation, such as identified prostate and reference volumes, and intensities of voxels of the 3D functional image (e.g., SPECT image). This quantification is discussed in more detail herein, for example, in the subsection below entitled, "Uptake metrics". For example, for use in computing a target to background ratio (TBR) value for the subject, as described herein, the Segmentation Service 1104 may identify a prostate maximum intensity voxel, along with a background value. The prostate maximum intensity voxel is a voxel identified as having a maximum intensity within a set of voxels of the 3D functional image corresponding to the identified prostate volume. In certain embodiments, as described herein, voxels of the 3D functional image corresponding to the identified prostate volume are corrected for cross-talk (also referred to as bleed) from a bladder of the subject, and the prostate maximum intensity voxel is identified following correction for bladder cross-talk. The background value used for determination of the TBR value is an average over intensities of a plurality of voxels of the 3D functional image that correspond to a reference volume, such as a volume corresponding to a left gluteal muscle of the subject, within the 3D anatomical image. As described herein, typically all voxels corresponding to the identified reference volume are used to compute the background value.

Data corresponding to the quantification performed by the Segmentation Service 1104 may be included in the segmentation output data. For example, quantification results may be included in a quantification result dictionary, as shown in the .json format example below:

```
{
"prostate_max": 988.0,
"prostate_max_pos": {
"z": 92,
"y": 74,
"x": 67
},
"background": 9.056859205776174,
}
```

Keys of the quantification result dictionary in the above example are as follows: "prostate_max" stores an intensity of the prostate maximum intensity voxel; "prostate_max_pos" stores a location of the prostate maximum intensity voxel in the SPECT image; and "background" stores the background value.

Figure 12:
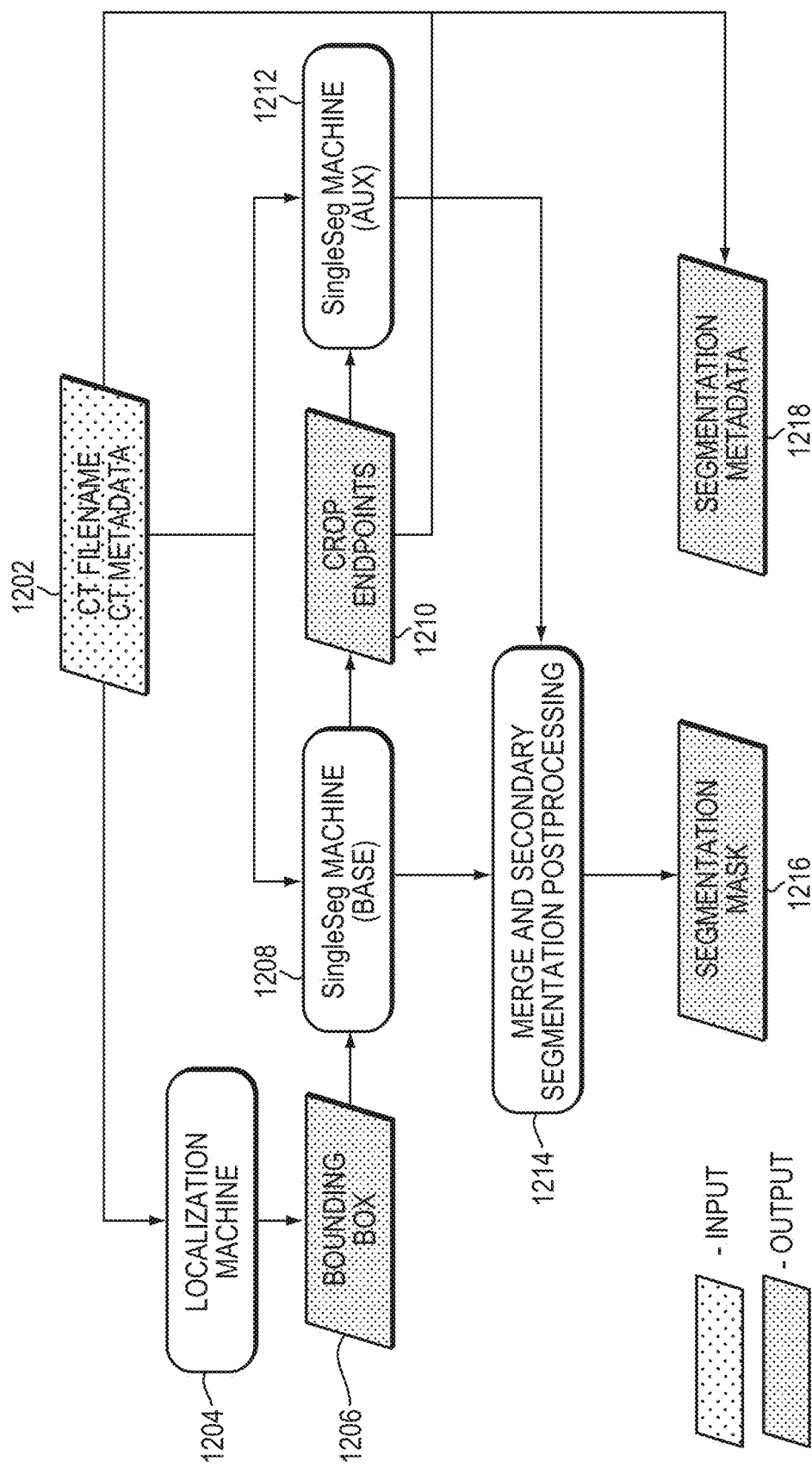
FIG. 12 is a block flow diagram showing an example architecture of modules for performing CNN-based image segmentation, according to an illustrative embodiment.

Example Segmentation Service Architecture Including CNN Module Organization and Interaction FIG. 12 shows an example architecture 1200 of modules for performing the CNN-based image segmentation as described herein. The example architecture 1200 includes a first machine learning module (referred in FIG. 12 as "Localization Machine") 1204 for identifying an initial VOI, and a second machine learning module (referred to as "SingleSegMachine (base)" in FIG. 12, short for "base Single Segmentation Machine") 1208 for identifying a prostate volume, additional tissue volumes, and a reference volume as described herein. Inputs and outputs of the first and second machine learning modules are also shown, along with several additional modules, including auxiliary machine learning modules (referred to as SingleSegMachine (aux) in FIG. 12, short for "auxiliary Single Segmentation Machine") 1212 and a module 1214 for merging outputs of the second machine learning module (base Single Segmentation Machine) and any auxiliary machine learning modules (auxiliary Single Segmentation Machines) and performing postprocessing. Outputs generated by the module organization shown in FIG. 12 include a segmentation mask set 1216 that identifies various tissue volumes in a 3D anatomical image (e.g., a CT image) and segmentation metadata 1218.

As described herein, the first machine learning module 1204 receives as input a CT image 1202 and produces a bounding box that identifies an initial VOI corresponding to a pelvic region of the subject. The second machine learning module 1208 receives, as input, the initial VOI along with the CT image 1202. The second machine learning module 1208 may add a crop margin to the initial VOI (e.g., add a margin about the initial bounding box to expand the bounding box) and provide the crop endpoints to auxiliary machine learning modules. As described herein, the second machine learning module 1208 identifies a prostate volume within the initial VOL The second machine learning module 1208 may also identify additional tissue volumes corresponding to additional tissue regions within the subject, such as a left gluteal muscle, a bladder, and left and right hip bones. A tissue volume corresponding to a left gluteal muscle of the subject may be used as a reference volume, for example to compute a background value in determining a TBR value for the subject, as described herein. A tissue volume corresponding to a bladder of the subject may be used for correcting intensity values of voxels of a SPECT image for bladder cross-talk, for example as described herein, in section B "Correcting for Bladder Intensity Bleed Through". Identified tissue volumes corresponding to a left and right hip bone of the subject may be used for postprocessing.

In certain embodiments, as described herein, performance may be improved by using, in addition to the second machine learning module 1208, one or more auxiliary machine learning modules 1212 that perform image segmentation in a similar fashion to the second machine learning module, identifying a prostate volume and additional tissue volumes (e.g., as shown in FIGS. 12, 1208 and 1212). These auxiliary tissue volumes, identified by the auxiliary machine learning modules, may be merged, via module 1214, with the base tissue volumes (the prostate volume and any additional tissue volumes) identified using the second machine learning module 1208.

In certain embodiments, the first and second machine learning modules, and any auxiliary machine learning modules, are implemented as trained CNN modules. Each trained CNN module may be represented (e.g., via computer code) as a directory that comprises an associated trained neural network with model structure and weights. Neural network libraries, such as Keras, can be used to represent trained CNN modules in this manner. The dictionary representing a particular CNN module may also include metadata that describes any preprocessing to be performed on an image before it is fed as input to the particular CNN module. Metadata describing how the neural network model was built and trained may also be included.

Accordingly, a particular CNN module may perform steps such as (1) loading and preprocessing an image, given an image file name and image metadata; (2) feeding the preprocessed image through the associated trained neural network (e.g., as included in the directory representing the particular CNN module) to obtain a raw prediction output (e.g., a map that includes, for each of one or more voxels of the CT image, a likelihood (e.g., probability) that that voxel belongs to a particular category as determined by a trained neural network); and (3) postprocess the raw prediction output. As described herein, the first machine learning module 1204 may postprocess the raw prediction output produced by its associated trained neural network to determine crop endpoints of a bounding box corresponding to an initial VOL The second machine learning module 1208 may postprocess the raw prediction output produced by its associated trained neural network to determine a segmentation mask set that labels voxels of the CT image with values (e.g., numerical values) that indicate a particular tissue volume to which they correspond or identify the voxels as background, as determined by the second machine learning module.

Figure 13:
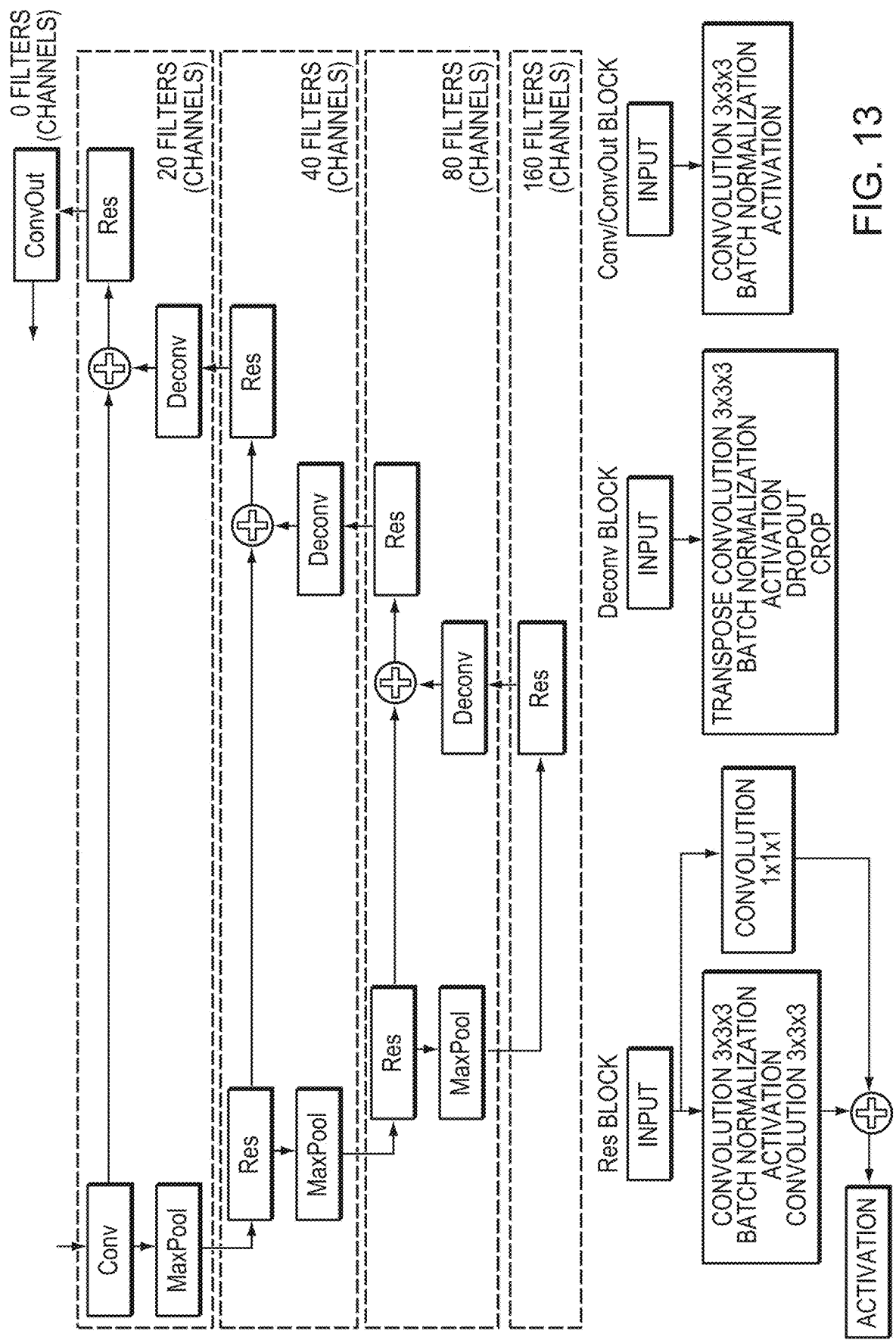
FIG. 13 is a block flow diagram showing a structure of a CNN, according to an illustrative embodiment.
Figure 14:
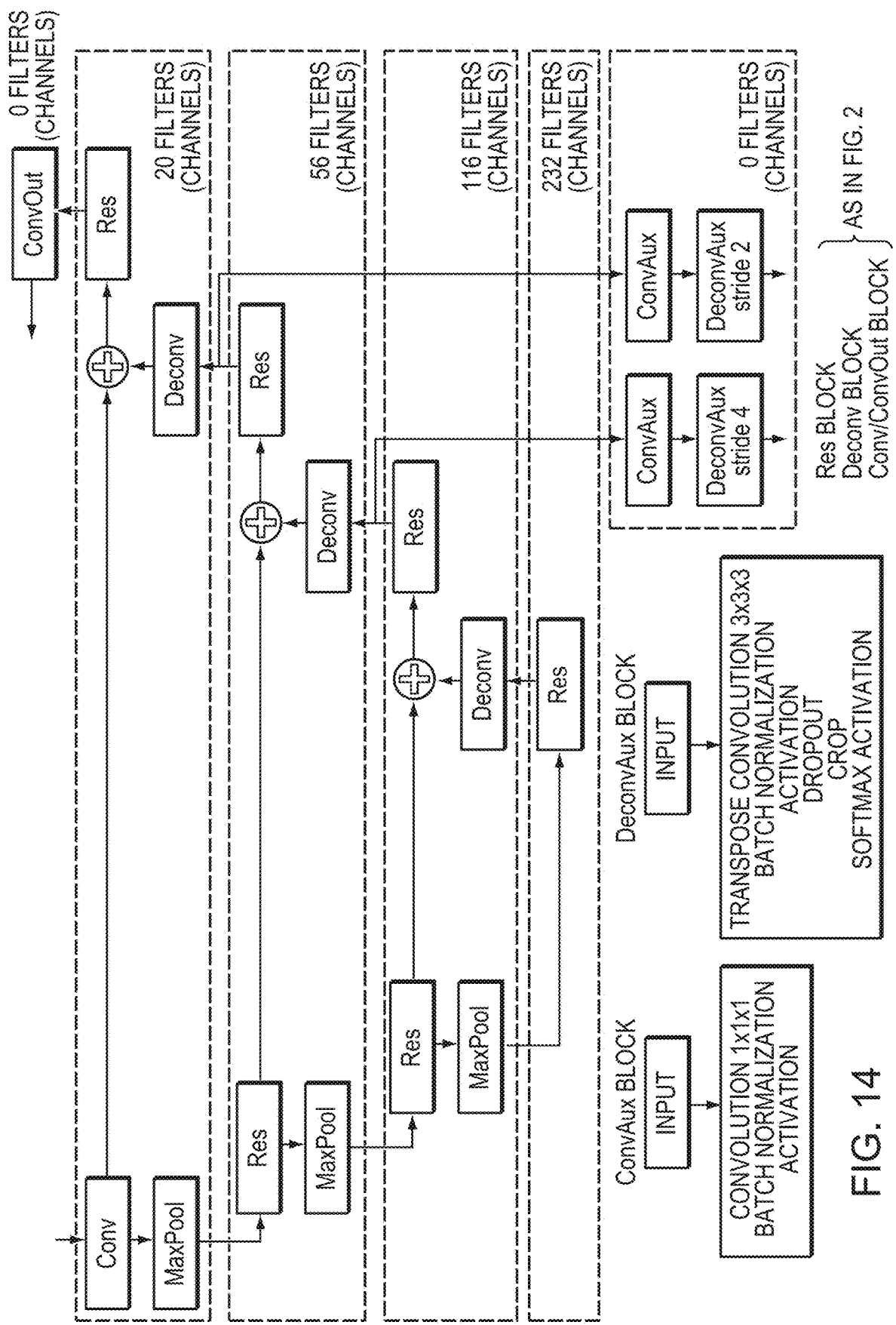
FIG. 14 is a block flow diagram showing a structure of a CNN that performs auxiliary predictions, according to an illustrative embodiment.

An example model structure of a CNN module implementation of the first machine learning module (Localization Machine in FIG. 12) 1204 is shown in FIG. 13. An example model structure of a CNN module implementation of the second machine learning module (Single Segmentation Machine in FIG. 12) 1208 is shown in FIG. 14.

Example first machine learning module (Localization Machine) Implementation

As described herein, the first machine learning module identifies an initial VOI—e.g., a "bounding box" that identifies a region of the CT image that corresponds to a pelvic region of the subject, which includes pelvic bones of the subject, along with tissue regions such as a prostate, a bladder, a rectum, and left and right gluteal muscles. An identification of the bounding box (e.g., crop endpoints) is provided to the second machine learning module, as well as any auxiliary machine learning modules, allowing them to limit their processing to a small, specific, target region of the CT image as opposed to having to operate on and process the entire CT image. This reduces the amount of data processed by these machine learning modules, which perform computationally intensive fine segmentation, thereby improving their performance and efficiency.

In an example implementation of the first machine learning module in accordance with approach 3 as described herein, Localization Machine 1204 in FIG. 12 extracts a bounding box (to identify the initial VOI) from a coarse segmentation of a CT image performed by its associated trained neural network (a CNN), referred to as a Localization CNN.

In certain embodiments, the CT image is preprocessed to prepare it for segmentation by the Localization CNN. A configuration file may be used to specify the preprocessing steps and parameters. The preprocessing may include steps such as cropping the CT image to remove one or more regions that correspond to surrounding air, normalizing intensities of voxels in the CT image, and resizing the CT image (e.g., to produce a resized CT image that conforms to a fixed input size expected by the Localization CNN). The intensity normalization preprocessing step adjusts intensities of voxels of the CT image to produce a particular mean and standard deviation of intensities over all voxels of the CT image. For example, voxel intensities of the CT image may be normalized by subtracting a first fixed value and then dividing by a second fixed value, to produce a CT image in which a mean intensity over all voxels is specific mean value (e.g., 0) and a standard deviation of intensities over all voxels is a specific standard deviation value (e.g., 1). The resizing step may be performed by sampling the CT image.

The Localization CNN receives the preprocessed CT image as input and passes it through a series of layers as shown in FIG. 13. The output of the Localization CNN is a coarse segmentation, e.g., represented via a first segmentation mask set, that classifies voxels of the preprocessed CT image as belonging to one of four categories, three representing particular tissue regions: (i) a sacrum and coccyx, (ii) a left hip bone, (iii) a right hip bone, and a fourth category, (iv) background (e.g., everything else). This coarse segmentation is obtained from a raw prediction map generated by the Localization CNN. The raw prediction map has a same shape—that is a same set of voxels as the preprocessed CT image received as input, but with four channels. Each channel corresponds to a particular classification category—(i) sacrum and coccyx, (ii) left hip bone, (iii) right hip bone, and (iv) background. Each channel represents a probability map for the classification category to which it corresponds. That is, each particular channel corresponding to a particular classification category includes, for each voxel of the preprocessed CT image, a likelihood value representing probability that the voxel belongs to that particular category (e.g., represents a physical volume inside the tissue region that the category represents, or represents background). Accordingly, for each voxel, a sum over the likelihood values for that voxel in each channel is 1.

To determine the first segmentation mask set that classifies each voxel as belonging to a particular category, each voxel of the preprocessed CT image is assigned to the category (e.g., tissue region or background) having a largest likelihood value (e.g., probability) for that voxel. The determined first segmentation mask set has a same shape as the preprocessed CT image, and labels each voxel with a value identifying the category that it is classified as belonging to. For example, a particular voxel may be labeled with a numerical value, such as 1, 2, or 3 corresponding to categories (i), (ii), and (iii) as described above, or a value 0 zero if it is classified as a background voxel.

A bounding box that identifies an initial VOI may be determined from the first segmentation mask set as a smallest box (e.g., rectangular volume) that comprises all voxels labeled as belonging to categories (i)-(iii). Coordinates identifying the bounding box (e.g., coordinates of opposite corners of a rectangular volume corresponding to the bounding box) are determined and output as crop endpoints. In certain embodiments, wherein the preprocessed CT image input to the Localization CNN is a resized version of the original CT image, the coordinates identifying the bounding box are transformed to a coordinate system of the original CT image and output as crop endpoints.

Example Second Machine Learning Module (Segmentation Machine) Implementation

In the example architecture of FIG. 12, a second machine learning module, also referred to as a base Single Segmentation Machine 1208 (SingleSegMachine (base) in FIG. 12) performs a high-resolution segmentation of a CT image to identify a prostate volume corresponding to a prostate of the subject, along with additional tissue volumes corresponding to specific tissue regions, such as left and right gluteal muscles, a rectum, a bladder, a sacrum and coccyx, and left and right hip bones.

In certain embodiments, the CT image is preprocessed to prepare it for segmentation by the second machine learning module. As with Localization Machine 1204, a configuration file may be used to specify preprocessing steps and parameters. Preprocessing steps may include normalizing intensities of the CT image, similar to the approach described above with respect to Localization Machine 1204. The CT image may also be cropped using the crop endpoints that identify the initial VOI (bounding box) and are output by the Localization Machine 1204, to produce a reduced, fixed size preprocessed CT image input for providing as input to a trained neural network (a trained CNN) associated with and implemented in Single Segmentation Machine 1208. Preprocessing may also include a resizing step.

Similar to the Localization CNN of the Localization Machine, the Single Segmentation Machine implements a trained CNN, referred to as a Segmentation CNN, that receives as input the preprocessed CT image. The Segmentation CNN passes the preprocessed CT image through a series of layers, and outputs a second raw prediction map. Similar to the raw prediction map produced by the Localization CNN, the second raw prediction map includes multiple channels, each corresponding to a different particular category into which each voxel of the input CT image is to be classified. Each channel represents a probability map for the classification category to which it corresponds and includes, for each voxel of the preprocessed CT image, a likelihood value corresponding to a probability (as determined by the Segmentation CNN) that the voxel belongs to that category.

As described above, the second raw prediction map output by the Segmentation CNN comprises a channel corresponding to a prostate of the subject. The second raw prediction map may include other channels, corresponding to various additional tissue regions, such as a left gluteal muscle, a right gluteal muscle, a rectum, a urinary bladder, a sacrum and coccyx, a left hip bone, and a right hip bone. The second raw prediction map may also include a background channel.

Certain variants of high-resolution segmentation CNN's give predictions from multiple levels of the network, resulting in multiple probability maps per category. These multiple probability maps are referred to as auxiliary predictions. The CNN model structure shown in FIG. 13 corresponds to a model structure that does not produce auxiliary predictions, and the CNN model structure shown in FIG. 14 is for a model that produces auxiliary predictions. In certain embodiments, while a number of filters in a top layer (e.g., 20 filters in FIGS. 13 and 28 filters in FIG. 14) may vary, a number of filters in subsequent, lower layers doubles each layer down. In certain embodiments, the Segmentation CNN produces a single probability map, and does not produce any auxiliary predictions. In certain embodiments, the Segmentation CNN produces auxiliary predictions.

In certain embodiments, when the Segmentation CNN produces auxiliary prediction map, likelihood values for each category as included in the second raw prediction map and each auxiliary probability map are averaged together, such that for a particular voxel, a single likelihood value for each category is determined.

In certain embodiments, to determine a second, fine segmentation mask set that classifies each voxel as belonging to a particular category, each voxel of the preprocessed CT image is assigned to the highest probability value. In certain embodiments, a number of labels in the fine segmentation mask set is reduced, such that only certain tissue volumes, such as a prostate volume and a reference volume (e.g., a left gluteal muscle volume) are included in the fine segmentation mask set.

Auxiliary Single Segmentation Machines

In certain embodiments, one or more auxiliary machine learning modules are used to produce auxiliary fine segmentation mask sets, similar to the fine segmentation mask set generated by the second machine learning module. These auxiliary fine segmentation mask sets identify a same set of tissue volumes as the fine segmentation mask set generated by the second machine learning module. In this manner, the second machine learning module generates a base fine segmentation mask set, and the one or more auxiliary machine learning modules each generate an auxiliary fine segmentation mask set, thereby providing a parallel set of classifications for voxels of the CT image.

In certain embodiments, for each category representing a particular tissue region, a corresponding base fine segmentation mask (e.g., that identifies a volume in the CT image determined via the base Single Segmentation Machine as corresponding to the particular tissue region) of or determined using the base fine segmentation mask set and one or more corresponding auxiliary fine segmentation masks (e.g., each identifying a volume of the CT image determined via an auxiliary Single Segmentation Machine as corresponding to the same particular tissue region) are merged, to produce a merged fine segmentation mask. For example, for a particular category, certain voxels in the one or more auxiliary fine segmentation masks may be identified (e.g., labeled) as belonging to the particular category, but not belong to a set of voxels in the base fine segmentation mask that are identified as belonging to the particular category. These voxels may be added (e.g., by labeling them as such) to the set of voxels identified as belonging to the particular category in the base fine segmentation mask to produce the final merged fine segmentation mask. For example, in the architecture shown in FIG. 12, base Single Segmentation Machine 1208 produces a base fine segmentation mask and one or more auxiliary Single Segmentation Machine(s) 1212 each produces an auxiliary segmentation mask. The base fine segmentation mask produced by base Single Segmentation Machine 1208 is merged with the one or more auxiliary fine segmentation masks produced by the auxiliary Single Segmentation Machine(s) 1212 by module 1214 to produce a final fine segmentation mask set 1216 comprising a final fine segmentation mask for each category.

In certain embodiments, one or more of the final fine segmentation masks are filtered such that only a largest connected part is retained. In certain embodiments, when filtering to retain only a largest connected component of a prostate segmentation mask (e.g., a final fine segmentation mask that identifies a volume of the CT image corresponding to a prostate of the subject) is performed, a subset of connected components of the prostate segmentation mask is considered. The subset comprises only components that (i) have a center of mass lying in between the hip bones' centers of mass in a left-right direction of an axial plane (x direction) and (ii) lie within a bounding box defined so that the left and right hip bones are just contained.

iv. Uptake Metrics

Referring to step 110 of process 100 in FIG. 1, one or more uptake metrics are determined, from which diagnosis or staging of a condition (e.g., prostate cancer) may be informed or automatically rendered. The one or more uptake metrics are determined using the 3D functional image and the prostate volume identified within the VOI of the 3D anatomical image. For example, a quantity of radiopharmaceutical in the prostate of the subject may be computed based on intensity values of voxels of the 3D functional image that correspond to the prostate volume identified within the VOI of the 3D anatomical image. This may involve computing a sum (e.g., a weighted sum), an average, and/or a maximum of intensities of voxels of the 3D functional image representing a physical volume occupied by the prostate of the subject. In certain embodiments, this involves computing a normalization value based on intensity values of voxels of the 3D functional image that correspond to a reference volume identified within the 3D anatomical image. For example, the normalization value for intensities identified in the prostate may be normalized using intensity values of one or more voxels that correspond to the gluteal muscles, or another reference volume within the VOI (or, in certain embodiments, elsewhere within the 3D anatomical image). The uptake metrics, then, can be converted to an identification of whether or not the subject has prostate cancer and/or a quantification of risk that the subject has prostate cancer, and/or a staging of the disease (e.g., as part of disease tracking over time), which may be used by the medical practitioner in advising treatment options, and/or monitoring efficacy of administered therapy, for example.

Target to Background Ratio

In certain embodiments, one or more uptake metrics determined include(s) a target to background ratio (TBR) value for the subject. Determining the TBR value comprises determining (i) a target intensity value using intensity values of one or more voxels of the 3D functional image (e.g., PET or SPECT image) that correspond to the prostate volume identified within the initial VOI of the 3D anatomical image (e.g., CT image), and (ii) determining a background intensity value using intensity values of one or more voxels of the 3D functional image that correspond to an identified reference volume. The TBR value is computed as a ratio of the target intensity value to the background intensity value.

In particular, in certain embodiments, the target intensity value is a maximum of intensities of the voxels of the 3D functional image (e.g., PET or SPECT image) that correspond to the identified prostate volume. As described above, a prostate maximum intensity voxel corresponding to a voxel identified as having a maximum intensity within a set of voxels of the 3D functional image corresponding to the identified prostate volume. The target value may then be taken as the intensity of the prostate maximum intensity voxel. The background intensity value may be computed as an average over intensities of a plurality of voxels of the 3D functional image that correspond to the identified reference volume. As described herein, a gluteal muscle, such as a left gluteal muscle, or a portion thereof, may be used as the identified reference volume.

For example, TBR values may be computed from a SPECT/CT image for a subject recorded following administration of a radiopharmaceutical such as 1404 to the subject. The SPECT image corresponds to the 3D functional image and the CT image corresponds to the anatomical image. The image segmentation approaches described herein may be used to identify, within the CT image, a prostate volume along with a reference volume corresponding to a left gluteal muscle of the subject. A prostate segmentation mask and a left gluteal muscle segmentation mask may be used to identify the prostate volume and the left gluteal reference volume, respectively.

The prostate volume segmentation mask identifies voxels of the CT image that are classified as belonging to a prostate of the subject via the machine learning segmentation approaches described herein. In certain embodiments, in order to identify voxels of the SPECT image that correspond to the identified prostate volume within the CT image, voxels of the prostate segmentation mask are mapped to corresponding voxels of the SPECT image. Since the prostate segmentation mask identifies voxels in the CT image, it may have a different resolution from the SPECT image (e.g., since the SPECT and CT images may have different resolutions). Interpolation (e.g., bilinear interpolation) and/or sampling may be used to match a resolution of the prostate segmentation mask to the resolution of the SPECT image, such that each voxel of the prostate segmentation mask maps to a particular corresponding voxel of the SPECT image. In this manner, a SPECT prostate mask that identifies voxels in the SPECT image that correspond to the prostate volume identified within the CT image is obtained. A SPECT left gluteal muscle mask that identifies those voxels in the SPECT image that correspond to the identified left gluteal muscle reference volume in the CT image may be obtained in a similar fashion.

The SPECT left gluteal muscle mask may be used to determine the background intensity value. In particular, intensities of voxels in the SPECT image identified by the SPECT left gluteal muscle mask are extracted and partitioned into quartiles. The background value is computed as a mean over the extracted left gluteal muscle voxel intensities that fall within a first and third quartile. Other approaches for computing a background value, such as computing an overall mean or a median over all extracted left gluteal muscle voxel intensities, may also be used. The above described approach of partitioning the extracted left gluteal muscle voxel intensities into quartiles, was found to be more stable against outliers than computing an overall mean and more precise than a median (e.g., since the intensities are discretized and many of them have a same value). The determined background intensity value may be output and stored in a result dictionary, e.g., under a key 'background'.

The target intensity value may be computed using the SPECT prostate mask. A prostate maximum intensity voxel may be identified as a voxel of the SPECT prostate mask and having a maximal SPECT image intensity. The target intensity value is determined as the intensity of the prostate maximum intensity voxel. Both the target value intensity value and a location of the prostate maximum intensity voxel may be stored. For example, a result dictionary may store the target intensity value and the prostate maximum intensity voxel location under keys such as "prostate_max" and "prostate_max_position", respectively. In certain embodiments, intensities of voxels of the SPECT image corresponding to the identified prostate volume are corrected for bladder "cross-talk" or "bleed" as described in section B below, prior to determining the target intensity value, such that, for example, the maximum intensity stored is a maximum corrected intensity and the prostate maximum intensity voxel is a voxel of the SPECT prostate mask having a maximum corrected intensity.

In certain embodiments, a prostate cancer status for a subject may be determined by comparing a determined TBR value for the subject with one or more threshold values. In particular, a determined TBR value may be compared with a particular threshold value (e.g., a cutoff threshold) to distinguish between patients who have clinically significant prostate cancer (e.g., assigned a status of clinically significant) from those who do not (e.g., assigned a status of clinically non-significant). Example 4 below shows an example approach for determining a TBR threshold value based on TBR values computed from reference images, in order to obtain a desired sensitivity and specificity.

B. Correcting for Bladder Intensity Bleed Through

Figure 15:
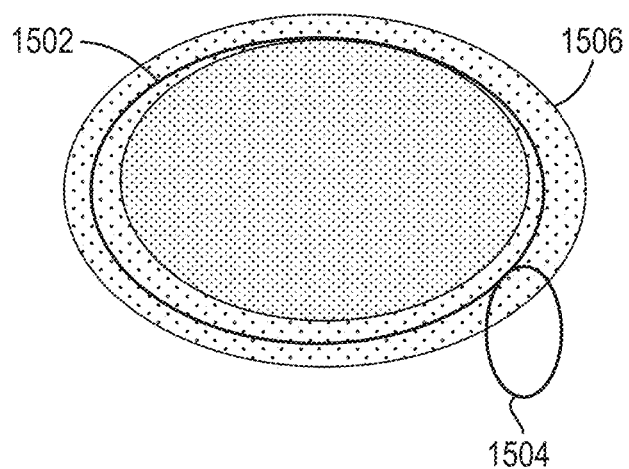
FIG. 15 is a schematic illustrating cross-talk between a bladder and a prostate of a subject, according to an illustrative embodiment.
Figure 17A:
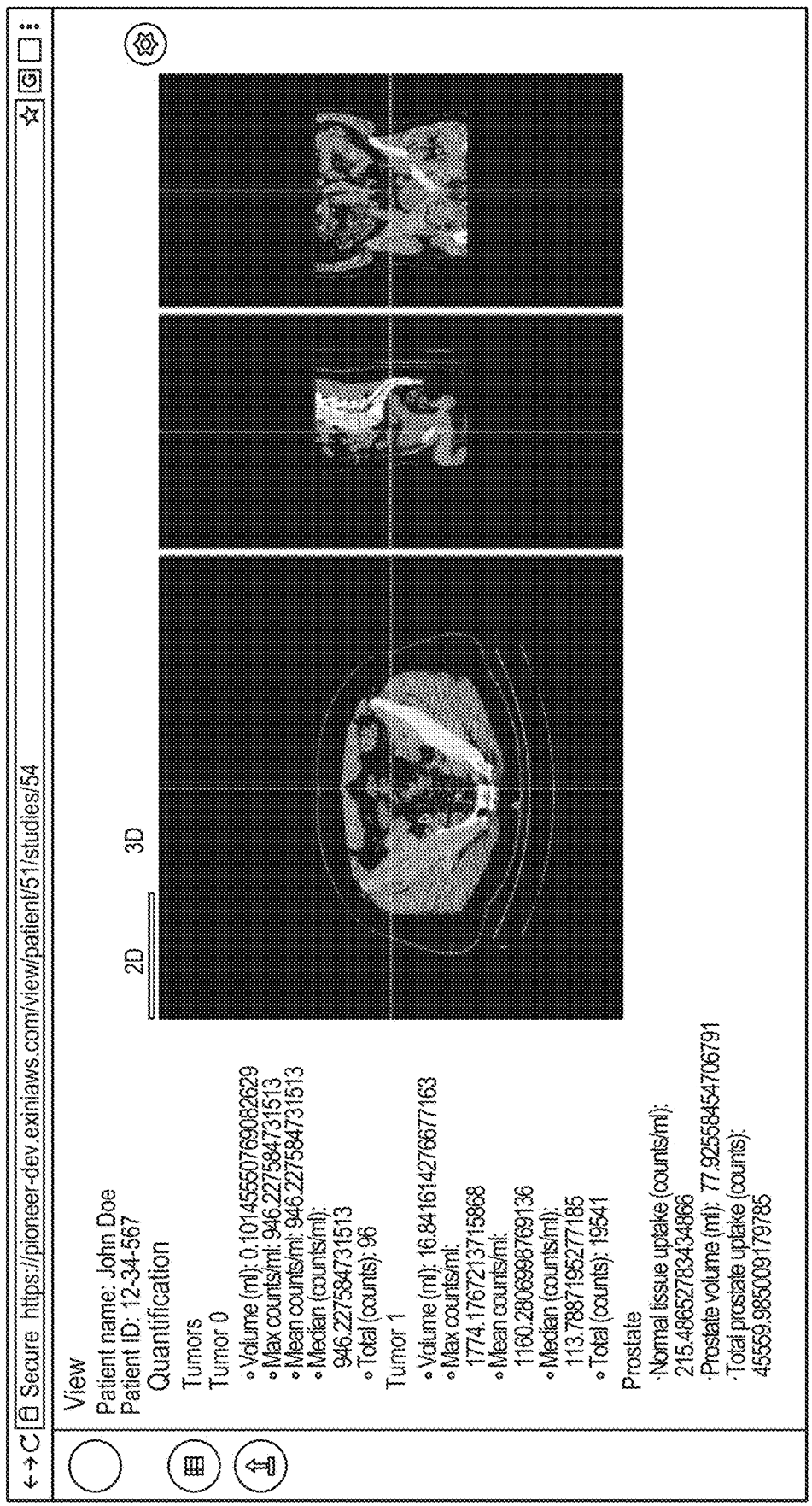
FIG. 17A is a screenshot of a GUI for reviewing patient image data showing a window comprising a set of images each showing a different 2D cross sectional view of a CT image of a subject overlaid with a SPECT image of the subject and graphics representing identified tissue volumes, according to an illustrative embodiment.
Figure 17B:
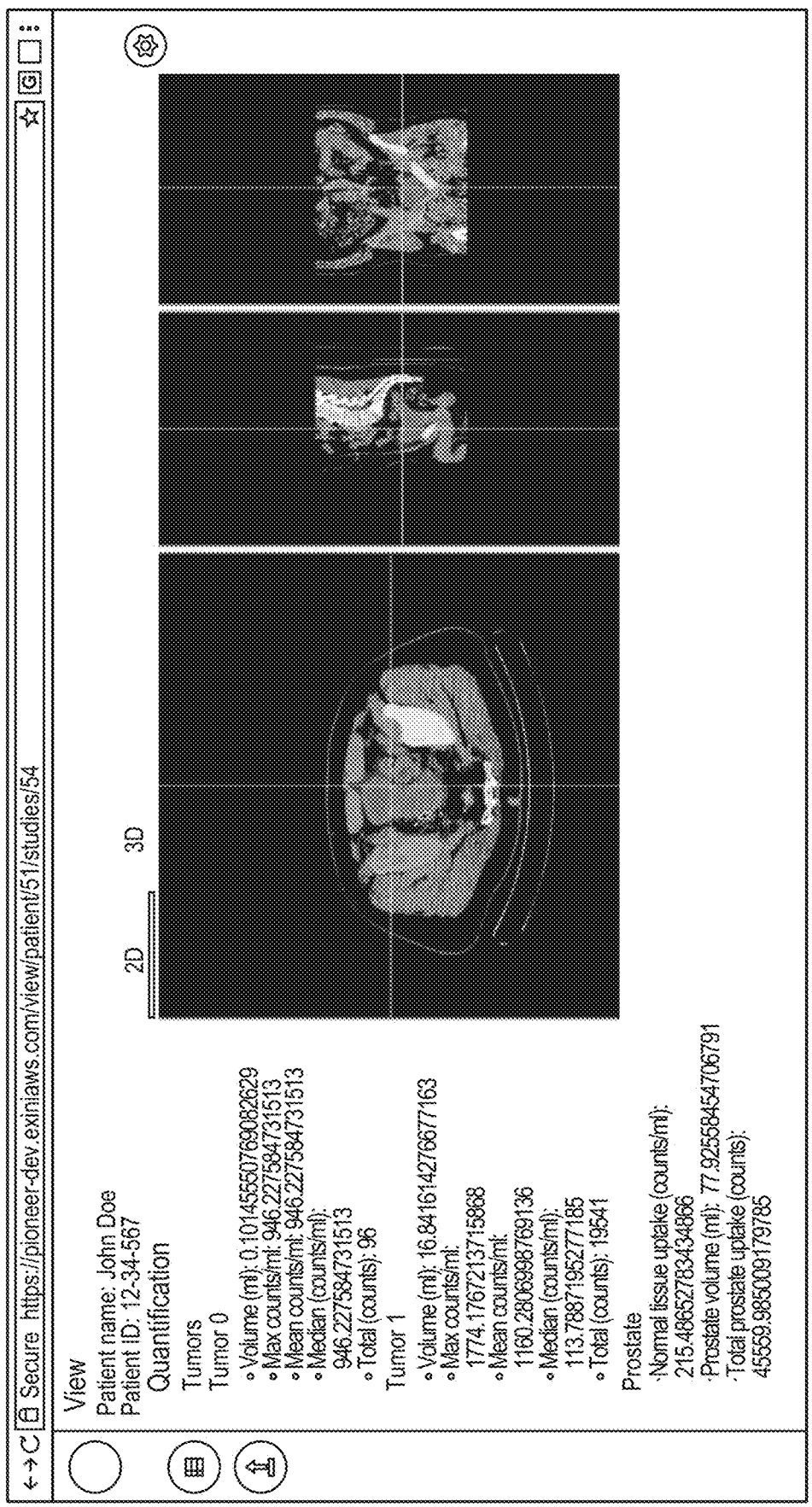
FIG. 17B is a screenshot of a GUI for reviewing patient image data showing a window comprising a set of images each showing a different 2D cross sectional view of a CT image of a subject overlaid with a SPECT image of the subject and graphics representing identified tissue volumes, according to an illustrative embodiment.
Figure 17C:
FIG. 17C is a screenshot of a GUI for reviewing patient image data showing a window comprising a set of images each showing a different 2D cross sectional view of a CT image of a subject overlaid with a SPECT image of the subject and graphics representing identified tissue volumes, according to an illustrative embodiment.
Figure 17D:
FIG. 17D is a screenshot of a GUI for reviewing patient image data showing a window comprising a set of images each showing a different 2D cross sectional view of a CT image of a subject overlaid with a SPECT image of the subject and graphics representing identified tissue volumes, according to an illustrative embodiment.
Figure 17E:
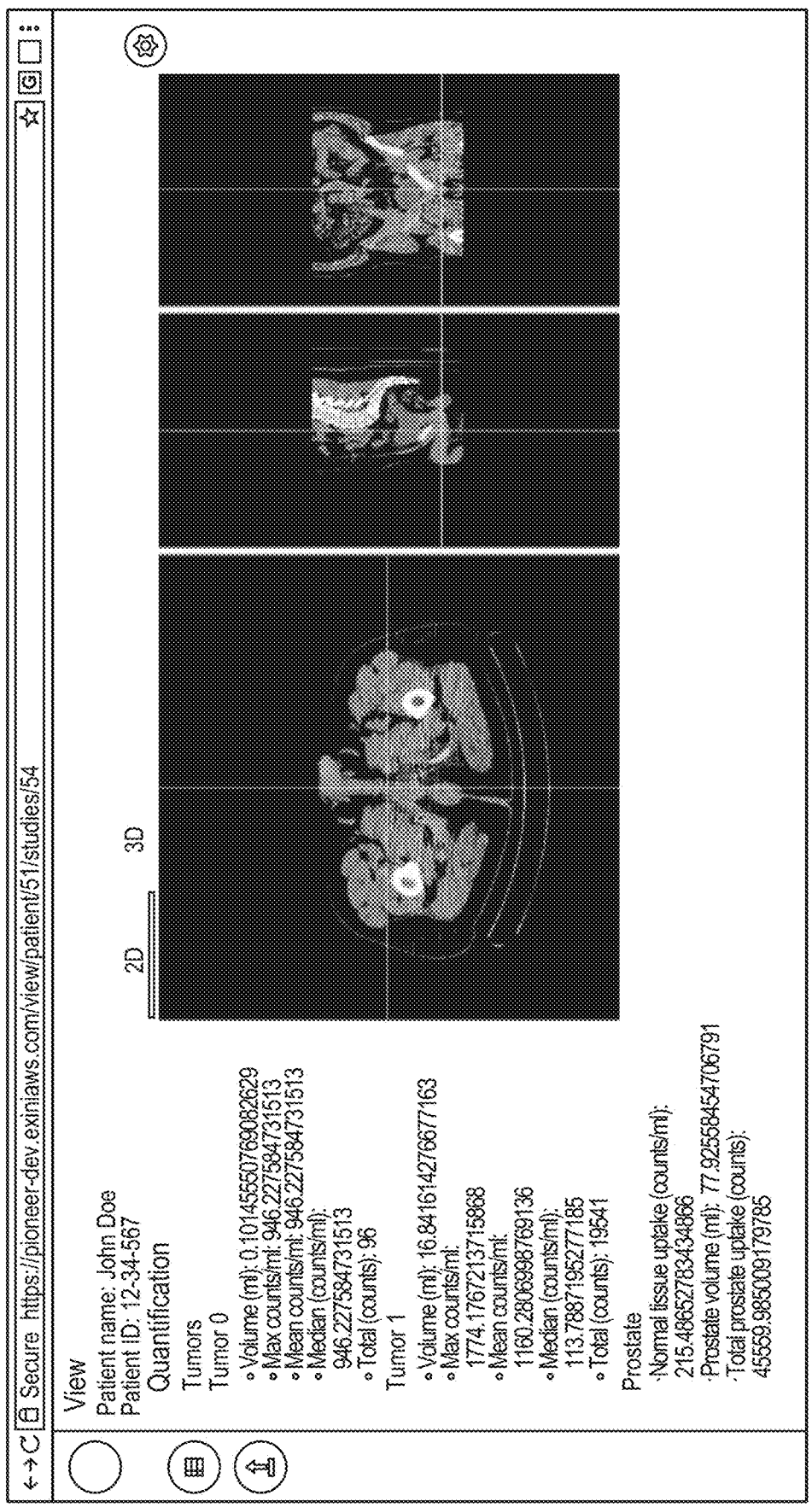
FIG. 17E is a screenshot of a GUI for reviewing patient image data showing a window comprising a set of images each showing a different 2D cross sectional view of a CT image of a subject overlaid with a SPECT image of the subject and graphics representing identified tissue volumes, according to an illustrative embodiment.

FIG. 15. is a schematic illustrating cross-talk of imaging agent intensity from a bladder to a prostate of a subject. In the figure, reference 1502 is a bladder, 1506 is the cross-talk/intensity that bleeds from the bladder, and 1504 is the prostate. Certain imaging agents comprising a PSMA binding agent have high uptake in the bladder, which may affect the identification of diseased tissue (e.g., prostate cancer). For example, uptake of a radionuclide labelled PSMA binding agent by the bladder may result in scattering in the 3D functional image, and may reduce accuracy of the measured imaging agent intensity in the prostate, which is located near the bladder. By training a second CNN for detailed segmentation of both the prostate and the bladder of a subject, it is possible to accurately, automatically account for a 'bleed through' or 'cross-talk' effect and/or other effects caused by uptake of the imaging agent by the bladder. Furthermore, by training the second CNN for identification of a reference region in the 3D anatomical image, e.g., the gluteal muscles, it is possible to more accurately weight/normalize imaging agent intensity measurements and improve the accuracy and diagnostic value of the uptake measurements in the prostate of the subject.

i. Bladder Dilation

In certain embodiments, bladder cross-talk correction includes a step wherein an identified bladder volume is dilated (e.g., via morphological dilation) with two iterations. This dilation may be used to prohibit high intensities very close to the segmented urinary bladder to be used for determination of a target intensity value in computing a TBR value (e.g., selected as a maximal intensity), and also to stabilize a bladder suppression approach described below.

ii. Bladder Suppression Computation

In certain embodiments, a bladder suppression method is used to remove intensity bleed from the bladder to other regions of the functional image. An amount of suppression, that is, intensity bleed to remove from a particular voxel of the functional image is dependent on a distance from that voxel to a core bladder region, corresponding to a region of the bladder having high intensity voxels.

In certain embodiments, bladder suppression is made if a maximum functional image intensity within a volume of the functional image identified as corresponding to a bladder (e.g., corresponding to a bladder volume identified within a 3D anatomical image; e.g. as identified via a urinary bladder mask) is more than a specific multiplier value times a determined background intensity value. As described herein, a background intensity value may be determined based on intensities of voxels of the 3D functional image corresponding to a reference volume identified within the 3D anatomical image, for example a gluteal muscle volume. For example, bladder suppression may be performed if a maximum functional image intensity within a region corresponding to the identified bladder volume is 15 times a determined background value (e.g., the bladder-to-background ratio should be at least 15).

In certain embodiments, bladder suppression is computed from and applied to a portion of the 3D functional image that lies within a bladder suppression bounding box of a specific size about the identified bladder volume. For example, a bladder suppression bounding box that contains the urinary bladder with a margin of a predetermined size in a particular direction (e.g., 40 mm in the vertical direction) and is a same number of voxels in the other directions may be determined.

For example, after masking out a region of the 3D functional image corresponding the prostate, the core bladder region may be determined as a region of the 3D functional image within the bladder suppression bounding box comprising voxels having intensities within a specific fraction of a maximum intensity within the bounding box (e.g., not including voxels of the masked out prostate region). For example, the core bladder region may be determined as the region comprising voxels having intensities greater than or equal to 50% of the maximum intensity within the bladder suppression bounding box. The core bladder region may include high-intensity regions that were not included in the original bladder mask.

In certain embodiments, one or more bladder intensity bleed functions are determined to perform bladder suppression and thereby correct intensities of voxels of the 3D functional image for bladder cross-talk. For example, the 3D functional image may be cropped using the bladder suppression bounding box and a determined background intensity value subtracted from intensities of voxels within the cropped image region. Sample intensities are then collected to determine how bladder intensity (e.g., intensity originating from radiopharmaceutical uptake within a bladder of the subject) decreases as one moves away from the bladder. The samples are collected starting at an extreme top, an extreme front, an extreme right and an extreme left of the core bladder region and then moving straight up, forward, right or left respectively, one voxel at a time. If an edge of the cropped image region is encountered, extrapolated intensities may be used as samples, for example linear extrapolation from a previous two or more samples.

The intensity samples provide four curves of intensity (e.g., sets of sampled intensity data points) decrease from the bladder core, to each of which a template function may be fit to establish four bladder intensity bleed functions that model bladder intensity variation as a function of distance from the core bladder region. Before further analysis, such as fitting, outlier removal may be performed, for example to remove the curve farthest away from the others. A template function such as an n-th degree polynomial (e.g., a $5^{th}$ degree polynomial) is fitted to the data points in the remaining three curves, resulting in a function modelling the bladder intensity bleed as a function of the distance to the core bladder. This bladder intensity bleed function describes how much should be subtracted from the original intensities to obtain corrected intensities, depending on the distance to the core bladder region.

In certain embodiments, to decrease a risk that the bladder intensity bleed function underestimates bleed in the direction of the bladder (the bleed might vary to some extent between different directions), before fitting to the sampled intensity data points, the distances are multiplied with an expansion factor (e.g., ranging from 1 to 2; e.g., 1.2), so that the fit bladder intensity bleed function is stretched out. Risk of underestimating bladder intensity bleed may also be reduced by multiplying the sampled intensity data points by a scaling factor. The scaling factor may be variable scaling factor having a value that depends on the bladder-to-background intensity ratio. For example, a scaling factor that has a particular value when the bladder to background ratio is sufficiently high and increases (e.g., linearly) with lower bladder-to-background ratios may be used. For example, the sample intensities may be multiplied with a factor that is 1.2 when the bladder-to background ratio is sufficiently high and for lower bladder-to-background ratios increases linearly from 0 for a bladder-to-background ratio of 15. This approach of multiplying the sampled intensity data points with a scaling factor also improves robustness of the bladder suppression approach.

In certain embodiments, a reach of bladder suppression, that is, a farthest distance from the bladder where it is applied, is based on where the decay rate of the function is sufficiently small. If the decay rate never gets sufficiently small then the distance is chosen as a length of the intensity sample vectors. In certain embodiments, it is ensured that bladder suppression at all distances is non-negative.

Once determined, the bladder intensity bleed function may be evaluated at locations of various voxels of the 3D functional image, for example at voxel locations corresponding to locations within the prostate of the subject, to determine a bladder intensity bleed value for each particular voxel location. Accordingly, an intensity of a particular voxel may be corrected for bladder cross-talk by subtracting, from the intensity of the particular voxel, a determined bladder intensity bleed value at a location of the particular voxel. Intensities of voxels at various locations within the 3D functional image, for example at locations corresponding to an identified prostate volume (e.g., identified within a 3D anatomical image), may be corrected for bladder cross-talk in this manner.

iii. Corrected Prostate Maximal Intensity and Location

In certain embodiments, the bladder suppression approach described herein is used to correct intensity values of voxels of the 3D functional image that correspond a prostate volume identified within the 3D anatomical image, and uptake metrics, such as a TBR value, are determined using the corrected intensity values.

C. Visualizing Image Data and Computed Uptake Metrics

Figure 16A:
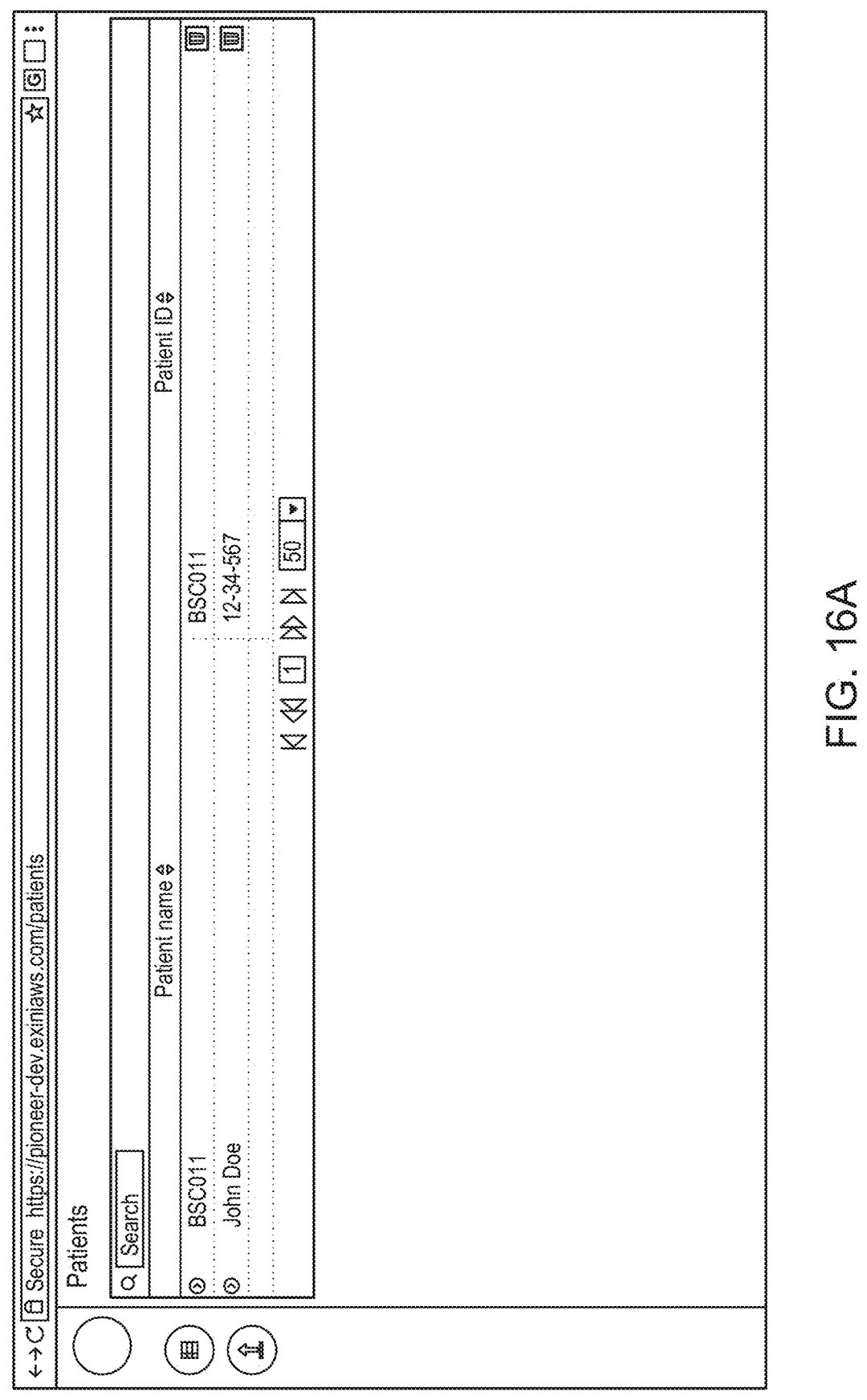

FIG. 16A shows a window of the GUI interface with two subjects (patients) listed. The user can select a desired subject to process and view their image data.

Figure 16B:
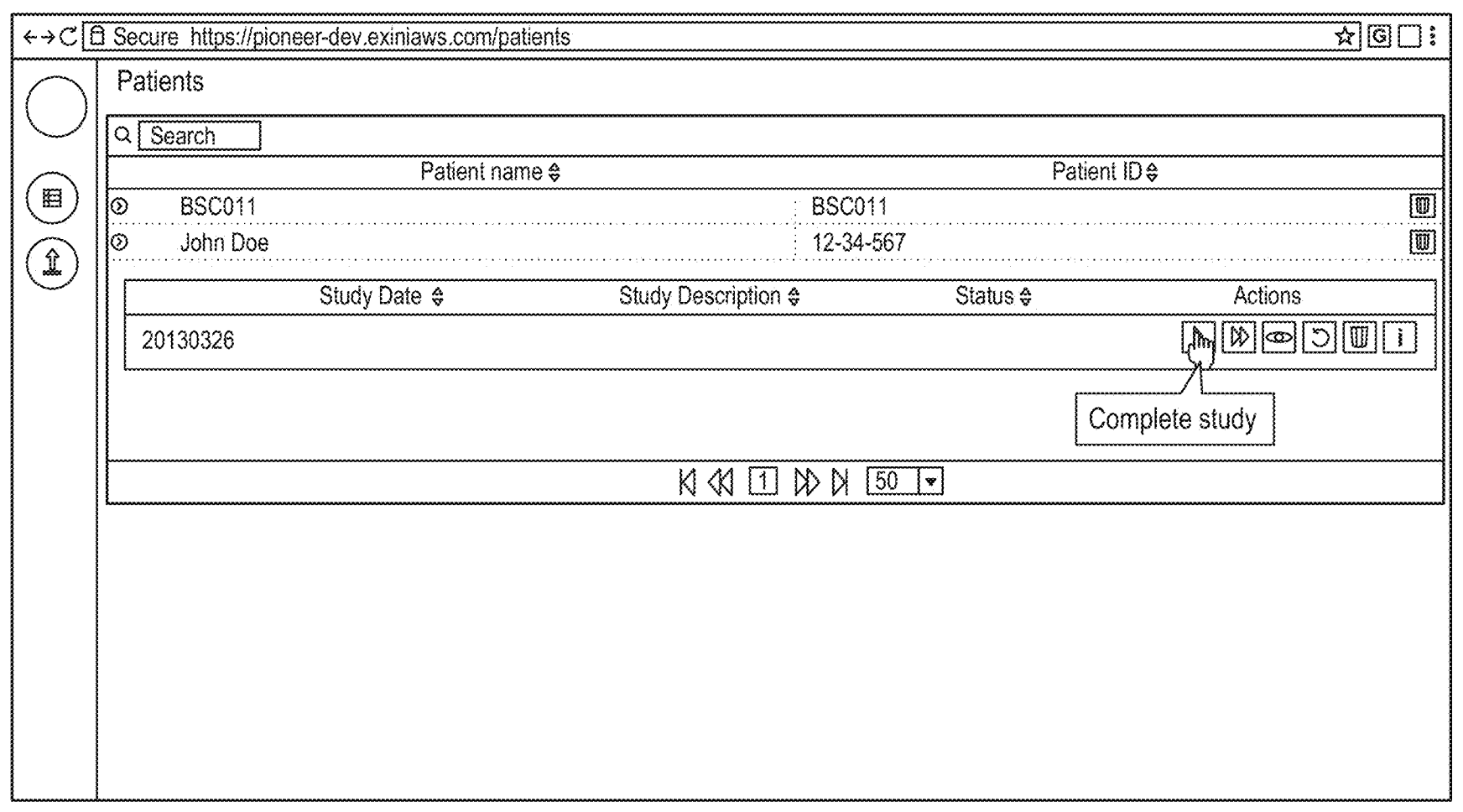

FIG. 16B shows an exemplary GUI with graphical control elements for processing and navigating subject data, which appears after the user selected the subject "John Doe". The user clicks a selectable button element to complete processing of image data for the selected subject.

Figure 16C:
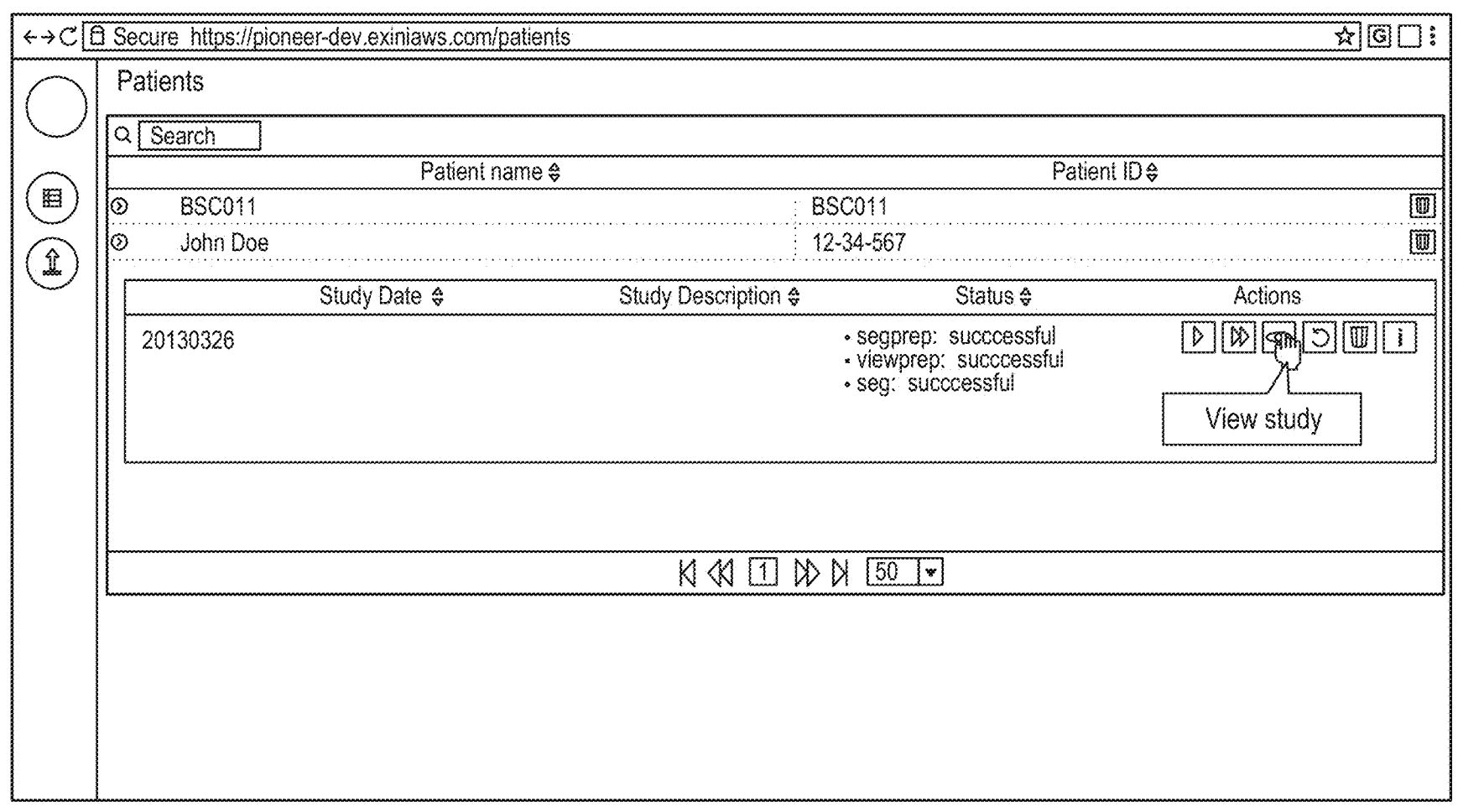

In FIG. 16C, after processing of the selected subject's image data is complete, the user clicks another selectable button to view the processed image data and computed uptake metrics.

In FIGS. 17A-17E a 2D viewer is displayed. FIGS. 17A-17E show a set of 2D cross-sectional views of CT image data overlaid with the SPECT image as well as graphics representing identified tissue volumes—specifically, a prostate and pelvic bones. The user can scan through the cross sectional slices as shown in the figures.

Figure 18A:
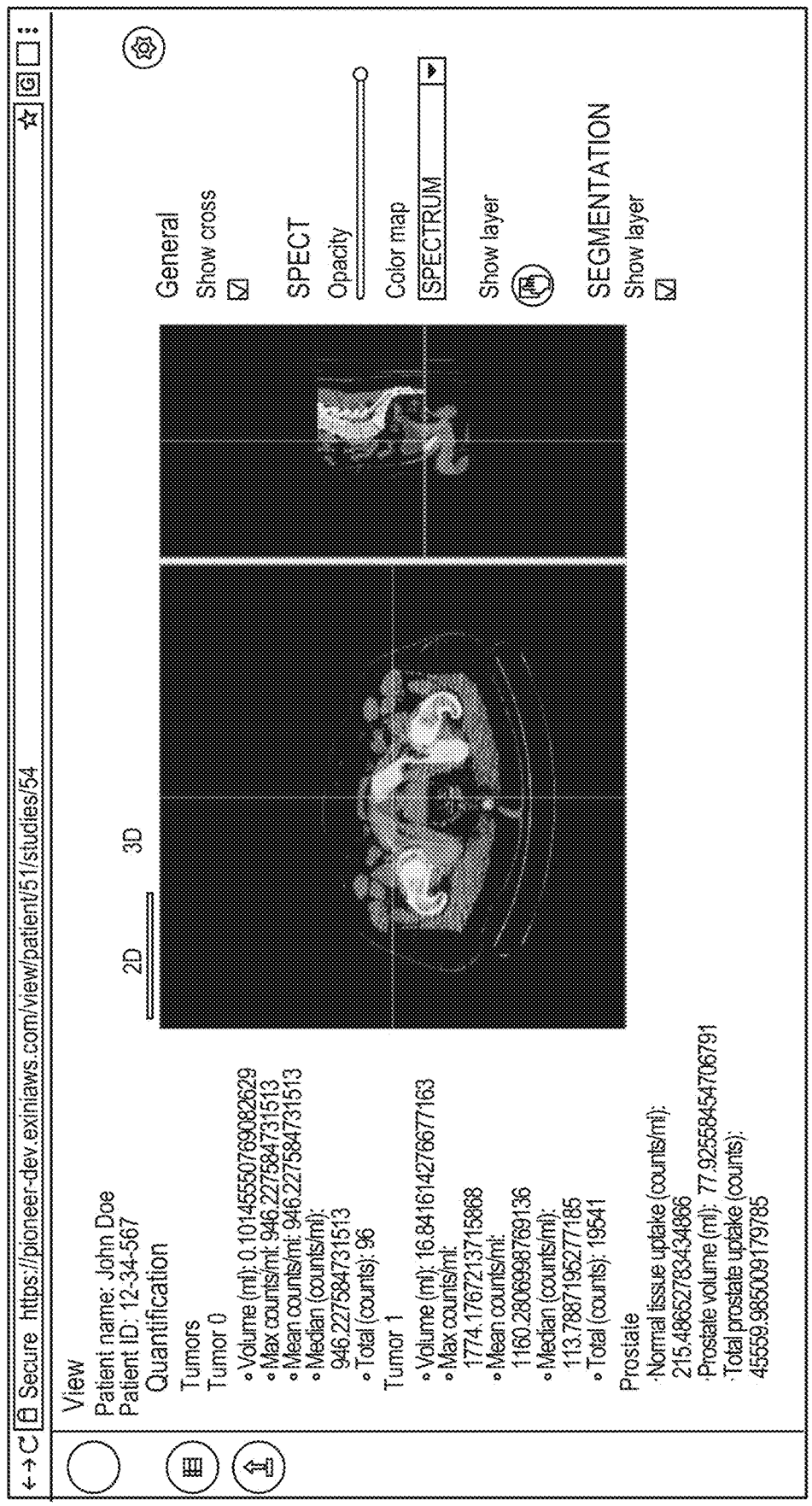
FIG. 18A is a screenshot of a GUI for reviewing patient image data showing a window comprising a graphical control element for toggling display of selectable layers illustrating a user toggling of a SPECT image layer off, according to an illustrative embodiment.
Figure 18B:
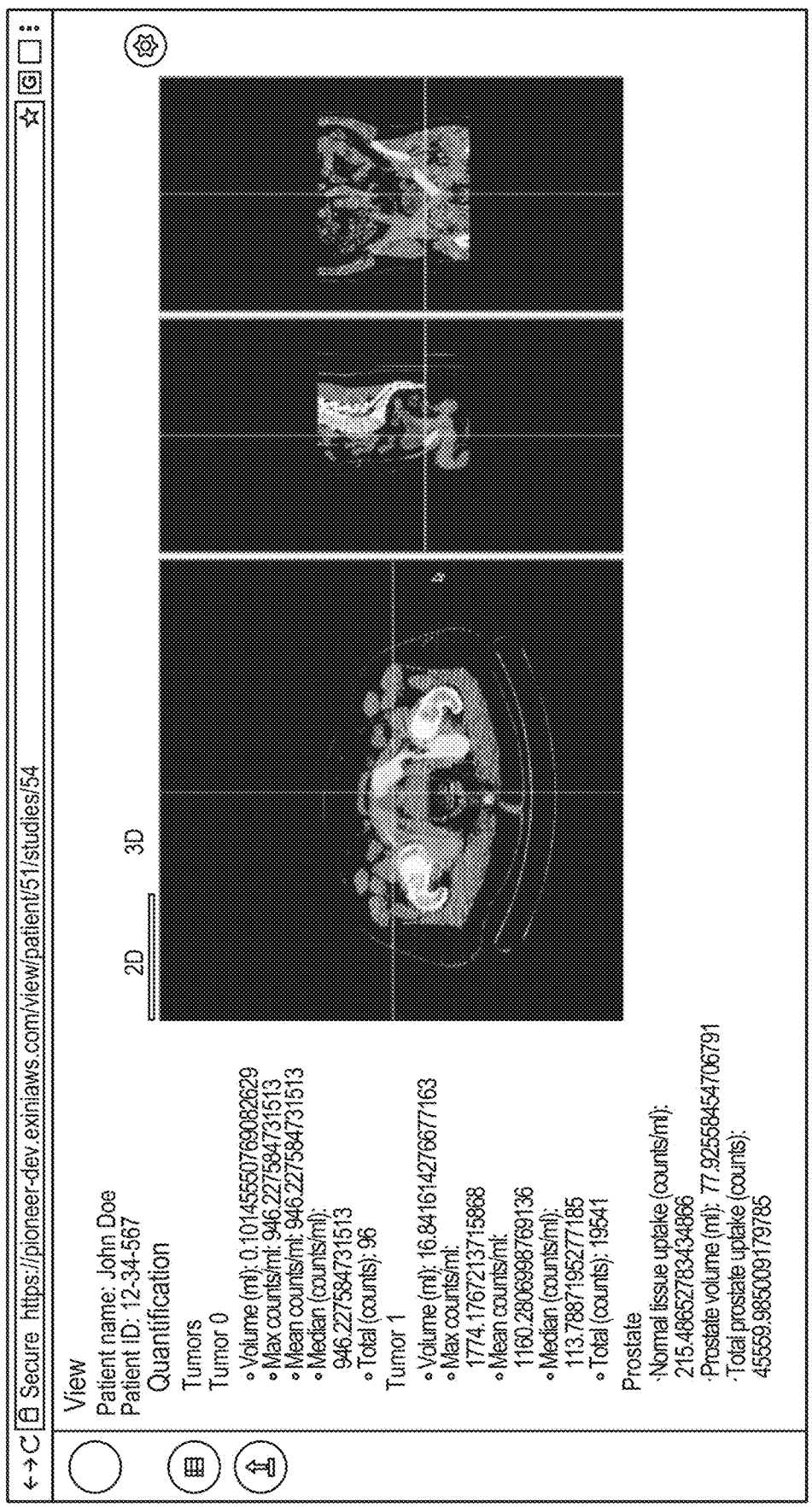
FIG. 18B is a screenshot of a GUI for reviewing patient image data showing a window comprising a set of images each showing a different 2D cross sectional view of a CT image of a subject overlaid with graphics representing identified tissue volumes, according to an illustrative embodiment.
Figure 18C:
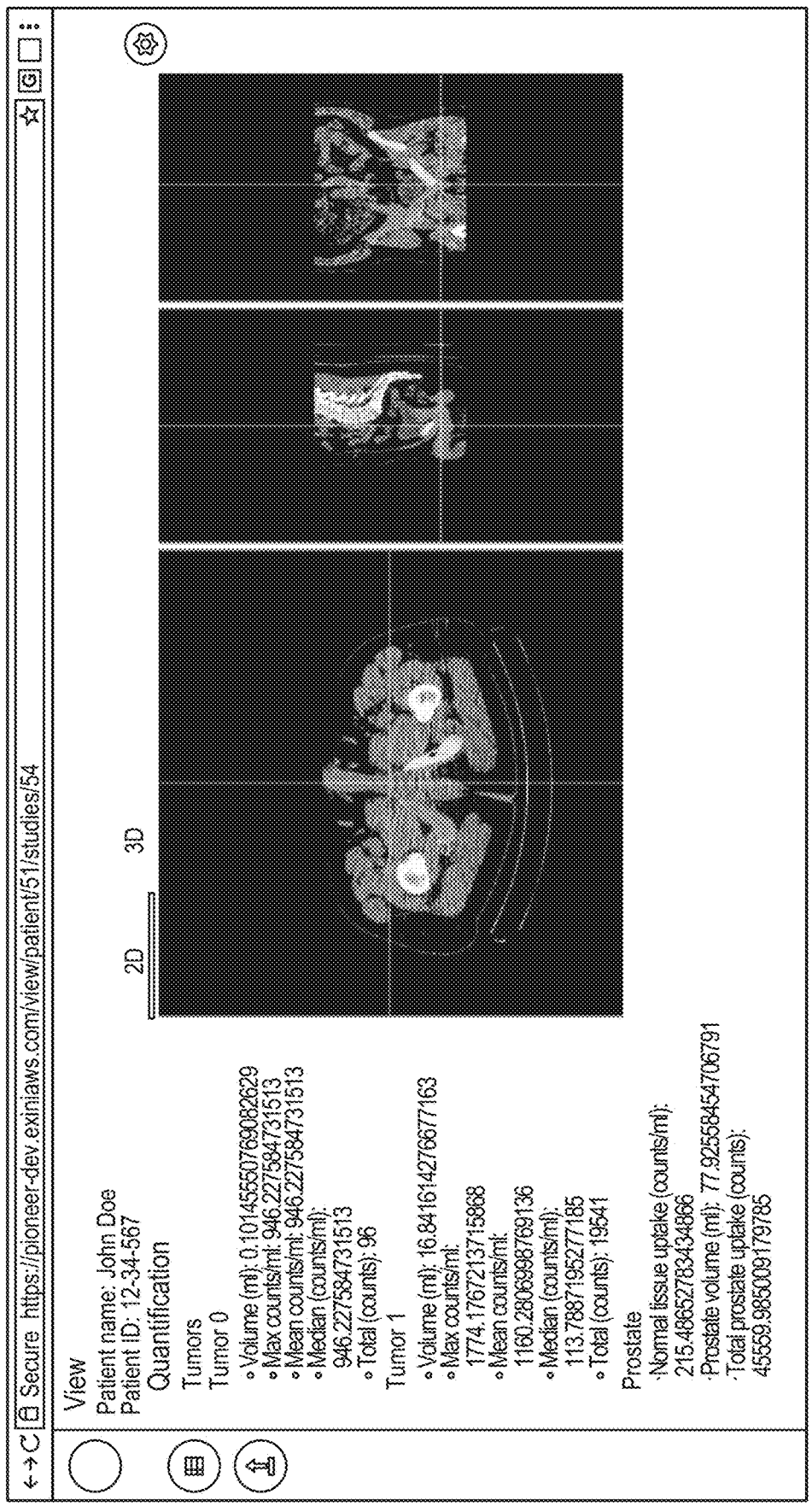
FIG. 18C is a screenshot of a GUI for reviewing patient image data showing a window comprising a set of images each showing a different 2D cross sectional view of a CT image of a subject overlaid with graphics representing identified tissue volumes, according to an illustrative embodiment.
Figure 18D:
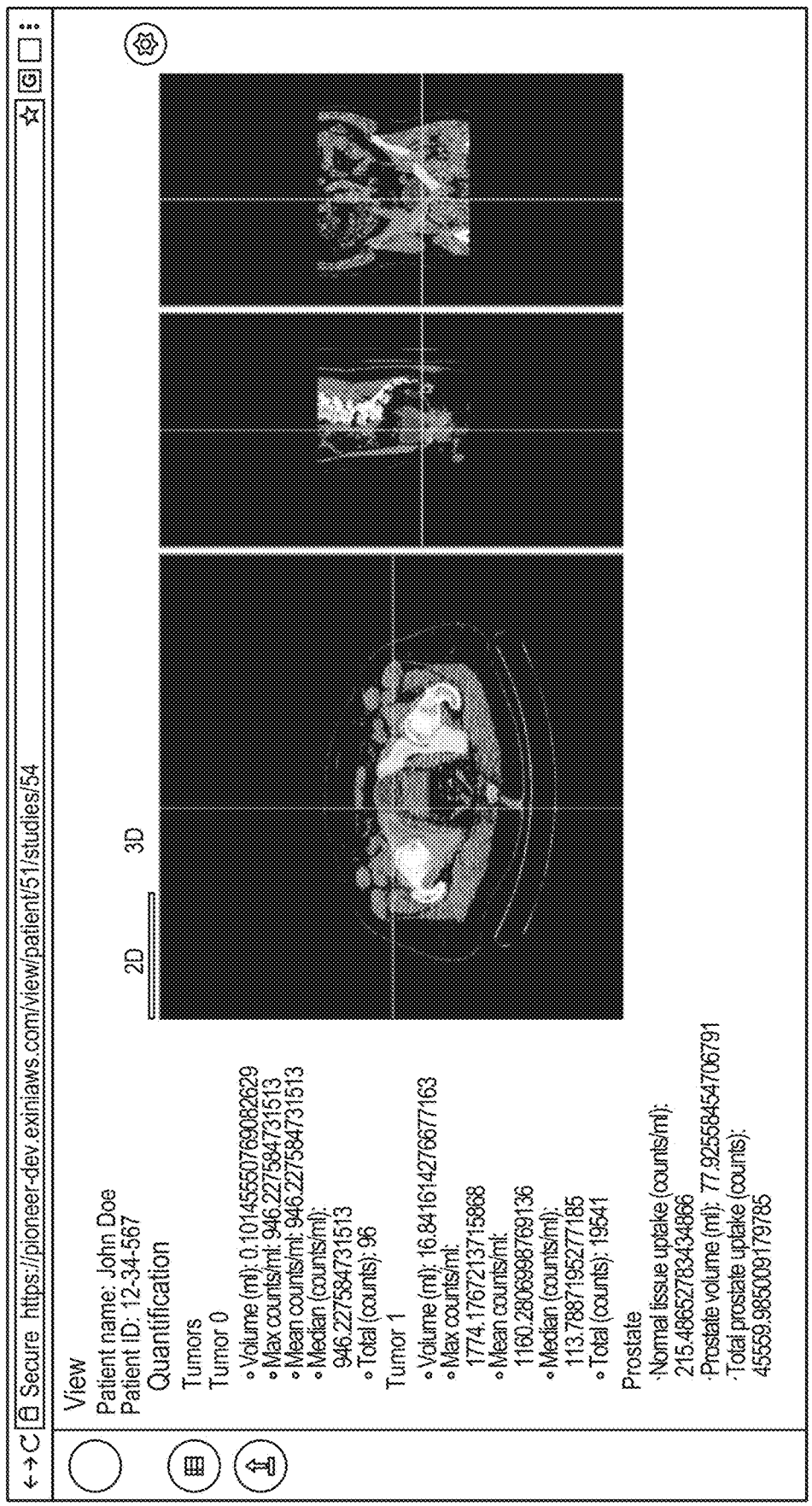
FIG. 18D is a screenshot of a GUI for reviewing patient image data showing a window comprising a set of images each showing a different 2D cross sectional view of a CT image of a subject overlaid with graphics representing identified tissue volumes, according to an illustrative embodiment.
Figure 18E:
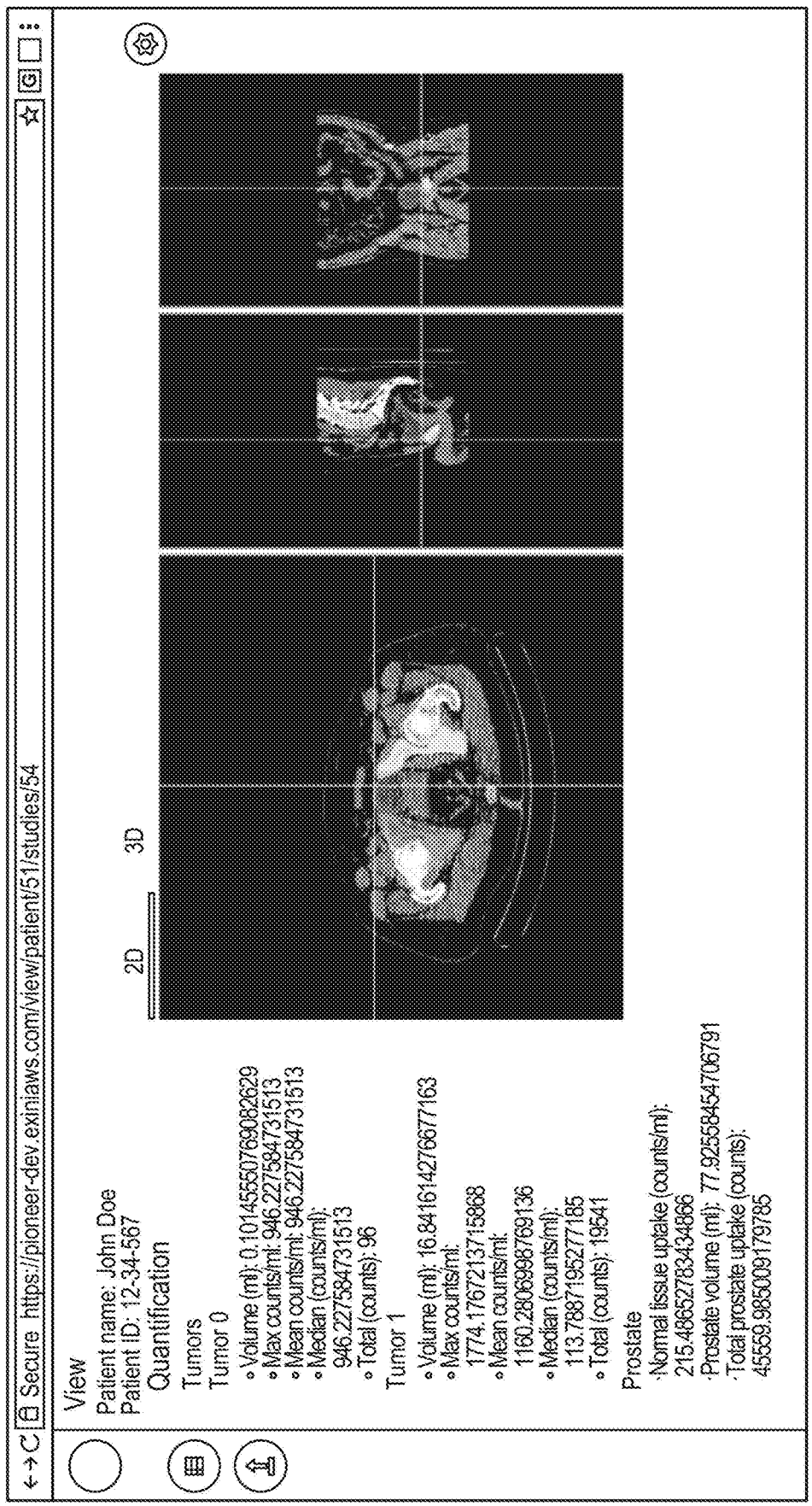
FIG. 18E is a screenshot of a GUI for reviewing patient image data showing a window comprising a set of images each showing a different 2D cross sectional view of a CT image of a subject overlaid with graphics representing identified tissue volumes, according to an illustrative embodiment.
Figure 18F:
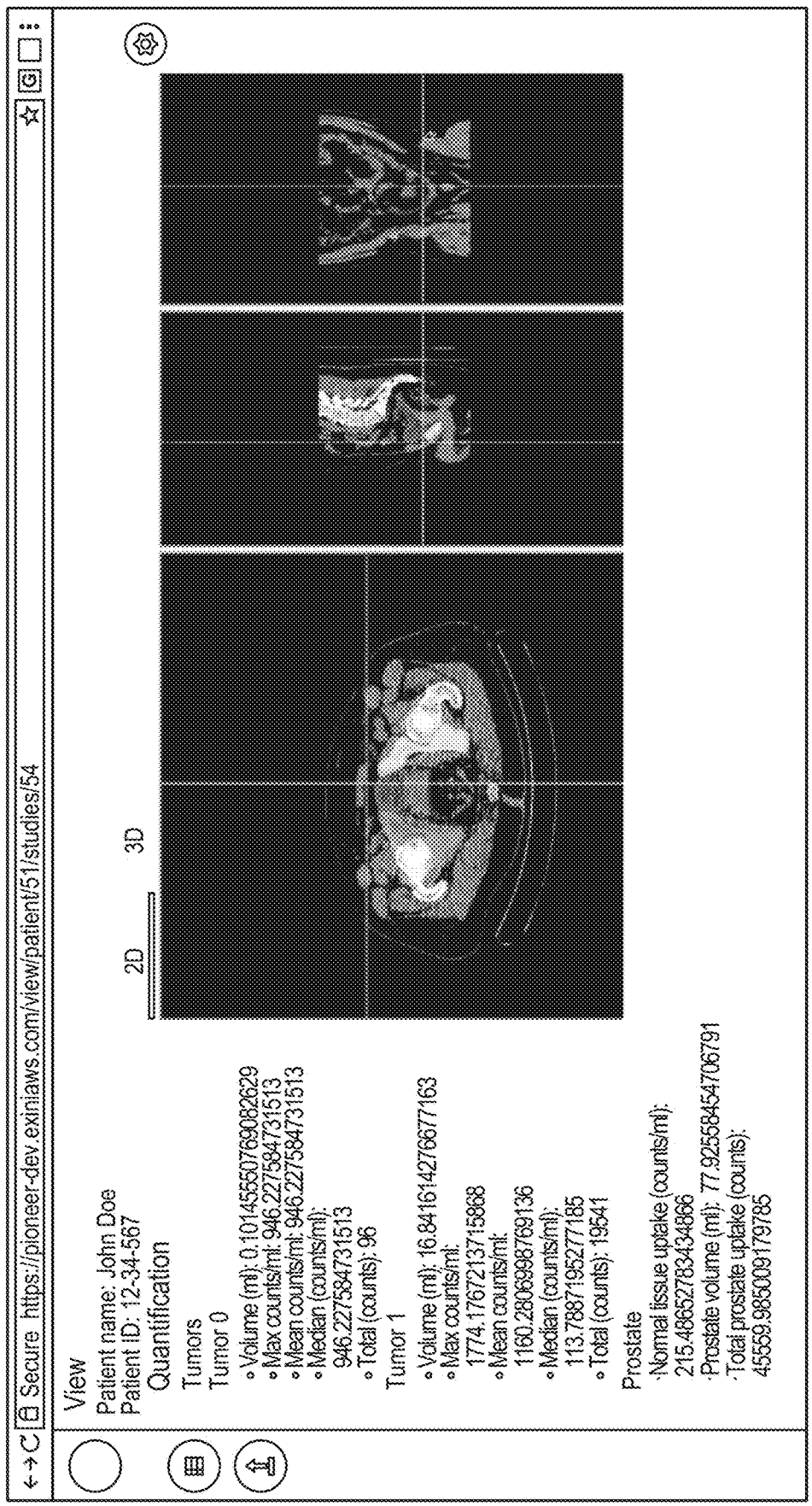
FIG. 18F is a screenshot of a GUI for reviewing patient image data showing a window comprising a set of images each showing a different 2D cross sectional view of a CT image of a subject overlaid with graphics representing identified tissue volumes, according to an illustrative embodiment.

The CT image and SPECT image are rendered as selectable layers which can be toggled on and off. The graphics representing identified tissue volumes are also rendered as a selectable segmentation layer. In FIG. 18A the user toggles display of the SPECT image layer off, such that only the CT image and segmentation layers are displayed. In FIGS. 18B-18F the user scans through the cross sections.

Figure 19A:
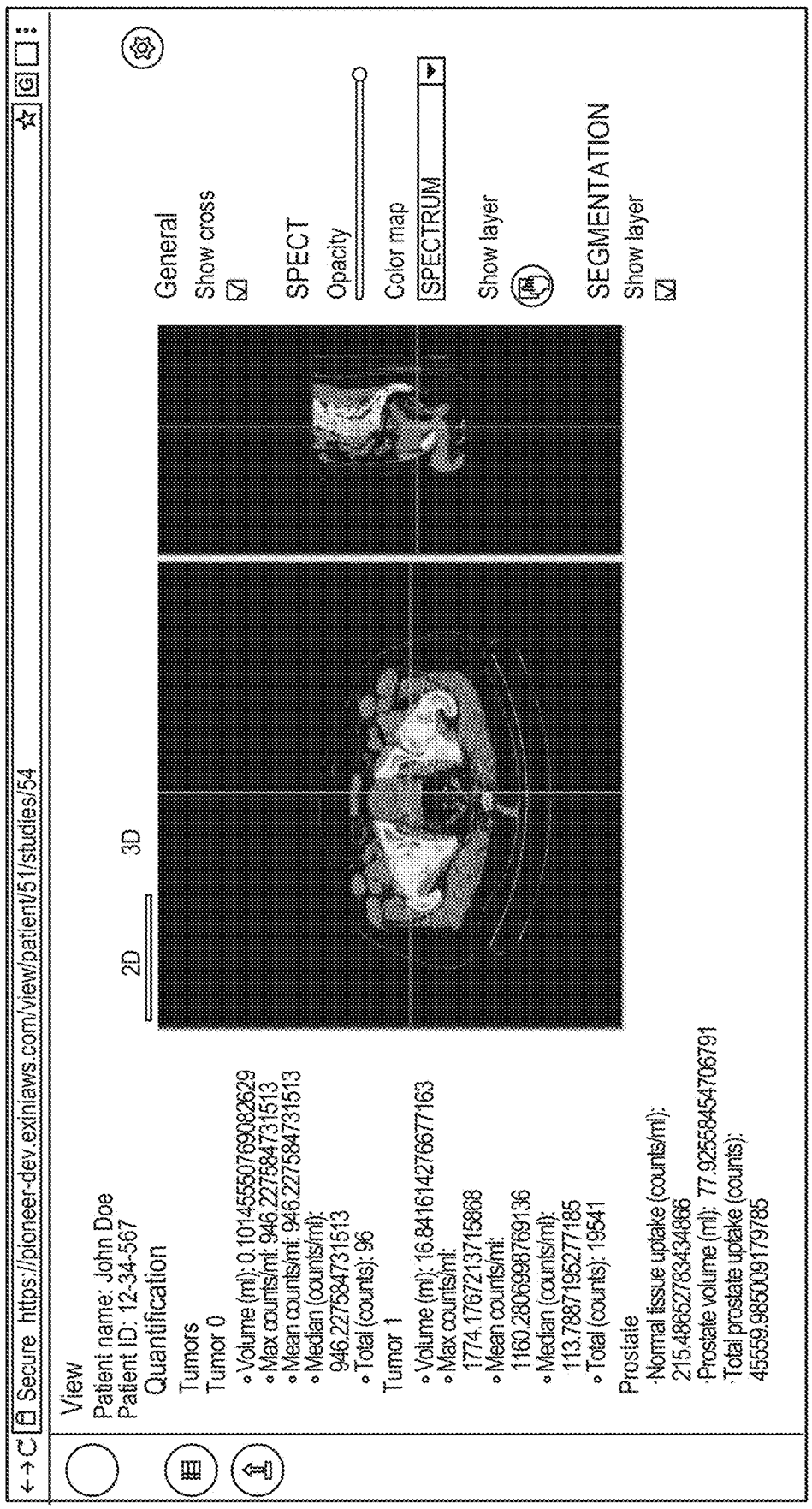
FIG. 19A is a screenshot of a GUI for reviewing patient image data showing a window comprising a graphical control element for toggling display of selectable layers illustrating a user toggling of a SPECT image layer and a segmentation layer on and off, respectively, according to an illustrative embodiment.
Figure 19B:
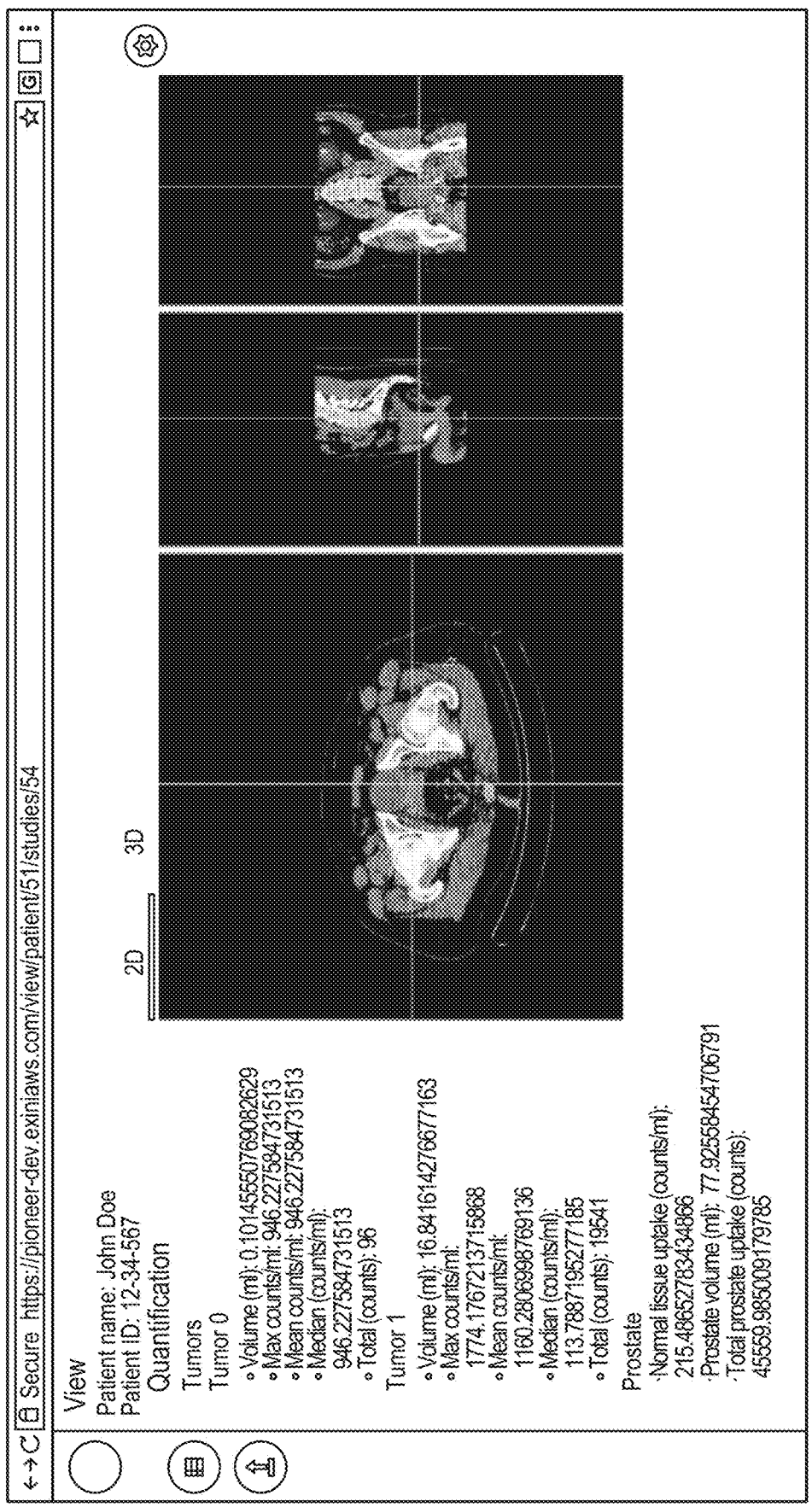
FIG. 19B is a screenshot of a GUI for reviewing patient image data showing a window comprising a set of images each showing a different 2D cross sectional view of a CT image of a subject overlaid with a SPECT image of the subject, according to an illustrative embodiment.
Figure 19C:
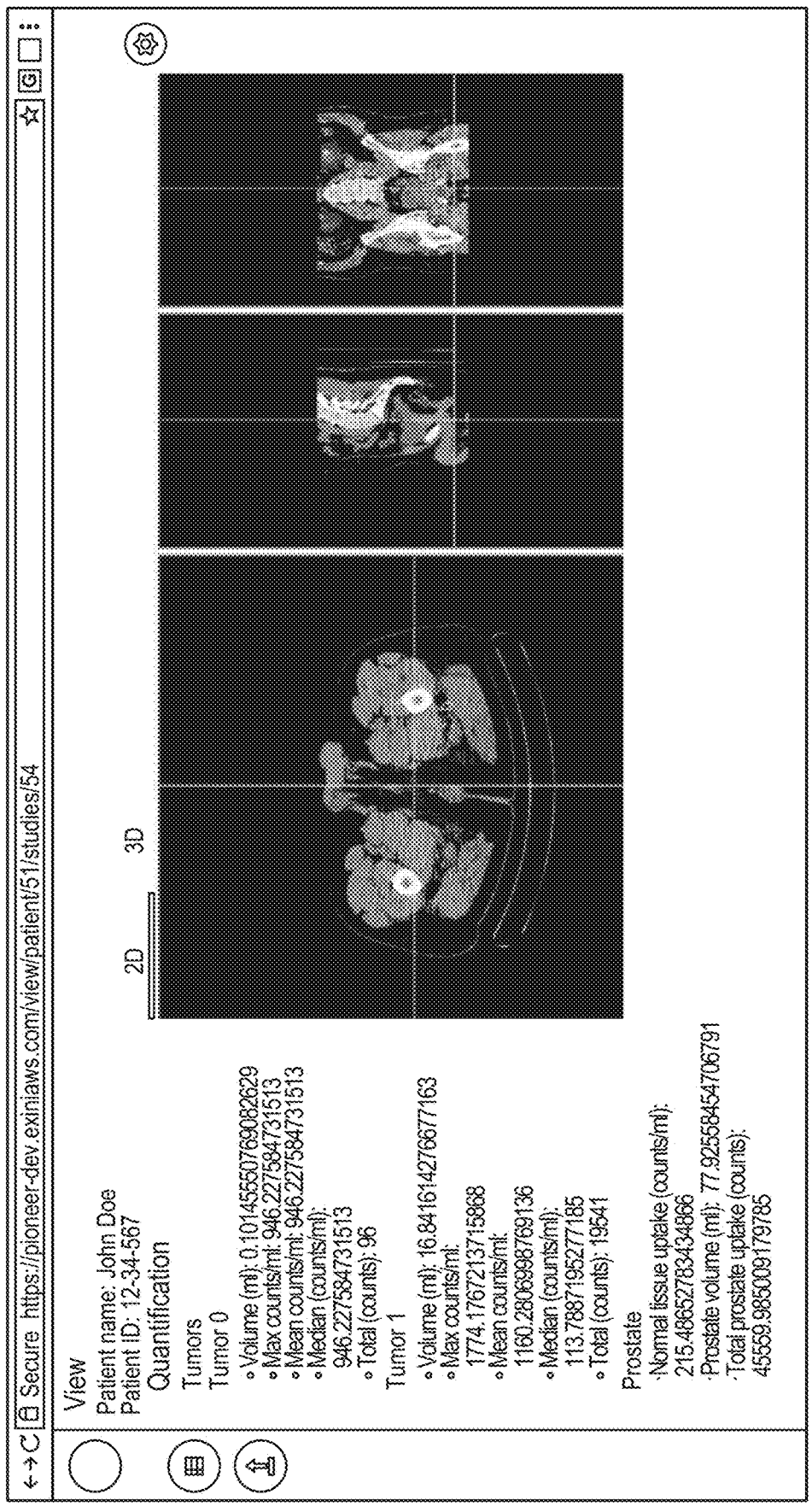
FIG. 19C is a screenshot of a GUI for reviewing patient image data showing a window comprising a set of images each showing a different 2D cross sectional view of a CT image of a subject overlaid with a SPECT image of the subject, according to an illustrative embodiment.
Figure 19D:
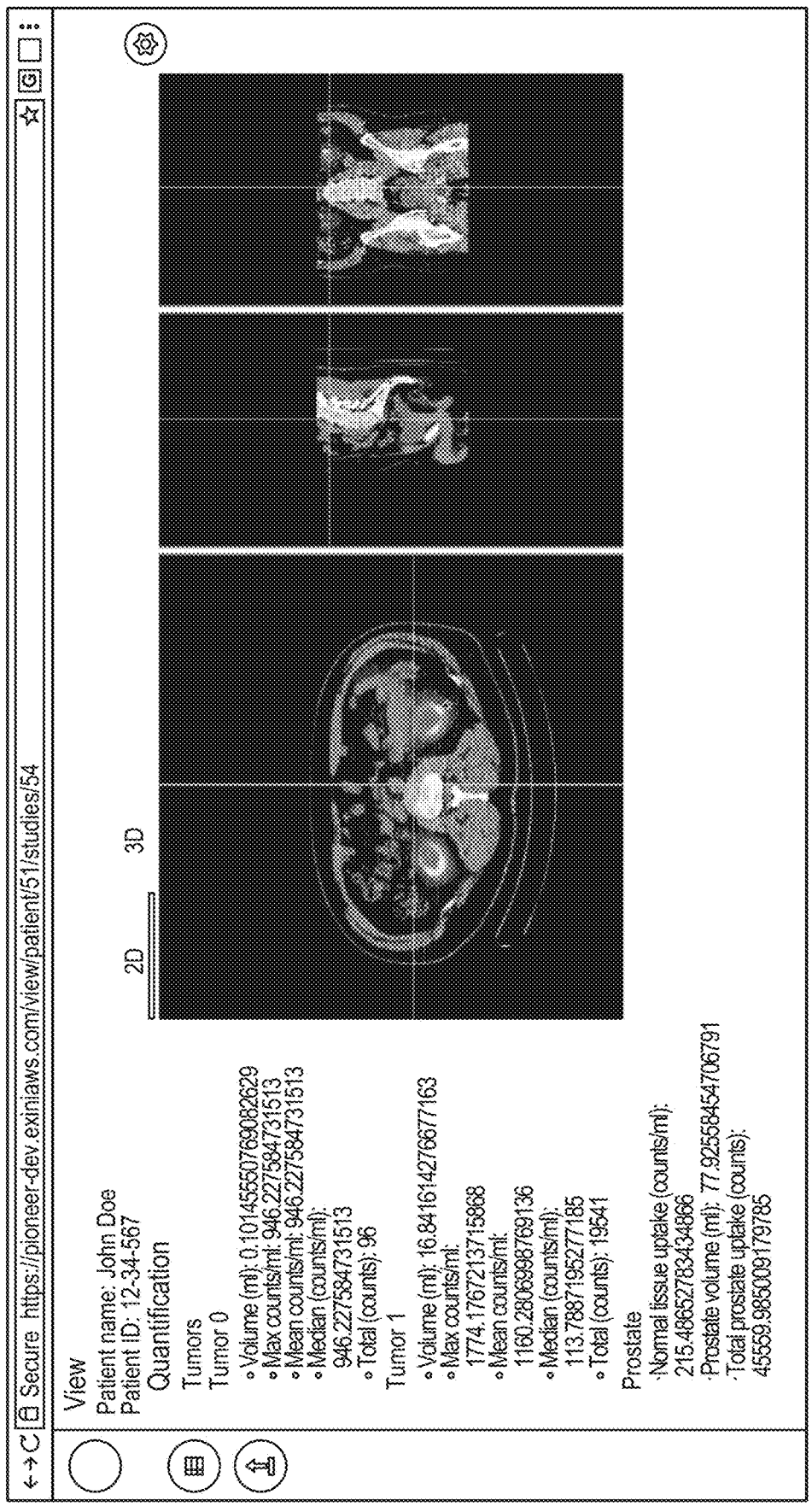
FIG. 19D is a screenshot of a GUI for reviewing patient image data showing a window comprising a set of images each showing a different 2D cross sectional view of a CT image of a subject overlaid with a SPECT image of the subject, according to an illustrative embodiment.

In FIG. 19A the user toggles display of the SPECT image layer on, and the segmentation layer off. FIGS. 19B-19D show the user scanning through the cross-sectional views again, this time with only the CT image and the SPECT image layers displayed.

Figure 20A:
FIG. 20A is a screenshot of a GUI for reviewing patient image data showing a window comprising an image showing a 3D view of a CT image of a subject comprising a graphical representation of soft tissue overlaid with a SPECT image of the subject, according to an illustrative embodiment.
Figure 20B:
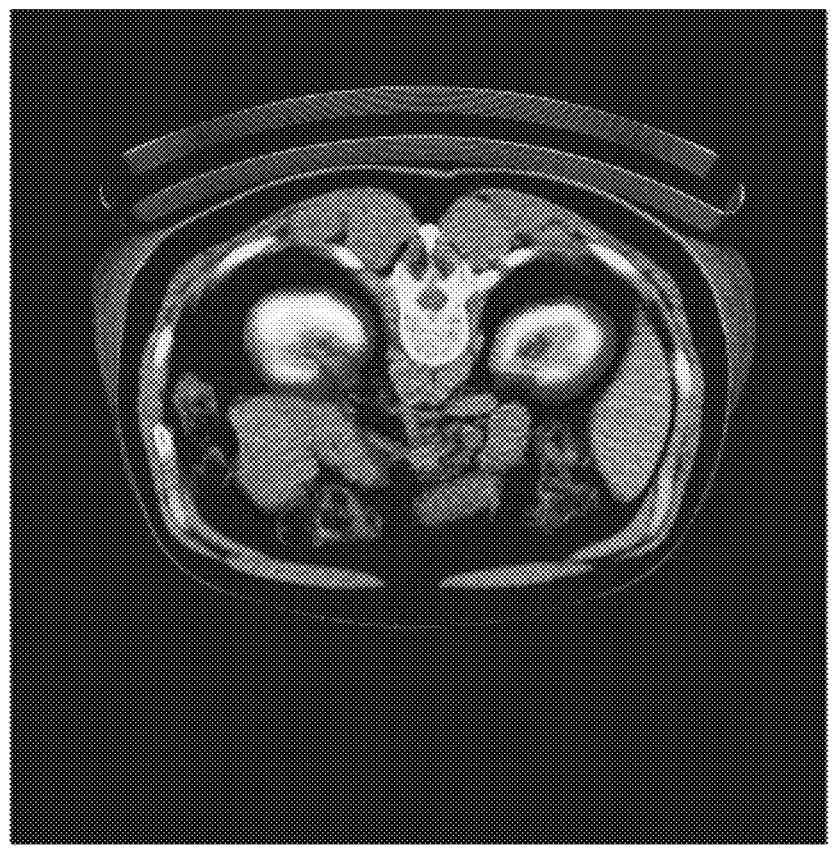
FIG. 20B is a screenshot of a GUI for reviewing patient image data showing a window comprising an image showing a 3D view of a CT image of a subject comprising a graphical representation of soft tissue overlaid with a SPECT image of the subject, according to an illustrative embodiment.
Figure 20C:
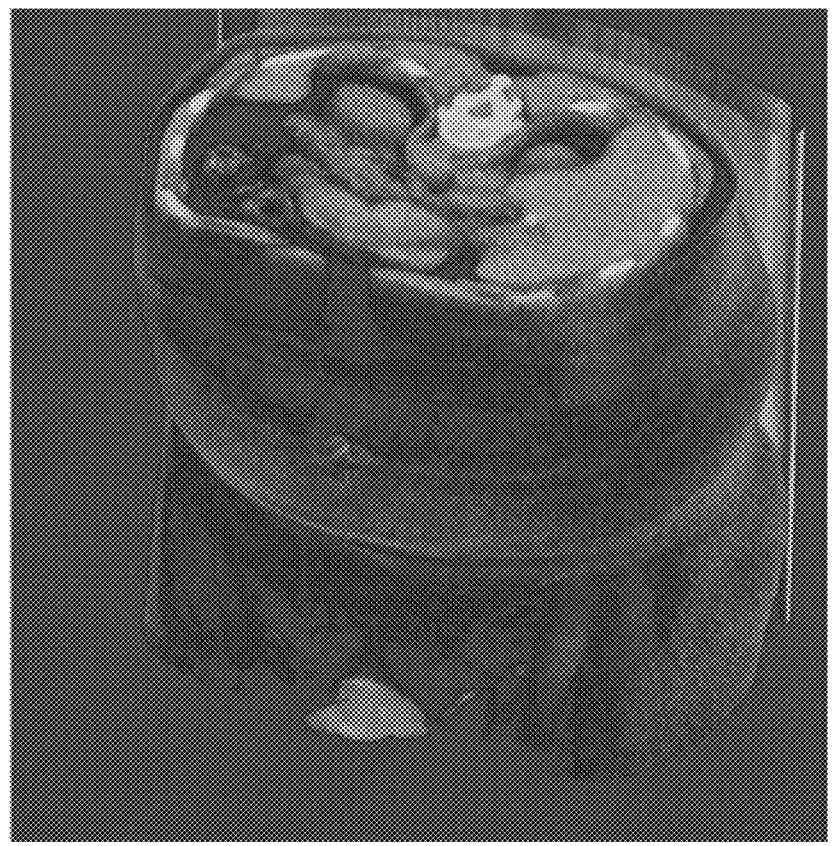
FIG. 20C is a screenshot of a GUI for reviewing patient image data showing a window comprising an image showing a 3D view of a CT image of a subject comprising a graphical representation of soft tissue overlaid with a SPECT image of the subject, according to an illustrative embodiment.

FIGS. 20A-20C show a rotatable and sliceable 3D viewer for viewing the CT image along with overlaid with SPECT image data, wherein the CT image comprises a graphical representation of soft-tissue.

Figure 21A:
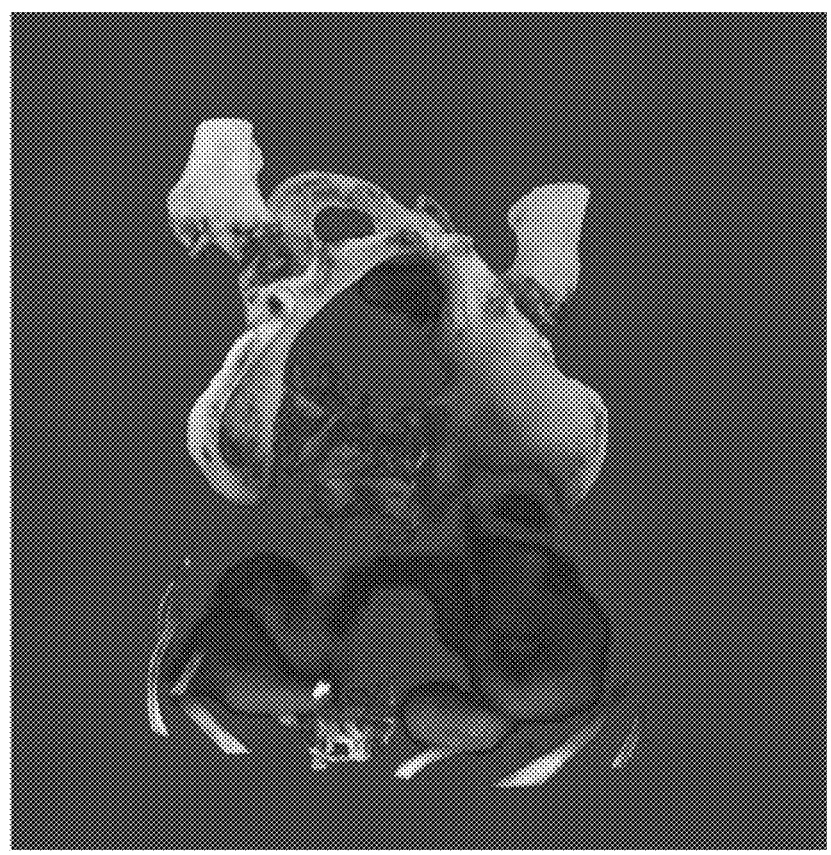
FIG. 21A is a screenshot of a GUI for reviewing patient image data showing a window comprising an image showing a 3D view of a CT image of a subject comprising a graphical representation of bone overlaid with a SPECT image of the subject, according to an illustrative embodiment.
Figure 21B:
FIG. 21B is a screenshot of a GUI for reviewing patient image data showing a window comprising an image showing a 3D view of a CT image of a subject comprising a graphical representation of bone overlaid with a SPECT image of the subject, according to an illustrative embodiment.
Figure 22A:
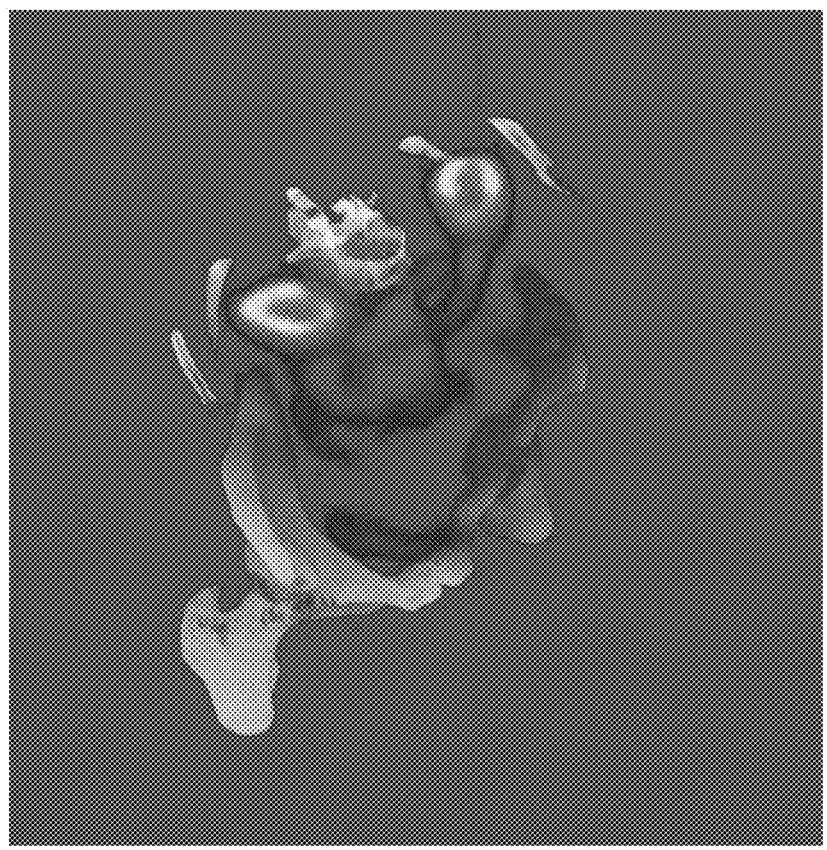
FIG. 22A is a screenshot of a GUI for reviewing patient image data showing a window comprising an image showing a 3D view of a CT image of a subject comprising a graphical representation of bone overlaid with a SPECT image of the subject, according to an illustrative embodiment.
Figure 22B:
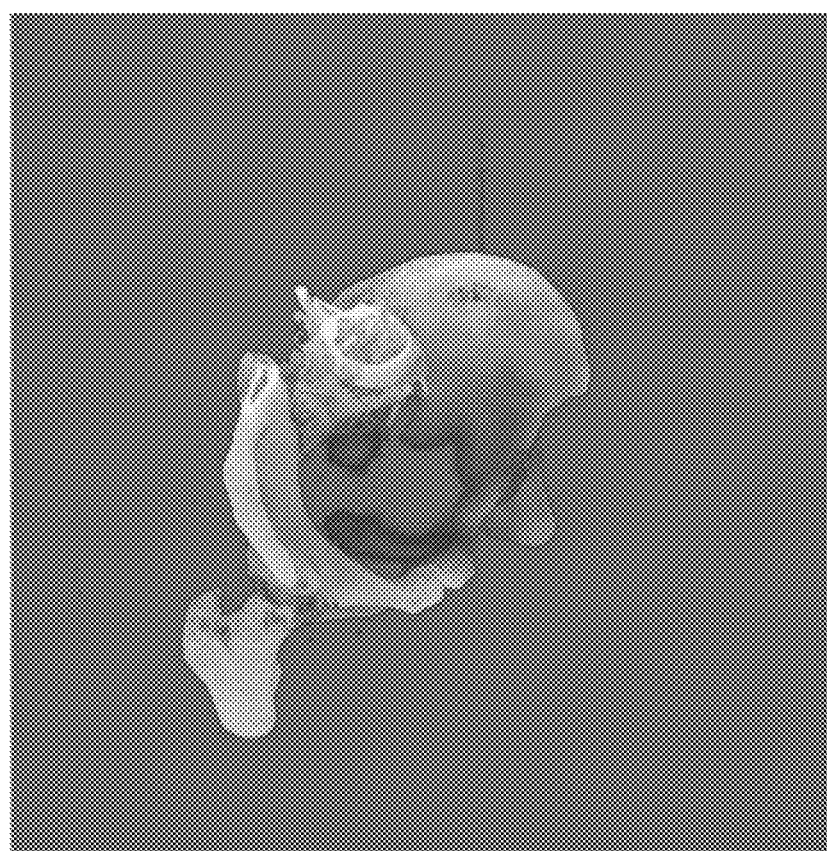
FIG. 22B is a screenshot of a GUI for reviewing patient image data showing a window comprising an image showing a 3D view of a CT image of a subject comprising a graphical representation of bone overlaid with a SPECT image of the subject, according to an illustrative embodiment.
Figure 22C:
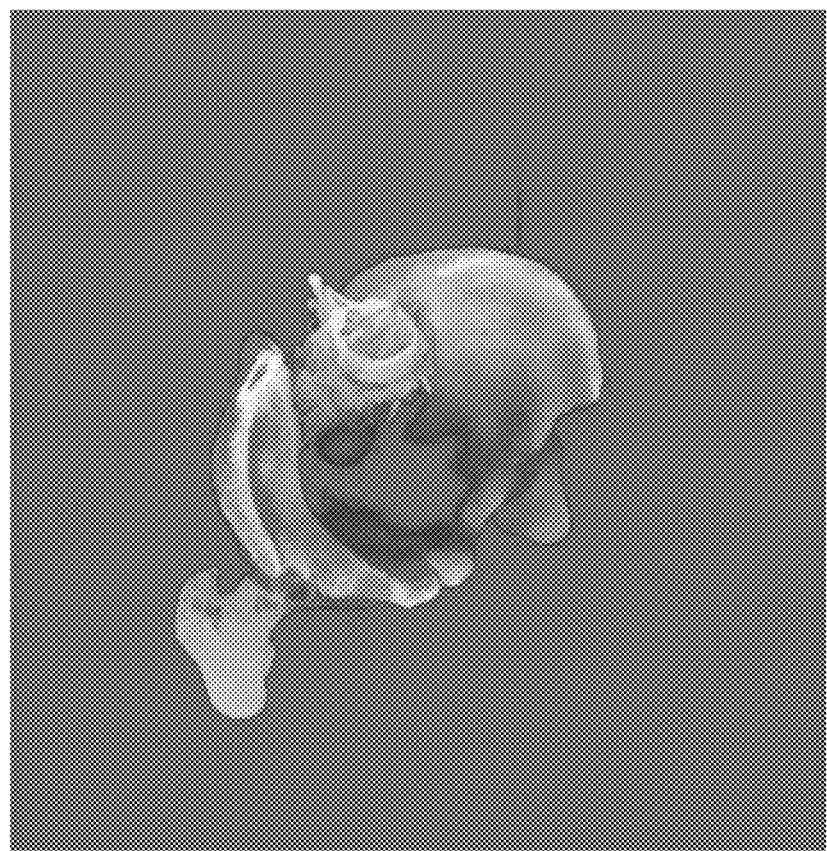
FIG. 22C is a screenshot of a GUI for reviewing patient image data showing a window comprising an image showing a 3D view of a CT image of a subject comprising a graphical representation of bone overlaid with a SPECT image of the subject and graphics representing identified tissue volumes, according to an illustrative embodiment.
Figure 22D:
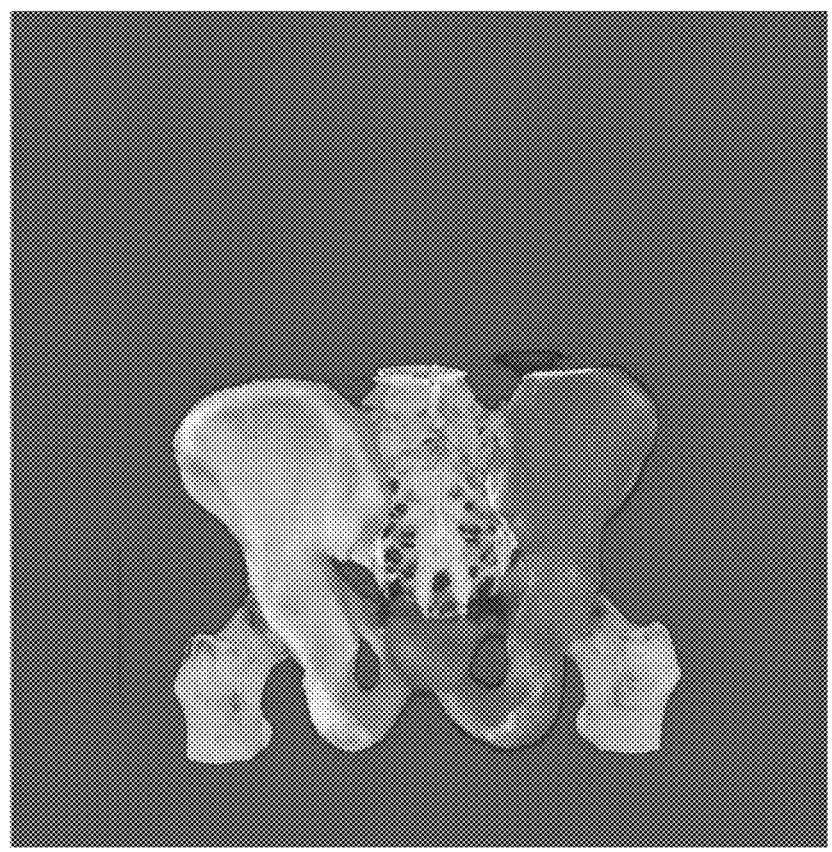
FIG. 22D is a screenshot of a GUI for reviewing patient image data showing a window comprising an image showing a 3D view of a CT image of a subject comprising a graphical representation of bone overlaid with a SPECT image of the subject and graphics representing identified tissue volumes, according to an illustrative embodiment.
Figure 22E:
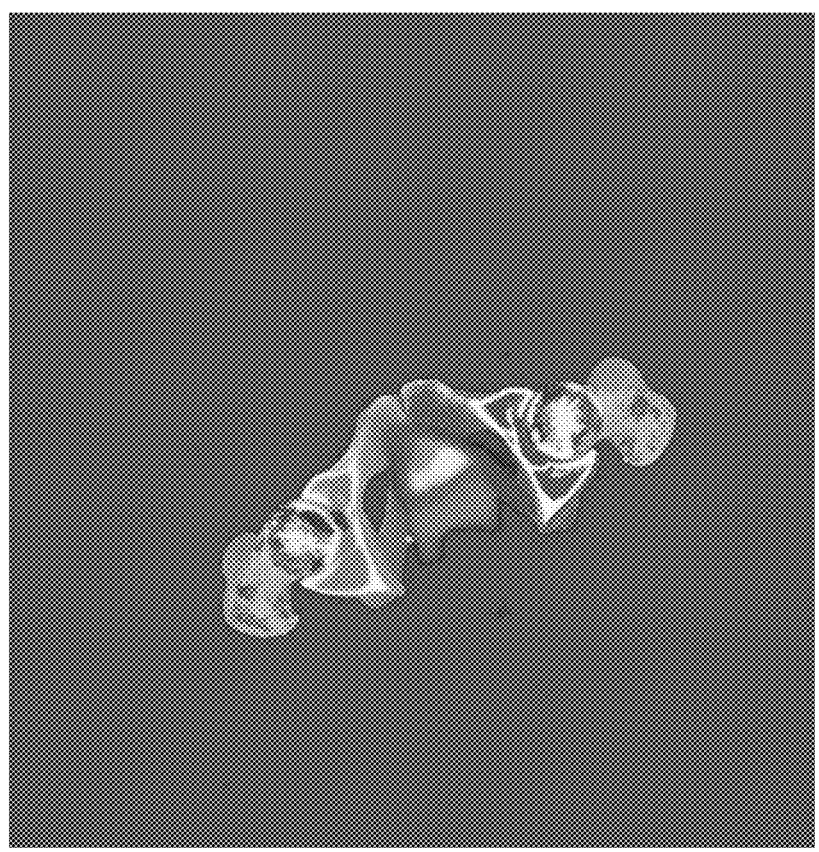
FIG. 22E is a screenshot of a GUI for reviewing patient image data showing a window comprising an image showing a 3D view of a CT image of a subject comprising a graphical representation of bone overlaid with a SPECT image of the subject and graphics representing identified tissue volumes, according to an illustrative embodiment.
Figure 22F:
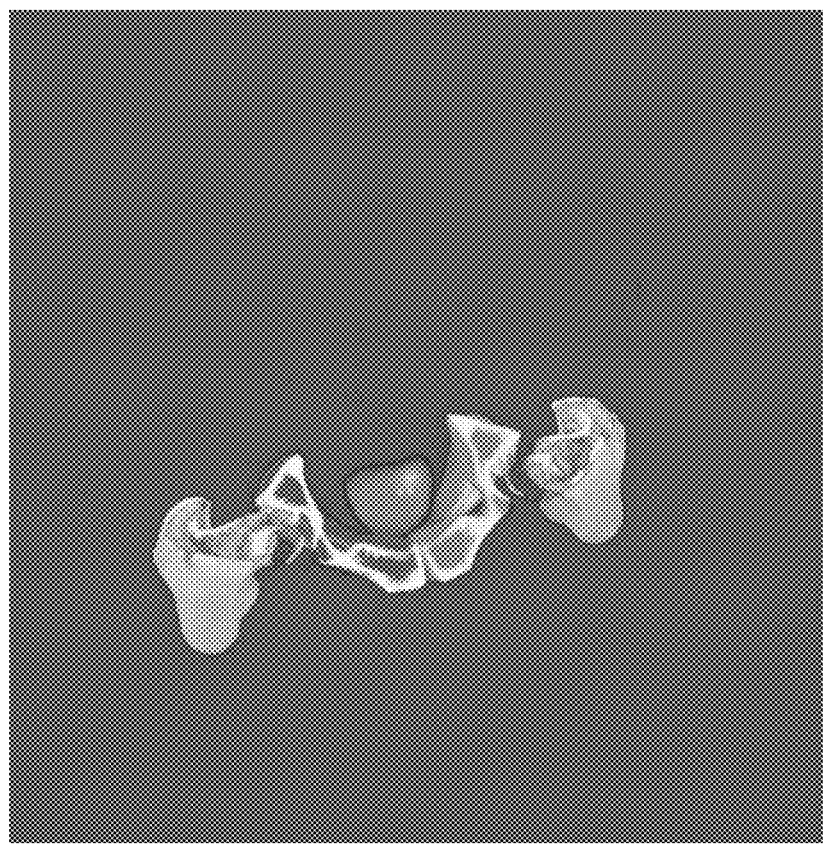
FIG. 22F is a screenshot of a GUI for reviewing patient image data showing a window comprising an image showing a 3D view of a CT image of a subject comprising a graphical representation of bone overlaid with a SPECT image of the subject and graphics representing identified tissue volumes, according to an illustrative embodiment.

FIGS. 21A-21B also show the rotatable and sliceable 3D viewer, this time with only a graphical representation of bone in the CT image displayed.

FIGS. 22A-22F show how a user can use the 3D viewer to inspect the image data and automated identification of the prostate and other additional tissue regions. The user slices down to focus on the pelvic region in FIG. 22B and turns on the segmentation layer to display graphics representing the identified prostate volume and pelvic bone volumes overlaid on the CT image as colorized regions. The user can slice and rotate the image to view the bright spots of the SPECT image intensity in the prostate region (purple volume).

Figure 23A:
FIG. 23A is a screenshot of a GUI for reviewing patient image data showing a window comprising an image showing a 3D view of a CT image of a subject comprising a graphical representation of bone overlaid with a SPECT image of the subject, according to an illustrative embodiment.
Figure 23B:
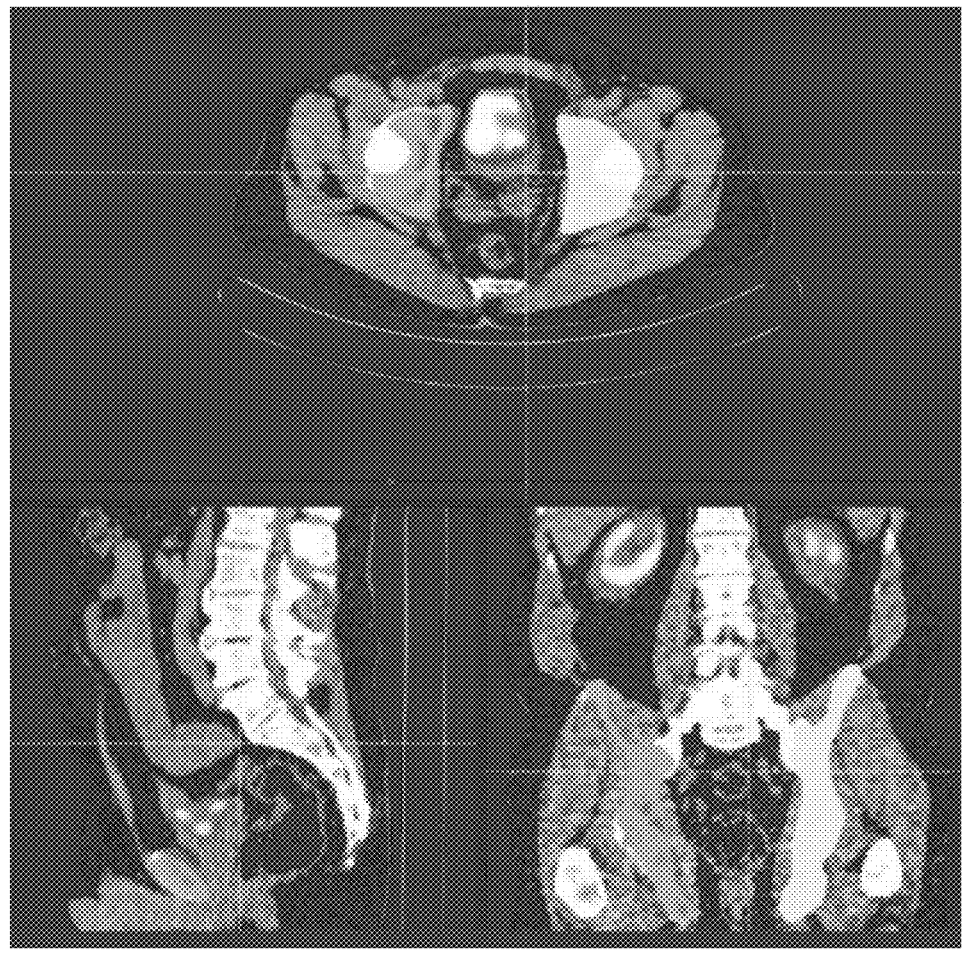
FIG. 23B is a screenshot of a GUI for reviewing patient image data showing a window comprising an image showing a 3D view of a CT image of a subject comprising a graphical representation of bone overlaid with a SPECT image of the subject, according to an illustrative embodiment.

FIGS. 23A and 23B show the viewer, but with a black background to improve contrast and mimic a radiologist scan.

FIG. 24 shows a report (e.g., an auto-generated report) with various uptake metrics.

D. User Interface, Quality Control, and Reporting

In certain embodiments, the systems and methods described herein are implemented as part of a GUI-based workflow that allows a user, such as a medical practitioner (e.g., a radiologist, a technician) to upload images of patients (subjects), initiate an automated analysis in accordance with the approaches described herein, in which a prostate volume is identified in a 3D anatomical image and used to determine uptake metrics using corresponding voxels of a 3D functional image. The user may then view results of the automated analysis, including the determined uptake metrics and any prognostic values determined therefrom. The user may be guided through a quality control workflow, in which they choose to approve or disapprove the results of the automated analysis, and, if the results are approved, generate a report for the patient. The quality control workflow may also allow the user to manually adjust and update the results of the automated analysis, for example via an interaction with the GUI, and generate a report based on the manually updated results.

Figure 25:
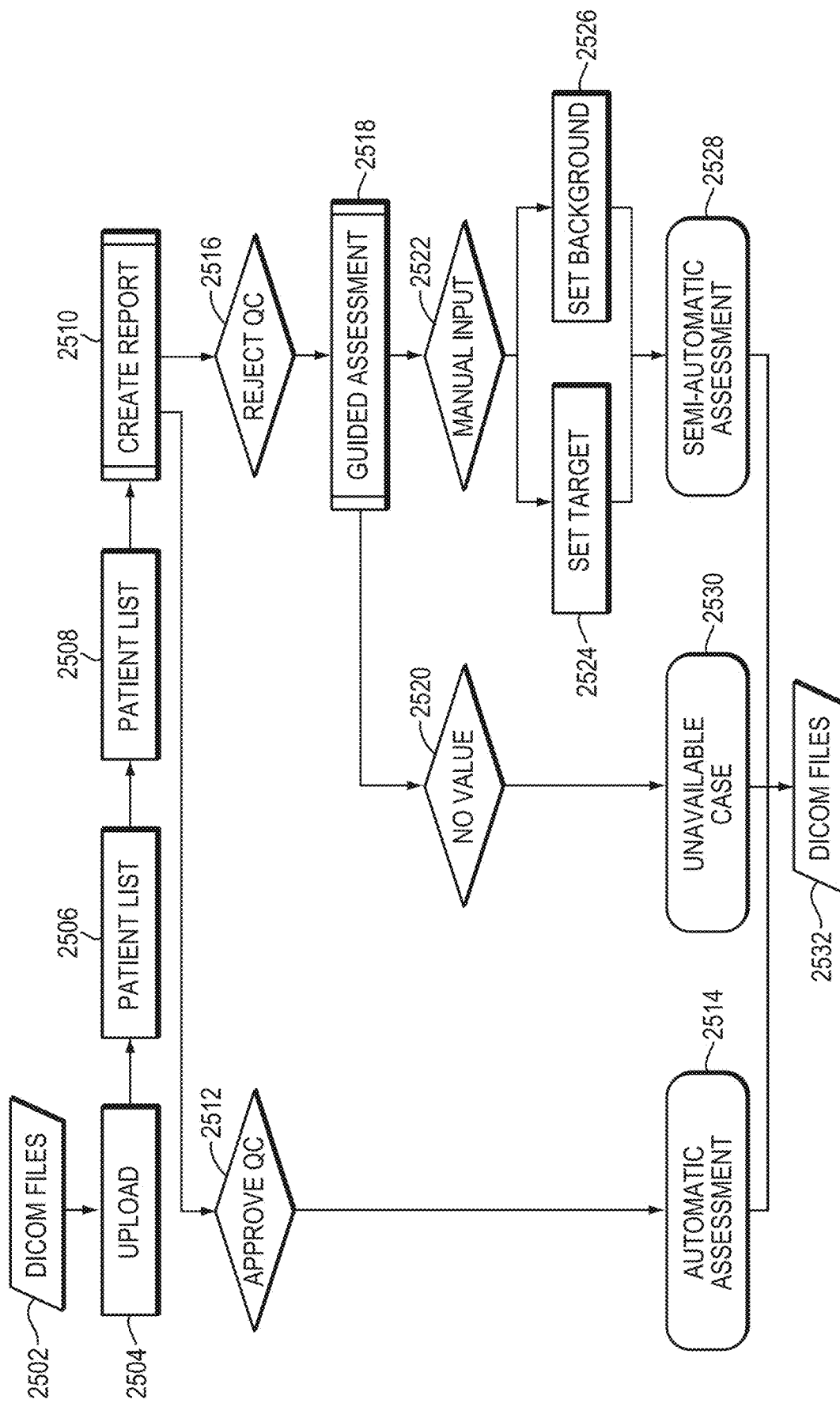
FIG. 25 is a block flow diagram showing a workflow for user interaction with a GUI in which the user reviews images, segmentation results, and uptake metrics, and generates reports, according to an illustrative embodiment.
Figure 26A:
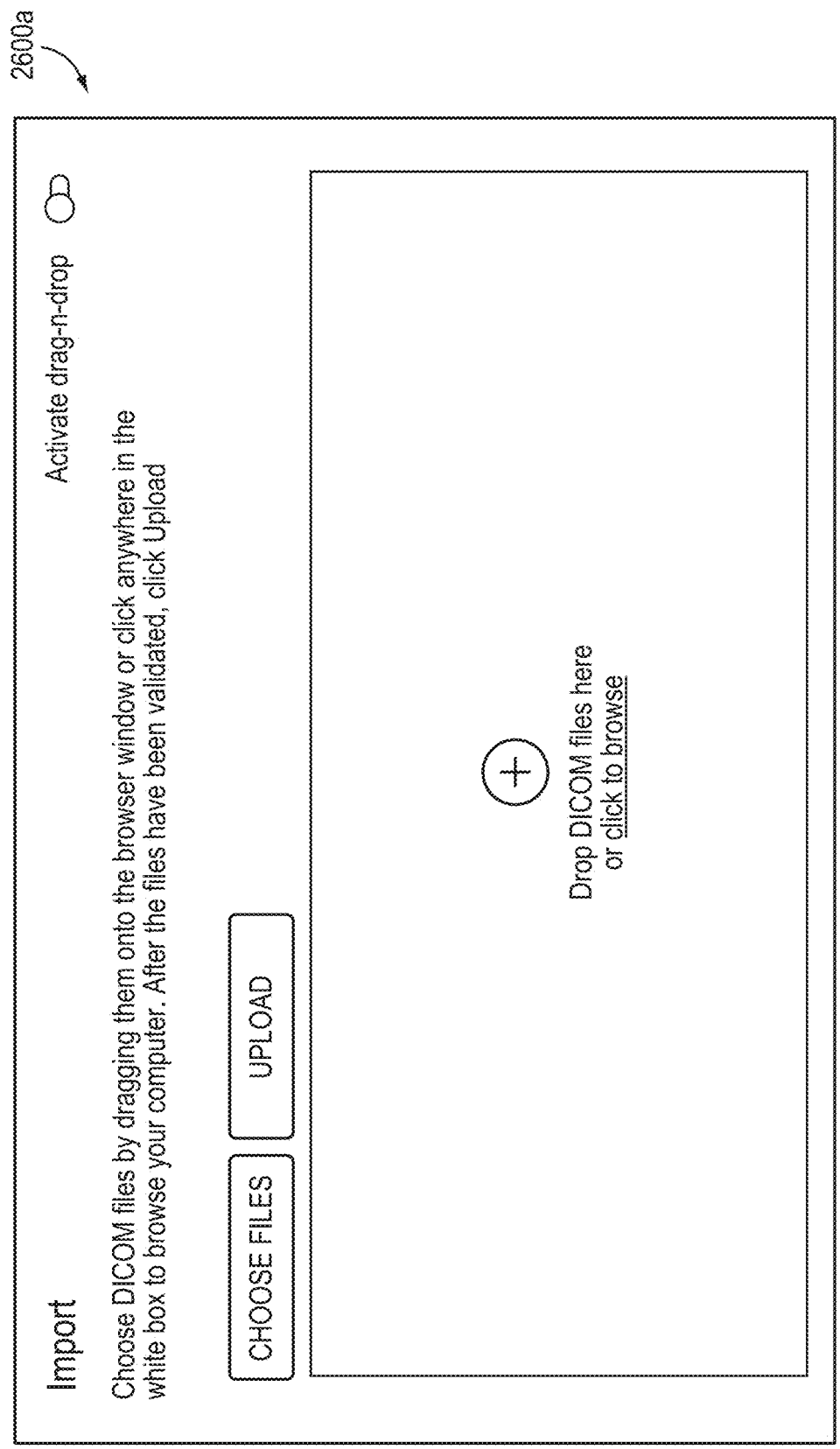
FIG. 26A is a screenshot of a view of a GUI window that allows a user to upload images, according to an illustrative embodiment.
Figure 26B:
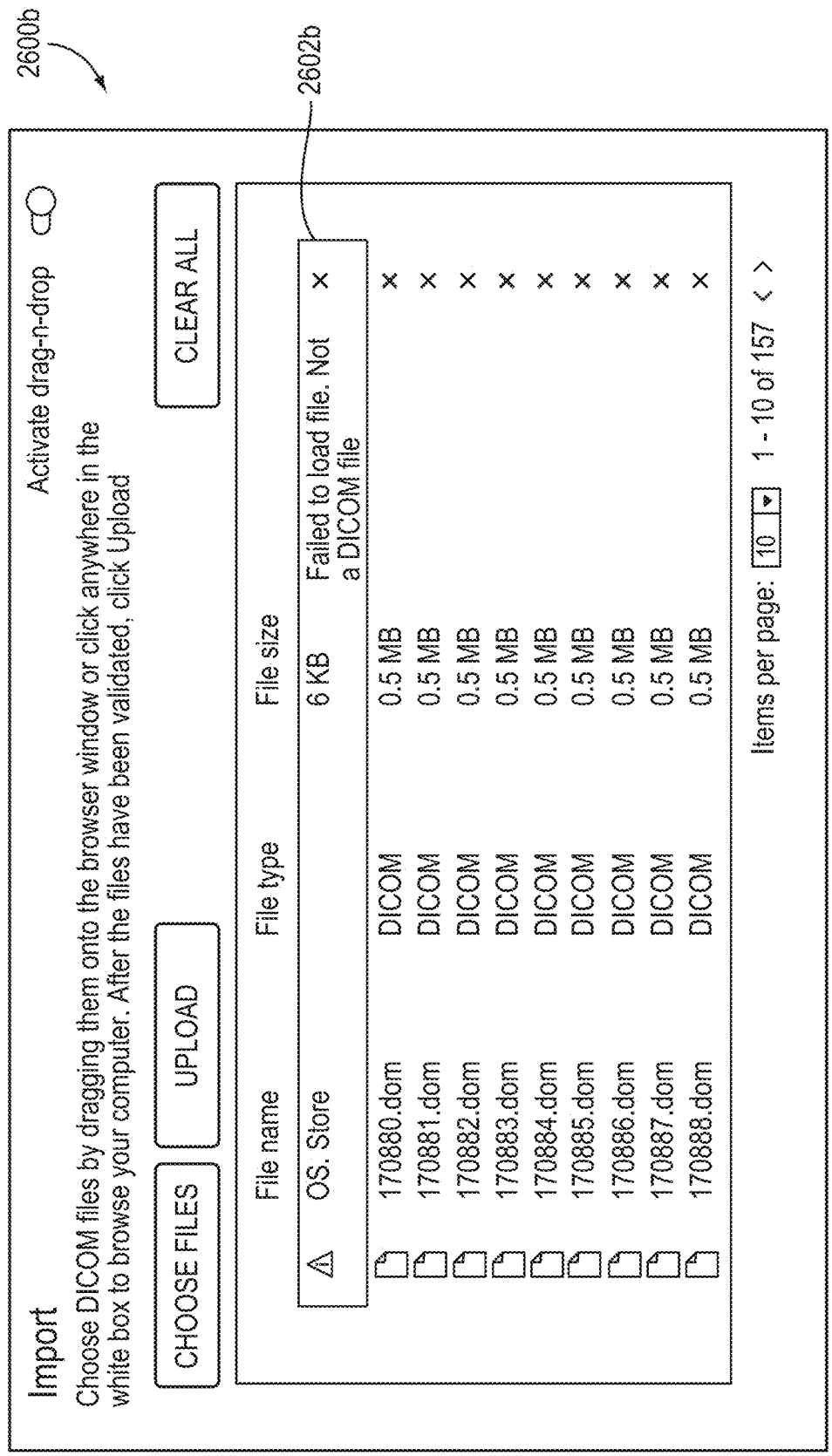
FIG. 26B is a screenshot of a view of a GUI window showing a listing of images uploaded by a user, according to an illustrative embodiment.

FIG. 25 shows an example workflow 2500, used in certain embodiments for analysis of SPECT/CT images. As shown in FIG. 25, the user may upload 2504 SPECT/CT images that conform to a specific accepted standard format 2502, specifically the DICOM standard in the example of FIG. 25. FIG. 26A shows an example GUI window 2600a of a web-based portal that allows a user to upload 2504 images. FIG. 26B shows an updated view 2600b of the GUI window shown in FIG. 26A, in which several images have been selected for upload, and checked for conformance with the DICOM standard. One image is identified as not conforming to the DICOM standard, and indicated as failed to upload 2602b.

Figure 27C:
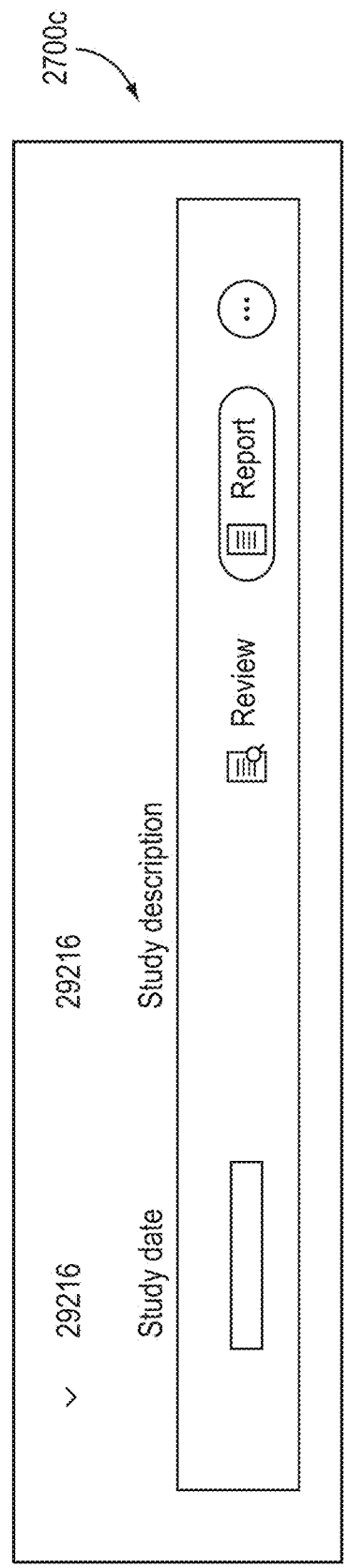
FIG. 27C is a screenshot of a view of a GUI window showing a selected patient and menu providing a user with options for reviewing study data and generating a report, according to an illustrative embodiment.

Returning to FIG. 25, in another step 2506, the user may view a list of patients for which images have been uploaded. FIG. 27A shows a view 2700a of a GUI window listing patients via anonymized numerical identifiers. FIG. 27B shows another view 2700b of the GUI window shown in FIG. 27A, in which a row of the patient list corresponding to a specific patient is highlighted for selection. FIG. 27C shows another view 2700c of the GUI, wherein upon selection of the row corresponding to the specific patient, a menu listing studies performed for the specific patient is displayed, including selectable buttons that allow the user to review image data for the study and generate a report.

In certain embodiments, the user review of the image data, along with any automated analysis results performed using the image data, is a prerequisite for generating a report. The user review of image data and automated analysis may be required to validate accuracy of image segmentation. For example, as shown in FIG. 25, following viewing of the patient list 2506 and selection of a patient, in a next step 2508, the user reviews the image data for the patient and results of automated processing as described herein.

Figure 28A:
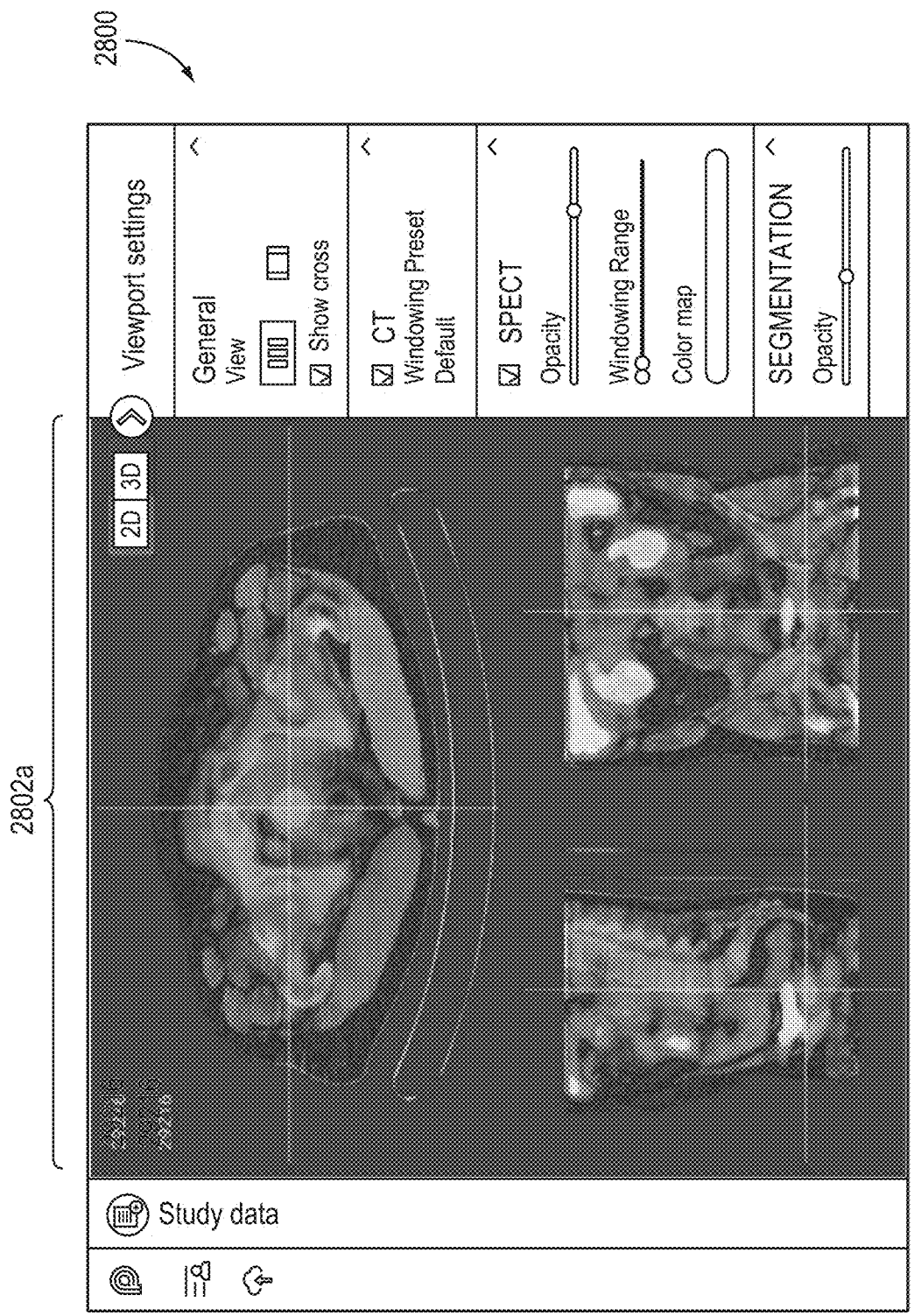
FIG. 28A is a screenshot of a GUI for reviewing patient image data showing a window comprising an image showing a 3D view of a CT image of a subject comprising a graphical representation of bone overlaid with a SPECT image of the subject and graphics representing identified tissue volumes, according to an illustrative embodiment.
Figure 28B:
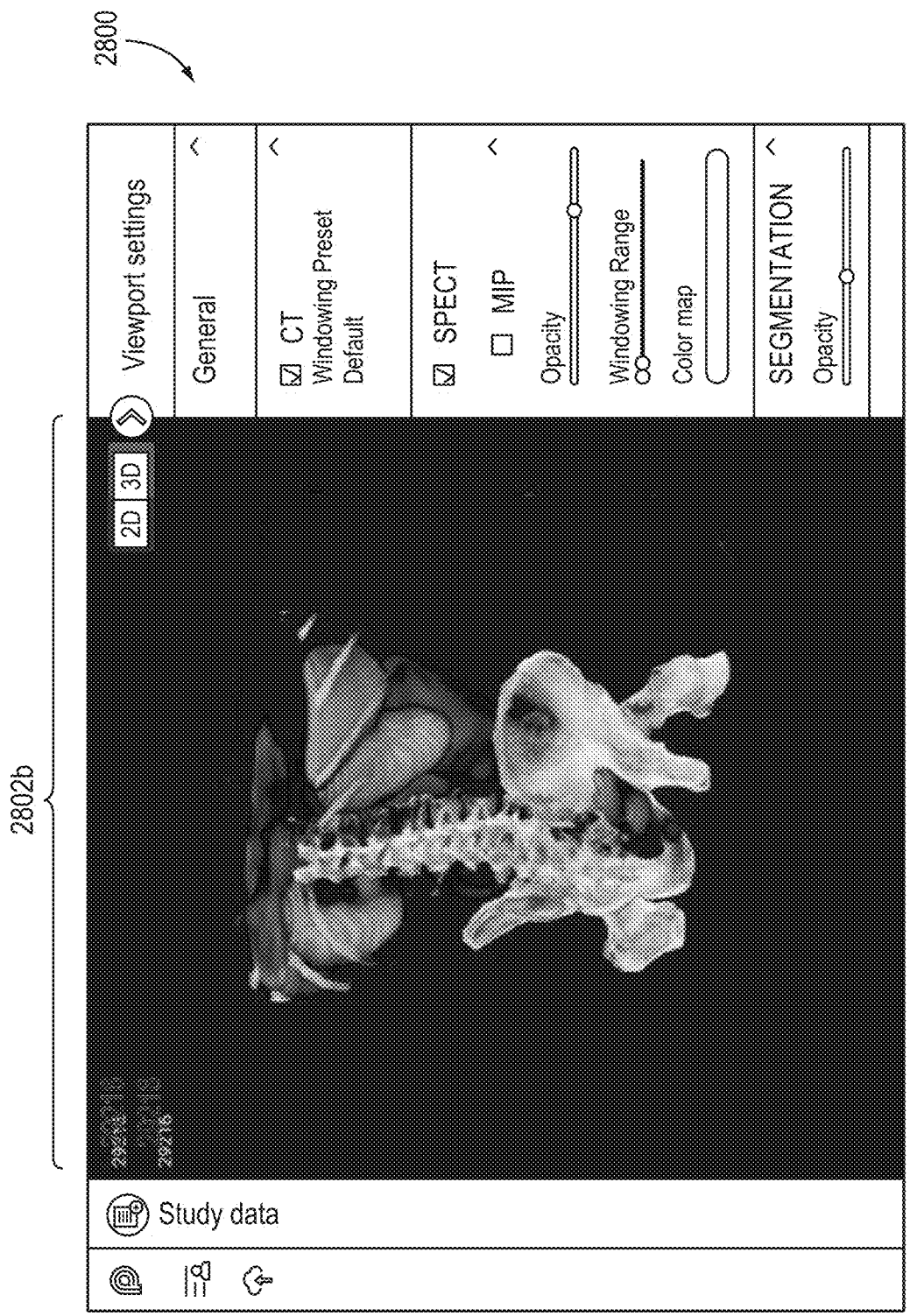
FIG. 28B is a screenshot of a GUI for reviewing patient image data showing a window comprising an image showing a 3D view of a CT image of a subject comprising a graphical representation of bone overlaid with a SPECT image of the subject, according to an illustrative embodiment.

In particular, in the review step 2508 of the workflow 2500 shown in FIG. 25, a user examines SPECT/CT image data for the selected patient using a GUI based viewer. The user may select to view and examine the SPECT/CT image data as a set of 2D slices or as a 3D rendering. FIG. 28A shows a view of the GUI viewer 2800 in which the SPECT/CT image data is displayed as a set of 2D slices 2802a. FIG. 28B shows a view of the GUI based viewer 2800 in which the SPECT/CT image data is displayed as a 3D rendering 2802b.

As shown in FIG. 28A and FIG. 28B, GUI viewer 2800 displays the SPECT image and the CT image as selectable layers, overlaid on each other. The user may select one layer at a time, to view the SPECT and/or CT image alone, or may select both a CT layer and a SPECT layer to view the SPECT image overlaid on the CT image. The user may adjust an opacity of the SPECT image, e.g., to emphasize or deemphasize the SPECT image features overlaid on the CT image. The user may also view a segmentation layer that shows locations of various tissue regions identified via the second machine learning module within the CT image, as described herein. In this manner, the user may, for example, validate the image segmentation performed by the second machine learning module via visual inspection of the CT image layer and the segmentation layer.

Figure 29A:
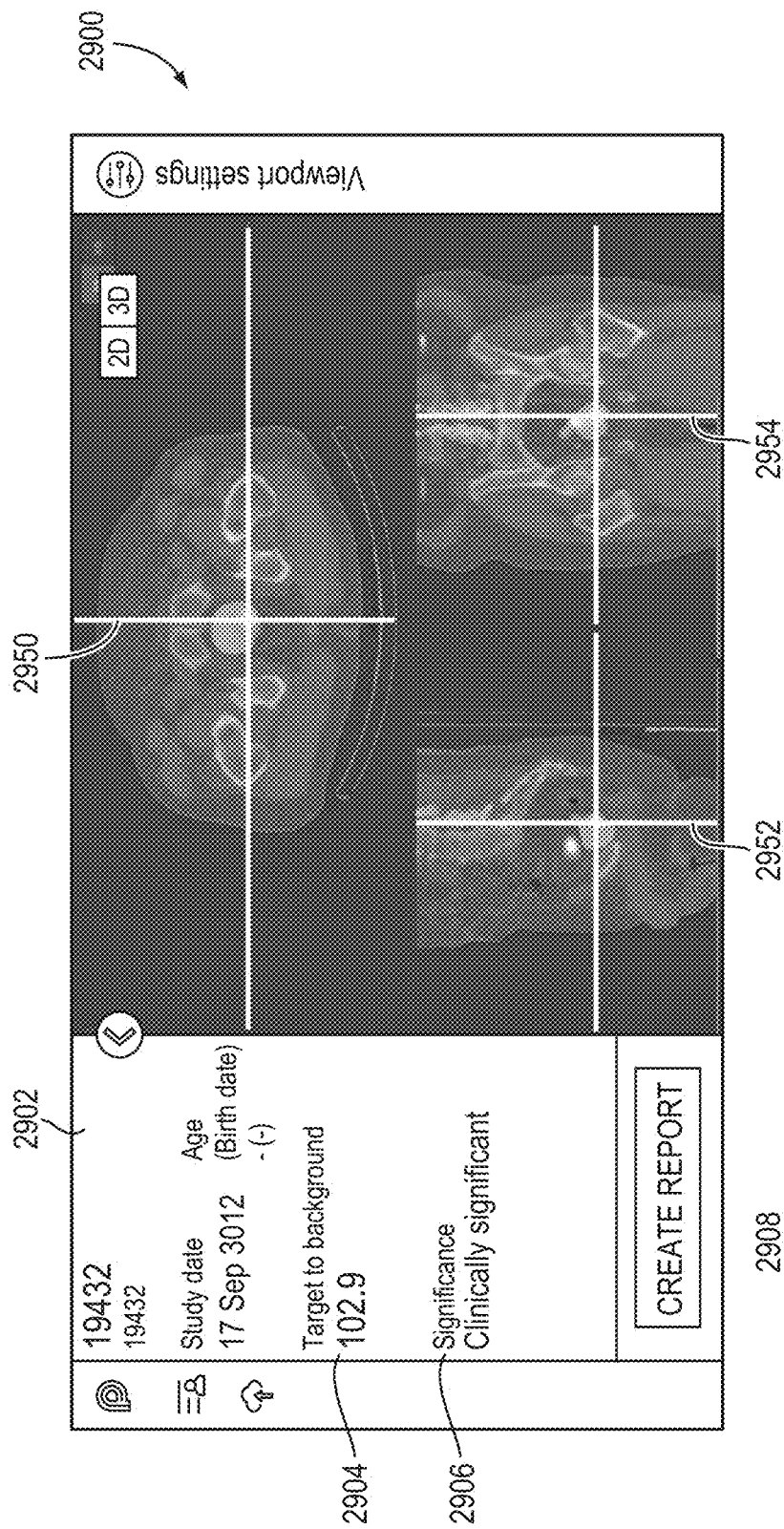
FIG. 29A is a screenshot of a GUI for reviewing patient image data showing a window for reviewing a determined uptake metric, according to an illustrative embodiment.

The user may also view and validate the one or more uptake metrics determined via the automated image analysis approaches described herein. For example, FIG. 29A shows a GUI view 2900 in which a panel 2902 of the GUI displays an automatically determined TBR value 2904 for the patient. The panel also displays a determined TBR based classification 2906, indicating that the TBR value is associated with clinically significant prostate cancer.

In certain embodiments, in order to aid in the user validation of the determined uptake metrics, a graphical element is displayed within the GUI to indicate a location of a voxel of the identified prostate volume. For example, as described herein, when a TBR value is computed as a ratio of a target intensity value to a background intensity value, a maximal intensity of voxels in the SPECT image corresponding to the identified prostate volume is identified. Accordingly, the GUI may display a graphical element that indicates a location of a voxel of the SPECT image corresponding to the identified prostate volume and having a maximal intensity in comparison with other voxels of the SPECT image that correspond to the identified prostate volume. In this manner, a position of a maximum SPECT intensity voxel corresponding to a location within the prostate volume is displayed to the user. The user may then visually verify, for example by inspection of the relation of the graphical element in comparison with the CT image, that this maximum SPECT intensity voxel indeed lies within the prostate of the subject. For example, as shown in FIG. 29A, a set of cross-hair graphical elements 2950, 2952, and 2954 identifying a location of the maximum SPECT intensity voxel are overlaid on the 2D slices shown in the image viewer.

Figure 29B:
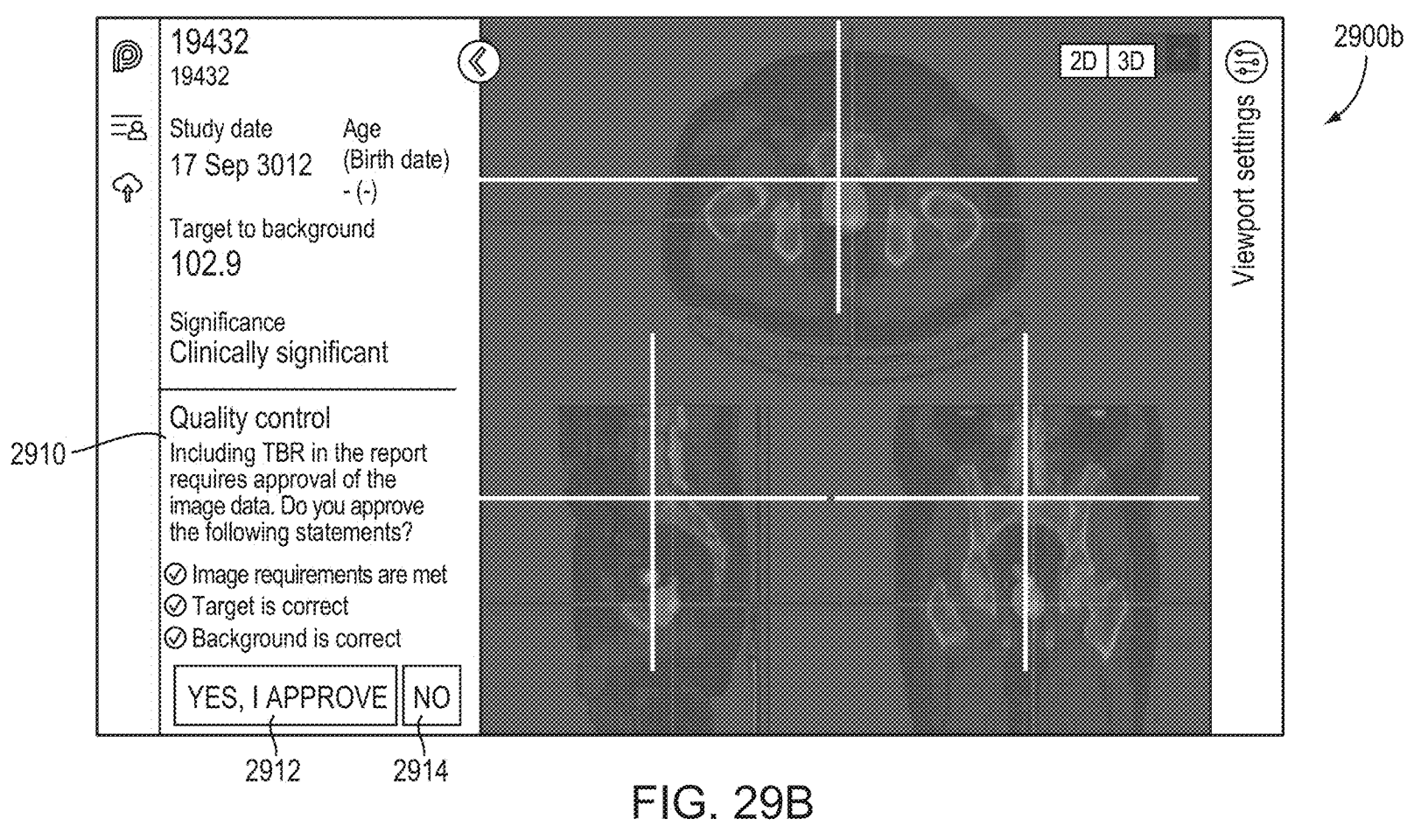

Returning to FIG. 25, in another step 2510, the user may choose to generate a report summarizing analysis performed for the patient using the uploaded SPECT/CT images, and be guided through a quality control workflow. For example, as shown in FIG. 29A, the user may select (e.g., click) a create report button 2908 of the GUI. Upon the user selection of the create report button 2908, a quality control graphical widget 2910 is displayed as shown in FIG. 29B. The quality control graphical widget 2910 may guide a user to check if various acceptance criteria are met. For example, the quality control graphical widget 2910 guides a user to check that image requirements are met, and that a target value and background value, as used in determining a TBR value, are correct. The user may approve the automated analysis results, via selection of button 2912, or may disapprove the automated analysis results, via selection of button 2914.

Figure 29C:
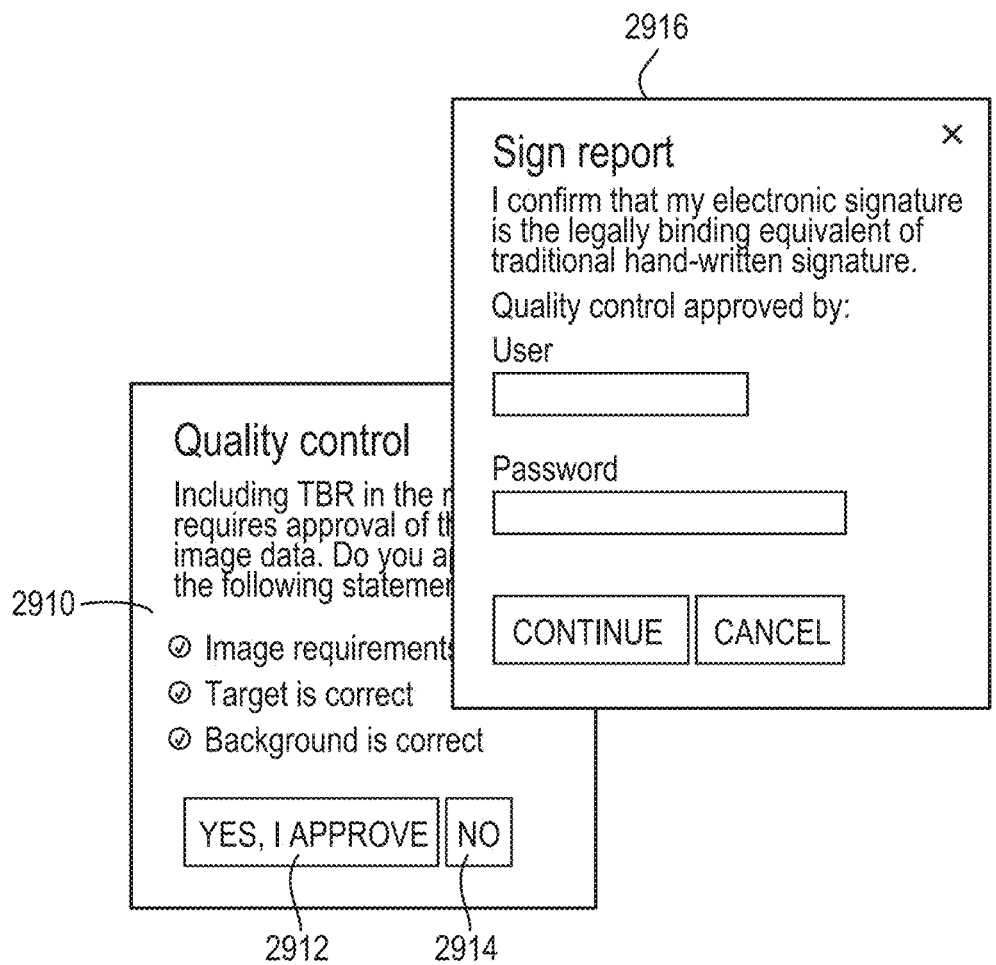
FIG. 29C is a screenshot of a view of a quality control graphical widget allowing a user to sign a generated report, according to an illustrative embodiment.

As shown in FIG. 25, following user approval of the quality control check 2512, the automated assessment results 2514 are used to generate a report 2532 for the patient. As shown in FIG. 29C, prior to generation a report, the user may be presented with a widget 2916 requesting their confirmation of approval of the quality control. FIG. 29D shows an example report 2900d. The report may include an identification of the quality control criteria 2918, along with an identification of the user that approved the quality control and signed the report 2920.

As shown in FIG. 25, if the user disapproves 2516 the automated determination of the uptake metric (e.g., TBR), the quality control widget may begin a guided assessment 2518 workflow. In the guided assessment workflow, the user may manually update values used in determining the one or more uptake metrics via a manual interaction with the GUI. The user may also provide an input that indicates that the images for the patient cannot be used for accurately determining uptake metrics may also be received via the quality control widget. For example, following a user input corresponding to disapproval of the quality control, a GUI element such as that shown in FIG. 29E may be presented to the user. The GUI element 2900e shown in FIG. 29E allows the user to select whether no TBR value can be determined for the patient, via selection of button 2922, or whether they would like to manually update the target and background intensity values used for the TBR value calculation, via selection of button 2924.

For example, if the user determines (e.g., via visual inspection of the images) that the images are of too poor quality to use for accurate determination of a TBR value, the user may select button 2922 in GUI element 2900e to identify the case as unevaluable. As shown in FIG. 25, follow receipt of the user identification of the case as unevaluable 2520, the case is marked as unevaluable 2530, and a report 2532 is produced that identifies quality control as rejected. FIG. 29F shows an example of graphics and text 2900f that may be included in such a report to identify the quality control as rejected.

In certain embodiments, the user may elect to update the target and/or background intensity values used for determining the TBR value via a manual interaction with the GUI. Once a user input indicating that they wish to update the target and/or background intensity values is received 2522, they are guided to manually set a target value 2524 and/or a background value 2526. FIG. 29G shows a view 2900g of a manual input graphical widget displayed to the user to allow them to set a target and/or background value. The user may click on button 2926 to manually set the target intensity value via interaction with the GUI. Upon selection of button 2926, the user is presented with a voxel selection graphical element that allows them to select a voxel of the SPECT image to use as the maximum intensity voxel in computing the TBR value. For example, the user may be provided with a movable cross-hair that allows them to locate positions in the SPECT and CT images, such as the cross-hairs shown in FIG. 29A. The user may move the cross-hairs and/or click on locations within the viewer to select a particular voxel to use as the maximum intensity voxel. As shown in FIG. 29H, an updated view 2900h of the manual input graphical widget may show an intensity value 2930 of the selected maximum intensity voxel that will be used as an updated target intensity value for computing an updated TBR value.

The user may also select button 2928 to set a background value to use in computing the TBR value. Upon selection of button 2928, the user may be presented with a voxel selection element and guided to select multiple voxels that they identify (e.g., based on visual inspection of the CT image layer and/or segmentation layer displayed in the GUI viewer) as belonging to the left gluteal muscle. Since the background intensity value for computing TBR is an average over intensities of multiple voxels of the SPECT image corresponding to physical locations within the left gluteal muscle, the user may be guided to select a sufficient number of voxels to ensure an accurate background intensity value is determined. For example, as shown in the view 2900h of the manual input graphical widget shown in FIG. 29H, when the user is selecting voxels to use in determining an update background intensity value, a number of samples may be displayed along with the updated value of the background intensity 2932. In certain embodiments, the user is required to select at least a predefined number of samples (e.g., 100), and the displayed background intensity value and number of samples 2932 includes a visual indication (e.g., color change) to let the user know once a sufficient number of samples has been selected.

Returning to FIG. 25, once the user has completed manual input of an updated target value and/or an updated background intensity value, an updated TBR value is computed using the updated values and stored as a semi-automatic assessment 2528. A report 2532 may then be generate using the semi-automatic assessment results.

E. Example Cloud-Based Architecture and Service Organization

In certain embodiments, the systems and methods described herein are implemented as a cloud-based application. The cloud-based application may use multiple modules to implement various functionalities, such as a client facing module that provides an interface for receiving input from a user and presenting them with image data and results. The client facing module may, in turn, interface with other modules, such as a segmentation service module that performs automated image segmentation to identify a prostate volume and compute uptake metrics as described herein.

Figure 30:
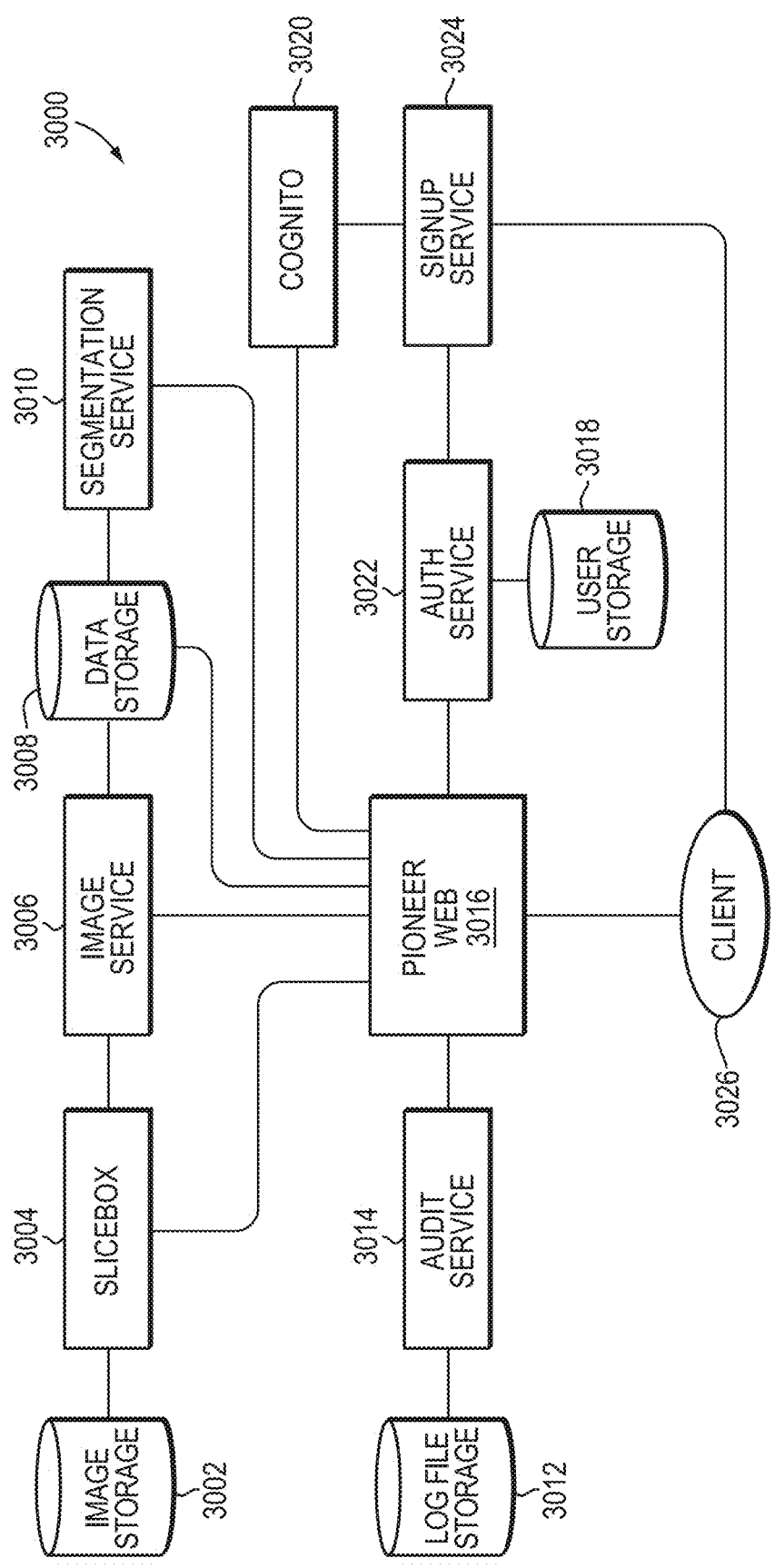
FIG. 30 is a block diagram showing a microservice network architecture for performing image segmentation to identify prostate volumes within images, determine uptake metrics, and provide results to a client, according to an illustrative embodiment.

FIG. 30 shows an example microservice network architecture 3000 for implementing the systems and methods described herein as a cloud-based application. The particular example microservice network is used in the example cloud-based application referred to as Pioneer, as described herein. In the example microservice network architecture 3000 of FIG. 30, microservice Pioneer web 3016 is a client facing module that serves a client 3026 to provide them with an interface (e.g., by serving code instruction such as javascript and HTML) for interacting with stored images and analysis results. Pioneer web 3016 also communicates with other microservices, as shown in FIG. 30. Audit service 3014 logs events and saves event logs in a log file storage database 3012. Cognito 3020 stores and authenticates users. Auth service 3022 tracks user groups and customer product registrations. Signup service 3024 is a front-end service that allows users to sign up, e.g., for use of the cloud-based system. Slicebox 3004 stores image files in a standardized DICOM format, including 3D anatomical images such as CT images, and 3D functional images such as SPECT and PET images. Images are stored in image storage database 3002. Image service 3006 reads images (e.g, DICOM files) and stores images and image metadata in a specific (e.g., convenient; e.g., standardized) format. Segmentation service 3010 performs automated image segmentation and uptake metric determination as described herein. Segmentation service 3010 fetches image data prepared by image service 3006 from data storage database 3008, performs image segmentation and uptake metric determination, and stores results in the data storage database 3008.

The architecture shown in FIG. 30 can be used to implement applications and platforms described herein on a variety of datacenters, including publicly available datacenters. The datacenter provides infrastructure in the form of servers and networks and provides services for e.g. networking, messaging, authentication, logging and storage. The architecture 3000 for the application uses a series of functional units with limited scope referred to as microservices. Each microservice handles an isolated set of tasks such as image storage, calculation of a risk index, identification of medical image type, and other tasks. Services (e.g., microservices) can communicate with each other using standard protocols such as Hypertext Transfer Protocol (HTTP).

Organizing the application into a network of microservices, as shown in the architecture 3000 of FIG. 30, allows for parts of the platform to be scaled individually to meet high demand and to ensure minimal downtime. In certain embodiments, such an architecture allows for components to be improved or replaced without affecting other parts of the application, or platforms that include the application along with others.

Figure 31:
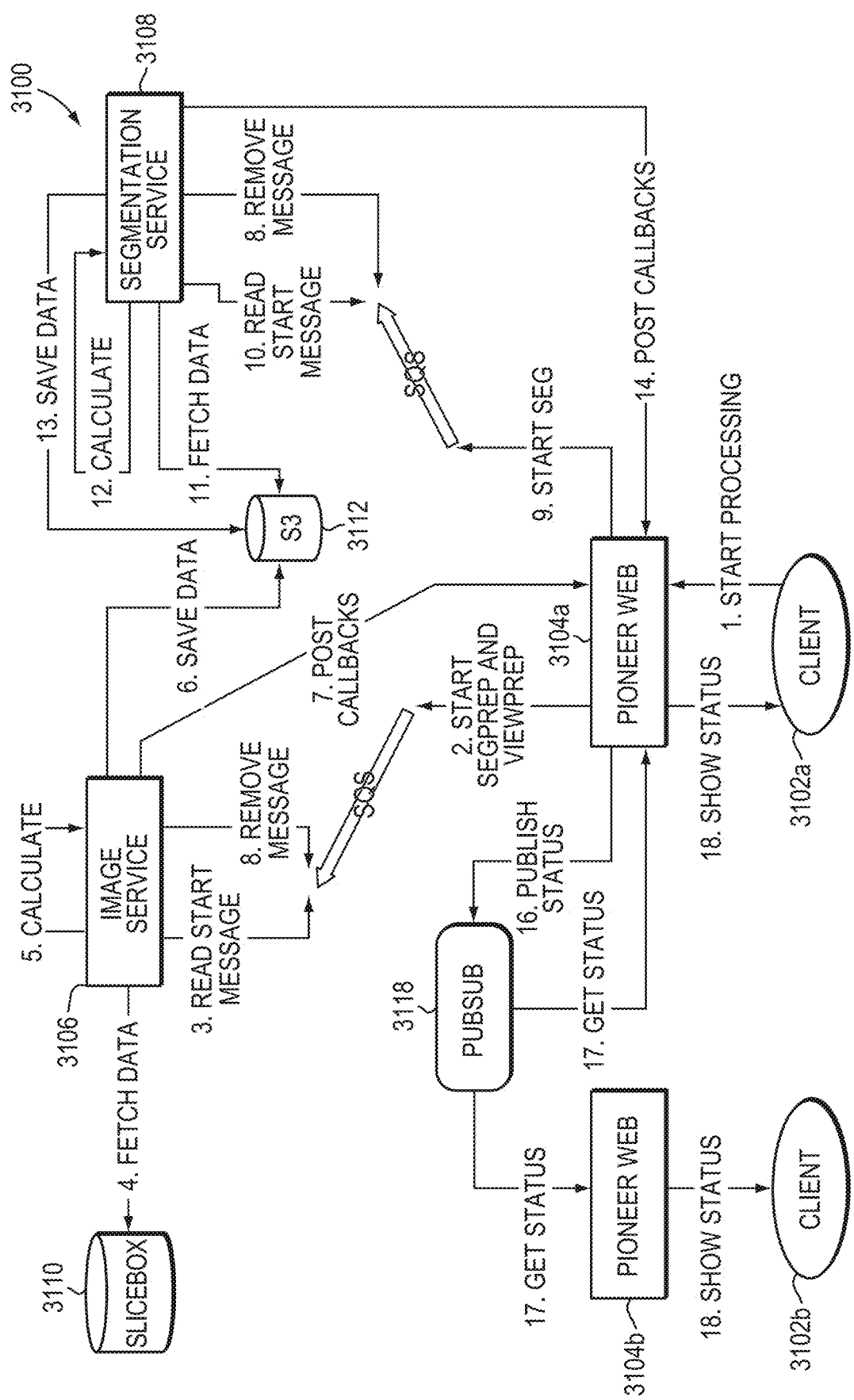
FIG. 31 is a block flow diagram showing dataflow between microservices of a cloud-based application in order to process a study by performing image segmentation and determining uptake metrics, according to an illustrative embodiment.

FIG. 31 is a block flow diagram showing an example dataflow 3100 for performing automated segmentation and analysis of CT/SPECT images using a microservice network such as the one shown in FIG. 30. Images uploaded by a user are stored in slicebox 3110. A user may initiate processing of a study (e.g., images for a patient) to initiate automated image segmentation and analysis, for example via an interaction with Pioneer web 3104a via a client 3102a. Processing of a study may also begin automatically (e.g., following uploading of images; e.g., at regular time intervals). As shown in FIG. 31, once processing of a study is initiated, Pioneer web 3104a interacts with Image service 3106 to initiate preparation (e.g., preprocessing; e.g., formatting) of image data for automated segmentation and analysis. Image service 3106 saves preprocessed images in database S3 3112. Pioneer web 3104a initiates image segmentation and analysis by Segmentation service (e.g., by sending a SQS message). Segmentation service 3108 fetches image data comprising a 3D anatomical image and a 3D functional image, such as a CT/SPECT image, from S3 3112. Segmentation service 3108 performs image segmentation to identify tissue volumes, including a prostate volume, within the 3D anatomical image, and uses the identified tissue volumes and the 3D functional image to compute one or more uptake metrics as described herein. Results of the automated image segmentation and uptake metric determination are saved in S3 3112. Segmentation service posts a callback to Pioneer web 3104a indicating whether results were successfully obtained or if an error/exception occurred. Upon receipt of the callback, Pioneer web 3104a publishes an updated status for the study on channel Pubsub 3118. Multiple Pioneer web services 3104a and 3104b may receive the status update for the study and notify clients 3102a and 3102b with which they interact of the status update.

Figure 32:
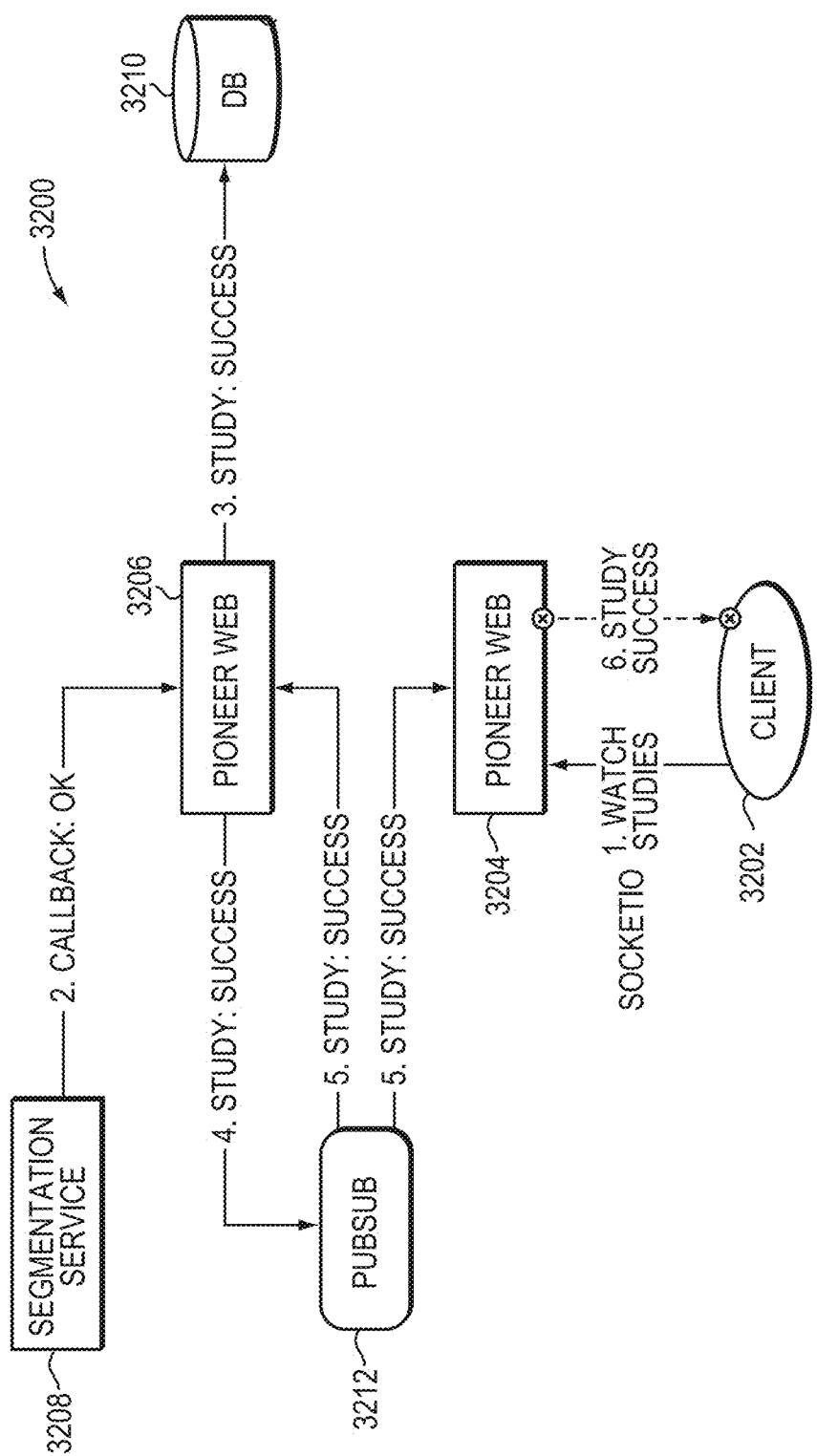
FIG. 32 is a block flow diagram showing communication between microservices of a cloud-based application and a client, according to an illustrative embodiment.

FIG. 32 shows a data flow 3200 between microservices showing how a client may request statuses of studies and be notified of study status updates in a manner similar to that described above with reference to FIG. 31. As shown in FIG. 32, a client 3202 may send study ids to a Pioneer web service instance 3204 that receives status updates via Pub/Sub channel 3212. Callbacks for completed calculations (e.g., completed image segmentation and uptake metric analysis as described herein) may enter Pioneer web from any Segmentation service 3208. A status for a completed calculation for a study may be saved in a database 3210 and an updated status for the study is sent to the Pub/Sub channel 3212. All Pioneer web instances (e.g., 3204 and 3206) subscribe to the status updates and may provide a status update (e.g., a notification of a completed calculation for the study) to a client 3202 with which they interact.

In certain embodiments, for example as described above with respect to FIG. 30 and FIG. 31, implementations of the systems and methods described herein may include an Image service module that performs image data preprocessing and formatting, for example to provide appropriately formatted image data to a Segmentation service that performs automated image segmentation and uptake metric determination.

The image service module may preprocess different images from various modalities, including 3D functional and 3D anatomical images, to standardize and format the images. For example, preprocessing of a 3D functional image (e.g., a nuclear medicine image, such as a SPECT image), may include performing basic compliance checks and interpreting voxel intensity values as specified in a standard format (e.g., DICOM PS3 NM Image IOD). Frames of the 3D functional image may be arranged in a particular order corresponding to a direction along the subject, such as a head-to-feet order. A position may be adjusted to represent an outer corner of a first voxel. Attributes from the 3D functional image that may be needed in further processing may also be extracted.

Preprocessing of a 3D anatomical image, such as a CT image, may also include performing basic compliance checks and interpreting voxel intensity values as specified in a standard format (e.g., DICOM PS3 NM Image IOD). Slices of the 3D anatomical image may be arranged in a particular order corresponding to a direction along the subject, such as a head-to-feet order. Cropping bounds to remove one or more regions of the 3D anatomical image that correspond to air around an imaged patient may also be determined. A position may be adjusted to represent an outer corner of a first voxel. Attributes from the 3D anatomical image that may be needed in further processing may also be extracted.

Figure 33:
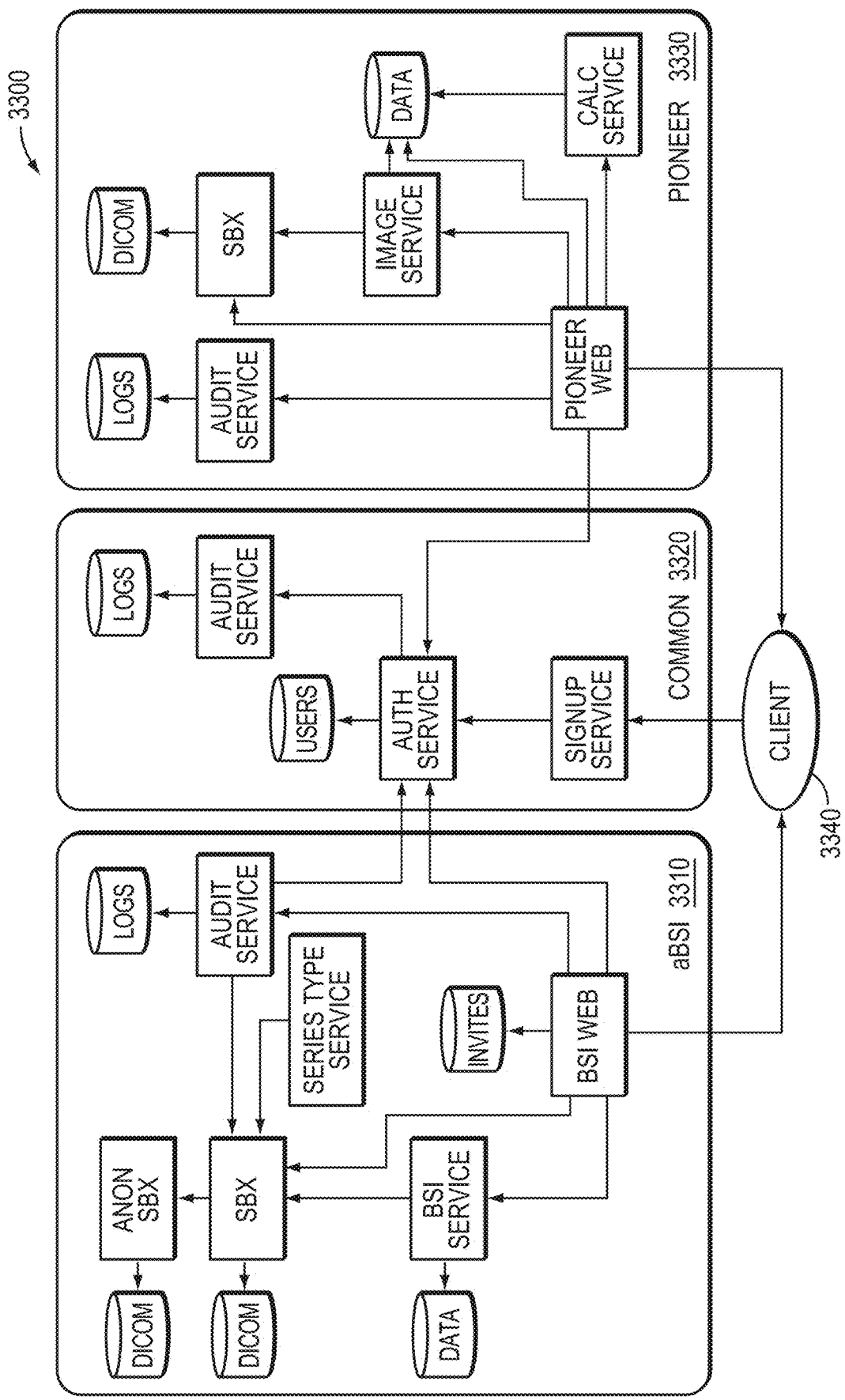
FIG. 33 is a block diagram of an example architecture for implementing a cloud-based platform comprising a cloud-based application for performing image segmentation and computing uptake metrics in accordance with the systems and methods described herein, according to an illustrative embodiment.

FIG. 33 shows an architecture 3300 illustrating how a cloud-based application implementing the image segmentation and analysis approaches described herein, may be combined with other systems for performing other types of image analysis, to provide a cloud-based platform that a client/user may use to multiple image analysis applications. The architecture 3300 shown in FIG. 33 includes a set 3320 of microservices that are common between two or more applications. The left 3310 and right 3330 panels show microservices in two applications. Microservice network 3330 implements a version of the Pioneer cloud-based application, as described herein, and provides for automated analysis of CT/SPECT images, calculation of uptake metrics, such as TBR, and generation of reports. The microservice network 3310 shown in the left panel implements web-based application, referred to as aBSI, that analyzes whole-body scans obtained with a gamma camera, and computes an automated bone scan index (BSI). Further details regarding aBSI and automated BSI determination are provided in U.S. patent application Ser. No. 15/794,220, filed Oct. 10, 2017, the content of which is hereby incorporated by reference in its entirety.

Figure 34:
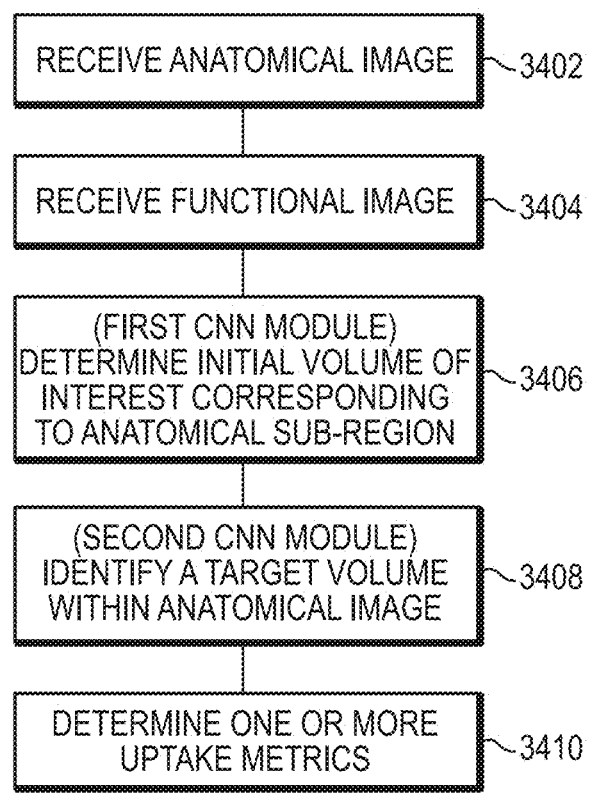
FIG. 34 is a block diagram showing a process for automatically identifying 3D target volumes within 3D images and determining uptake metrics indicative of radiopharmaceutical uptake therein, according to an illustrative embodiment.

F. Identifying Other Target Volumes of Interest and Computing Uptake Metrics With regard to FIG. 34, the approaches described herein can be used to identify other target volumes, e.g., lungs, lymph nodes, bone, liver. Other image types can be used. Various radiopharmaceuticals can be used to generate 3D functional images. For example, in certain embodiments, 1404 is the imaging agent used for SPECT images, and, in certain embodiments, PyL is the imaging agent used for PET images. In one embodiment, imaging is performed over the whole body of the subject for detection of disease (e.g., tumors) in tissue, e.g., in lymph nodes. The total number of tumors and/or the size and/or another metric associated with the spreading and/or quantity of diseased tissue (e.g., cancer) is/are determined automatically using methods described herein. For example, in process 3400 a 3D anatomical image and a corresponding 3D functional image are received at steps 3402 and 3404, respectively. A first CNN may be used to efficiently identify 3406 one or more sub-regions of an initial 3D anatomical image for more detailed segmentation by a second CNN 3408, and the corresponding 3D functional image is analyzed within the identified one or more sub-regions to quantify overall imaging agent uptake and/or to provide a computed metric indicative of the level and/or extent of disease in the subject 3410.

G. Example 1: Automated Detection and Quantification of Prostatic PSMA Uptake from SPECT/CT Imaging In this example, 99mTc MIP-1404, a small-molecule inhibitor of prostate-specific membrane antigen (PSMA) was used to detect clinically significant disease in prostate cancer. An objective of this example was to develop a deep learning model for the automatic detection and quantification of prostatic MIP-1404 uptake in SPECT/CT images.

A deep-learning algorithm was developed based on convolutional neural networks for automatically segmenting the prostate and pelvic bones from CT images. The algorithm as designed to process both high- and low-dose CT images as well as whole and part body field of views, with no manual interaction necessary. The training material consisted of 100 diagnostic CT images (all male) with complete and distinct segmentations, performed manually, for relevant anatomical regions. The algorithm was validated on the MIP-1404 phase II study including 102 high-risk prostate cancer patients who all underwent PSMA imaging prior to radical prostatectomy. All validation scans were quantified manually using the OsiriX medical image viewer (Pixmeo SARL), by measuring the maximum uptake in a circular ROI placed inside the prostate in the slice and region with highest uptake values determined visually. The automatic algorithm uses its volumetric segmentations to measure uptake at every voxel in the prostate, and registers the maximum uptake. The Pearson correlation coefficient was used to assess the concordance between manual and automated quantification of prostatic uptake.

The algorithm based on the lining material had 2.7 million parameters and was optimized using Adam, a variant of gradient descent. In the test set, 1404 images of 34 patients (33%; 34/102) were excluded due to excessive CT artifacts, incomplete data and/or data format problems. Computation time on the evaluable patients (N=68) was 13 seconds (per case) on commodity hardware. The automated maximum uptake value was significantly correlated to the manually obtained in the prostate (r=0.95, 95% CI=[0.91,0.97]; slope=0.89, 95% CI=[0.80,0.98]; p<0.0001). The algorithm was fully automated and deterministic, resulting in 100% repeatability.

This example demonstrates the feasibility of an objective and automated measure of MIP-1404 uptake in the prostate.

H. Example 2: Technical and Clinical Performance of Automated Segmentation and Uptake Metric Determination Example 2 shows evaluation of technical and clinical performance of an embodiment automated image segmentation and uptake metric determination approaches described herein implement via an example cloud-based application referred to as Pioneer. To establish the hypothesis generating algorithm for Pioneer, MIP-1404 SPECT/CT image data from two clinical studies were used, including healthy volunteers (a phase 1 study: MIP-1404-1301) and patients with prostate cancer who had histopathology data available following radical prostatectomy (a phase 2 study: MIP-1404-201). Data comparing the receiver operating characteristic plot (ROC), sensitivity, specificity, positive and negative predictive values produced by Pioneer with those obtained by traditional manual reads, showed that Pioneer could be a useful tool to assist radiologists in MIP-1404 image interpretation; thereby facilitating the evaluation of patients with prostate cancer.

i. Technical Performance

The analytical verification of the algorithm's segmentation and quantification performance criteria and the motivation was prospectively defined as detailed in OTHA-2262 and OTHA-2263, respectively. Total of sixty-one 1404 SPECT/CT images and standard for care read from nuclear medicine physician was used as benchmark to evaluate the analytical performance. All manual reads were done independently and blindly to the technical performance acceptance criteria.

The prostate segmentation performance test demonstrated mean dice of 0.77 and a standard deviation of 0.012. The lower endpoint of the one sided 95% confidence interval was 0.75, higher than the pre-defined threshold in OTHA-2262 (0.70). The background (gluteus maximus left) segmentation performance test demonstrated mean dice of 0.94 and a standard deviation of 0.002. The lower endpoint of the one sided 95% confidence interval was 0.94, higher than the pre-defined threshold in OTHA-2262 (0.80).

Only in four of the total 61 (6.6%) of the target locations predicted by the automated Pioneer software were classified by the human expert (nuclear medicine reader) as faulty. The outcome was better than that specified in OTHA-2263.

ii. Clinical Performance

In a retrospective ad hoc analysis of clinical performance, fourteen healthy volunteers (phase 1 study MIP-1404-1301) and 105 subjects with prostate cancer patients (phase 2 study MIP-1404-201) were combined in a single cohort for analysis with Pioneer. Subjects in MIP-1404-201 who received prior therapy for prostate cancer were excluded.

Images that had CT artifacts or could not be reconstructed for automated analysis were also excluded. A total of 75 images were evaluated from 61 subjects with prostate cancer and 14 normal volunteers.

Pioneer's automated assessment was evaluated against the histopathological truth standard for those who had been diagnosed with prostate cancer and had undergone radical prostatectomy following MIP-1404 SPECT/CT imaging. For healthy volunteers the assumption was made that they had no prostate cancer based on their normal PSA and pelvic MRI at the time of study. Spearman's rho was used to assess the correlation with Gleason score. Area under the receiver operating characteristic (ROC) curve was employed to determine the performance of the algorithm in detecting prostate cancer in the prostate gland. Sensitivity and specificity was determined from the optimal threshold/cutoff value from the ROC curve.

The automated quantitative assessment of the 1404 images correlated with Gleason score (rho: 0.54; p<0.0001). The ROC curve demonstrated an AUC of 0.80 (95% CI: 67-94). The optimal threshold for the binary TBR-based result in distinguishing clinically significant prostate cancer from clinically non-significant cancer or normal prostate was determined to be 25. Using this threshold, Pioneer distinguished clinically significant from clinically non-significant prostate cancer or normal prostates with a sensitivity of 75% and specificity of 80% using 1404 SPECT/CT images from the MIP-1404-1301 and MIP-1404-201 studies.

Accordingly, Pioneer improves on manual reads by providing (i) more objective and reproducible read performance across all diagnostic endpoints, and (ii) point estimates for key diagnostic performance parameters, e.g. sensitivity, specificity, that have been shown to be consistently >70% using histopathology as the truth standard.

I. Example 3: Example Cloud Based Software for Automated and Semi-Automated Analysis of 1404 CT/SPECT Images Example 3 is an example of a cloud-based software platform, referred to as Pioneer that implements an embodiment of the automated image analysis approaches described herein. Pioneer is a cloud-based software platform, implemented according to regulatory and data safety standards, where users can upload 1404 SPECT/CT image data, view it using 2-dimensional and 3-dimensional medical image viewers accessed through the user's ordinary internet browser, and review and export TBR values. The software also provides a quality control workflow where users can assess the quality of the analysis with options to reject and/or adjust the automated analysis.

Thus, under the supervision of the user, the software employs an artificial intelligence algorithm to automatically identify and analyze the regions of interest (ROIs). Pioneer extracts image data from the ROIs to provide an objective analysis—Target to background (TBR)—based on uptake in the prostate and background. Since signals in the prostate are often obscured by signals from the urinary bladder (MIP-1404 being excreted in urine), capability was also built in the software to segment the bladder and suppress bladder associated signals, thus enabling prostatic signals to be measured more accurately.

The non-clinical performance data of Pioneer include verification and validation (V&V) assessments, including definition of test methods. Pre-determined acceptance criteria were designed to ensure, at a minimum, equivalent performance with state of the art (manual assessment). The verification included software unit testing, integration testing and software system testing with functional testing of all software requirements. The validation process was performed to ensure that the system meets the user requirements specification. The V&V test results showed that Pioneer meets its intended use, user and software requirements.

J. Example 4: Selection of TBR Threshold for Clinically Significant Findings Example 4 is an example showing how a TBR threshold value for partitioning patient prostate cancer pathology into clinically significant and clinically non-significant classifications can be determined.

Two datasets of SPECT/CT images were combined to select an appropriate threshold value. A first dataset comprised images of healthy individuals, taken from a phase I study of the 1404 drug. This dataset contained originally 14 images. Segmentation of a prostate within the images was performed in accordance with the approaches described herein and two images where segmentation of the prostate clearly failed were excluded, resulting in 12 remaining images. A second data set comprised images of individuals with prostate cancer, originating from a phase II study of the 1404 drug. The images were partitioned based on the subject's Gleason grades on histopathology from radical prostatectomy. A total Gleason Score of 7 or above was considered clinically significant and total Gleason Score 6 or below was considered clinically non-significant. This dataset contained originally 65 images (63 clinically significant, 2 clinically non-significant), after excluding one image where the image did not cover the entire pelvic region and one image where the segmentation of prostate had clearly failed, 63 remained (61 clinically significant, 2 clinically non-significant).

In summary, 14 images without clinically significant pathology and 61 images with clinically significant pathology were used.

A software package implementing an embodiment of the automated image segmentation and uptake metric determination approaches described herein, ctseg package version 1.0.0rcIII, was used to compute TBR values for the images.

Figure 35B:
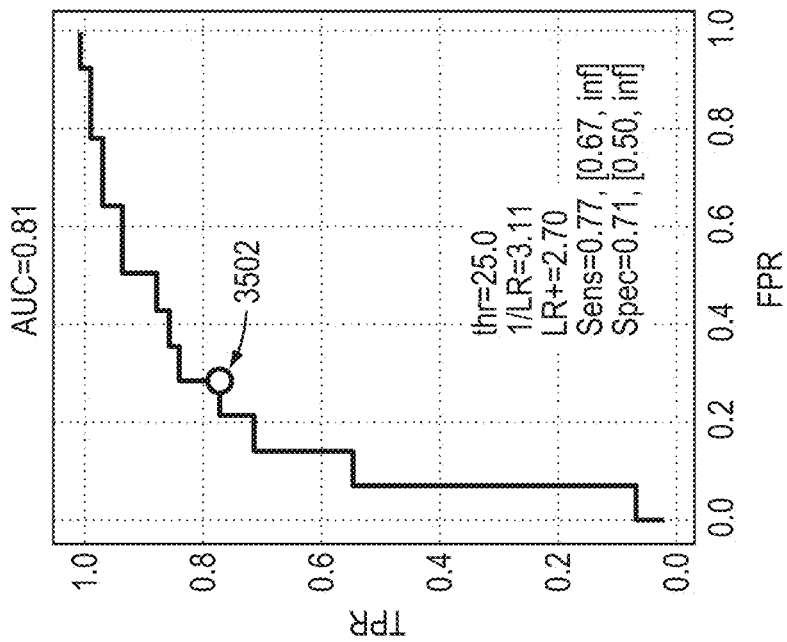
FIG. 35B is an ROC curve determined based on varying a TBR threshold computed in accordance with the systems and methods described herein.
Figure 35A:
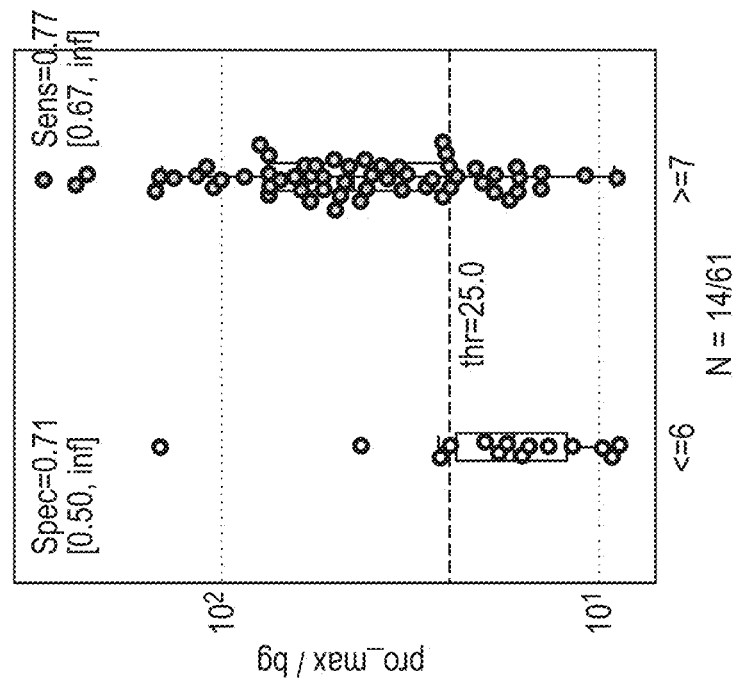
FIG. 35A is a swarm plot of clinically non-significant and clinically significant images.

FIG. 35A shows a swarm plot of clinically non-significant (<=6 on the x-axis) and clinically significant images (>=7 on the x-axis). A threshold of 25 gives a sensitivity of 0.77 (lower endpoint of Jeffreys one-sided 95% confidence interval is 0.67) and a specificity of 0.71 (lower endpoint of Jeffreys one-sided 95% confidence interval is 0.50) on the test data. FIG. 35B shows a ROC curve based on varying the TBR threshold. The point for TBR threshold 25 is marked 3502 (red circular marker).

As shown in FIGS. 35A and 35B, a threshold value of 25 provided a value for distinguishing between patients who do have clinically significant prostate cancer and those who do not. However, since there are few data points very close to the threshold, the estimates of sensitivity and specificity are not robust to small random variations in data. To get more robust estimates, the R package 'scdensity' was used to estimate smooth unimodal densities for the distribution of log TBR values for clinically non-significant and significant images respectively. From this, estimates for sensitivity and specificity were computed for different TBR thresholds, see Table 1.

TABLE 1

Robust estimates of sensitivity and specificity for different TBR thresholds.

| TBR threshold | Specificity | Sensitivity |
| --- | --- | --- |
| 22 | 0.68 | 0.79 |
| 23 | 0.70 | 0.78 |
| 24 | 0.73 | 0.76 |
| 25 | 0.75 | 0.75 |
| 26 | 0.76 | 0.73 |
| 27 | 0.78 | 0.72 |
| 28 | 0.79 | 0.70 |

Accordingly, based on the analysis described in this example, a TBR threshold of 25 was selected based on a desired specificity and sensitivity. These preliminary studies based on Phase 1 and Phase 2 data have shown improved diagnostic accuracy of MIP-1404 SPECT/CT using the automated method in comparison to manual reads.

K. Example 5: Application of AI to Phase 3 Study MIP-1404-3301 ("proSPECT-AS")

MIP1404-3301 is a pivotal phase 3 multicenter trial of $^{99m}$Tc-MIP1404 Injection for the detection of prostate cancer. MIP-1404-3301 is titled "A Phase 3 Study to Evaluate the Safety and Efficacy of 1404 SPECT/CT Imaging to Detect Clinically Significant Prostate Cancer in Men with Biopsy Proven Low-Grade Prostate Cancer who are Candidates for Active Surveillance". Cohort A patients were men with biopsy-proven low to intermediate grade prostate cancer (Gleason score 3+3 or 3+4) who were candidates for active surveillance but elected to have radical prostatectomy. Cohort B patients were biopsy-proven very low risk prostate cancer patients who scheduled to undergo routine re-biopsy as part or routine active surveillance. The phase 3 study was initiated in December 2015, and enrollment is now complete. The computer-assisted diagnosis (CADx) software device is to be used as the primary reading methodology to analyze the primary end-points in Study MIP-1404-3301.

There are two co-primary endpoints:

Specificity of $^{99m}$Tc-MIP1404 to detect clinically significant prostate cancer when compared to histopathology following radical prostatectomy (cohort A) or prostate biopsy (cohort B) using automated reading technology;

Sensitivity of $^{99m}$Tc-MIP1404 to detect clinically significant prostate cancer when compared to histopathology following radical prostatectomy (cohort A) or prostate biopsy (cohort B) using automated reading technology.

The 1404 image data from the Phase 3 trial were collected by a central imaging core laboratory. The image analysis is conducted by a radiologist using the automated software device. The medical software device is used in the assessment and characterization of prostate cancer, using a radioactive PSMA targeting imaging agent, for example as a Computer Aided Detection (CADe) device. The analysis is useful in estimating the risk for clinically significant prostate cancer in a patients. The device is also useful as a combination product comprising 1404 radioactive diagnostic agent indicated for the imaging of patients with prostate cancer in combination with the automated software device, for the automated assessment, characterization and diagnosis of prostate cancer, for example as a Computer-aided Diagnostic (CADx) device. The 1404 imaging results help estimate the risk for clinically significant prostate cancer in these patients. The software uses artificial intelligence to automatically segment the image data into distinct anatomical regions and then analyzes the volumetric regions of interest (ROI). The software extracts quantitative data from ROIs to assist in determining the presence or absence of clinically significant prostate cancer. The software device is used to assist radiologist and physicians in the assessment, characterization and quantification of prostate cancer in SPECT/CT and PET/CT images. The device is indicated for evaluation of patients presenting high-risk or low-risk screening, diagnostic imaging workup, or evaluation of extent of disease. The results from the image analysis are useful in guiding treatment decisions for the patients by the physicians.

L. Example 6: Training and Validation of Convolutional Neural Networks Implemented by the First Machine Learning Module (Localization Machine) and Second Machine Learning Module (Segmentation Machine)

Example 5 is an example showing training and validation of CNN modules used to segment CT images to identify various tissue volumes, including a prostate volume, in accordance with the aspects and embodiments described herein. In this example, the neural networks were defined and trained using the Keras framework with the Tensorflow backend.

i. Training and Validation Data

The training and validation data comprised CT images coupled with semi-automated segmentations corrected by a radiologist delineating all or some of the following body parts: (i) a prostate; (ii) a urinary bladder; (iii) a rectum; (iv) a left gluteus maximus; (v) a right gluteus maximus; (vi) a left hip bone; (vii) a right hip bone; and (viii) a sacrum and coccyx To train a localization CNN, 90 high quality CT images were used with segmentations of all the body parts above. For training a segmentation CNN for high resolution segmentation of left gluteus maximus, these and 10 images of the same type were used. For training a segmentation CNN for high resolution segmentation of the prostate, an additional data set of 73 lower-quality images with more anatomical variation in prostate and urinary bladder (due to disease) was used. These additional images were matched with segmentations of the prostate and the urinary bladder only. Pseudo labels for rectum, left and right hip bone, and sacrum and coccyx were generated for these 73 images. The pseudo labels are predicted labels generated using a previously trained network (a network trained on the 100 high quality CT images). The pseudo labels were merged with the manual labels before training.

ii. Training Configuration

Each training run was defined by a configuration file named config.json. The configuration file included parameters for: (i) which data set is used; (ii) data preprocessing; (iii) partitioning data into training and validation sets; (iv) model structure; and (v) training hyperparameters.

This configuration file is used when the trained model is used for inference, to ensure that the same image preprocessing is done during inference as during training.

iii. Preprocessing

The configuration file defines which preprocessing steps are applied during training. Several preprocessing steps were included. Cropping preprocessing steps were performed to remove surrounding air for localization training and to crop out a bounding box defined by pelvic bones, urinary bladder, rectum and prostate for segmentation. A fixed intensity normalization step was performed by subtraction of a fixed value and then division by another fixed value, where the values are chosen so that on average the intensities of voxels in the images have a mean intensity 0 and a standard deviation 1. Images were also reshaped to a fixed size by resampling. For localization, the resolution in each direction decreased by a factor of 4 for an image with median sizes in each direction. For high-resolution segmentation the resolution does not change for an image with median sizes in each dimension. Other preprocessing steps included one-hot-encoding of segmentation labels, segmentation label reweighting as defined in section iv. "Optimization", below, and data augmentation, as defined in section iv. "Optimization", below.

Some preprocessing steps are performed offline in order to speed up the training, resulting in preprocessed data sets. The config.json that belongs to the training only defines those preprocessing steps that are done online.

For localization training, the preprocessing steps for the offline preprocessing is stored in a separate file meta_data/prep_config.json in the trained CNN directory.

iv. Optimization

The loss function used for training is voxel-wise categorical cross entropy, weighted such that all voxel belonging to one class (in the true labeling) together have the same weight as all voxels belonging to any other class (when the label frequencies equal the median frequencies across the data set). This approach balances the classes and is important for prostate segmentation since the prostate is very small in comparison to, e.g., the background.

The loss is optimized using mini-batch descent with the Adam optimizer for around 2000-3000 epochs. The batch size equals 1. A batch size of 1 means that batch normalization turns into instance normalization (since the batch is only one sample). For improved performance, instance normalization is enforced also during inference.

The learning rate is determined by a learning rate schedule with a very low learning rate (e.g., $1 \times 10^{-5}$) for the first few epochs, then decreasing in steps from a high learning rate (e.g. $1 \times 10^{-2}$). After 250 epochs the learning rate is halved, then halved again after 500 more epochs, then halved again after 1000 more epochs. To decrease overfitting, dropout is used. Dropout rates vary between 0.2 and 0.5 for different networks (but the rate same in all places where it is applied for a given network, as shown, for example, in FIG. 13 and FIG. 14). Appropriate rates of dropout are based on experience from multiple trainings and how it affects the difference in performance on training and validation sets.

A training approach where the training image data is augmented by adding random distortions was used prevent the neural networks from focusing on fine details in the images. Training the neural networks (e.g., the localization CNN and segmentation CNN) in this manner allows them to handle (e.g., perform effective localization and/or segmentation of) images with image artifacts that are not present or not common in the training data.

The random distortions added to augment the training data include additive or multiplicative noise and added smoothed salt noise. These random distortions are applied independently with certain probabilities. These random distortions are scheduled to be not used for the first few hundred epochs so that the network first learns to handle images without artifacts, then the noise level is gradually increased. The intensity distortions are only applied to the 100 high-quality CT images, not the 73 low-quality images since they already have artifacts.

The localization CNN is trained to handle (e.g., receive as input) whole-body images as well as different partial-body images. To this end, augmentation with random crops of the image (always keeping the entire pelvic bounding box) is used.

v. Computational Resources

The localization trainings were done on a Nvidia GeForce GTX 1050, where a training took a few hours.

The high resolution segmentation trainings were done on a Nvidia GeForce GTX 1080 Ti, where training took 2-3 days.

vi. Model Selection

To optimize neural network structures and select hyper parameters for the training it is necessary to have metrics measuring performance. The main metric for evaluating the progress of training is Sorensen-Dice score (referred to hereafter as "Dice score"): the weighted score (weighting described above in section iv. "Optimization") or the score for individual body parts (prostate or left gluteus maximus).

When aggregating results over multiple images, most often averages of evaluated Dice scores are used (e.g., as metrics). In certain cases, a frequency of images with Dice scores below a certain level is used.

For each localization training run, the model that had best average weighted Dice score for the training images was selected. For segmentation trainings used to train the segmentation neural network to segment the prostate, the Dice score for prostate was used as a basis for selection. For segmentation trainings used to train the segmentation neural network to segment the left gluteus maximus the Dice score for left gluteus maximus was a basis for selection. For segmentation trainings with auxiliary predictions, the Dice scores were based on the prediction from the main output—that is, the output which is present also when there are no auxiliary predictions.

When training the localization CNN, 30% of the 90 CT images were reserved for validation, such that performance of the localization CNN could be evaluated using images that it was not trained on. To train the segmentation CNN for high-resolution prostate segmentation, 23 of the low-quality CT images were set aside for validation, such that only 50 of the low quality images were used in training (resulting in 150 CT images for training in total).

Metrics corresponding to a precision in cropping was used when selecting between different localization trainings. Cropping precision was evaluated based on several metrics/ aspects. In particular, one metric was that as few images as possible of the 90 training and validation images should need a crop margin above 0.1 to encompass the entire pelvic bones. Another metric was that an error in distance to the bounding box walls should be as small as possible (evaluated by looking at box plots of errors). Another metric was that on 102 low-quality CT images (without ground truth segmentations available), 2D projections of them with the coarse segmentation and final bounding box overlaid should show good agreement between segmentation and anatomy, especially that the appropriate region was covered.

When selecting between different high-resolution segmentation trainings, the following metrics/aspects were considered: (i) Dice scores for training and validation data; (ii) precision and recall for prostate for training and validation data; (iii) overlap between ground-truth bladder and predicted prostate; and (iv) examples of segmentations overlaid on CT-images in a CT image viewer where one can scroll through the slices in the sagittal, axial and coronal planes.

Accordingly, this example provides an example of an approach that can be used to train neural network models used in the localization machine learning module (first machine learning module) and segmentation machine learning modules (second machine learning module and any auxiliary segmentation machine learning modules) described herein.

M. Imaging Agents

In certain embodiments, 3D functional images are nuclear medicine images that use imaging agents comprising radiopharmaceuticals. Nuclear medicine images are obtained following administration of a radiopharmaceutical to a patient, and provide information regarding the distribution of the radiopharmaceutical within the patient. Radiopharmaceuticals are compounds that comprise a radionuclide.

Nuclear medicine images (e.g., PET scans; e.g., SPECT scans; e.g., whole-body scans; e.g. composite PET-CT images; e.g., composite SPECT-CT images) detect radiation emitted from the radionuclides of radiopharmaceuticals to form an image. The distribution of a particular radiopharmaceutical within a patient may be determined by biological mechanisms such as blood flow or perfusion, as well as by specific enzymatic or receptor binding interactions. Different radiopharmaceuticals may be designed to take advantage of different biological mechanisms and/or particular specific enzymatic or receptor binding interactions and thus, when administered to a patient, selectively concentrate within particular types of tissue and/or regions within the patient.

Greater amounts of radiation are emitted from regions within the patient that have higher concentrations of radiopharmaceutical than other regions, such that these regions appear brighter in nuclear medicine images. Accordingly, intensity variations within a nuclear medicine image can be used to map the distribution of radiopharmaceutical within the patient. This mapped distribution of radiopharmaceutical within the patient can be used to, for example, infer the presence of cancerous tissue within various regions of the patient's body.

For example, upon administration to a patient, technetium 99m methylenediphosphonate ($^{99m}$Tc MDP) selectively accumulates within the skeletal region of the patient, in particular at sites with abnormal osteogenesis associated with malignant bone lesions. The selective concentration of radiopharmaceutical at these sites produces identifiable hotspots—localized regions of high intensity in nuclear medicine images. Accordingly, presence of malignant bone lesions associated with metastatic prostate cancer can be inferred by identifying such hotspots within a whole-body scan of the patient. Risk indices that correlate with patient overall survival and other prognostic metrics indicative of disease state, progression, treatment efficacy, and the like, can be computed based on automated analysis of intensity variations in whole-body scans obtained following administration of $^{99m}$Tc MDP to a patient. In certain embodiments, other radiopharmaceuticals can also be used in a similar fashion to $^{99m}$Tc MDP.

In certain embodiments, the particular radiopharmaceutical used depends on the particular nuclear medicine imaging modality used. For example $^{18}$F sodium fluoride (NaF) also accumulates in bone lesions, similar to $^{99m}$Tc MDP, but can be used with PET imaging. In certain embodiments, PET imaging may also utilize a radioactive form of the vitamin choline, which is readily absorbed by prostate cancer cells.

In certain embodiments, radiopharmaceuticals that selectively bind to particular proteins or receptors of interest—particularly those whose expression is increased in cancerous tissue may be used. Such proteins or receptors of interest include, but are not limited to tumor antigens, such as CEA, which is expressed in colorectal carcinomas, Her2/neu, which is expressed in multiple cancers, BRCA 1 and BRCA 2, expressed in breast and ovarian cancers; and TRP-1 and -2, expressed in melanoma.

For example, human prostate-specific membrane antigen (PSMA) is upregulated in prostate cancer, including metastatic disease. PSMA is expressed by virtually all prostate cancers and its expression is further increased in poorly differentiated, metastatic and hormone refractory carcinomas. Accordingly, radiopharmaceuticals corresponding to PSMA binding agents (e.g., compounds that a high affinity to PSMA) labelled with one or more radionuclide(s) can be used to obtain nuclear medicine images of a patient from which the presence and/or state of prostate cancer within a variety of regions (e.g., including, but not limited to skeletal regions) of the patient can be assessed. In certain embodiments, nuclear medicine images obtained using PSMA binding agents are used to identify the presence of cancerous tissue within the prostate, when the disease is in a localized state. In certain embodiments, nuclear medicine images obtained using radiopharmaceuticals comprising PSMA binding agents are used to identify the presence of cancerous tissue within a variety of regions that include not only the prostate, but also other organs and tissue regions such as lungs, lymph nodes, and bones, as is relevant when the disease is metastatic.

In particular, upon administration to a patient, radionuclide labelled PSMA binding agents selectively accumulate within cancerous tissue, based on their affinity to PSMA. In a similar manner to that described above with regard to $^{99m}$Tc MDP, the selective concentration of radionuclide labelled PSMA binding agents at particular sites within the patient produces detectable hotspots in nuclear medicine images. As PSMA binding agents concentrate within a variety of cancerous tissues and regions of the body expressing PSMA, localized cancer within a prostate of the patient and/or metastatic cancer in various regions of the patient's body can be detected, and evaluated. As described in the following, risk indices that correlate with patient overall survival and other prognostic metrics indicative of disease state, progression, treatment efficacy, and the like, can be computed based on automated analysis of intensity variations in nuclear medicine images obtained following administration of a PSMA binding agent radiopharmaceutical to a patient.

A variety of radionuclide labelled PSMA binding agents may be used as radiopharmaceutical imaging agents for nuclear medicine imaging to detect and evaluate prostate cancer. In certain embodiments, the particular radionuclide labelled PSMA binding agent that is used depends on factors such as the particular imaging modality (e.g., PET; e.g., SPECT) and the particular regions (e.g., organs) of the patient to be imaged. For example, certain radionuclide labelled PSMA binding agents are suited for PET imaging, while others are suited for SPECT imaging. For example, certain radionuclide labelled PSMA binding agents facilitate imaging a prostate of the patient, and are used primarily when the disease is localized, while others facilitate imaging organs and regions throughout the patient's body, and are useful for evaluating metastatic prostate cancer.

A variety of PSMA binding agents and radionuclide labelled versions thereof are described in U.S. Pat. Nos. 8,778,305, 8,211,401, and 8,962,799, each of which are incorporated herein by reference in their entireties.

i. PET Imaging Radionuclide Labelled PSMA Binding Agents

In certain embodiments, the radionuclide labelled PSMA binding agent is a radionuclide labelled PSMA binding agent appropriate for PET imaging.

In certain embodiments, the radionuclide labelled PSMA binding agent comprises [18F]DCFPyL (also referred to as PyL™; also referred to as DCFPyL-18F):

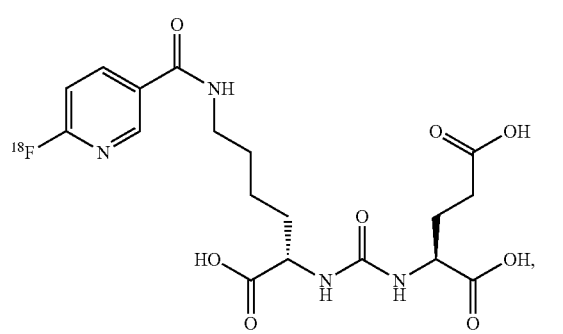

[18F]DCFPyL or a pharmaceutically acceptable salt thereof.

In certain embodiments, the radionuclide labelled PSMA binding agent comprises [18F]DCFBC:

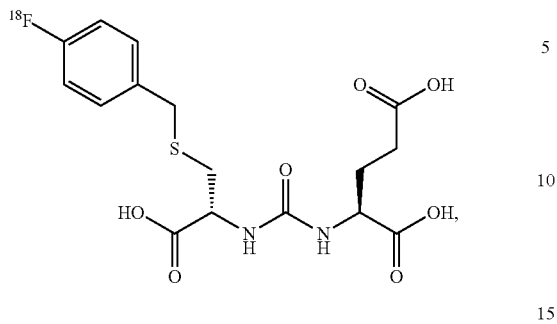

[18F]DCFBC or a pharmaceutically acceptable salt thereof.

In certain embodiments, the radionuclide labelled PSMA binding agent comprises $^{68}$Ga-PSMA-HBED-CC (also referred to as $^{68}$Ga-PSMA-11):

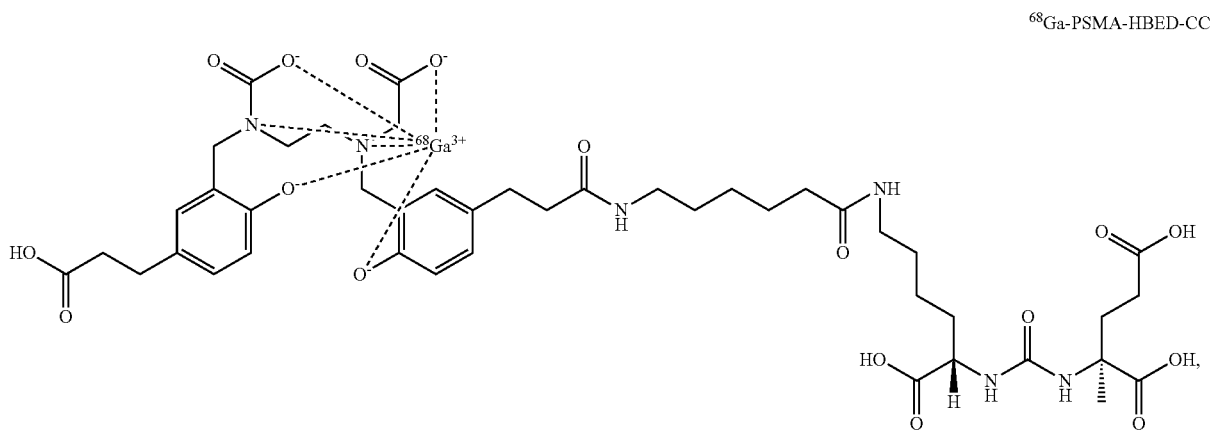

$^{68}$Ga-PSMA-HBED-CC or a pharmaceutically acceptable salt thereof.

In certain embodiments, the radionuclide labelled PSMA binding agent comprises PSMA-617:

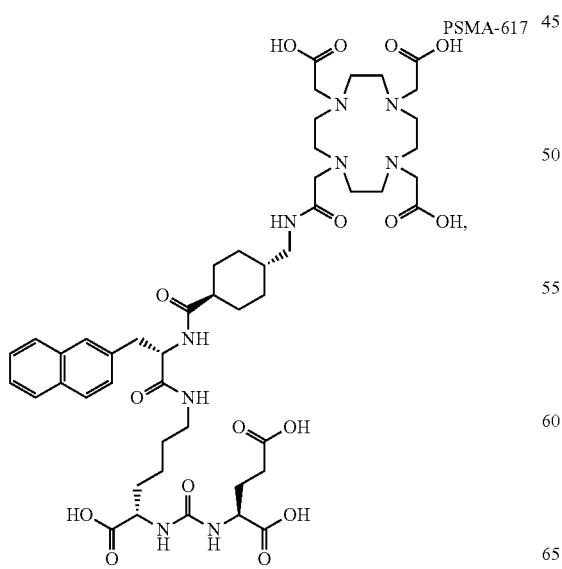

PSMA-617 or a pharmaceutically acceptable salt thereof. In certain embodiments, the radionuclide labelled PSMA binding agent comprises $^{68}$Ga-PSMA-617, which is PSMA-617 labelled with $^{68}$Ga, or a pharmaceutically acceptable salt thereof. In certain embodiments, the radionuclide labelled PSMA binding agent comprises $^{177}$Lu-PSMA-617, which is PSMA-617 labelled with $^{177}$Lu, or a pharmaceutically acceptable salt thereof.

In certain embodiments, the radionuclide labelled PSMA binding agent comprises PSMA-I&T:

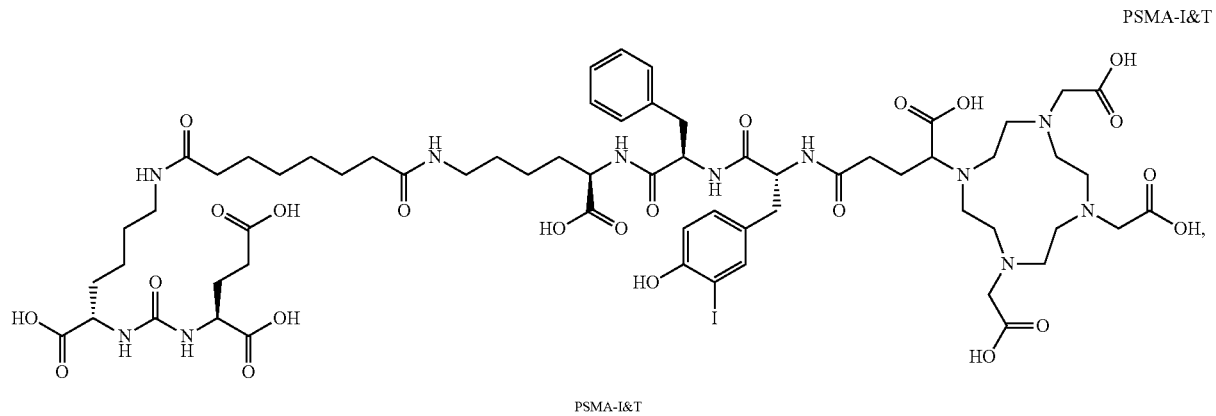 [SMILES: O=C(O)CC[C@H](NC(=O)N[C@@H](CCCCNC(=O)CCCCCCC(=O)NCCCC[C@@H](NC(=O)[C@@H](Cc1ccccc1)NC(=O)[C@@H](Cc1ccc(O)c(I)c1)NC(=O)CCC(C(=O)O)N1CCN(CC(=O)O)CCN(CC(=O)O)CCN(CC(=O)O)CC1)C(=O)O)C(=O)O)C(=O)O]

PSMA-I&T or a pharmaceutically acceptable salt thereof. In certain embodiments, the radionuclide labelled PSMA binding agent comprises $^{68}$Ga-PSMA-I&T, which is PSMA-I&T labelled with $^{68}$Ga, or a pharmaceutically acceptable salt thereof.

In certain embodiments, the radionuclide labelled PSMA binding agent comprises PSMA-1007:

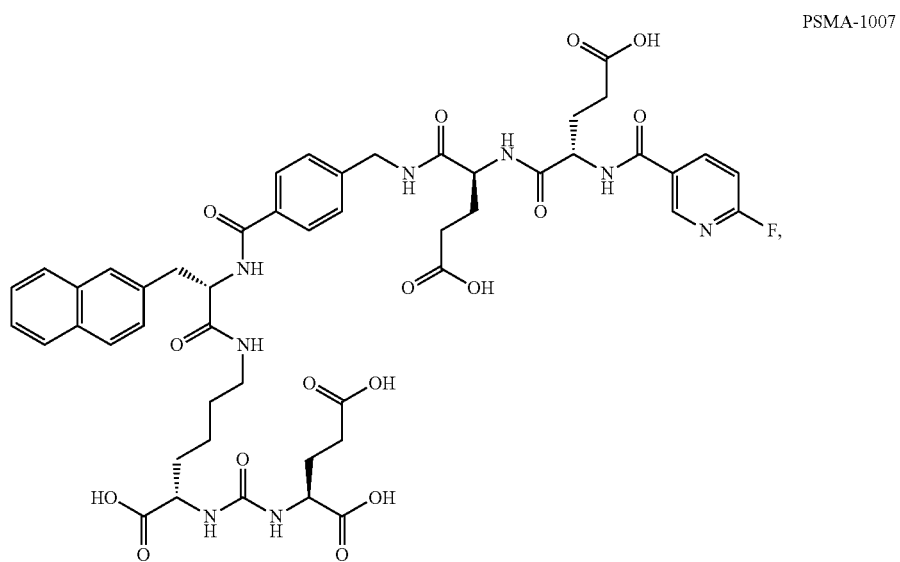 [SMILES: O=C(O)CC[C@H](NC(=O)N[C@@H](CCCCNC(=O)[C@H](Cc1ccc2ccccc2c1)NC(=O)c1ccc(CNC(=O)[C@H](CCC(=O)O)NC(=O)[C@H](CCC(=O)O)NC(=O)c2ccc(F)nc2)cc1)C(=O)O)C(=O)O]

PSMA-1007 or a pharmaceutically acceptable salt thereof. In certain embodiments, the radionuclide labelled PSMA binding agent comprises $^{18}$F-PSMA-1007, which is PSMA-1007 labelled with $^{18}$F, or a pharmaceutically acceptable salt thereof.

ii. SPECT Imaging Radionuclide Labelled PSMA Binding Agents

In certain embodiments, the radionuclide labelled PSMA binding agent is a radionuclide labelled PSMA binding agent appropriate for SPECT imaging.

In certain embodiments, the radionuclide labelled PSMA binding agent comprises 1404 (also referred to as MIP-1404):

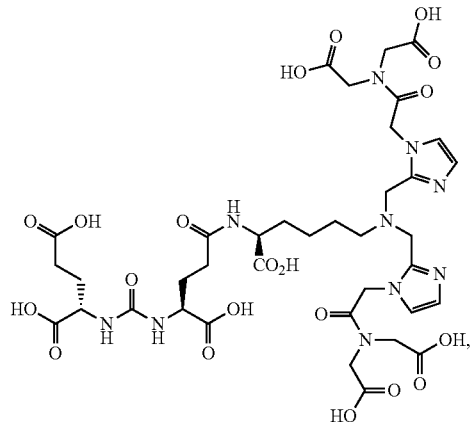

or a pharmaceutically acceptable salt thereof.

In certain embodiments, the radionuclide labelled PSMA binding agent comprises 1405 (also referred to as MIP-1405):

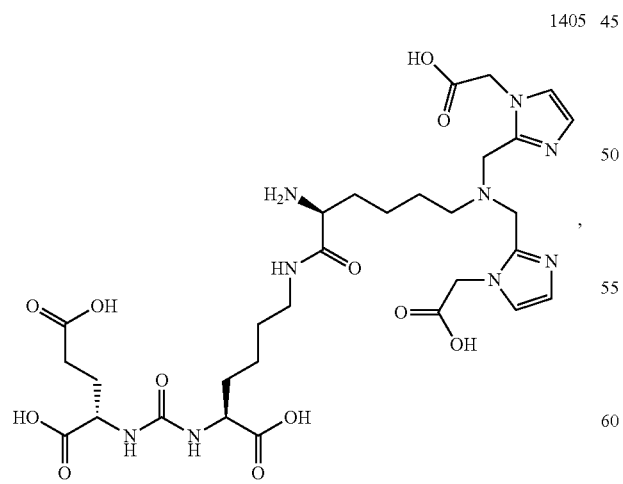

or a pharmaceutically acceptable salt thereof.

In certain embodiments, the radionuclide labelled PSMA binding agent comprises 1427 (also referred to as MIP-1427):

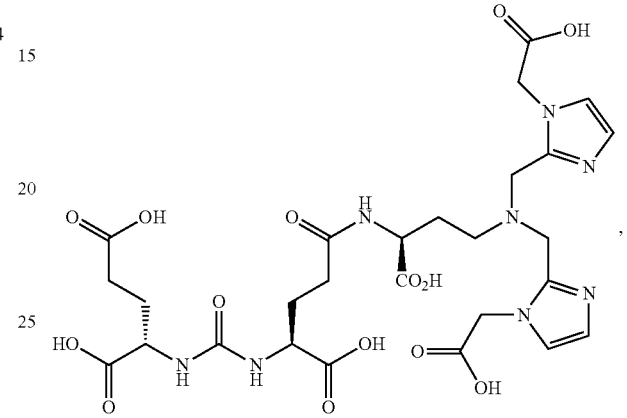

or a pharmaceutically acceptable salt thereof.

In certain embodiments, the radionuclide labelled PSMA binding agent comprises 1428 (also referred to as MIP-1428):

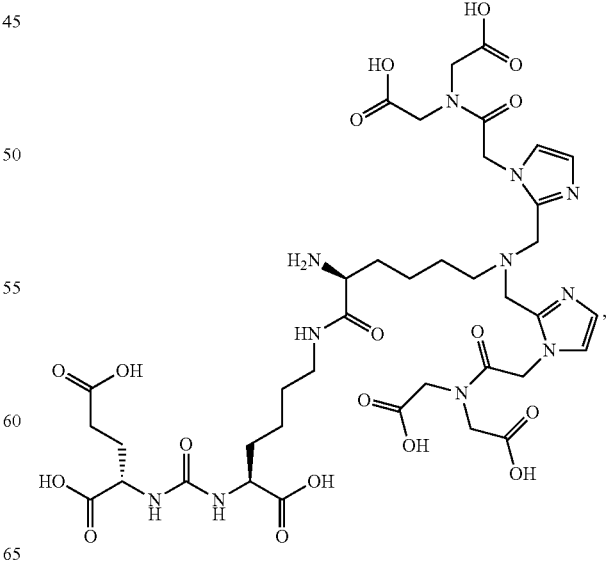

or a pharmaceutically acceptable salt thereof.

In certain embodiments, the PSMA binding agent is labelled with a radionuclide by chelating it to a radioisotope of a metal [e.g., a radioisotope of technetium (Tc) (e.g., technetium-99m ($^{99m}$Tc)); e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu) (e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)].

In certain embodiments, 1404 is labelled with a radionuclide (e.g., chelated to a radioisotope of a metal). In certain embodiments, the radionuclide labelled PSMA binding agent comprises $^{99m}$Tc-MIP-1404, which is 1404 labelled with (e.g., chelated to) $^{99m}$Tc:

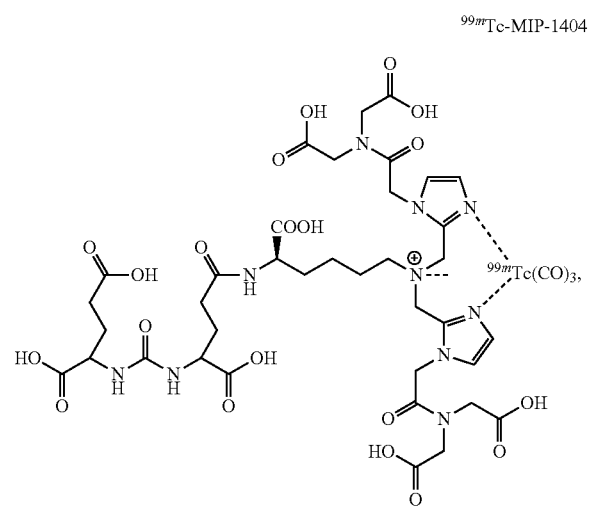

or a pharmaceutically acceptable salt thereof. In certain embodiments, 1404 may be chelated to other metal radioisotopes [e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu)(e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)] to form a compound having a structure similar to the structure shown above for $^{99m}$Tc-MIP-1404, with the other metal radioisotope substituted for $^{99m}$Tc.

In certain embodiments, 1405 is labelled with a radionuclide (e.g., chelated to a radioisotope of a metal). In certain embodiments, the radionuclide labelled PSMA binding agent comprises $^{99m}$Tc-MIP-1405, which is 1405 labelled with (e.g., chelated to) $^{99m}$Tc:

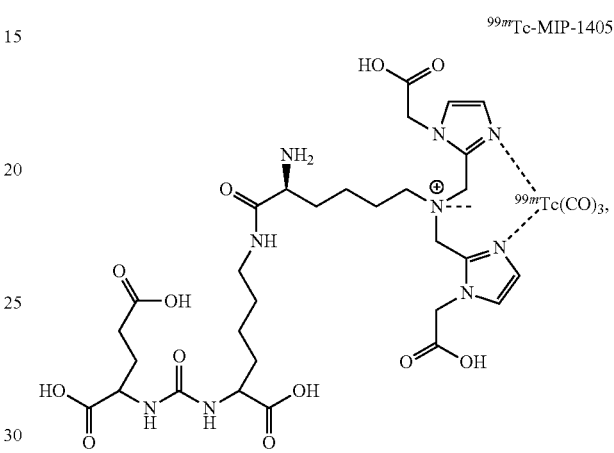

or a pharmaceutically acceptable salt thereof. In certain embodiments, 1405 may be chelated to other metal radioisotopes [e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu)(e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)] to form a compound having a structure similar to the structure shown above for $^{99m}$Tc-MIP-1405, with the other metal radioisotope substituted for $^{99m}$Tc.

In certain embodiments, 1427 is labelled with (e.g., chelated to) a radioisotope of a metal, to form a compound according to the formula below:

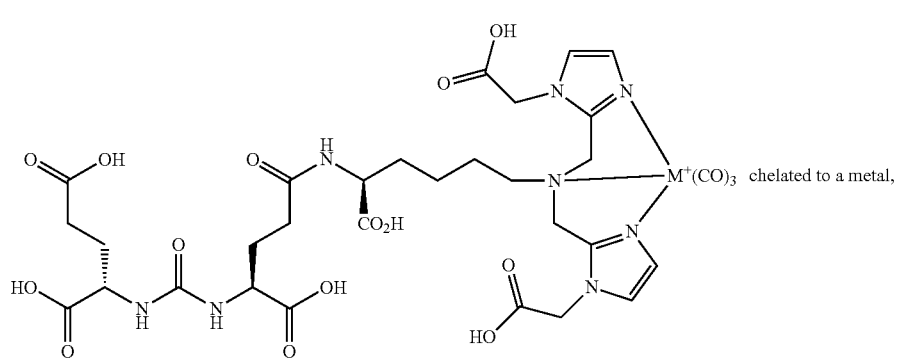

or a pharmaceutically acceptable salt thereof, wherein M is a metal radioisotope [e.g., a radioisotope of technetium (Tc) (e.g., technetium-99m ($^{99m}$Tc)); e.g., a radioisotope of rhenium (Re) (e.g., rhenium-188 $^{188}$Re); (e.g., rhenium-186 ($^{186}$Re)); e.g., a radioisotope of yttrium (Y) (e.g., $^{90}$Y); e.g., a radioisotope of lutetium (Lu)(e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)] with which 1427 is labelled.

In certain embodiments, 1428 is labelled with (e.g., chelated to) a radioisotope of a metal, to form a compound according to the formula below:

or a pharmaceutically acceptable salt thereof. In certain embodiments, the radionuclide labelled PSMA binding agent comprises $^{99m}$Tc-PSMA I&S, which is PSMA I&S labelled with $^{99m}$Tc, or a pharmaceutically acceptable salt thereof.

N. Computer System and Network Architecture

Figure 36:
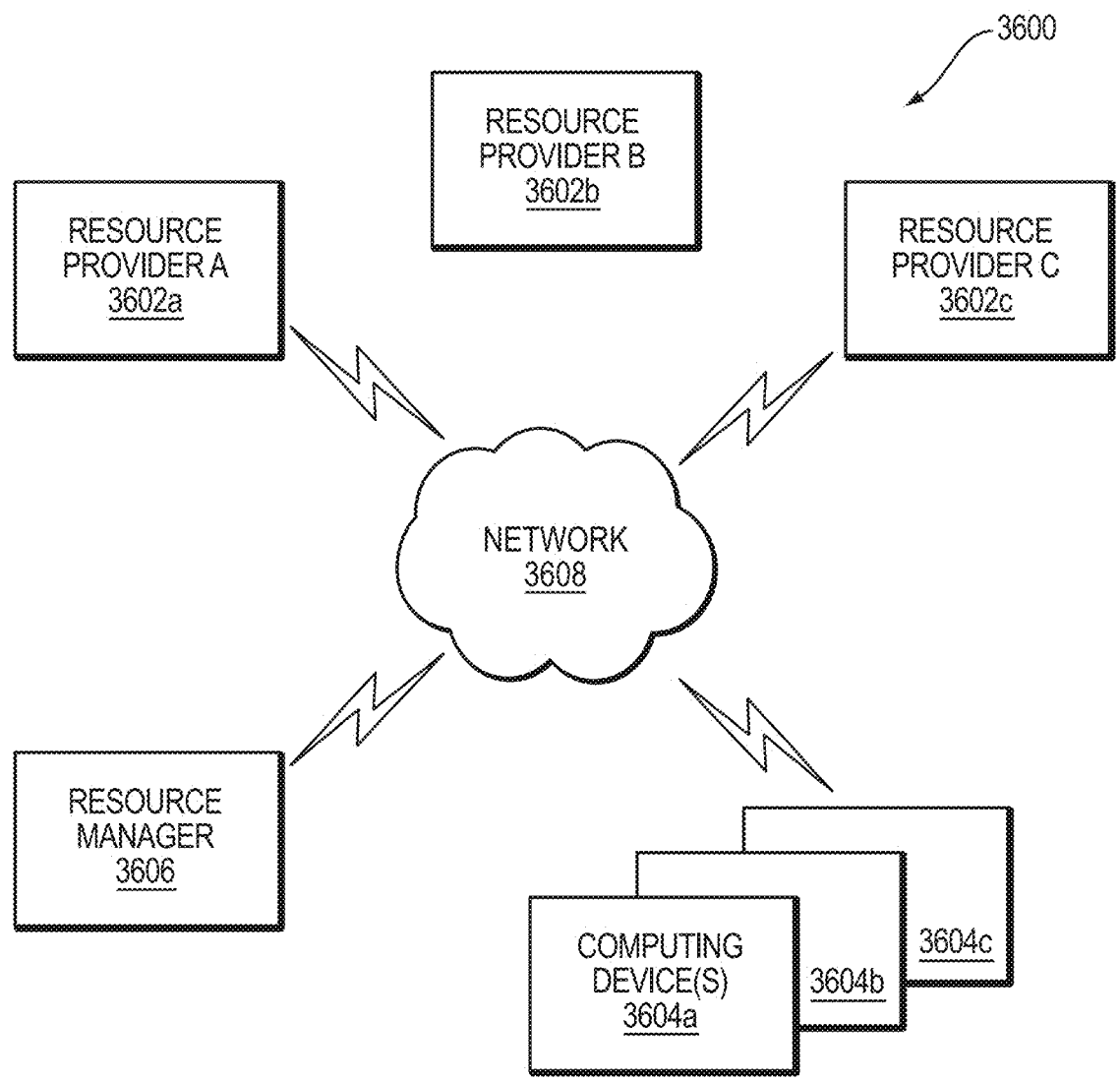
FIG. 36 is a block diagram of an exemplary cloud computing environment, used in certain embodiments.

As shown in FIG. 36, an implementation of a network environment 3600 for use in providing systems, methods, and architectures described herein is shown and described. In brief overview, referring now to FIG. 36, a block diagram of an exemplary cloud computing environment 3600 is

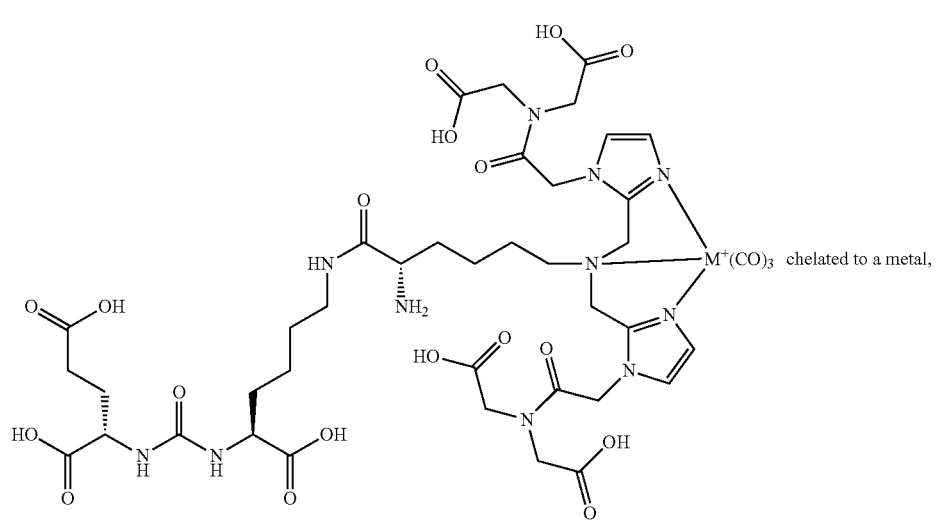

1428 or a pharmaceutically acceptable salt thereof, wherein M is a metal radioisotope [e.g., a radioisotope of technetium (Tc) (e.g., technetium-99m ($^{99m}$Tc)); e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu)(e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)] with which 1428 is labelled.

In certain embodiments, the radionuclide labelled PSMA binding agent comprises PSMA I&S:

shown and described. The cloud computing environment 3600 may include one or more resource providers 3602a, 3602b, 3602c (collectively, 3602). Each resource provider 3602 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each

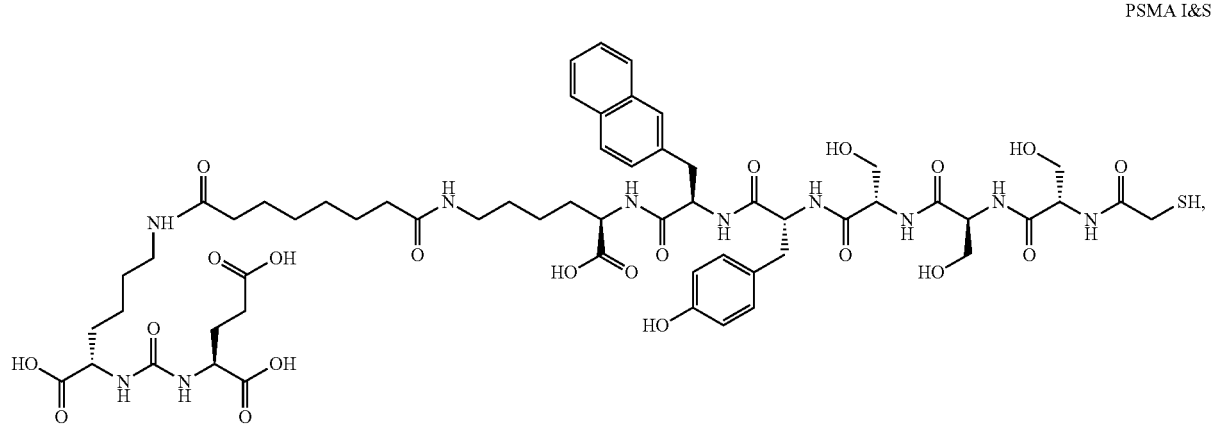 [SMILES: O=C(O)CC[C@H](NC(=O)N[C@@H](CCCCNC(=O)CCCCCCC(=O)NCCCC[C@@H](NC(=O)[C@@H](Cc1ccc2ccccc2c1)NC(=O)[C@@H](Cc1ccc(O)cc1)NC(=O)[C@H](CO)NC(=O)[C@H](CO)NC(=O)[C@H](CO)NC(=O)CS)C(=O)O)C(=O)O)C(=O)O]

PSMA I&S resource provider 3602 may be connected to any other resource provider 3602 in the cloud computing environment 3600. In some implementations, the resource providers 3602 may be connected over a computer network 3608. Each resource provider 3602 may be connected to one or more computing device 3604a, 3604b, 3604c (collectively, 3604), over the computer network 3608.

The cloud computing environment 3600 may include a resource manager 3606. The resource manager 3606 may be connected to the resource providers 3602 and the computing devices 3604 over the computer network 3608. In some implementations, the resource manager 3606 may facilitate the provision of computing resources by one or more resource providers 3602 to one or more computing devices 3604. The resource manager 3606 may receive a request for a computing resource from a particular computing device 3604. The resource manager 3606 may identify one or more resource providers 3602 capable of providing the computing resource requested by the computing device 3604. The resource manager 3606 may select a resource provider 3602 to provide the computing resource. The resource manager 3606 may facilitate a connection between the resource provider 3602 and a particular computing device 3604. In some implementations, the resource manager 3606 may establish a connection between a particular resource provider 3602 and a particular computing device 3604. In some implementations, the resource manager 3606 may redirect a particular computing device 3604 to a particular resource provider 3602 with the requested computing resource.

Figure 37:
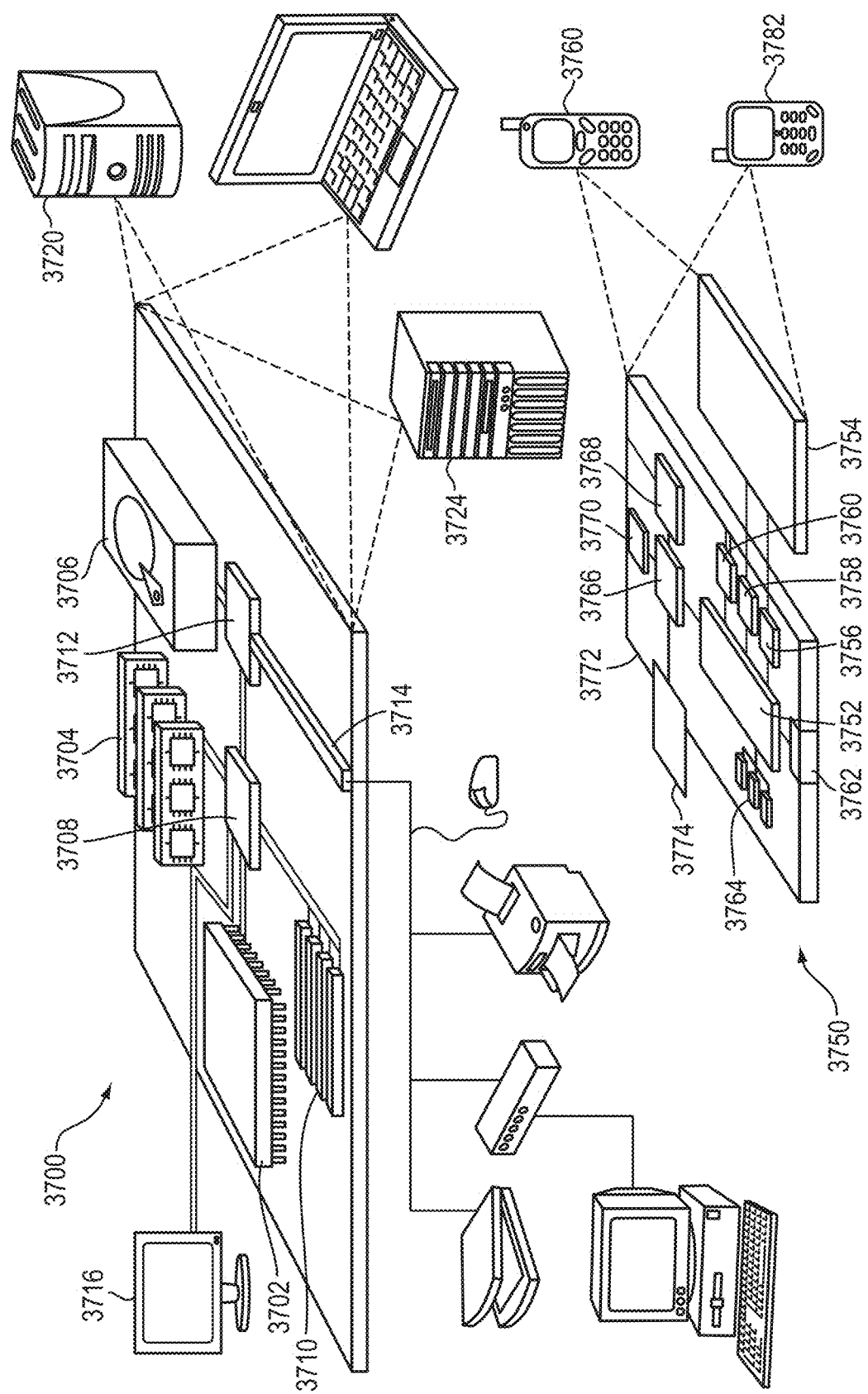
FIG. 37 is a block diagram of an example computing device and an example mobile computing device used in certain embodiments.

FIG. 37 shows an example of a computing device 3700 and a mobile computing device 3750 that can be used to implement the techniques described in this disclosure. The computing device 3700 is intended to represent various forms of digital computers, such as laptops, desktops, workstations, personal digital assistants, servers, blade servers, mainframes, and other appropriate computers. The mobile computing device 3750 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 3700 includes a processor 3702, a memory 3704, a storage device 3706, a high-speed interface 3708 connecting to the memory 3704 and multiple high-speed expansion ports 3710, and a low-speed interface 3712 connecting to a low-speed expansion port 3714 and the storage device 3706. Each of the processor 3702, the memory 3704, the storage device 3706, the high-speed interface 3708, the high-speed expansion ports 3710, and the low-speed interface 3712, are interconnected using various busses, and may be mounted on a common motherboard or in other manners as appropriate. The processor 3702 can process instructions for execution within the computing device 3700, including instructions stored in the memory 3704 or on the storage device 3706 to display graphical information for a GUI on an external input/output device, such as a display 3716 coupled to the high-speed interface 3708. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plural-ity of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 3704 stores information within the computing device 3700. In some implementations, the memory 3704 is a volatile memory unit or units. In some implementations, the memory 3704 is a non-volatile memory unit or units. The memory 3704 may also be another form of computer-readable medium, such as a magnetic or optical disk.

The storage device 3706 is capable of providing mass storage for the computing device 3700. In some implementations, the storage device 3706 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 3702), perform one or more methods, such as those described above. The instructions can also be stored by one or more storage devices such as computer- or machine-readable mediums (for example, the memory 3704, the storage device 3706, or memory on the processor 3702).

The high-speed interface 3708 manages bandwidth-intensive operations for the computing device 3700, while the low-speed interface 3712 manages lower bandwidth-intensive operations. Such allocation of functions is an example only. In some implementations, the high-speed interface 3708 is coupled to the memory 3704, the display 3716 (e.g., through a graphics processor or accelerator), and to the high-speed expansion ports 3710, which may accept various expansion cards (not shown). In the implementation, the low-speed interface 3712 is coupled to the storage device 3706 and the low-speed expansion port 3714. The low-speed expansion port 3714, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 3700 may be implemented in a number of different forms, as shown in the figure. For example, it may be implemented as a standard server 3720, or multiple times in a group of such servers. In addition, it may be implemented in a personal computer such as a laptop computer 3722. It may also be implemented as part of a rack server system 3724. Alternatively, components from the computing device 3700 may be combined with other components in a mobile device (not shown), such as a mobile computing device 3750. Each of such devices may contain one or more of the computing device 3700 and the mobile computing device 3750, and an entire system may be made up of multiple computing devices communicating with each other.

The mobile computing device 3750 includes a processor 3752, a memory 3764, an input/output device such as a display 3754, a communication interface 3766, and a transceiver 3768, among other components. The mobile computing device 3750 may also be provided with a storage device, such as a micro-drive or other device, to provide additional storage. Each of the processor 3752, the memory 3764, the display 3754, the communication interface 3766, and the transceiver 3768, are interconnected using various buses, and several of the components may be mounted on a common motherboard or in other manners as appropriate.

The processor 3752 can execute instructions within the mobile computing device 3750, including instructions stored in the memory 3764. The processor 3752 may be implemented as a chipset of chips that include separate and multiple analog and digital processors. The processor 3752 may provide, for example, for coordination of the other components of the mobile computing device 3750, such as control of user interfaces, applications run by the mobile computing device 3750, and wireless communication by the mobile computing device 3750.

The processor 3752 may communicate with a user through a control interface 3758 and a display interface 3756 coupled to the display 3754. The display 3754 may be, for example, a TFT (Thin-Film-Transistor Liquid Crystal Display) display or an OLED (Organic Light Emitting Diode) display, or other appropriate display technology. The display interface 3756 may comprise appropriate circuitry for driving the display 3754 to present graphical and other information to a user. The control interface 3758 may receive commands from a user and convert them for submission to the processor 3752. In addition, an external interface 3762 may provide communication with the processor 3752, so as to enable near area communication of the mobile computing device 3750 with other devices. The external interface 3762 may provide, for example, for wired communication in some implementations, or for wireless communication in other implementations, and multiple interfaces may also be used.

The memory 3764 stores information within the mobile computing device 3750. The memory 3764 can be implemented as one or more of a computer-readable medium or media, a volatile memory unit or units, or a non-volatile memory unit or units. An expansion memory 3774 may also be provided and connected to the mobile computing device 3750 through an expansion interface 3772, which may include, for example, a SIMM (Single In Line Memory Module) card interface. The expansion memory 3774 may provide extra storage space for the mobile computing device 3750, or may also store applications or other information for the mobile computing device 3750. Specifically, the expansion memory 3774 may include instructions to carry out or supplement the processes described above, and may include secure information also. Thus, for example, the expansion memory 3774 may be provide as a security module for the mobile computing device 3750, and may be programmed with instructions that permit secure use of the mobile computing device 3750. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 3752), perform one or more methods, such as those described above. The instructions can also be stored by one or more storage devices, such as one or more computer- or machine-readable mediums (for example, the memory 3764, the expansion memory 3774, or memory on the processor 3752). In some implementations, the instructions can be received in a propagated signal, for example, over the transceiver 3768 or the external interface 3762.

The mobile computing device 3750 may communicate wirelessly through the communication interface 3766, which may include digital signal processing circuitry where necessary. The communication interface 3766 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 3768 using a radio-frequency. In addition, short-range communication may occur, such as using a Bluetooth®, Wi-Fi™, or other such transceiver (not shown). In addition, a GPS (Global Positioning System) receiver module 3770 may provide additional navigation- and location-related wireless data to the mobile computing device 3750, which may be used as appropriate by applications running on the mobile computing device 3750.

The mobile computing device 3750 may also communicate audibly using an audio codec 3760, which may receive spoken information from a user and convert it to usable digital information. The audio codec 3760 may likewise generate audible sound for a user, such as through a speaker, e.g., in a handset of the mobile computing device 3750. Such sound may include sound from voice telephone calls, may include recorded sound (e.g., voice messages, music files, etc.) and may also include sound generated by applications operating on the mobile computing device 3750.

The mobile computing device 3750 may be implemented in a number of different forms, as shown in the figure. For example, it may be implemented as a cellular telephone 3780. It may also be implemented as part of a smart-phone 3782, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the various modules described herein can be separated, combined or incorporated into single or combined modules. The modules depicted in the figures are not intended to limit the systems described herein to the software architectures shown therein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for automatically processing 3D images to identify 3D volumes within the 3D images that correspond to a prostate of a subject and determining one or more uptake metrics indicative of radiopharmaceutical uptake therein, the method comprising:
   (a) receiving, by a processor of a computing device, a 3D anatomical image of the subject obtained using an anatomical imaging modality, wherein the 3D anatomical image comprises a graphical representation of tissue within a subject, at least a portion of which corresponds to a pelvic region of the subject;
   (b) receiving, by the processor, a 3D functional image of the subject obtained using a functional imaging modality, wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the pelvic region of the subject;
   (c) determining, by the processor, using a first module, an initial volume of interest (VOI) within the 3D anatomical image, the initial VOI corresponding to tissue within the pelvic region of the subject and excluding tissue outside the pelvic region of the subject;
   (d) identifying, by the processor, using a second module, a prostate volume within the initial VOI corresponding to the prostate of the subject; and
   (e) determining, by the processor, the one or more uptake metrics using the 3D functional image and the prostate volume identified within the initial VOI of the 3D anatomical image, and
   wherein the method comprises:
   identifying, by the processor, a reference volume within the 3D anatomical image, the reference volume corresponding to a reference tissue region within the subject; and
   at step (e), determining at least one of the one or more uptake metrics using the 3D functional image and the reference volume identified within the 3D anatomical image.

2. The method of claim 1, wherein the at least one of the one or more uptake metrics determined using the 3D functional image and the reference volume comprises a tumor to background ratio (TBR) value, and wherein determining the TBR value comprises:
   determining a target intensity value using intensity values of one or more voxels of the 3D functional image that correspond to the prostate volume identified within the initial VOI of the 3D anatomical image;
   determining a background intensity value using intensity values of one or more voxels of the 3D functional image that correspond to the reference volume identified within the 3D anatomical image; and
   determining, as the TBR value, a ratio of the target intensity value to the background intensity value.

3. The method of claim 2, comprising determining a prostate cancer status for the subject based on the TBR value in comparison with one or more threshold values.

4. The method of claim 3, wherein the one or more threshold values are determined using a plurality of reference TBR values, each reference TBR value associated with a particular classification prostate cancer status.

5. The method of claim 3, wherein the one or more threshold values are determined using a receiver operating characteristic (ROC) curve.

6. The method of claim 3, comprising determining the prostate cancer status for the subject to be (i) clinically significant if the TBR value is above a cutoff threshold or (ii) clinically non-significant if the TBR value is below the cutoff threshold.

7. The method of claim 1, the method comprising:
identifying, by the processor, a bladder volume within the 3D anatomical image corresponding to a bladder of the subject; and
at step (e), correcting for cross-talk from the bladder using intensities of voxels of the 3D functional image corresponding to the identified bladder volume within the 3D anatomical image.

8. The method of claim 7, wherein correcting for cross-talk from the bladder comprises:
determining one or more bladder intensity bleed functions that model a contribution of intensity originating from radiopharmaceutical within the bladder of the subject to intensity of one or more voxels of the 3D functional image corresponding to one or more regions of the 3D anatomical image that are outside of the identified bladder volume, wherein the one or more bladder intensity bleed functions model said contribution as a function of distance from the identified bladder volume; and
for each of one or more voxels of the 3D functional image corresponding to the identified prostate volume within the 3D anatomical image, adjusting an intensity of the voxel for bladder cross-talk using the one or more bladder intensity bleed functions.

9. The method of claim 1, comprising:
identifying, by the processor, a bladder volume within the 3D anatomical image corresponding to a bladder of the subject;
determining, by the processor, a dilated bladder volume by applying a morphological dilation operation to the identified bladder volume; and
at step (e), determining the one or more uptake metrics using intensity values of voxels of the 3D functional image that (i) correspond to the prostate volume identified within the VOI of the 3D anatomical image, but (ii) do not correspond to regions of the 3D anatomical image within the dilated bladder volume.

10. The method of claim 1, wherein the 3D functional image is a nuclear medicine image of the subject following administration to the subject of the radiopharmaceutical.

11. The method of claim 10, wherein the radiopharmaceutical comprises a PSMA binding agent.

12. The method of claim 10, wherein the nuclear medicine image is a single-photon emission computerized tomography (SPECT) scan of the subject obtained following administration to the subject of the radiopharmaceutical.

13. The method of claim 10, wherein the radiopharmaceutical comprises $^{99m}$Tc-MIP-1404.

14. The method of claim 1, the method comprising:
causing, by the processor, display of an interactive graphical user interface (GUI) for presentation to the user of a visual representation of the 3D anatomical image and/or the 3D functional image; and
(g) causing, by the processor, graphical rendering of, within the GUI, the 3D anatomical image and/or the 3D functional image as selectable and superimposable layers, such that either can be selected for display and rendered separately, or both selected for display and rendered together by overlaying the 3D anatomical image with the 3D functional image.

15. The method of claim 14, comprising causing display of, within the GUI, text and/or graphics representing the one or more uptake metrics determined in step (e) along with a quality control graphical widget for guiding the user through a quality control and reporting workflow for review and/or updating of the one or more uptake metrics.

16. The method of claim 15, comprising:
receiving, via the quality control graphical widget, a user input corresponding to an approval of automated determination of the one or more uptake metrics; and
responsive to the receipt of the user input corresponding to the approval of the automated determination of the one or more uptake metrics, generating, by the processor, a report for the subject comprising a representation of the one or more automatically determined uptake metrics.

17. The method of claim 15, comprising:
receiving, via the quality control graphical widget, a user input corresponding to disapproval of automated determination of the one or more uptake metrics;
responsive to receipt of the user input corresponding to the disapproval of the automated determination of the one or more uptake metrics, causing, by the processor, display of a voxel selection graphical element for user selection of one or more voxels of the 3D functional image for use in determining updated values of the one or more uptake metrics;
receiving, via the voxel selection graphical element, the user selection of one or more voxels of the 3D functional image for use in determining updated values of the one or more uptake metrics;
updating, by the processor, values of the one or more uptake metrics using the user selected voxels; and
generating, by the processor, a report for the subject comprising a representation of the one or more updated uptake metrics.

18. The method of claim 15, comprising:
receiving, via the quality control graphical widget, a user input corresponding to disapproval of automated determination of the one or more uptake metrics;
receiving, via the quality control graphical widget, a user input corresponding to a rejection of quality control; and
generating, by the processor, a report for the subject, wherein the report comprises an identification of the rejection of quality control.

19. The method of claim 14, wherein step (g) comprises causing graphical rendering of a selectable and superimposable segmentation layer comprising one or more identified specific tissue volumes within the 3D anatomical image, wherein upon selection of the segmentation layer for display, graphics representing the one or more specific tissue volumes are overlaid on the 3D anatomical image and/or the 3D functional image.

20. The method of claim 19, wherein the one or more specific tissue volumes comprise(s) the identified prostate volume.

21. The method of claim 14, the method comprising, at step (g), causing rendering of a 2D cross sectional view of the 3D anatomical image and/or the 3D functional image within an interactive 2D viewer, such that a position of the 2D cross sectional view is adjustable by the user.

22. The method of claim 14 the method comprising, at step (g), causing rendering of an interactive 3D view of the 3D anatomical image and/or the 3D functional image.

23. The method of claim 14, comprising causing display of, within the GUI, a graphical element indicating a location corresponding to a voxel of the identified prostate volume, thereby facilitating user review and/or quality control of the method.

24. The method of claim 1, wherein the first module receives the 3D anatomical image as input and outputs a plurality of coordinate values representing opposite corners of a rectangular volume within the 3D anatomical image.

25. The method of claim 1, wherein step (c) comprises determining, using the first module, a 3D pelvic bone mask that identifies a volume of the 3D anatomical image corresponding to pelvic bones of the subject.

26. The method of claim 1, wherein the first module is a Convolutional Neural Network (CNN) module.

27. The method of claim 1, wherein step (d) comprises using the second module to identify one or more additional tissue volumes within the 3D anatomical image, each volume corresponding to a specific tissue region within the subject, wherein the one or more additional tissue volumes correspond(s) to one or more specific tissue regions selected from the group consisting of:
a pelvic bone of the subject;
a bladder of the subject;
a rectum of the subject; and
a gluteal muscle of the subject.

28. The method of claim 27, wherein step (d) comprises using the second module to identify a set of one or more base tissue volumes, the one or more base tissue volumes comprising the identified prostate volume and the one or more additional tissue volumes, and wherein the method further comprises:
identifying, by the processor, using one or more auxiliary modules, one or more auxiliary tissue volumes within the 3D anatomical image, each auxiliary tissue volume corresponding to a base tissue volume identified by the second module; and
merging, by the processor, each auxiliary tissue volume with the corresponding base tissue volume identified by the second module.

29. The method of claim 1, wherein step (d) comprises using the second module to classify each voxel within the initial VOI as corresponding a particular tissue region of a set of different tissue regions within the subject.

30. The method of claim 29, wherein classifying each voxel within the initial VOI comprises:
determining, via the second module, for each of a plurality of voxels within the initial VOI, a set of likelihood values, wherein the set of likelihood values comprises, for each of one or more tissue regions of the tissue region set, a corresponding likelihood value that represents a likelihood that the voxel represents a physical volume within the tissue region; and
for each of the plurality of voxels within the initial VOI, classifying the voxel as corresponding to the particular tissue region based on the set of likelihood values determined for the voxel.

31. The method of claim 29, wherein the second module receives as input the initial VOI and outputs a plurality of values comprising, for each voxel within the initial VOI, at least one of (i), (ii), and (iii) as follows:
a value classifying the voxel;
(ii) a set of likelihood values for the voxel; and
(iii) a value identifying the voxel as not corresponding to any of a predetermined set of different tissue regions.

32. The method of claim 29, wherein the set of different tissue regions comprises one or more tissue regions selected from the group consisting of:
the prostate of the subject;
a pelvic bone of the subject;
a bladder of the subject;
a rectum of the subject; and
a gluteal muscle f the subject.

33. The method of claim 1, the method comprising determining, based on at least a portion of the one or more uptake metrics, one or more diagnostic or prognostic values for the subject.

34. The method of claim 33, wherein determining at least one of the one or more diagnostic or prognostic values comprises comparing an uptake metric to one or more threshold value(s).

35. The method of claim 33, wherein at least one of the one or more diagnostic or prognostic values estimates a risk for clinically significant prostate cancer in the subject.

36. The method of claim 1, wherein voxels of the 3D functional image are related to voxels of the 3D anatomical image via a known relationship.

37. The method of claim 1, wherein the first module is a first CNN (convolutional neural network) module and the second module is a second CNN module, wherein the second CNN module comprises a greater number of convolutional filters than the first CNN module.

38. The method of claim 1, comprising performing steps (a) and (c) for each of a plurality of 3D anatomical images to determine a plurality of initial VOIs, each within one of the plurality of 3D anatomical images, wherein a variability in sizes of the initial VOIs is less than a variability in sizes of the 3D anatomical images.

39. A system for automatically processing 3D images to identify 3D volumes within the 3D images that correspond to a prostate of a subject and determining one or more uptake metrics indicative of radiopharmaceutical uptake therein, the system comprising:
a processor; and
a memory having instructions stored thereon, wherein the instructions, when executed by the processor, cause the processor to:
(a) receive a 3D anatomical image of the subject obtained using an anatomical imaging modality, wherein the 3D anatomical image comprises a graphical representation of tissue within a subject, at least a portion of which corresponds to a pelvic region of the subject;
(b) receive a 3D functional image of the subject obtained using a functional imaging modality, wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the pelvic region of the subject;
(c) determine, using a first module, an initial volume of interest (VOI) within the 3D anatomical image, the initial VOI corresponding to tissue within the pelvic region of the subject and excluding tissue outside the pelvic region of the subject;
(d) identify, using a second module, a prostate volume within the initial VOI corresponding to the prostate of the subject; and (e) determine the one or more uptake metrics using the 3D functional image and the prostate volume identified within the initial VOI of the 3D anatomical image, and wherein the instructions, when executed by the processor, cause the processor to:
identify a reference volume within the 3D anatomical image, the reference volume corresponding to a reference tissue region within the subject; and
at step (e), determine at least one of the one or more uptake metrics using the 3D functional image and the reference volume identified within the 3D anatomical image.

40. A method for automatically processing 3D images to identify 3D volumes within the 3D images that correspond to a prostate of a subject and determining one or more uptake metrics indicative of radiopharmaceutical uptake therein, the method comprising:
(a) receiving, by a processor of a computing device, a 3D anatomical image of the subject obtained using an anatomical imaging modality, wherein the 3D anatomical image comprises a graphical representation of tissue within a subject, at least a portion of which corresponds to a pelvic region of the subject;
(b) receiving, by the processor, a 3D functional image of the subject obtained using a functional imaging modality, wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the pelvic region of the subject;
(c) determining, by the processor, using a first module, an initial volume of interest (VOI) within the 3D anatomical image, the initial VOI corresponding to tissue within the pelvic region of the subject and excluding tissue outside the pelvic region of the subject;
(d) identifying, by the processor, using a second module, a prostate volume within the initial VOI corresponding to the prostate of the subject; and
(e) determining, by the processor, the one or more uptake metrics using the 3D functional image and the prostate volume identified within the initial VOI of the 3D anatomical image, and
wherein the method further comprises:
identifying, by the processor, a bladder volume within the 3D anatomical image corresponding to a bladder of the subject; and
at step (e), correcting for cross-talk from the bladder using intensities of voxels of the 3D functional image corresponding to the identified bladder volume within the 3D anatomical image.

41. A method for automatically processing 3D images to identify 3D volumes within the 3D images that correspond to a prostate of a subject and determining one or more uptake metrics indicative of radiopharmaceutical uptake therein, the method comprising:
(a) receiving, by a processor of a computing device, a 3D anatomical image of the subject obtained using an anatomical imaging modality, wherein the 3D anatomical image comprises a graphical representation of tissue within a subject, at least a portion of which corresponds to a pelvic region of the subject;
(b) receiving, by the processor, a 3D functional image of the subject obtained using a functional imaging modality, wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the pelvic region of the subject;
(c) determining, by the processor, using a first module, an initial volume of interest (VOI) within the 3D anatomical image, the initial VOI corresponding to tissue within the pelvic region of the subject and excluding tissue outside the pelvic region of the subject;
(d) identifying, by the processor, using a second module, a prostate volume within the initial VOI corresponding to the prostate of the subject; and
(e) determining, by the processor, the one or more uptake metrics using the 3D functional image and the prostate volume identified within the initial VOI of the 3D anatomical image, and
wherein the method further comprises:
identifying, by the processor, a bladder volume within the 3D anatomical image corresponding to a bladder of the subject;
determining, by the processor, a dilated bladder volume by applying a morphological dilation operation to the identified bladder volume; and
at step (e), determining the one or more uptake metrics using intensity values of voxels of the 3D functional image that (i) correspond to the prostate volume identified within the VOI of the 3D anatomical image, but (ii) do not correspond to regions of the 3D anatomical image within the dilated bladder volume.

42. A method for automatically processing 3D images to identify 3D volumes within the 3D images that correspond to a prostate of a subject and determining one or more uptake metrics indicative of radiopharmaceutical uptake therein, the method comprising:
(a) receiving, by a processor of a computing device, a 3D anatomical image of the subject obtained using an anatomical imaging modality, wherein the 3D anatomical image comprises a graphical representation of tissue within a subject, at least a portion of which corresponds to a pelvic region of the subject;
(b) receiving, by the processor, a 3D functional image of the subject obtained using a functional imaging modality, wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the pelvic region of the subject;
(c) determining, by the processor, using a first module, an initial volume of interest (VOI) within the 3D anatomical image, the initial VOI corresponding to tissue within the pelvic region of the subject and excluding tissue outside the pelvic region of the subject;
(d) identifying, by the processor, using a second module, a prostate volume within the initial VOI corresponding to the prostate of the subject;
(e) determining, by the processor, the one or more uptake metrics using the 3D functional image and the prostate volume identified within the initial VOI of the 3D anatomical image;
causing, by the processor, display of an interactive graphical user interface (GUI) for presentation to the user of a visual representation of the 3D anatomical image and/or the 3D functional image; and (g) causing, by the processor, graphical rendering of, within the GUI, the 3D anatomical image and/or the 3D functional image as selectable and superimposable layers, such that either can be selected for display and rendered separately, or both selected for display and rendered together by overlaying the 3D anatomical image with the 3D functional image.

43. A method for automatically processing 3D images to identify 3D volumes within the 3D images that correspond to a prostate of a subject and determining one or more uptake metrics indicative of radiopharmaceutical uptake therein, the method comprising:

(a) receiving, by a processor of a computing device, a 3D anatomical image of the subject obtained using an anatomical imaging modality, wherein the 3D anatomical image comprises a graphical representation of tissue within a subject, at least a portion of which corresponds to a pelvic region of the subject;

(b) receiving, by the processor, a 3D functional image of the subject obtained using a functional imaging modality, wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the pelvic region of the subject;

(c) determining, by the processor, using a first module, an initial volume of interest (VOI) within the 3D anatomical image, the initial VOI corresponding to tissue within the pelvic region of the subject and excluding tissue outside the pelvic region of the subject;

(d) identifying, by the processor, using a second module, a prostate volume within the initial VOI corresponding to the prostate of the subject; and (e) determining, by the processor, the one or more uptake metrics using the 3D functional image and the prostate volume identified within the initial VOI of the 3D anatomical image;

wherein step (d) comprises using the second module to identify one or more additional tissue volumes within the 3D anatomical image, each volume corresponding to a specific tissue region within the subject, wherein the one or more additional tissue volumes correspond(s) to one or more specific tissue regions selected from the group consisting of:
  a pelvic bone of the subject;
  a bladder of the subject;
  a rectum of the subject; and
  a gluteal muscle of the subject; and
wherein the method further comprises:
  identifying, by the processor, using one or more auxiliary modules, one or more auxiliary tissue volumes within the 3D anatomical image, each auxiliary tissue volume corresponding to a base tissue volume identified by the second module; and
  merging, by the processor, each auxiliary tissue volume with the corresponding base tissue volume identified by the second module.

44. A method for automatically processing 3D images to identify 3D volumes within the 3D images that correspond to a prostate of a subject and determining one or more uptake metrics indicative of radiopharmaceutical uptake therein, the method comprising:

(a) receiving, by a processor of a computing device, a 3D anatomical image of the subject obtained using an anatomical imaging modality, wherein the 3D anatomical image comprises a graphical representation of tissue within a subject, at least a portion of which corresponds to a pelvic region of the subject;

(b) receiving, by the processor, a 3D functional image of the subject obtained using a functional imaging modality, wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the pelvic region of the subject;

(c) determining, by the processor, using a first module, an initial volume of interest (VOI) within the 3D anatomical image, the initial VOI corresponding to tissue within the pelvic region of the subject and excluding tissue outside the pelvic region of the subject;

(d) identifying, by the processor, using a second module, a prostate volume within the initial VOI corresponding to the prostate of the subject;

(e) determining, by the processor, the one or more uptake metrics using the 3D functional image and the prostate volume identified within the initial VOI of the 3D anatomical image; and determining, by the processor, based on at least a portion of the one or more uptake metrics, one or more diagnostic or prognostic values for the subject, wherein for at least one of the one or more diagnostic or prognostic values said determining comprises comparing an uptake metric to one or more threshold value(s).

45. A method for automatically processing 3D images to identify 3D volumes within the 3D images that correspond to a prostate of a subject and determining one or more uptake metrics indicative of radiopharmaceutical uptake therein, the method comprising:

(a) receiving, by a processor of a computing device, a 3D anatomical image of the subject obtained using an anatomical imaging modality, wherein the 3D anatomical image comprises a graphical representation of tissue within a subject, at least a portion of which corresponds to a pelvic region of the subject;

(b) receiving, by the processor, a 3D functional image of the subject obtained using a functional imaging modality, wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the pelvic region of the subject;

(c) determining, by the processor, using a first module, an initial volume of interest (VOI) within the 3D anatomical image, the initial VOI corresponding to tissue within the pelvic region of the subject and excluding tissue outside the pelvic region of the subject;

(d) identifying, by the processor, using a second module, a prostate volume within the initial VOI corresponding to the prostate of the subject;

(e) determining, by the processor, the one or more uptake metrics using the 3D functional image and the prostate volume identified within the initial VOI of the 3D anatomical image; and determining, by the processor, based on at least a portion of the one or more uptake metrics, one or more diagnostic or prognostic values for the subject, wherein at least one of the one or more diagnostic or prognostic values estimates a risk for clinically significant prostate cancer in the subject.

46. A method for automatically processing 3D images to identify 3D volumes within the 3D images that correspond to a prostate of a subject and determining one or more uptake metrics indicative of radiopharmaceutical uptake therein, the method comprising:
(a) receiving, by a processor of a computing device, a 3D anatomical image of the subject obtained using an anatomical imaging modality, wherein the 3D anatomical image comprises a graphical representation of tissue within a subject, at least a portion of which corresponds to a pelvic region of the subject;
(b) receiving, by the processor, a 3D functional image of the subject obtained using a functional imaging modality, wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the pelvic region of the subject;
(c) determining, by the processor, using a first module, an initial volume of interest (VOI) within the 3D anatomical image, the initial VOI corresponding to tissue within the pelvic region of the subject and excluding tissue outside the pelvic region of the subject;
(d) identifying, by the processor, using a second module, a prostate volume within the initial VOI corresponding to the prostate of the subject; and
(e) determining, by the processor, the one or more uptake metrics using the 3D functional image and the prostate volume identified within the initial VOI of the 3D anatomical image,
wherein the first module is a first CNN (convolutional neural network) module and the second module is a second CNN module, wherein the second CNN module comprises a greater number of convolutional filters than the first CNN module.

47. A method for automatically processing 3D images to identify 3D volumes within the 3D images that correspond to a prostate of a subject and determining one or more uptake metrics indicative of radiopharmaceutical uptake therein, the method comprising:
(a) receiving, by a processor of a computing device, a 3D anatomical image of the subject obtained using an anatomical imaging modality, wherein the 3D anatomical image comprises a graphical representation of tissue within a subject, at least a portion of which corresponds to a pelvic region of the subject;
(b) receiving, by the processor, a 3D functional image of the subject obtained using a functional imaging modality, wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the pelvic region of the subject;
(c) determining, by the processor, using a first module, an initial volume of interest (VOI) within the 3D anatomical image, the initial VOI corresponding to tissue within the pelvic region of the subject and excluding tissue outside the pelvic region of the subject;
(d) identifying, by the processor, using a second module, a prostate volume within the initial VOI corresponding to the prostate of the subject; and
(e) determining, by the processor, the one or more uptake metrics using the 3D functional image and the prostate volume identified within the initial VOI of the 3D anatomical image,
wherein the method comprises performing steps (a) and (c) for each of a plurality of 3D anatomical images to determine a plurality of initial VOIs, each within one of the plurality of 3D anatomical images, wherein a variability in sizes of the initial VOIs is less than a variability in sizes of the 3D anatomical images.

48. A system for automatically processing 3D images to identify 3D volumes within the 3D images that correspond to a prostate of a subject and determining one or more uptake metrics indicative of radiopharmaceutical uptake therein, the system comprising:
a processor; and
a memory having instructions stored thereon, wherein the instructions, when executed by the processor, cause the processor to:
(a) receive a 3D anatomical image of the subject obtained using an anatomical imaging modality, wherein the 3D anatomical image comprises a graphical representation of tissue within a subject, at least a portion of which corresponds to a pelvic region of the subject;
(b) receive a 3D functional image of the subject obtained using a functional imaging modality, wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the pelvic region of the subject;
(c) determine, using a first module, an initial volume of interest (VOI) within the 3D anatomical image, the initial VOI corresponding to tissue within the pelvic region of the subject and excluding tissue outside the pelvic region of the subject;
(d) identify, using a second module, a prostate volume within the initial VOI corresponding to the prostate of the subject; and
(e) determine the one or more uptake metrics using the 3D functional image and the prostate volume identified within the initial VOI of the 3D anatomical image, and
wherein the instructions further cause the processor to:
identify a bladder volume within the 3D anatomical image corresponding to a bladder of the subject; and
at step (e), correct for cross-talk from the bladder using intensities of voxels of the 3D functional image corresponding to the identified bladder volume within the 3D anatomical image.

49. A system for automatically processing 3D images to identify 3D volumes within the 3D images that correspond to a prostate of a subject and determining one or more uptake metrics indicative of radiopharmaceutical uptake therein, the system comprising:
  a processor; and
  a memory having instructions stored thereon, wherein the instructions, when executed by the processor, cause the processor to:
    (a) receive a 3D anatomical image of the subject obtained using an anatomical imaging modality, wherein the 3D anatomical image comprises a graphical representation of tissue within a subject, at least a portion of which corresponds to a pelvic region of the subject;
    (b) receive a 3D functional image of the subject obtained using a functional imaging modality, wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the pelvic region of the subject;
    (c) determine, using a first module, an initial volume of interest (VOI) within the 3D anatomical image, the initial VOI corresponding to tissue within the pelvic region of the subject and excluding tissue outside the pelvic region of the subject;
    (d) identify, using a second module, a prostate volume within the initial VOI corresponding to the prostate of the subject; and
    (e) determine the one or more uptake metrics using the 3D functional image and the prostate volume identified within the initial VOI of the 3D anatomical image, and
  wherein the instructions further cause the processor to:
    identify a bladder volume within the 3D anatomical image corresponding to a bladder of the subject;
    determine a dilated bladder volume by applying a morphological dilation operation to the identified bladder volume; and
    at step (e), determine the one or more uptake metrics using intensity values of voxels of the 3D functional image that (i) correspond to the prostate volume identified within the VOI of the 3D anatomical image, but (ii) do not correspond to regions of the 3D anatomical image within the dilated bladder volume.

50. A system for automatically processing 3D images to identify 3D volumes within the 3D images that correspond to a prostate of a subject and determining one or more uptake metrics indicative of radiopharmaceutical uptake therein, the system comprising:
  a processor; and
  a memory having instructions stored thereon, wherein the instructions, when executed by the processor, cause the processor to:
    (a) receive a 3D anatomical image of the subject obtained using an anatomical imaging modality, wherein the 3D anatomical image comprises a graphical representation of tissue within a subject, at least a portion of which corresponds to a pelvic region of the subject;
    (b) receive a 3D functional image of the subject obtained using a functional imaging modality, wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the pelvic region of the subject;
    (c) determine, using a first module, an initial volume of interest (VOI) within the 3D anatomical image, the initial VOI corresponding to tissue within the pelvic region of the subject and excluding tissue outside the pelvic region of the subject;
    (d) identify, using a second module, a prostate volume within the initial VOI corresponding to the prostate of the subject;
    (e) determine the one or more uptake metrics using the 3D functional image and the prostate volume identified within the initial VOI of the 3D anatomical image;
    cause display of an interactive graphical user interface (GUI) for presentation to the user of a visual representation of the 3D anatomical image and/or the 3D functional image; and
    (g) cause graphical rendering of, within the GUI, the 3D anatomical image and/or the 3D functional image as selectable and superimposable layers, such that either can be selected for display and rendered separately, or both selected for display and rendered together by overlaying the 3D anatomical image with the 3D functional image.

51. A system for automatically processing 3D images to identify 3D volumes within the 3D images that correspond to a prostate of a subject and determining one or more uptake metrics indicative of radiopharmaceutical uptake therein, the system comprising:
  a processor; and
  a memory having instructions stored thereon, wherein the instructions, when executed by the processor, cause the processor to:
    (a) receive a 3D anatomical image of the subject obtained using an anatomical imaging modality, wherein the 3D anatomical image comprises a graphical representation of tissue within a subject, at least a portion of which corresponds to a pelvic region of the subject;
    (b) receive a 3D functional image of the subject obtained using a functional imaging modality, wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the pelvic region of the subject;
    (c) determine, using a first module, an initial volume of interest (VOI) within the 3D anatomical image, the initial VOI corresponding to tissue within the pelvic region of the subject and excluding tissue outside the pelvic region of the subject;
    (d) identify, using a second module, a prostate volume within the initial VOI corresponding to the prostate of the subject; and
    (e) determine the one or more uptake metrics using the 3D functional image and the prostate volume identified within the initial VOI of the 3D anatomical image;
    wherein step (d) comprises using the second module to identify one or more additional tissue volumes within the 3D anatomical image, each volume corresponding to a specific tissue region within the subject, wherein the one or more additional tissue volumes correspond(s) to one or more specific tissue regions selected from the group consisting of:
- a pelvic bone of the subject;
- a bladder of the subject;
- a rectum of the subject; and
- a gluteal muscle of the subject; and wherein the instructions further cause the processor to:
identify, using one or more auxiliary modules, one or more auxiliary tissue volumes within the 3D anatomical image, each auxiliary tissue volume corresponding to a base tissue volume identified by the second module; and
merge each auxiliary tissue volume with the corresponding base tissue volume identified by the second module.

52. A system for automatically processing 3D images to identify 3D volumes within the 3D images that correspond to a prostate of a subject and determining one or more uptake metrics indicative of radiopharmaceutical uptake therein, the system comprising:
a processor; and
a memory having instructions stored thereon, wherein the instructions, when executed by the processor, cause the processor to:
(a) receive a 3D anatomical image of the subject obtained using an anatomical imaging modality, wherein the 3D anatomical image comprises a graphical representation of tissue within a subject, at least a portion of which corresponds to a pelvic region of the subject;
(b) receive a 3D functional image of the subject obtained using a functional imaging modality, wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the pelvic region of the subject;
(c) determine, using a first module, an initial volume of interest (VOI) within the 3D anatomical image, the initial VOI corresponding to tissue within the pelvic region of the subject and excluding tissue outside the pelvic region of the subject;
(d) identify, using a second module, a prostate volume within the initial VOI corresponding to the prostate of the subject;
(e) determine the one or more uptake metrics using the 3D functional image and the prostate volume identified within the initial VOI of the 3D anatomical image; and
(f) determine, based on at least a portion of the one or more uptake metrics, one or more diagnostic or prognostic values for the subject, wherein for at least one of the one or more diagnostic or prognostic values said determining comprises comparing an uptake metric to one or more threshold value(s).

53. A system for automatically processing 3D images to identify 3D volumes within the 3D images that correspond to a prostate of a subject and determining one or more uptake metrics indicative of radiopharmaceutical uptake therein, the system comprising:
a processor; and
a memory having instructions stored thereon, wherein the instructions, when executed by the processor, cause the processor to:
(a) receive a 3D anatomical image of the subject obtained using an anatomical imaging modality, wherein the 3D anatomical image comprises a graphical representation of tissue within a subject, at least a portion of which corresponds to a pelvic region of the subject;
(b) receive a 3D functional image of the subject obtained using a functional imaging modality, wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the pelvic region of the subject;
(c) determine, using a first module, an initial volume of interest (VOI) within the 3D anatomical image, the initial VOI corresponding to tissue within the pelvic region of the subject and excluding tissue outside the pelvic region of the subject;
(d) identify, using a second module, a prostate volume within the initial VOI corresponding to the prostate of the subject;
(e) determine the one or more uptake metrics using the 3D functional image and the prostate volume identified within the initial VOI of the 3D anatomical image; and
(f) determine, based on at least a portion of the one or more uptake metrics, one or more diagnostic or prognostic values for the subject, wherein at least one of the one or more diagnostic or prognostic values estimates a risk for clinically significant prostate cancer in the subject.

54. A system for automatically processing 3D images to identify 3D volumes within the 3D images that correspond to a prostate of a subject and determining one or more uptake metrics indicative of radiopharmaceutical uptake therein, the system comprising:
a processor; and
a memory having instructions stored thereon, wherein the instructions, when executed by the processor, cause the processor to:
(a) receive a 3D anatomical image of the subject obtained using an anatomical imaging modality, wherein the 3D anatomical image comprises a graphical representation of tissue within a subject, at least a portion of which corresponds to a pelvic region of the subject;
(b) receive a 3D functional image of the subject obtained using a functional imaging modality, wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the pelvic region of the subject;
(c) determine, using a first module, an initial volume of interest (VOI) within the 3D anatomical image, the initial VOI corresponding to tissue within the pelvic region of the subject and excluding tissue outside the pelvic region of the subject;

(d) identify, using a second module, a prostate volume within the initial VOI corresponding to the prostate of the subject; and (e) determine the one or more uptake metrics using the 3D functional image and the prostate volume identified within the initial VOI of the 3D anatomical image, wherein the first module is a first CNN (convolutional neural network) module and the second module is a second CNN module, wherein the second CNN module comprises a greater number of convolutional filters than the first CNN module.

55. A system for automatically processing 3D images to identify 3D volumes within the 3D images that correspond to a prostate of a subject and determining one or more uptake metrics indicative of radiopharmaceutical uptake therein, the system comprising:

a processor; and a memory having instructions stored thereon, wherein the instructions, when executed by the processor, cause the processor to:

(a) receive a 3D anatomical image of the subject obtained using an anatomical imaging modality, wherein the 3D anatomical image comprises a graphical representation of tissue within a subject, at least a portion of which corresponds to a pelvic region of the subject;

(b) receive a 3D functional image of the subject obtained using a functional imaging modality, wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the pelvic region of the subject;

(c) determine, using a first module, an initial volume of interest (VOI) within the 3D anatomical image, the initial VOI corresponding to tissue within the pelvic region of the subject and excluding tissue outside the pelvic region of the subject;

(d) identify, using a second module, a prostate volume within the initial VOI corresponding to the prostate of the subject; and (e) determine the one or more uptake metrics using the 3D functional image and the prostate volume identified within the initial VOI of the 3D anatomical image, wherein the instructions cause the processor to perform steps (a) and (c) for each of a plurality of 3D anatomical images to determine a plurality of initial VOIs, each within one of the plurality of 3D anatomical images, wherein a variability in sizes of the initial VOIs is less than a variability in sizes of the 3D anatomical images.

* * * * *